US008916589B2

(12) United States Patent
Hauel et al.

(10) Patent No.: US 8,916,589 B2
(45) Date of Patent: Dec. 23, 2014

(54) BRADYKININ B1-ANTAGONISTS

(75) Inventors: Norbert Hauel, Schemmerhofen (DE); Angelo Ceci, Mittelbiberach (DE); Enzo Cereda, Novi Ligure (IT); Henri Doods, Warthausen (DE); Ingo Konetzki, Warthausen (DE); Juergen Mack, Biberach (DE); Henning Priepke, Warthausen (DE); Annette Schuler-Metz, Ulm (DE); Rainer Walter, Biberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 614 days.

(21) Appl. No.: 12/675,224

(22) PCT Filed: Aug. 28, 2008

(86) PCT No.: PCT/EP2008/061263
§ 371 (c)(1),
(2), (4) Date: May 25, 2010

(87) PCT Pub. No.: WO2009/027450
PCT Pub. Date: Mar. 5, 2009

(65) Prior Publication Data
US 2011/0263626 A1 Oct. 27, 2011

(30) Foreign Application Priority Data

Aug. 29, 2007 (DE) .......................... 10 2007 041 042

(51) Int. Cl.
| | | |
|---|---|---|
| A61K 31/44 | (2006.01) |
| A61K 31/41 | (2006.01) |
| C07D 239/28 | (2006.01) |
| C07C 237/24 | (2006.01) |
| C07C 317/44 | (2006.01) |
| C07D 209/42 | (2006.01) |
| C07D 213/64 | (2006.01) |
| C07D 213/82 | (2006.01) |
| C07D 233/90 | (2006.01) |
| C07D 237/24 | (2006.01) |
| C07D 239/34 | (2006.01) |
| C07D 239/36 | (2006.01) |
| C07D 239/42 | (2006.01) |
| C07D 261/18 | (2006.01) |
| C07D 263/34 | (2006.01) |
| C07D 277/56 | (2006.01) |
| C07D 307/68 | (2006.01) |
| C07K 5/062 | (2006.01) |
| C07K 5/078 | (2006.01) |

(52) U.S. Cl.
CPC ............ *C07D 239/28* (2013.01); *C07C 237/24* (2013.01); *C07C 317/44* (2013.01); *C07D 209/42* (2013.01); *C07D 213/64* (2013.01); *C07D 213/82* (2013.01); *C07D 233/90* (2013.01); *C07D 237/24* (2013.01); *C07D 239/34* (2013.01); *C07D 239/36* (2013.01); *C07D 239/42* (2013.01); *C07D 261/18* (2013.01); *C07D 263/34* (2013.01); *C07D 277/56* (2013.01); *C07D 307/68* (2013.01); *C07K 5/06026* (2013.01); *C07K 5/06139* (2013.01); *C07C 2101/02* (2013.01)
USPC .......................................... 514/332; 514/359

(58) Field of Classification Search
USPC .................................. 514/339, 352
See application file for complete search history.

(56) References Cited

U.S. PATENT DOCUMENTS

| | | | |
|---|---|---|---|
| 6,689,778 B2 | 2/2004 | Bemis et al. | |
| 8,372,838 B2 | 2/2013 | Hauel et al. | |
| 8,450,306 B2 | 5/2013 | Hauel et al. | |
| 2008/0227823 A1* | 9/2008 | Pajouhesh et al. ............ | 514/339 |
| 2010/0197664 A1 | 8/2010 | Kauffmann-Hefner et al. | |
| 2010/0240669 A1 | 9/2010 | Hauel et al. | |

(Continued)

FOREIGN PATENT DOCUMENTS

| | | |
|---|---|---|
| CA | 2790952 A1 | 9/2011 |
| WO | 03065789 A2 | 8/2003 |

(Continued)

OTHER PUBLICATIONS

Kuduk et al.; Development of Orally Bioavailable and CNS Penetrant Biphenylaminocyclopropane Carboxamide Bradykinin B1 Receptor Antagonists; Journal of Medicinal Chemistry/ 2007; vol. 50; pp. 272-282.

(Continued)

*Primary Examiner* — San-Ming Hui
(74) *Attorney, Agent, or Firm* — Michael P. Morris; Anthony P. Bottino

(57) ABSTRACT

The present invention relates to compounds of general formula I (I)

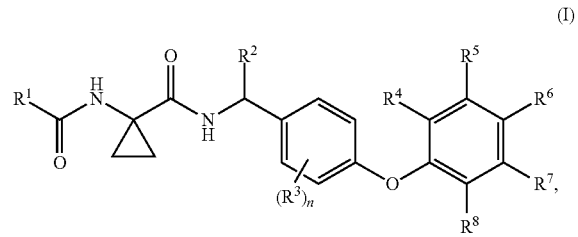

wherein n, $R^1$, $R^2$, $R^3$, $R^4$, $R^5$, $R^6$, $R^7$ and $R^8$ are defined as stated hereinafter, the enantiomers, the diastereomers, the mixtures thereof and the salts thereof, particularly the physiologically acceptable salts thereof with organic or inorganic acids or bases, which have valuable properties, the preparation thereof, the pharmaceutical compositions containing the pharmacologically effective compounds, the preparation thereof and the use thereof.

18 Claims, No Drawings

(56) References Cited

U.S. PATENT DOCUMENTS

2012/0142695 A1 6/2012 Hauel et al.
2012/0208823 A1 8/2012 Hauel et al.
2014/0038977 A1 2/2014 Hauel et al.

FOREIGN PATENT DOCUMENTS

| WO | 03066577 | A1 | 8/2003 |
| WO | 2004019868 | A2 | 3/2004 |
| WO | 2005016886 | A1 | 2/2005 |
| WO | 2005085198 | A2 | 9/2005 |
| WO | 2008050167 | A1 | 5/2008 |
| WO | 2009013299 | A2 | 1/2009 |
| WO | 2009021946 | A1 | 2/2009 |
| WO | 2011104203 | A1 | 9/2011 |
| WO | 2012022794 | A1 | 2/2012 |
| WO | 2012022795 | A1 | 2/2012 |

OTHER PUBLICATIONS

Kuduk et al.; Bradykinin B1 antagonists: SAR studies in the 2,3-diaminopyridine series; Bioorganic & Medicinal Chemistry Letters; 2005; No. 15; pp. 3925-3929.

Kuduk et al.; Bradykinin B1 antagonists: Biphenyl SAR studies in the cyclopropanecarboxamide series; Bioorganic & Medicinal Chemistry Letters; 2007; No. 17; pp. 3608-3612.

International Search Report, Form PCT/ISA/210, for corresponding PCT/EP2008/061263 ; date of mailing: Jan. 5, 2009.

Kuduk et al., 5-Piperazinyl pyridine carboxamide bradykinin B1 antagonists, Bioorganic & Medicinal Chemistry Letters 16, 2006, pp. 2791-2795.

Marceau et al, Bradykinin receptor ligands: Therapeutic perspectives, 3 Nature Review Drug Discovery, 2004, pp. 845-852.

* cited by examiner

BRADYKININ B1-ANTAGONISTS

The present invention relates to compounds of general formula I

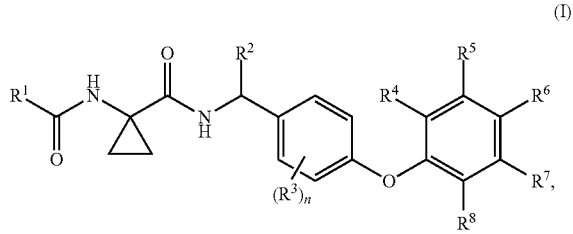

wherein n, $R^1$, $R^2$, $R^3$, $R^4$, $R^5$, $R^6$, $R^7$ and $R^8$ are defined as stated hereinafter, the enantiomers, the diastereomers, the mixtures thereof and the salts thereof, particularly the physiologically acceptable salts thereof with organic or inorganic acids or bases, which have valuable properties, the preparation thereof, the pharmaceutical compositions containing the pharmacologically effective compounds, the preparation thereof and the use thereof.

DETAILED DESCRIPTION OF THE INVENTION

In the above general formula I in a first embodiment $R^1$ denotes
  (a) a $C_{1-6}$-alkyl group optionally substituted by a group $R^{1.1}$,
  (b) a $C_{1-3}$-alkyl group wherein each methylene group is substituted by up to two fluorine atoms and each methyl group is substituted by up to three fluorine atoms,
  (c) a $C_{3-6}$-cycloalkyl group optionally substituted by a group $R^{1.2}$,
  (d) a $C_{2-6}$-alkenyl group,
  (e) a $C_{2-6}$-alkynyl group,
  (f) an aryl-$C_{0-2}$-alkylene group optionally substituted by 1, 2 or 3 groups $R^{1.3}$,
  (g) a five-membered heteroaryl group optionally substituted by 1, 2 or 3 groups $R^{1.4}$, which contains at least one N, O or S atom and optionally also contains one, two or three further N atoms and may additionally be benzo-fused,
  (h) a six-membered heteroaryl group optionally substituted by a group $R^{1.4}$, which contains one, two or three N atoms and may additionally be benzo-fused,
  (i) —O—$R^{1:1.1}$ or
  (j) —$NR^{1.1.3}R^{1.1.4}$,
$R^{1.1}$ denotes halogen, —$NO_2$, —CN, $C_{3-6}$-cycloalkyl, —$OR^{1.1.1}$, —$SR^{1.1.1}$, —$C(O)R^{1.1.1}$, —$S(O)_2$—$R^{1.1.2}$, —O—$S(O)_2$—$R^{1.1.2}$, —$CO_2R^{1.1.1}$, —O—$C(O)$—$R^{1.1.1}$, —$NR^{1.1.3}R^{1.1.4}$, —$NR^{1.1.3}$-$C(O)$—$R^{1.1.1}$, —$NR^{1.1.3}$-$C(O)$—$R^{1.1.1}$, —$NR^{1.1.3}$-$CO_2$—$R^{1.1.1}$, —$C(O)$—$NR^{1.1.3}R^{1.1.4}$,
$R^{1.1.1}$ denotes
  (a) H,
  (b) $C_{1-4}$-alkyl,
  (c) $C_{1-3}$-alkyl, wherein each methylene group is substituted by up to two fluorine atoms and each methyl group is substituted by up to three fluorine atoms,
  (d) a phenyl group optionally substituted by 1, 2 or 3 groups $R^{1.1.1.1}$,
  (e) $C_{3-6}$-cycloalkyl,
  (f) a pyridyl group optionally substituted by 1, 2 or 3 groups $R^{1.1.1.2}$,
$R^{1.1.1.1}$ independently of one another denote
  (b) halogen, —$NO_2$, —CN, —OH, —O—$C_{1-4}$-alkyl, $C_{3-6}$-cycloalkyl, $C_{1-4}$-alkyl,
  (c) $C_{1-3}$-alkyl, wherein each methylene group is substituted by up to two fluorine atoms and each methyl group is substituted by up to three fluorine atoms,
$R^{1.1.1.2}$ independently of one another denote halogen or $C_{1-4}$-alkyl,
$R^{1.1.2}$ denotes
  (a) $C_{1-4}$-alkyl,
  (b) $C_{1-3}$-alkyl, wherein each methylene group is substituted by up to two fluorine atoms and each methyl group is substituted by up to three fluorine atoms,
  (c) —O—$C_{1-4}$-alkyl,
  (d) a phenyl group optionally substituted by 1, 2 or 3 groups $R^{1.1.1.1}$,
$R^{1.1.3}$,
$R^{1.1.4}$ independently of one another denote
  (a) H,
  (b) a $C_{1-4}$-alkyl group optionally substituted by 1, 2 or 3 groups $R^{1.1.4.1}$,
  (c) a phenyl group optionally substituted by 1, 2 or 3 groups $R^{1.1.1.1}$,
  (d) $C_{3-6}$-cycloalkyl, or
$R^{1.1.3}$ and $R^{1.1.4}$ together with the N atom to which they are bound form a 4-, 5- or 6-membered heterocyclic ring, which may additionally contain a further heteroatom selected from N, O and S, or
$R^{1.1.3}$ and $R^{1.1.4}$ together with the N atom to which they are bound form a cyclic imide,
$R^{1.1.4.1}$ independently of one another denote halogen, —$NH_2$, —$NH(C_{1-4}$-alkyl), —$N(C_{1-4}$-alkyl)$_2$ or —$SO_2$—$R^{1.1.2}$,
$R^{1.2}$ denotes halogen, —$NO_2$, —CN or phenyl,
$R^{1.3}$ denotes
  (a) halogen, —$NO_2$, —CN, —$OR^{1.1.1}$, —$SR^{1.1.1}$, —$CO_2R^{1.1.1}$, $C_{1-6}$-alkyl,
  (b) $C_{1-3}$-alkyl, wherein each methylene group is substituted by up to two fluorine atoms and each methyl group is substituted by up to three fluorine atoms,
$R^{1.4}$ independently of one another denote
  (a) halogen, —$NO_2$, —CN, —$OR^{1.1.1}$, —$SR^{1.1.1}$, —S(O)—$R^{1.1.2}$, —$S(O)_2$—$R^{1.1.2}$, —$NR^{1.1.3}R^{1.1.4}$, $C_{1-6}$-alkyl,
  (b) $C_{1-3}$-alkyl, wherein each methylene group is substituted by up to two fluorine atoms and each methyl group is substituted by up to three fluorine atoms , or
  (c) an oxo group,
$R^2$ denotes
  (a) H or $C_{1-4}$-alkyl,
  (b) $C_{1-3}$-alkyl, wherein each methylene group is substituted by up to two fluorine atoms and each methyl group is substituted by up to three fluorine atoms,
$R^3$ independently of one another denote
  (a) H, halogen, —CN, —OH, $C_{1-6}$-alkyl, $C_{3-7}$-cycloalkyl, —O—$C_{1-4}$-alkyl, —O—$CF_3$, —O—$C_{3-6}$-cycloalkyl, —$N(C_{1-3}$-alkyl)$_2$, —$C(O)$—$NH_2$, —$(SO_2)NH_2$, —$SO_2$—$C_{1-3}$-alkyl,
  (b) $C_{1-3}$-alkyl, wherein each methylene group is substituted by up to two fluorine atoms and each methyl group is substituted by up to three fluorine atoms,
$R^4$, $R^5$,
$R^6$, $R^7$,
$R^8$ independently of one another denote
  (a) H, halogen, —CN, —OH, (b) $C_{1-6}$-alkyl, wherein two adjacent substituents together may denote a trimethylene or tetramethylene group,
(c) $C_{1-3}$-alkyl, wherein each methylene group is substituted by up to two fluorine atoms and each methyl group is substituted by up to three fluorine atoms,
(d) $C_{3-7}$-cycloalkyl,
(e) —O—$C_{1-6}$-alkyl, wherein two adjacent substituents may denote a methylenedioxy or ethylenedioxy group,
(f) —O—$CF_3$, —O—$C_{3-7}$-cycloalkyl,
(g) —$NH_2$, —NH($C_{1-3}$-alkyl), —N($C_{1-3}$-alkyl)$_2$,
(h) —C(O)—$R^{8.1}$,
(i) —$SO_2$—$R^{8.2}$,
(j) a five-membered heteroaryl group optionally substituted by one or two $C_{1-3}$-alkyl groups which is selected from among pyrrolyl, oxazolyl, isoxazolyl, oxadiazolyl, thiazolyl, isothiazolyl, thiadiazolyl, imidazolyl, pyrazolyl, triazolyl and tetrazolyl,
(k) a six-membered heteroaryl group optionally substituted by one or two $C_{1-3}$-alkyl groups which is selected from among pyridyl, pyrimidinyl, pyrazinyl, pyridazinyl and triazinyl, $R^{8.1}$ denotes —$NH_2$, —NH($C_{1-6}$-alkyl),—N($C_{1-6}$-alkyl)$_2$, N-acetidinyl, N-pyrrolidinyl, N-piperidinyl, N-morpholinyl, —OH, —O—$C_{1-8}$-alkyl, —O—$C_{3-7}$-cycloalkyl, $R^{8.2}$ denotes —$NH_2$, —NH($C_{1-6}$-alkyl),—N($C_{1-6}$-alkyl)$_2$, N-acetidinyl, N-pyrrolidinyl, N-piperidinyl, N-morpholinyl and n denotes one of the numbers 0, 1, 2, 3 or 4,
the enantiomers, the diastereomers, the mixtures thereof and the salts thereof, particularly the physiologically acceptable salts thereof with organic or inorganic acids or bases.

A further embodiment of the present invention comprises the compounds of the above general formula I, wherein $R^2$, $R^3$, $R^4$, $R^5$, $R^6$, $R^7$, $R^8$ and n are defined as mentioned hereinbefore in the first embodiment and
$R^1$ denotes
(a) a $C_{1-6}$-alkyl group optionally substituted by a group $R^{1.1}$,
(b) a $C_{1-3}$-alkyl group wherein each methylene group is substituted by up to two fluorine atoms and each methyl group is substituted by up to three fluorine atoms,
(c) a $C_{3-6}$-cycloalkyl group optionally substituted by a group $R^{1.2}$,
(d) a phenyl group optionally substituted by 1, 2 or 3 groups $R^{1.3}$,
(e) a five-membered heteroaryl group optionally substituted by a group $R^{1.4}$, which contains at least one N, O or S atom and which optionally additionally contains one, two or three further N atoms, or
(f) a six-membered heteroaryl group optionally substituted by a group $R^{1.4}$, which contains one, two or three N atoms, $R^{1.1}$ denotes $C_{3-6}$-cycloalkyl, —$OR^{1.1.1}$, —$NR^{1.1.3}R^{1.1.4}$, —C(O)—$NR^{1.1.3}R^{1.1.4}$, —CN, —$CO_2R^{1.1.1}$, —$S(O)_2$—$C_{1-6}$-alkyl or —O—$S(O)_2$—$C_{1-6}$-alkyl, $R^{1.1.1}$ denotes
(a) H,
(b) $C_{1-4}$-alkyl,
(c) $C_{1-3}$-alkyl, wherein each methylene group is substituted by up to two fluorine atoms and each methyl group is substituted by up to three fluorine atoms, or
(d) $C_{3-6}$-cycloalkyl, $R^{1.1.3}$,
$R^{1.1.4}$ independently of one another denote
(a) H,
(b) $C_{1-4}$-alkyl or
(c) $C_{3-6}$-cycloalkyl, and $R^{1.2}$ denotes halogen, —$NO_2$, —CN or phenyl,
$R^{1.3}$ denotes
(a) halogen, —$NO_2$, —CN, —$OR^{1.1.1}$, —$SR^{1.1.1}$, —$CO_2R^{1.1.1}$, $C_{1-6}$-alkyl or
(b) $C_{1-3}$-alkyl, wherein each methylene group is substituted by up to two fluorine atoms and each methyl group is substituted by up to three fluorine atoms, and $R^{1.4}$ denotes
(a) halogen, —$NO_2$, —CN, —$OR^{1.1.1}$, —$SR^{1.1.1}$, —$NR^{1.1.3}R^{1.1.4}$, $C_{1-6}$-alkyl,
(b) $C_{1-3}$-alkyl, wherein each methylene group is substituted by up to two fluorine atoms and each methyl group is substituted by up to three fluorine atoms, or
(c) an oxo group, the enantiomers, the diastereomers, the mixtures thereof and the salts thereof, particularly the physiologically acceptable salts thereof with organic or inorganic acids or bases.

A further embodiment of the present invention comprises the compounds of the above general formula I, wherein
$R^1$ denotes
(a) a $C_{1-6}$-alkyl group optionally substituted by a group $R^{1.1}$,
(b) a $C_{1-3}$-alkyl group wherein each methylene group is substituted by up to two fluorine atoms and each methyl group is substituted by up to three fluorine atoms,
(c) a $C_{3-6}$-cycloalkyl group optionally substituted by a group $R^{1.2}$,
(d) a phenyl group optionally substituted by 1, 2 or 3 groups $R^{1.3}$,
(e) a five-membered heteroaryl group optionally substituted by a group $R^{1.4}$, which contains at least one N, O or S atom and which optionally additionally contains one, two or three further N atoms, or
(f) a six-membered heteroaryl group optionally substituted by a group $R^{1.4}$, which contains one, two or three N atoms, $R^{1.1}$ denotes $C_{3-6}$-cycloalkyl, —$OR^{1.1.1}$, —$NR^{1.1.3}R^{1.1.4}$, —C(O)—$NR^{1.1.3}R^{1.1.4}$, —CN, —$CO_2R^{1.1.1}$, —$S(O)_2$—$C_{1-6}$-alkyl or —O—$S(O)_2$—$C_{1-6}$-alkyl, $R^{1.1.1}$ denotes
(a) H,
(b) $C_{1-4}$-alkyl,
(c) $C_{1-3}$-alkyl, wherein each methylene group is substituted by up to two fluorine atoms and each methyl group is substituted by up to three fluorine atoms, or
(d) $C_{3-6}$-cycloalkyl, $R^{1.1.3}$,
$R^{1.1.4}$ independently of one another denote
(a) H,
(b) $C_{1-4}$-alkyl or
(c) $C_{3-6}$-cycloalkyl, $R^{1.2}$ denotes halogen, —$NO_2$, —CN or phenyl,
$R^{1.3}$ denotes
(a) halogen, —$NO_2$, —CN, —$OR^{1.1.1}$, —$SR^{1.1.1}$, —$CO_2R^{1.1.1}$, $C_{1-6}$-alkyl or
(b) $C_{1-3}$-alkyl, wherein each methylene group is substituted by up to two fluorine atoms and each methyl group is substituted by up to three fluorine atoms, $R^{1.4}$ denotes
(a) halogen, —$NO_2$, —CN, —$OR^{1.1.1}$, —$SR^{1.1.1}$, —$NR^{1.1.3}R^{1.1.4}$, $C_{1-6}$-alkyl,
(b) $C_{1-3}$-alkyl, wherein each methylene group is substituted by up to two fluorine atoms and each methyl group is substituted by up to three fluorine atoms, or
(c) an oxo group $R^2$ denotes H or $C_{1-3}$-alkyl,
$R^3$ independently of one another denote (a) H, halogen, $C_{1-3}$-alkyl, —O—$C_{1-3}$-alkyl or
(b) $C_{1-3}$-alkyl, wherein each methylene group is substituted by up to two fluorine atoms and each methyl group is substituted by up to three fluorine atoms, $R^4$ denotes H or halogen, $R^5$ denotes
(a) H, halogen,
(b) $C_{1-3}$-alkyl,
(c) $C_{1-3}$-alkyl, wherein each methylene group is substituted by up to two fluorine atoms and each methyl group is substituted by up to three fluorine atoms,
(d) —O—$C_{1-3}$-alkyl,
(e) —C(O)—O—$C_{1-3}$-alkyl or —C(O)—$NH_2$, $R^6$ denotes
(a) H, halogen,
(b) $C_{1-3}$-alkylene-$R^{6.1}$,
(c) $C_{1-3}$-alkyl, wherein each methylene group is substituted by up to two fluorine atoms and each methyl group is substituted by up to three fluorine atoms,
(d) —OH, —O—$C_{1-4}$-alkyl,
(e) —O—$CHF_2$, —O—$CF_3$,
(f) —C(O)—O—$R^{6.2}$, —CN, —C(O)—$CH_3$, —C(O)—$NH_2$ or
(g) pyrrolyl, $R^{6.1}$ denotes H, —OH,
$R^{6.2}$ denotes H, $C_{1-3}$-alkyl, $R^7$ denotes
(a) H, halogen,
(b) $C_{1-3}$-alkyl,
(c) $C_{1-3}$-alkyl, wherein each methylene group is substituted by up to two fluorine atoms and each methyl group is substituted by up to three fluorine atoms,
(d) —O—$C_{1-3}$-alkyl,
(e) —C(O)—$NH_2$ or —C(O)-pyrrolidinyl, and $R^8$ denotes
(a) H, halogen,
(b) $C_{1-4}$-alkyl,
(c) $C_{1-3}$-alkyl, wherein each methylene group is substituted by up to two fluorine atoms and each methyl group is substituted by up to three fluorine atoms,
(d) —O—$C_{1-3}$-alkyl,
(e) —O—$CF_3$,
(f) —CN, —C(O)—$NH_2$ or
(g) pyrrolyl, the enantiomers, the diastereomers, the mixtures thereof and the salts thereof, particularly the physiologically acceptable salts thereof with organic or inorganic acids or bases.

A further embodiment of the present invention comprises the compounds of the above general formula I, wherein $R^2$, $R^3$, $R^4$, $R^5$, $R^6$, $R^7$, $R^8$ and n are defined as mentioned hereinbefore in the first embodiment and $R^1$ denotes
(a) a $C_{1-6}$-alkyl group optionally substituted by a group $R^{1.1}$,
(b) a $C_{1-3}$-alkyl group wherein each methylene group is substituted by up to two fluorine atoms and each methyl group is substituted by up to three fluorine atoms,
(c) a phenyl group optionally substituted by 1, 2 or 3 groups $R^{1.3}$,
(d) a five-membered heteroaryl group optionally substituted by a group $R^{1.4}$, which is selected from among furanyl, isoxazolyl, isothiazolyl, oxazolyl, thiazolyl, pyrazolyl, thiadiazolyl, oxadiazolyl, triazolyl, tetrazolyl, imidazolyl, indolyl, thienyl, pyrrolyl, benzimidazolyl, benzoxazolyl, benzothiazolyl and benzisoxazinyl, or
(e) a six-membered heteroaryl group optionally substituted by a group $R^{1.4}$, which is selected from among pyridyl, pyrimidinyl, pyridazinyl, pyrazinyl, triazinyl, quinazolinyl and quinoxazinyl, $R^{1.1}$ denotes $C_{3-6}$-cycloalkyl, —$OR^{1.1.1}$, —$NR^{1.1.3}R^{1.1.4}$, —C(O)—$NR^{1.1.3}R^{1.1.4}$, —CN, —$CO_2R^{1.1.1}$, —$S(O)_2$—$C_{1-6}$-alkyl or —O—$S(O)_2$—$C_{1-6}$-alkyl, $R^{1.1.1}$ denotes
(a) H,
(b) $C_{1-4}$-alkyl,
(c) $C_{1-3}$-alkyl, wherein each methylene group is substituted by up to two fluorine atoms and each methyl group is substituted by up to three fluorine atoms, or
(d) $C_{3-6}$-cycloalkyl, $R^{1.1.3}$,
$R^{1.1.4}$ independently of one another denote
(a) H,
(b) $C_{1-4}$-alkyl or
(c) $C_{3-6}$-cycloalkyl, $R^{1.3}$ denotes
(a) halogen, —$NO_2$, —CN, —$OR^{1.1.1}$, —$SR^{1.1.1}$, —$CO_2R^{1.1.1}$, $C_{1-6}$-alkyl or
(b) $C_{1-3}$-alkyl, wherein each methylene group is substituted by up to two fluorine atoms and each methyl group is substituted by up to three fluorine atoms, and $R^{1.4}$ denotes
(a) halogen, —$NO_2$, —CN, —$OR^{1.1.1}$, —$SR^{1.1.1}$, $C_{1-6}$-alkyl,
(b) $C_{1-3}$-alkyl, wherein each methylene group is substituted by up to two fluorine atoms and each methyl group is substituted by up to three fluorine atoms, or
(c) an oxo group, the enantiomers, the diastereomers, the mixtures thereof and the salts thereof, particularly the physiologically acceptable salts thereof with organic or inorganic acids or bases.

A further embodiment of the present invention comprises the compounds of the above general formula I, wherein $R^2$, $R^3$, $R^4$, $R^5$, $R^6$, $R^7$, $R^8$ and n are defined as mentioned hereinbefore in the first embodiment and $R^1$ denotes a group selected from

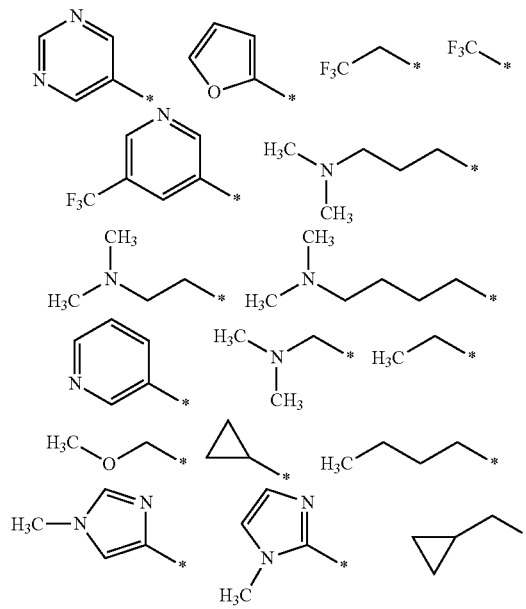

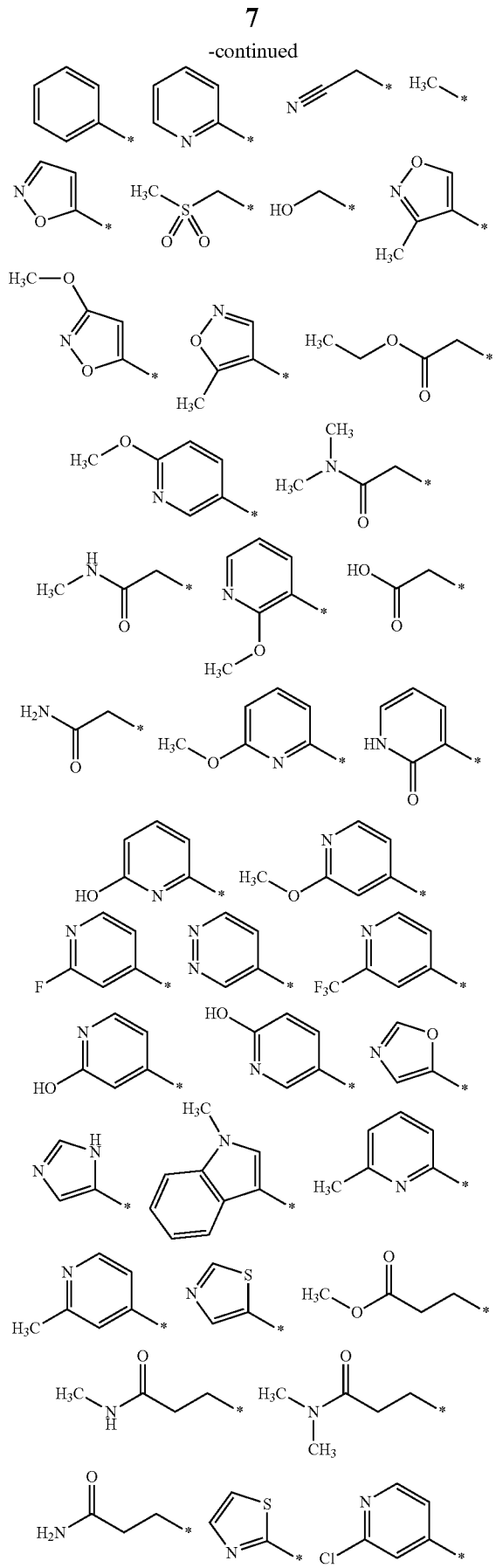

the enantiomers, the diastereomers, the mixtures thereof and the salts thereof, particularly the physiologically acceptable salts thereof with organic or inorganic acids or bases.

A further embodiment of the present invention comprises the compounds of the above general formula I, wherein $R^1$, $R^3$, $R^4$, $R^5$, $R^6$, $R^7$, $R^8$ and n are defined as mentioned hereinbefore in the first embodiment and $R^2$ denotes H or $C_{1-3}$-alkyl, the enantiomers, the diastereomers, the mixtures thereof and the salts thereof, particularly the physiologically acceptable salts thereof with organic or inorganic acids or bases.

A further embodiment of the present invention comprises the compounds of the above general formula I, wherein $R^1$, $R^2$, $R^4$, $R^5$, $R^6$, $R^7$, $R^8$ and n are defined as mentioned hereinbefore in the first embodiment and $R^3$ independently of one another denote
 (a) H, halogen, $C_{1-3}$-alkyl, —O—$C_{1-3}$-alkyl or
 (b) $C_{1-3}$-alkyl, wherein each methylene group is substituted by up to two fluorine atoms and each methyl group is substituted by up to three fluorine atoms, the enantiomers, the diastereomers, the mixtures thereof and the salts thereof, particularly the physiologically acceptable salts thereof with organic or inorganic acids or bases.

A further embodiment of the present invention comprises the compounds of the above general formula I, wherein $R^1$, $R^2$, $R^3$, $R^5$, $R^6$, $R^7$, $R^8$ and n are defined as mentioned hereinbefore in the first embodiment and $R^4$ denotes H or halogen, the enantiomers, the diastereomers, the mixtures thereof and the salts thereof, particularly the physiologically acceptable salts thereof with organic or inorganic acids or bases.

A further embodiment of the present invention comprises the compounds of the above general formula I, wherein $R^1$, $R^2$, $R^3$, $R^4$, $R^6$, $R^7$, $R^8$ and n are defined as mentioned hereinbefore in the first embodiment and $R^5$ denotes
 (a) H, halogen,
 (b) $C_{1-3}$-alkyl,
 (c) $C_{1-3}$-alkyl, wherein each methylene group is substituted by up to two fluorine atoms and each methyl group is substituted by up to three fluorine atoms,
 (d) —O—$C_{1-3}$-alkyl,
 (e) —C(O)—O—$C_{1-3}$-alkyl or —C(O)—$NH_2$, the enantiomers, the diastereomers, the mixtures thereof and the salts thereof, particularly the physiologically acceptable salts thereof with organic or inorganic acids or bases.

A further embodiment of the present invention comprises the compounds of the above general formula I, wherein $R^1$, $R^2$, $R^3$, $R^4$, K $R^5$, $R^7$, $R^8$ and n are defined as mentioned hereinbefore in the first embodiment and
$R^6$ denotes
- (a) H, halogen,
- (b) $C_{1-3}$-alkylene-$R^{6.1}$,
- (c) $C_{1-3}$-alkyl, wherein each methylene group is substituted by up to two fluorine atoms and each methyl group is substituted by up to three fluorine atoms,
- (d) —OH, —O—$C_{1-4}$-alkyl,
- (e) —O—$CHF_2$, —O—$CF_3$,
- (f) —C(O)—O—$R^{6.2}$, —CN, —C(O)—$CH_3$, —C(O)—$NH_2$ or
- (g) pyrrolyl, $R^{6.1}$ denotes H or —OH and
$R^{6.2}$ denotes H or $C_{1-3}$-alkyl,
the enantiomers, the diastereomers, the mixtures thereof and the salts thereof, particularly the physiologically acceptable salts thereof with organic or inorganic acids or bases.

A further embodiment of the present invention comprises the compounds of the above general formula I, wherein $R^1$, $R^2$, $R^3$, $R^4$, $R^5$, $R^6$, $R^8$ and n are defined as mentioned hereinbefore in the first embodiment and
$R^7$ denotes
- (a) H, halogen,
- (b) $C_{1-3}$-alkyl,
- (c) $C_{1-3}$-alkyl, wherein each methylene group is substituted by up to two fluorine atoms and each methyl group is substituted by up to three fluorine atoms,
- (d) —O—$C_{1-3}$-alkyl,
- (e) —C(O)—$NH_2$ or —C(O)-pyrrolidinyl, the enantiomers, the diastereomers, the mixtures thereof and the salts thereof, particularly the physiologically acceptable salts thereof with organic or inorganic acids or bases.

A further embodiment of the present invention comprises the compounds of the above general formula I, wherein $R^1$, $R^2$, $R^3$, $R^4$, $R^5$, $R^6$, $R^7$ and n are defined as mentioned hereinbefore in the first embodiment and
$R^8$ denotes
- (a) H, halogen,
- (b) $C_{1-4}$-alkyl,
- (c) $C_{1-3}$-alkyl, wherein each methylene group is substituted by up to two fluorine atoms and each methyl group is substituted by up to three fluorine atoms,
- (d) —O—$C_{1-3}$-alkyl,
- (e) —O—$CF_3$,
- (f) —CN, —C(O)—$NH_2$ or
- (g) pyrrolyl, the enantiomers, the diastereomers, the mixtures thereof and the salts thereof, particularly the physiologically acceptable salts thereof with organic or inorganic acids or bases.

A further embodiment of the present invention comprises the compounds of the above general formula I wherein
$R^1$ denotes a group selected from

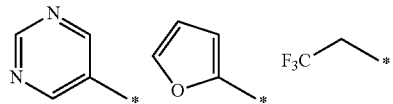

$R^2$ denotes H or —$CH_3$,
$R^3$ denotes H, F, —$CF_3$, —$CH_3$ or —O—$CH_3$,
$R^4$ denotes H or Cl, $R^5$ denotes H, Cl, $C_{1-3}$-alkyl, —$CF_3$, —O—$C_{1-3}$-alkyl, —C(O)—O—$C_{1-3}$-alkyl or —C(O)—$NH_2$,
$R^6$ denotes H, F, Cl, $C_{1-3}$-alkyl, —$CF_3$, —O—$C_{1-4}$-alkyl, —$OCF_3$, —C(O)—$NH_2$ or pyrrolyl,
$R^7$ denotes H, F, Cl, $C_{1-3}$-alkyl, —$CF_3$, —O—$C_{1-3}$-alkyl, —C(O)—$NH_2$ or —C(O)-pyrrolidinyl and
$R^8$ denotes H, F, Cl, Br, $C_{1-4}$-alkyl, —$CF_3$, —O—$C_{1-3}$-alkyl, —$OCF_3$, —C(O)—$NH_2$, —$OCF_3$ or pyrrolyl, the enantiomers, the diastereomers, the mixtures thereof and the salts thereof, particularly the physiologically acceptable salts thereof with organic or inorganic acids or bases.

A further embodiment of the present invention comprises the compounds of the above general formula I wherein
$R^1$ denotes a group selected from

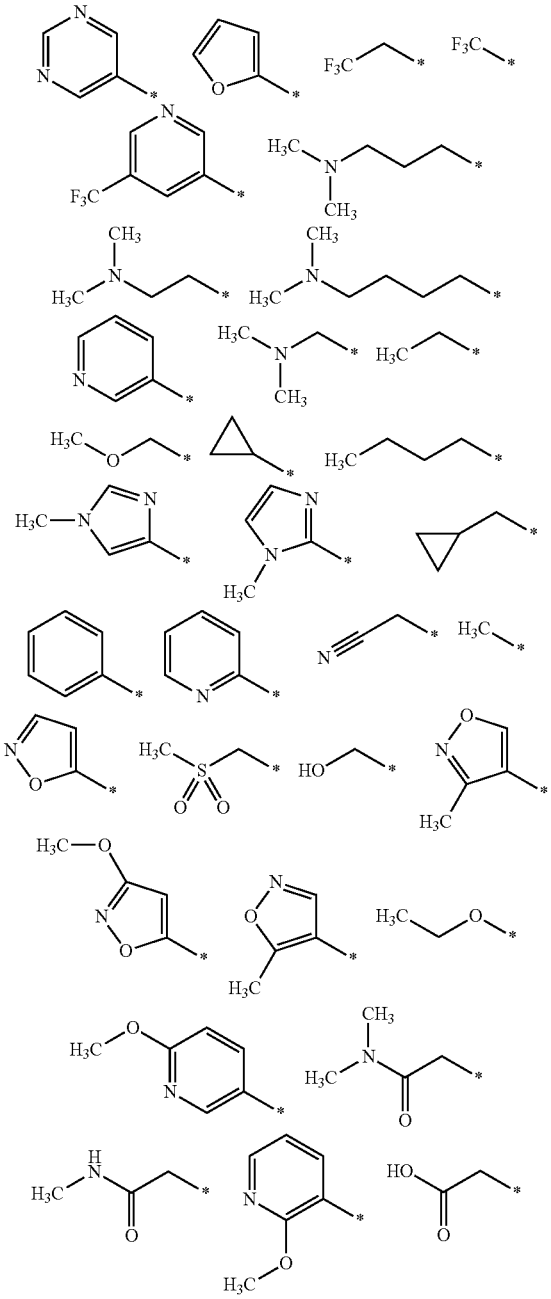

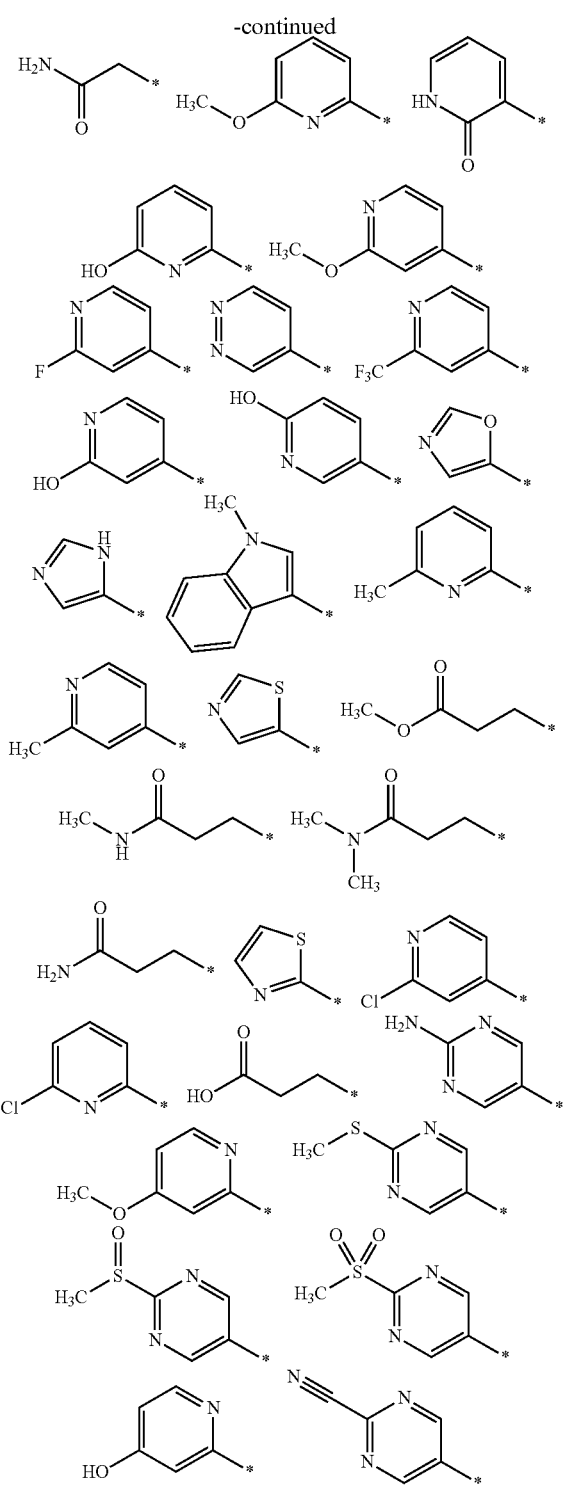

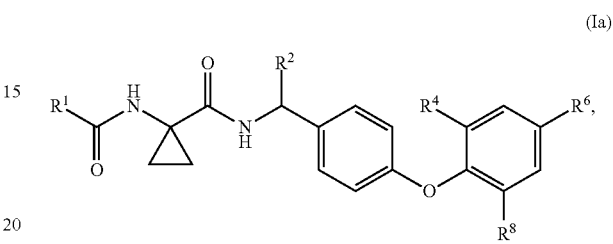

$R^2$ denotes H, —CH$_3$ or —C$_2$H$_5$,
$R^3$ denotes H, F, Cl, —CF$_3$, —CH$_3$ or —O—CH$_3$,
$R^4$ denotes H or Cl,
$R^5$ denotes H, Cl, C$_{1-3}$-alkyl, —CF$_3$, —O—C$_{1-3}$-alkyl, —C(O)—O—C$_{1-3}$-alkyl or —C(O)—NH$_2$,
$R^6$ denotes H, F, Cl, Br, —CN, C$_{1-3}$-alkyl, —CF$_3$, —COOH, —COO—C$_{1-3}$-alkyl, —CH(OH)CH$_3$, —OH, —O—C$_{1-4}$-alkyl, —OCF$_3$, —OCHF$_2$, —C(O)—CH$_3$, —C(O)—NH$_2$ or pyrrolyl,
$R^7$ denotes H, F, Cl, C$_{1-3}$-alkyl, —CF$_3$, —O—C$_{1-3}$-alkyl, —C(O)—NH$_2$ or —C(O)-pyrrolidinyl and
$R^8$ denotes H, F, Cl, Br, —CN, C$_{1-4}$-alkyl, —CF$_3$, —O—C$_{1-3}$-alkyl, —OCF$_3$, —C(O)—NH$_2$, —OCF$_3$ or pyrrolyl,
the enantiomers, the diastereomers, the mixtures thereof and the salts thereof, particularly the physiologically acceptable salts thereof with organic or inorganic acids or bases.

A further embodiment of the present invention comprises the compounds of general formula Ia, (Ia)

wherein
$R^1$ denotes a C$_{1-6}$-alkyl group optionally substituted by a group $R^{1.1}$,
$R^{1.1}$ denotes halogen, —NO$_2$, —CN, C$_{3-6}$-cycloalkyl, —OR$^{1.1.1}$, —SR$^{1.1.1}$, —C(O)R$^{1.1.1}$, —S(O)$_2$—R$^{1.1.2}$, —O—S(O)$_2$—R$^{1.1.1}$, —CO$_2$R$^{1.1.1}$, —O—C(O)—R$^{1.1.1}$, —NR$^{1.1.3}$R$^{1.1.4}$, —NR$^{1.1.3}$-C(O)—R$^{1.1.1}$, —NR$^{1.1.3}$-C(O)—R$^{1.1.1}$, —NR$^{1.1.3}$-CO$_2$—R$^{1.1.1}$ or —C(O)—NR$^{1.1.3}$R$^{1.1.4}$,
$R^{1.1.1}$ denotes
 (a) H,
 (b) C$_{1-4}$-alkyl,
 (c) C$_{1-3}$-alkyl, wherein each methylene group is substituted by up to two fluorine atoms and each methyl group is substituted by up to three fluorine atoms, or
 (d) C$_{3-6}$-cycloalkyl,
$R^{1.1.2}$ denotes
 (a) C$_{1-4}$-alkyl,
 (b) C$_{1-3}$-alkyl, wherein each methylene group is substituted by up to two fluorine atoms and each methyl group is substituted by up to three fluorine atoms, or
 (c) —O—C$_{1-4}$-alkyl,
$R^{1.1.3}$,
$R^{1.1.4}$ independently of one another denote
 (a) H,
 (b) a C$_{1-4}$-alkyl group optionally substituted by 1, 2 or 3 groups $R^{1.1.4.1}$ or
 (c) C$_{3-6}$-cycloalkyl,
$R^2$ denotes
 (a) H, C$_{1-4}$-alkyl or
 (b) C$_{1-3}$-alkyl, wherein each methylene group is substituted by up to two fluorine atoms and each methyl group is substituted by up to three fluorine atoms,
$R^4$ denotes H or halogen,
$R^6$ denotes
 (a) H, halogen,
 (b) C$_{1-3}$-alkylene-R$^{6.1}$,
 (c) C$_{1-3}$-alkyl, wherein each methylene group is substituted by up to two fluorine atoms and each methyl group is substituted by up to three fluorine atoms,
 (d) —OH, —O—C$_{1-4}$-alkyl,
 (e) —O—CHF$_2$, —O—CF$_3$,
 (f) —C(O)—O—R$^{6.2}$, —CN, —C(O)—CH$_3$, —C(O)—NH$_2$ or
 (g) pyrrolyl, $R^{6.1}$ denotes H, —OH,
R6.2 denotes H, $C_{1-3}$-alkyl, and
$R^8$ denotes
(a) H, halogen,
(b) $C_{1-4}$-alkyl,
(c) $C_{1-3}$-alkyl, wherein each methylene group is substituted by up to two fluorine atoms and each methyl group is substituted by up to three fluorine atoms,
(d) —O—$C_{1-3}$-alkyl,
(e) —O—$CF_3$,
(f) —CN, —C(O)—$NH_2$ or
(g) pyrrolyl,
the enantiomers, the diastereomers, the mixtures thereof and the salts thereof, particularly the physiologically acceptable salts thereof with organic or inorganic acids or bases.

A further embodiment of the present invention comprises the compounds of general formula Ia, wherein
$R^1$ denotes a group selected from

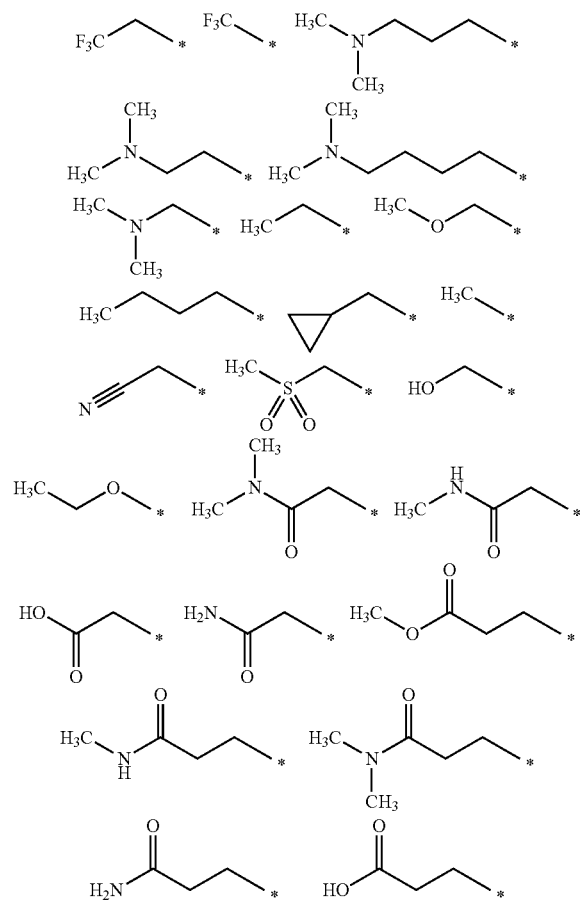

$R^2$ denotes H, —$CH_3$ or —$C_2H_5$,
$R^4$ denotes H or Cl,
$R^6$ denotes Cl or —O—$C_{1-4}$-alkyl, and
$R^8$ denotes F or —$CF_3$,
the enantiomers, the diastereomers, the mixtures thereof and the salts thereof, particularly the physiologically acceptable salts thereof with organic or inorganic acids or bases.

A further embodiment of the present invention comprises the compounds of general formula Ia,

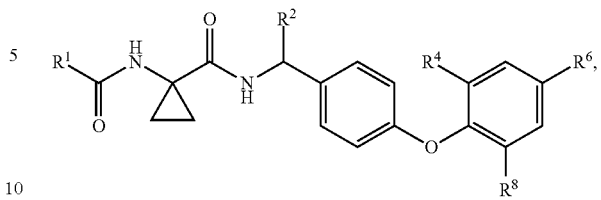

(Ia)

wherein
$R^1$ denotes
(a) a five-membered heteroaryl group optionally substituted by 1, 2 or 3 groups $R^{1.4}$, which contains at least one N, O or S atom and which optionally additionally contains one, two or three further N atoms and which may additionally be benzo-condensed, or
(b) a six-membered heteroaryl group optionally substituted by a group $R^{1.4}$, which contains one, two or three N atoms and which may additionally be benzo-condensed,
$R^{1.4}$ independently of one another denote
(a) halogen, —$NO_2$, —CN, —$OR^{1.1.1}$, —$SR^{1.1.1}$, —S(O)$_2$—$R^{1.1.2}$, —S(O)$_2$—$R^{1.1.2}$, —$NR^{1.1.3}R^{1.1.4}$, $C_{1-6}$-alkyl or
(b) $C_{1-3}$-alkyl, wherein each methylene group is substituted by up to two fluorine atoms and each methyl group is substituted by up to three fluorine atoms,
$R^{1.1.1}$ denotes
(a) H,
(b) $C_{1-4}$-alkyl,
(c) $C_{1-3}$-alkyl, wherein each methylene group is substituted by up to two fluorine atoms and each methyl group is substituted by up to three fluorine atoms, or
(d) $C_{3-6}$-cycloalkyl,
$R^{1.1.2}$ denotes
(a) $C_{1-4}$-alkyl,
(b) $C_{1-3}$-alkyl, wherein each methylene group is substituted by up to two fluorine atoms and each methyl group is substituted by up to three fluorine atoms, or
(c) —O—$C_{1-4}$-alkyl,
$R^{1.1.3}$,
$R^{1.1.4}$ independently of one another denote
(a) H,
(b) a $C_{1-4}$-alkyl group optionally substituted by 1, 2 or 3 groups $R^{1.1.4.1}$,
(c) $C_{3-6}$-cycloalkyl, or
$R^2$ denotes
(a) H, $C_{1-4}$-alkyl or
(b) $C_{1-3}$-alkyl, wherein each methylene group is substituted by up to two fluorine atoms and each methyl group is substituted by up to three fluorine atoms,
$R^4$ denotes H or halogen,
$R^6$ denotes
(a) H, halogen,
(b) $C_{1-3}$-alkylene-$R^{6.1}$,
(c) $C_{1-3}$-alkyl, wherein each methylene group is substituted by up to two fluorine atoms and each methyl group is substituted by up to three fluorine atoms,
(d) —OH, —O—$C_{1-4}$-alkyl,
(e) —O—$CHF_2$, —O—$CF_3$,
(f) —C(O)—O—$R^{6.2}$, —CN, —C(O)—$CH_3$, —C(O)—$NH_2$ or
(g) pyrrolyl,
$R^{6.1}$ denotes H, —OH,
$R^{6.2}$ denotes H, $C_{1-3}$-alkyl, and R⁸ denotes
(a) H, halogen,
(b) $C_{1-4}$-alkyl,
(c) $C_{1-3}$-alkyl, wherein each methylene group is substituted by up to two fluorine atoms and each methyl group is substituted by up to three fluorine atoms,
(d) —O—$C_{1-3}$-alkyl,
(e) —O—$CF_3$,
(f) —CN, —C(O)—$NH_2$ or
(g) pyrrolyl,
the enantiomers, the diastereomers, the mixtures thereof and the salts thereof, particularly the physiologically acceptable salts thereof with organic or inorganic acids or bases.

A further embodiment of the present invention comprises the compounds of general formula Ia, wherein
$R^1$ denotes a group selected from

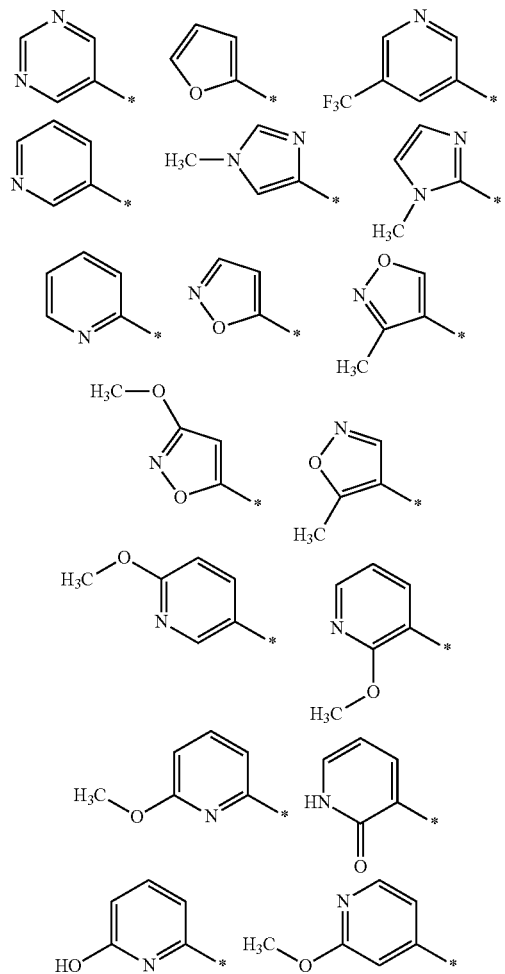

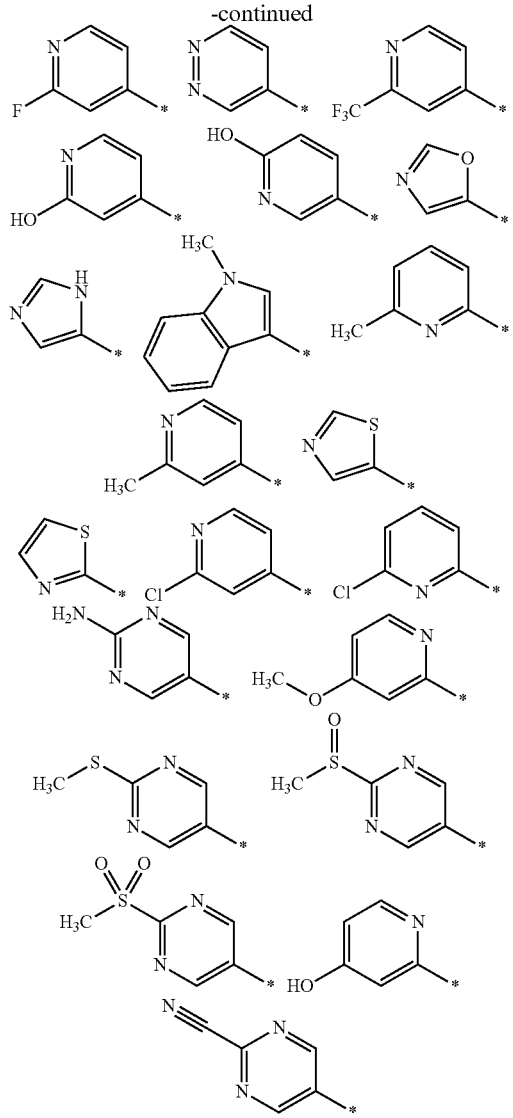

$R^2$ denotes H, —$CH_3$ or —$C_2H_5$,
$R^4$ denotes H or Cl,
$R^6$ denotes F, Cl, Br, —CN, —$CH_3$, —$CF_3$, —COOH, —COO—$CH_3$, —CH(OH)$CH_3$, —OH, —O—$CH_3$, —$OCF_3$, —$OCHF_2$, —C(O)—$CH_3$, —C(O)—$NH_2$ or pyrrolyl, and
$R^8$ denotes H, F, Cl, Br, —CN, $C_{1-4}$-alkyl, —$CF_3$, —O—$C_{1-3}$-alkyl, —$OCF_3$, —C(O)—$NH_2$, —$OCF_3$ or pyrrolyl,
the enantiomers, the diastereomers, the mixtures thereof and the salts thereof, particularly the physiologically acceptable salts thereof with organic or inorganic acids or bases.

The following are mentioned as examples of most particularly preferred compounds of the above general formula I:

| No. | Structure |
|---|---|
| (1) | 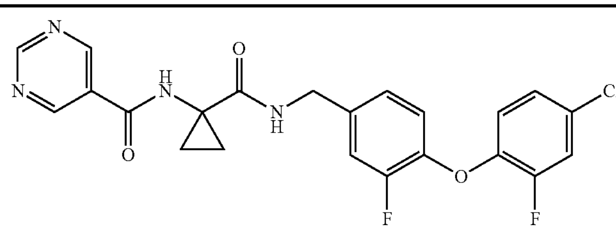 |

-continued
| No. | Structure |
|---|---|
| (2) | 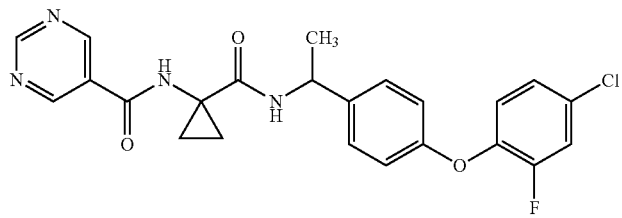 [SMILES: CC(NC(=O)C1(NC(=O)c2cncnc2)CC1)c1ccc(Oc2ccc(Cl)cc2F)cc1] |
| (3) | 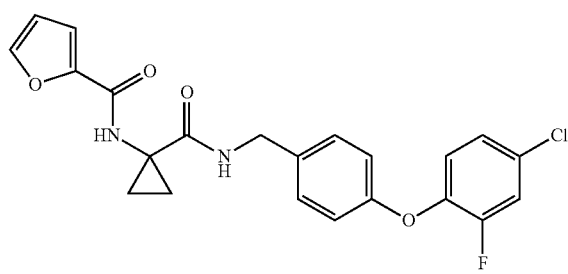 [SMILES: O=C(NC1(C(=O)NCc2ccc(Oc3ccc(Cl)cc3F)cc2)CC1)c1ccco1] |
| (4) | 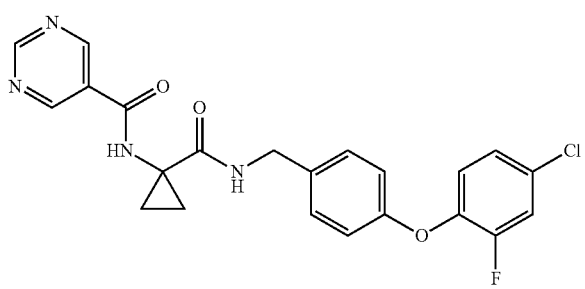 [SMILES: O=C(NC1(C(=O)NCc2ccc(Oc3ccc(Cl)cc3F)cc2)CC1)c1cncnc1] |
| (5) | 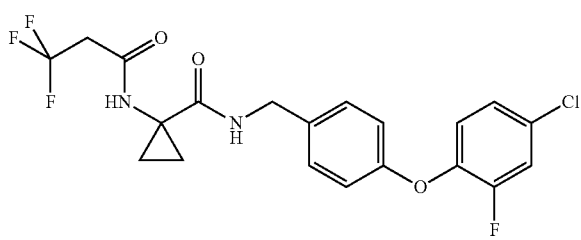 [SMILES: O=C(CC(F)(F)F)NC1(C(=O)NCc2ccc(Oc3ccc(Cl)cc3F)cc2)CC1] |
| (6) | 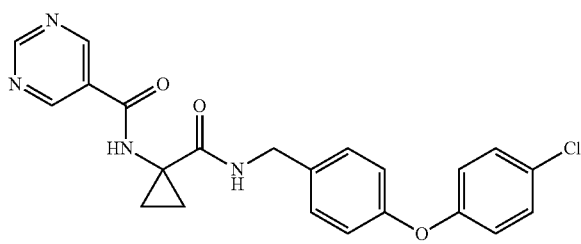 [SMILES: O=C(NC1(C(=O)NCc2ccc(Oc3ccc(Cl)cc3)cc2)CC1)c1cncnc1] |
| (7) | 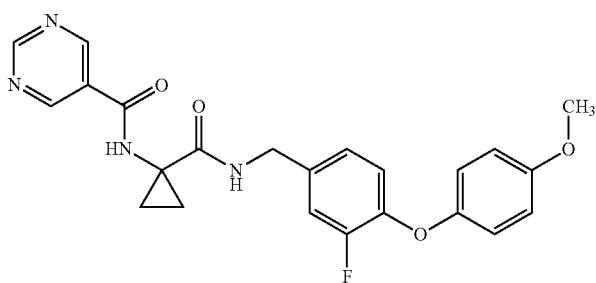 [SMILES: COc1ccc(Oc2ccc(CNC(=O)C3(NC(=O)c4cncnc4)CC3)cc2F)cc1] |

-continued
| No. | Structure |
|---|---|
| (8) | 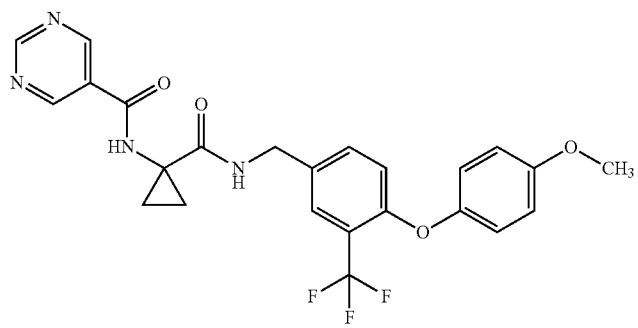 [SMILES: COc1ccc(Oc2ccc(CNC(=O)C3(NC(=O)c4cncnc4)CC3)cc2C(F)(F)F)cc1] |
| (9) | 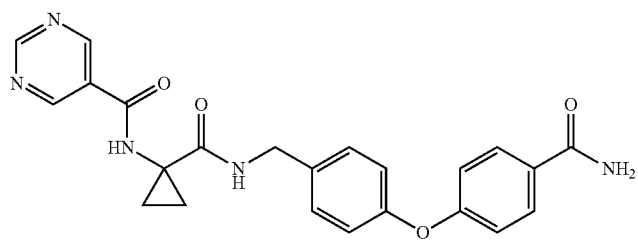 [SMILES: NC(=O)c1ccc(Oc2ccc(CNC(=O)C3(NC(=O)c4cncnc4)CC3)cc2)cc1] |
| (10) | 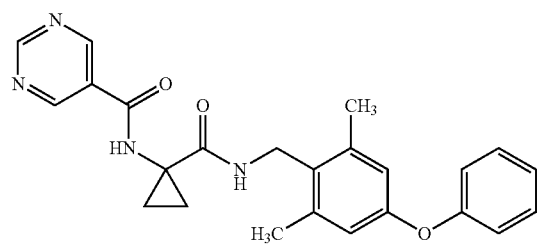 |
| (11) | 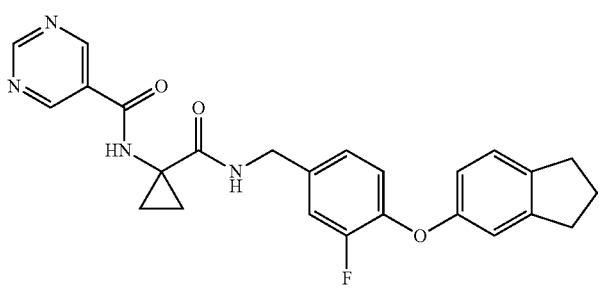 |
| (12) | 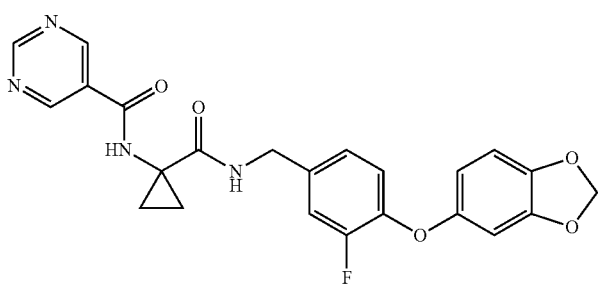 [SMILES: O=C(NC1(C(=O)NCc2ccc(Oc3ccc4c(c3)OCO4)c(F)c2)CC1)c1cncnc1] |

-continued
| No. | Structure |
|---|---|
| (13) | 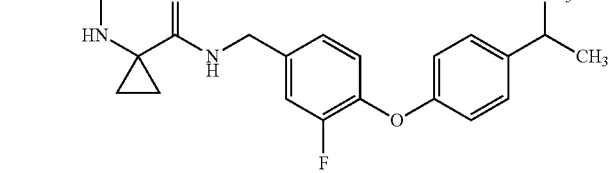 |
| (14) | 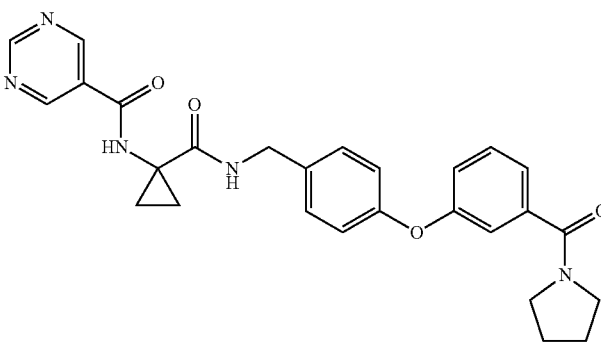 |
| (15) | 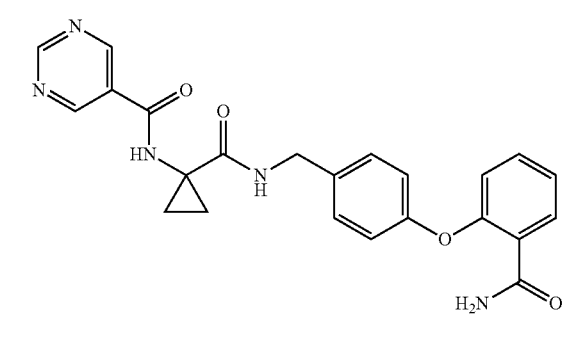 [SMILES: NC(=O)c1ccccc1Oc1ccc(CNC(=O)C2(NC(=O)c3cncnc3)CC2)cc1] |
| (16) | 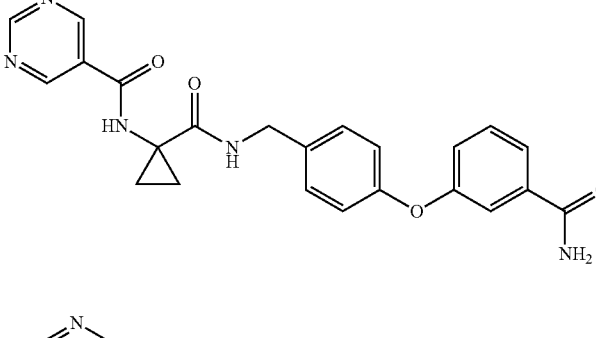 |
| (17) | 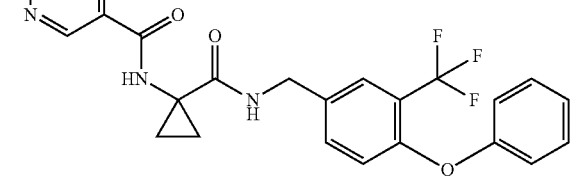 |

| No. | Structure |
|---|---|
| (18) | 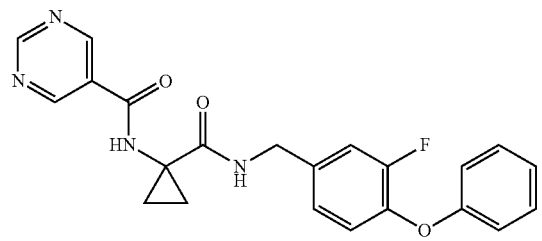 [SMILES: O=C(NC1(C(=O)NCc2ccc(Oc3ccccc3)c(F)c2)CC1)c1cncnc1] |
| (19) | 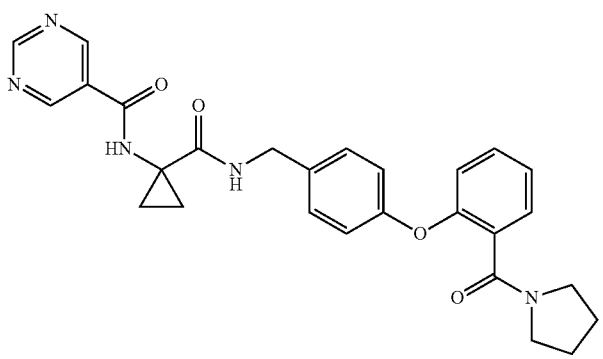 [SMILES: O=C(NC1(C(=O)NCc2ccc(Oc3ccccc3C(=O)N3CCCC3)cc2)CC1)c1cncnc1] |
| (20) | 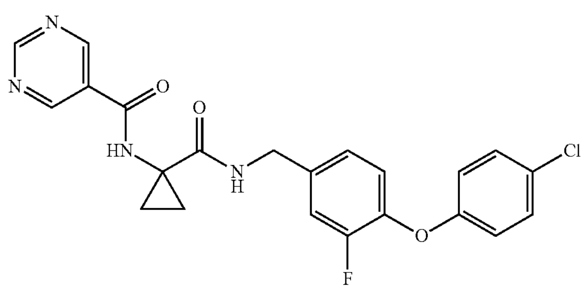 [SMILES: O=C(NC1(C(=O)NCc2ccc(Oc3ccc(Cl)cc3)c(F)c2)CC1)c1cncnc1] |
| (21) | 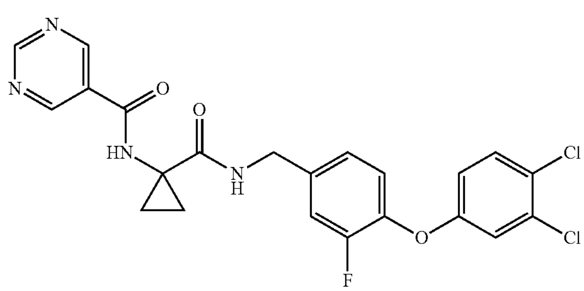 [SMILES: O=C(NC1(C(=O)NCc2ccc(Oc3ccc(Cl)c(Cl)c3)c(F)c2)CC1)c1cncnc1] |
| (22) | 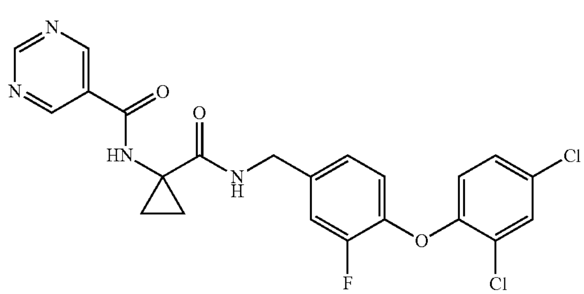 [SMILES: O=C(NC1(C(=O)NCc2ccc(Oc3ccc(Cl)cc3Cl)c(F)c2)CC1)c1cncnc1] |

| No. | Structure |
|---|---|
| (23) | 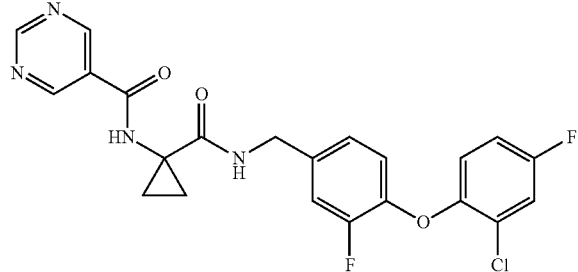 [SMILES: O=C(NC1(C(=O)NCc2ccc(Oc3ccc(F)cc3Cl)c(F)c2)CC1)c1cncnc1] |
| (24) | 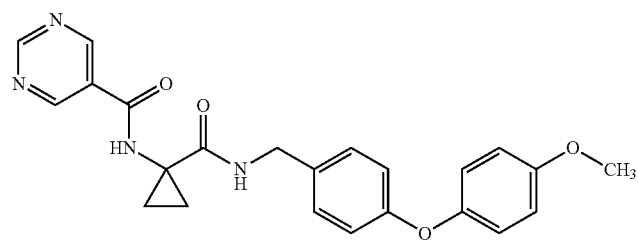 [SMILES: COc1ccc(Oc2ccc(CNC(=O)C3(NC(=O)c4cncnc4)CC3)cc2)cc1] |
| (25) | 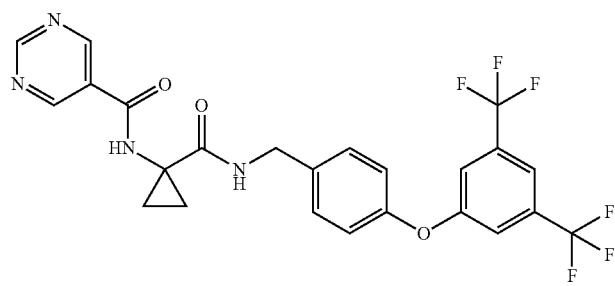 [SMILES: O=C(NC1(C(=O)NCc2ccc(Oc3cc(C(F)(F)F)cc(C(F)(F)F)c3)cc2)CC1)c1cncnc1] |
| (26) | 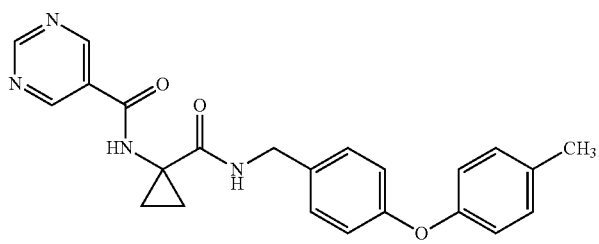 [SMILES: Cc1ccc(Oc2ccc(CNC(=O)C3(NC(=O)c4cncnc4)CC3)cc2)cc1] |
| (27) | 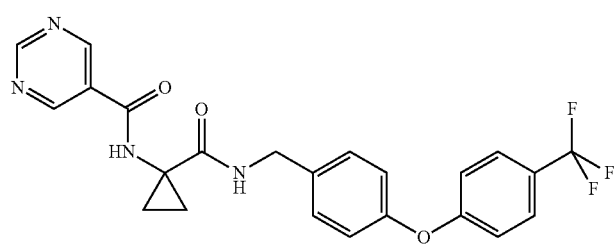 [SMILES: O=C(NC1(C(=O)NCc2ccc(Oc3ccc(C(F)(F)F)cc3)cc2)CC1)c1cncnc1] |

| No. | Structure |
|---|---|
| (28) | 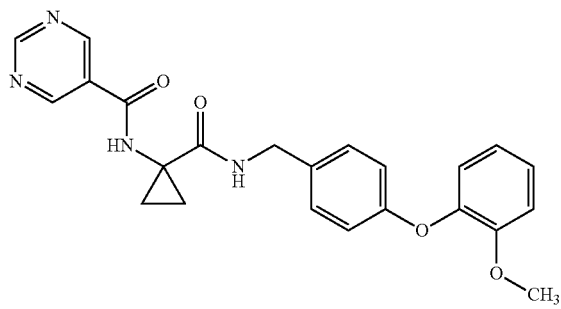 [SMILES: COc1ccccc1Oc1ccc(CNC(=O)C2(NC(=O)c3cncnc3)CC2)cc1] |
| (29) | 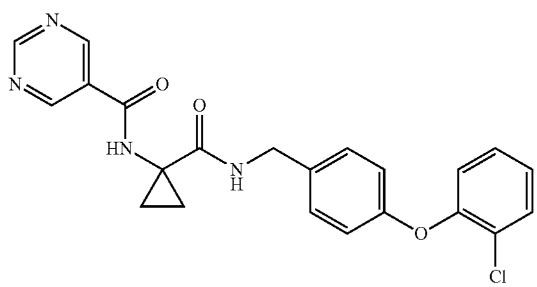 [SMILES: O=C(NC1(C(=O)NCc2ccc(Oc3ccccc3Cl)cc2)CC1)c1cncnc1] |
| (30) | 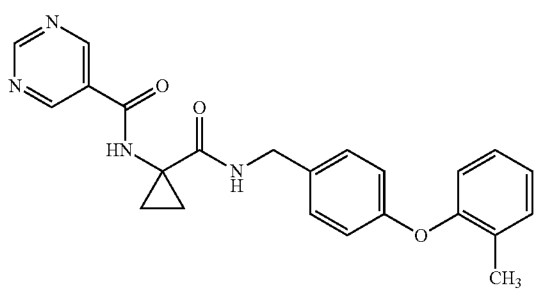 [SMILES: Cc1ccccc1Oc1ccc(CNC(=O)C2(NC(=O)c3cncnc3)CC2)cc1] |
| (31) | 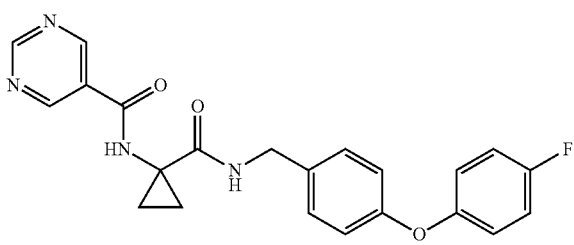 [SMILES: O=C(NC1(C(=O)NCc2ccc(Oc3ccc(F)cc3)cc2)CC1)c1cncnc1] |
| (32) | 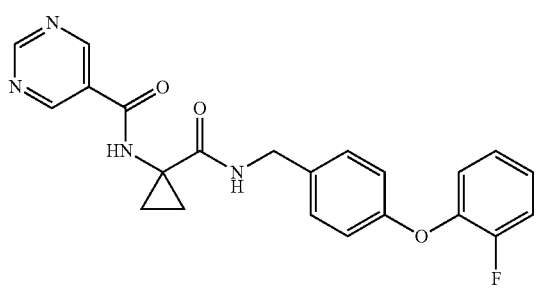 [SMILES: O=C(NC1(C(=O)NCc2ccc(Oc3ccccc3F)cc2)CC1)c1cncnc1] |

| No. | Structure |
|---|---|
| (33) | 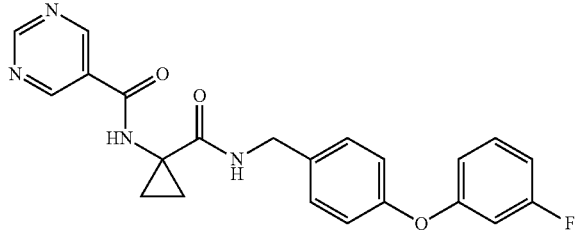 [SMILES: O=C(NC1(C(=O)NCc2ccc(Oc3cccc(F)c3)cc2)CC1)c1cncnc1] |
| (34) | 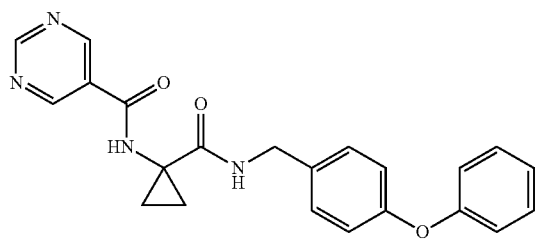 [SMILES: O=C(NC1(C(=O)NCc2ccc(Oc3ccccc3)cc2)CC1)c1cncnc1] |
| (35) | 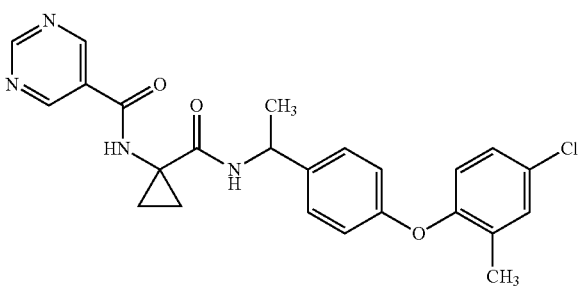 [SMILES: Cc1cc(Cl)ccc1Oc1ccc(C(C)NC(=O)C2(NC(=O)c3cncnc3)CC2)cc1] |
| (36) | 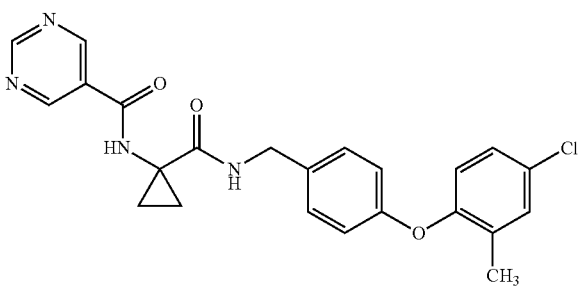 [SMILES: Cc1cc(Cl)ccc1Oc1ccc(CNC(=O)C2(NC(=O)c3cncnc3)CC2)cc1] |
| (37) | 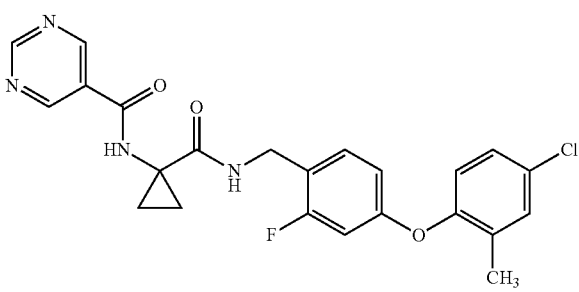 [SMILES: Cc1cc(Cl)ccc1Oc1ccc(CNC(=O)C2(NC(=O)c3cncnc3)CC2)c(F)c1] |

-continued
| No. | Structure |
|---|---|
| (38) | 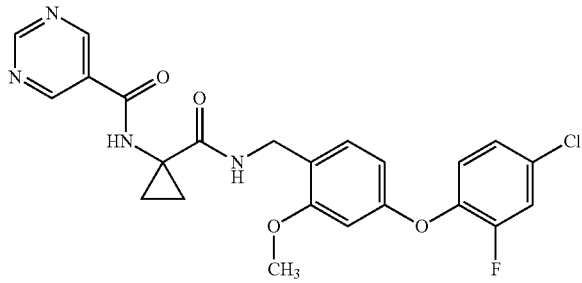 [SMILES: COc1cc(Oc2ccc(Cl)cc2F)ccc1CNC(=O)C1(NC(=O)c2cncnc2)CC1] |
| (39) | 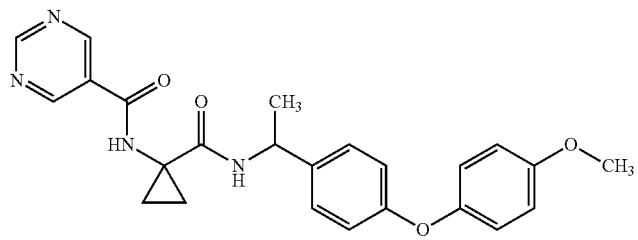 [SMILES: COc1ccc(Oc2ccc(C(C)NC(=O)C3(NC(=O)c4cncnc4)CC3)cc2)cc1] |
| (40) | 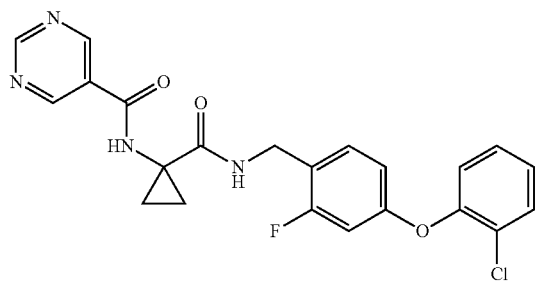 [SMILES: O=C(NC1(C(=O)NCc2ccc(Oc3ccccc3Cl)cc2F)CC1)c1cncnc1] |
| (41) | 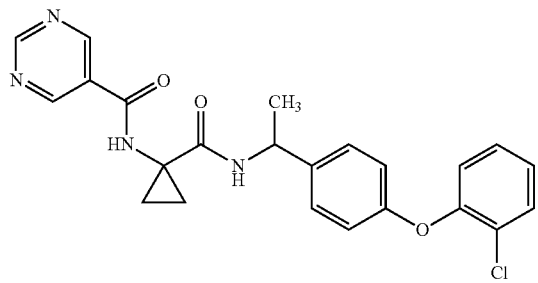 [SMILES: CC(NC(=O)C1(NC(=O)c2cncnc2)CC1)c1ccc(Oc2ccccc2Cl)cc1] |
| (42) | 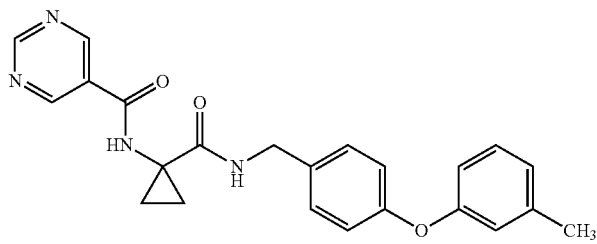 |
| (43) | 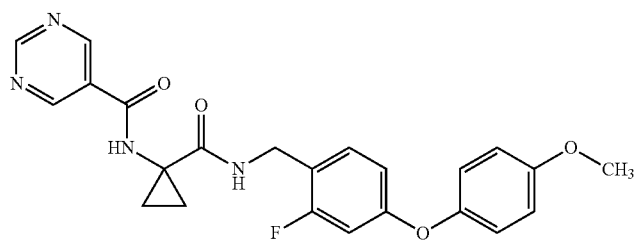 [SMILES: COc1ccc(Oc2ccc(CNC(=O)C3(NC(=O)c4cncnc4)CC3)c(F)c2)cc1] |

| No. | Structure |
|---|---|
| (44) | 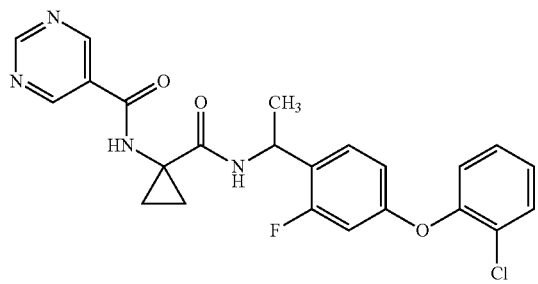 |
| (45) | 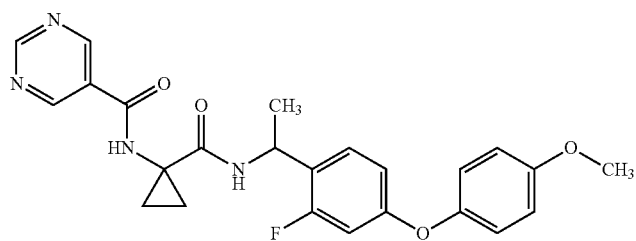 [SMILES: COc1ccc(Oc2ccc(C(C)NC(=O)C3(NC(=O)c4cncnc4)CC3)c(F)c2)cc1] |
| (46) | 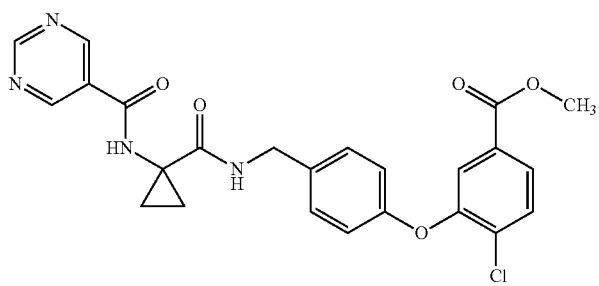 [SMILES: COC(=O)c1ccc(Cl)c(Oc2ccc(CNC(=O)C3(NC(=O)c4cncnc4)CC3)cc2)c1] |
| (47) | 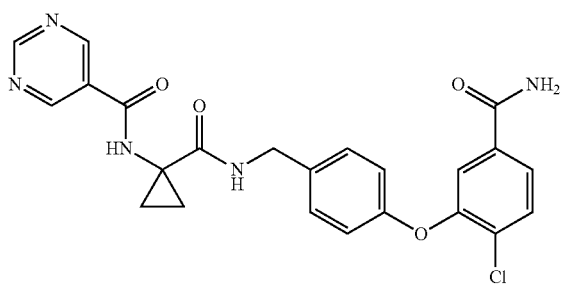 [SMILES: NC(=O)c1ccc(Cl)c(Oc2ccc(CNC(=O)C3(NC(=O)c4cncnc4)CC3)cc2)c1] |
| (48) | 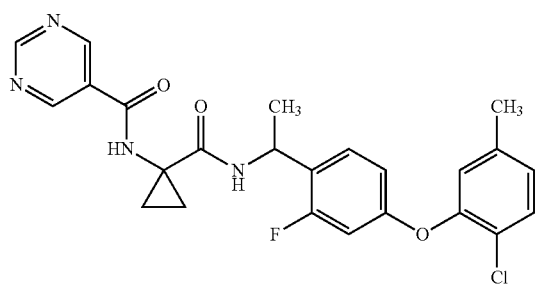 [SMILES: Cc1ccc(Cl)c(Oc2ccc(C(C)NC(=O)C3(NC(=O)c4cncnc4)CC3)c(F)c2)c1] |

| No. | Structure |
|---|---|
| (49) | 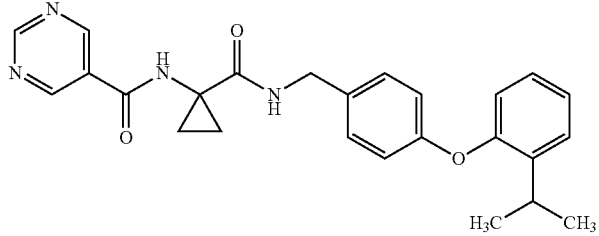 [SMILES: CC(C)c1ccccc1Oc1ccc(CNC(=O)C2(NC(=O)c3cncnc3)CC2)cc1] |
| (50) | 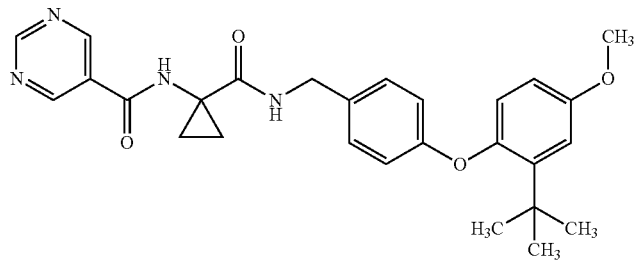 [SMILES: COc1ccc(Oc2ccc(CNC(=O)C3(NC(=O)c4cncnc4)CC3)cc2)c(C(C)(C)C)c1] |
| (51) | 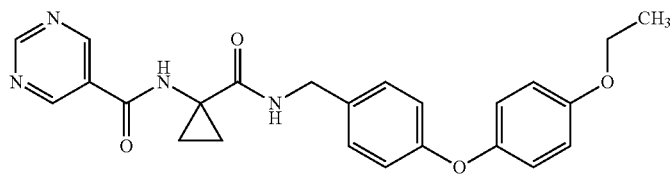 [SMILES: CCOc1ccc(Oc2ccc(CNC(=O)C3(NC(=O)c4cncnc4)CC3)cc2)cc1] |
| (52) | 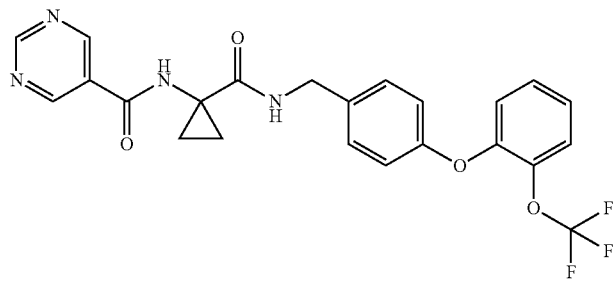 [SMILES: O=C(NC1(C(=O)NCc2ccc(Oc3ccccc3OC(F)(F)F)cc2)CC1)c1cncnc1] |
| (53) | 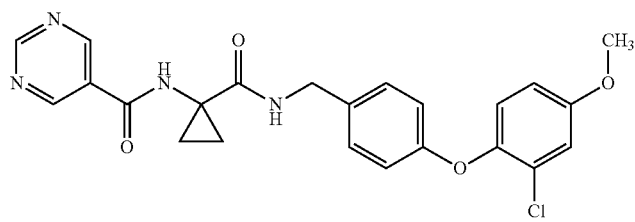 |
| (54) | 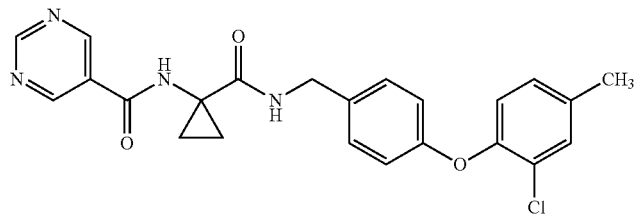 [SMILES: Cc1ccc(Oc2ccc(CNC(=O)C3(NC(=O)c4cncnc4)CC3)cc2)c(Cl)c1] |

| No. | Structure |
|---|---|
| (55) | 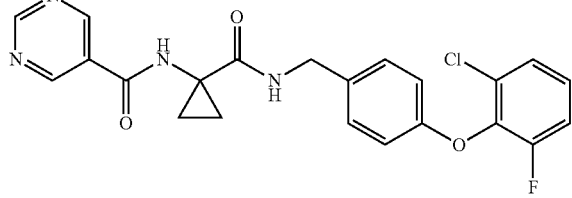 |
| (56) | 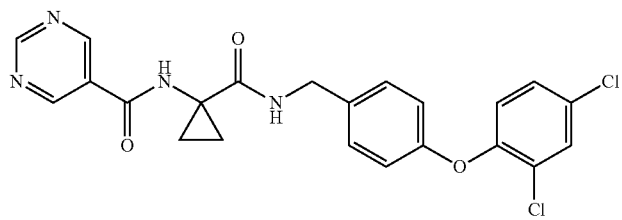 [SMILES: O=C(NC1(C(=O)NCc2ccc(Oc3ccc(Cl)cc3Cl)cc2)CC1)c1cncnc1] |
| (57) | 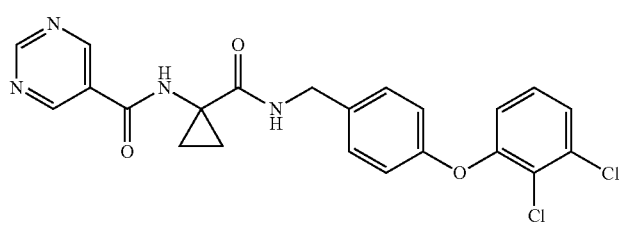 [SMILES: O=C(NC1(C(=O)NCc2ccc(Oc3cccc(Cl)c3Cl)cc2)CC1)c1cncnc1] |
| (58) | 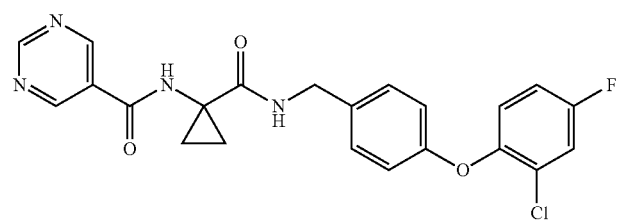 [SMILES: O=C(NC1(C(=O)NCc2ccc(Oc3ccc(F)cc3Cl)cc2)CC1)c1cncnc1] |
| (59) | 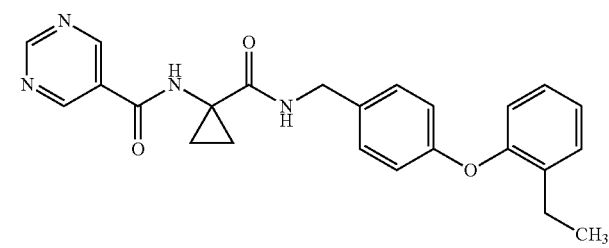 |
| (60) | 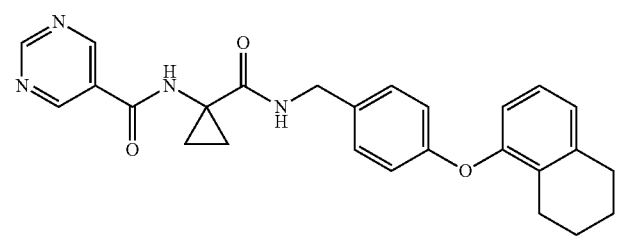 [SMILES: O=C(NC1(C(=O)NCc2ccc(Oc3cccc4c3CCCC4)cc2)CC1)c1cncnc1] |
| (61) | 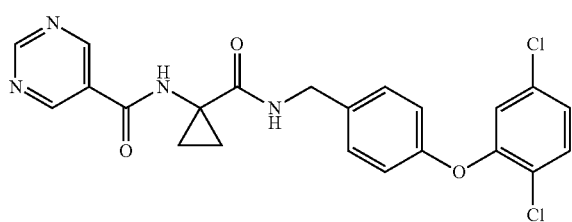 [SMILES: O=C(NC1(C(=O)NCc2ccc(Oc3cc(Cl)ccc3Cl)cc2)CC1)c1cncnc1] |

US 8,916,589 B2
39    40
-continued
| No. | Structure |
|---|---|
| (62) | 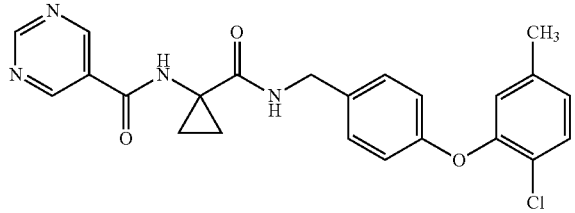 |
| (63) | 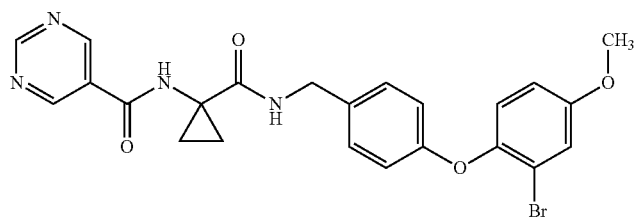 [SMILES: COc1ccc(Oc2ccc(CNC(=O)C3(NC(=O)c4cncnc4)CC3)cc2)c(Br)c1] |
| (64) | 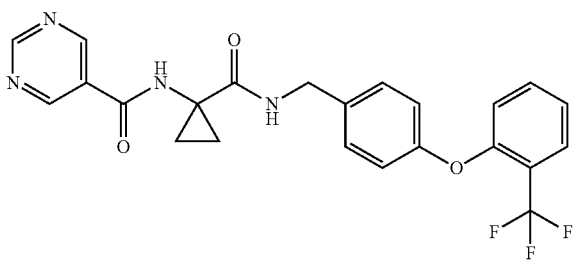 [SMILES: O=C(NC1(C(=O)NCc2ccc(Oc3ccccc3C(F)(F)F)cc2)CC1)c1cncnc1] |
| (65) | 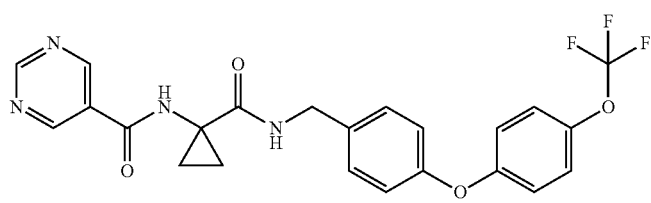 [SMILES: O=C(NC1(C(=O)NCc2ccc(Oc3ccc(OC(F)(F)F)cc3)cc2)CC1)c1cncnc1] |
| (66) | 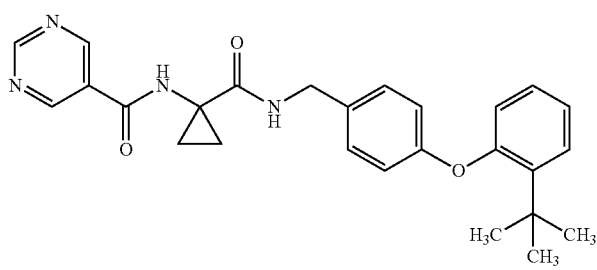 [SMILES: CC(C)(C)c1ccccc1Oc1ccc(CNC(=O)C2(NC(=O)c3cncnc3)CC2)cc1] |
| (67) | 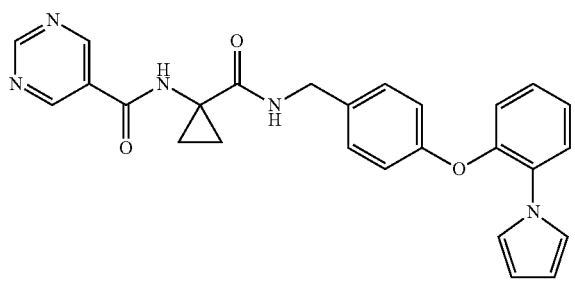 [SMILES: O=C(NC1(C(=O)NCc2ccc(Oc3ccccc3-n3cccc3)cc2)CC1)c1cncnc1] |

| No. | Structure |
|---|---|
| (68) | 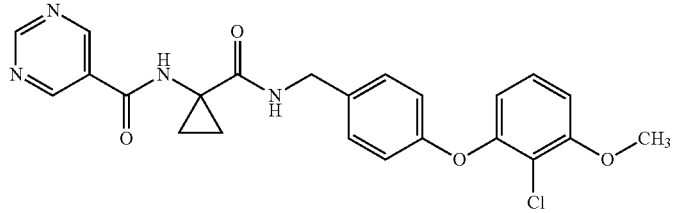 [SMILES: COc1cccc(Oc2ccc(CNC(=O)C3(NC(=O)c4cncnc4)CC3)cc2)c1Cl] |
| (69) | 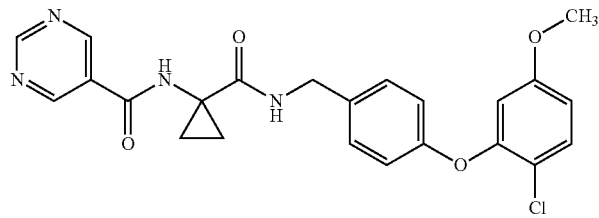 [SMILES: COc1ccc(Cl)c(Oc2ccc(CNC(=O)C3(NC(=O)c4cncnc4)CC3)cc2)c1] |
| (70) | 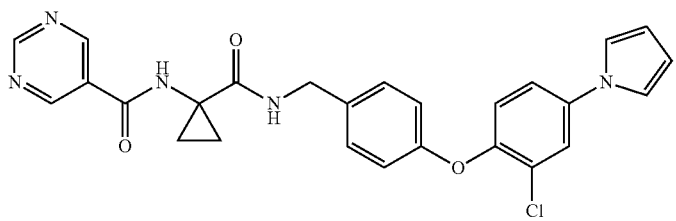 [SMILES: O=C(NC1(C(=O)NCc2ccc(Oc3ccc(-n4cccc4)cc3Cl)cc2)CC1)c1cncnc1] |
| (71) | 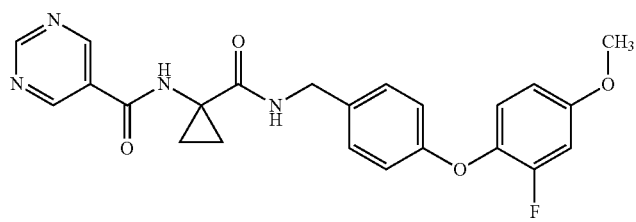 [SMILES: COc1ccc(Oc2ccc(CNC(=O)C3(NC(=O)c4cncnc4)CC3)cc2)c(F)c1] |
| (72) | 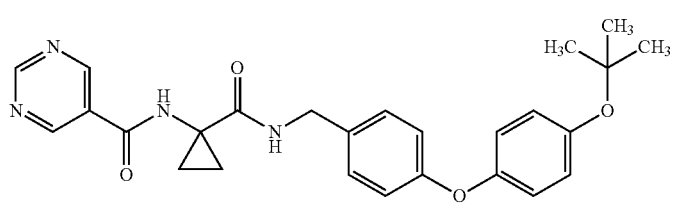 [SMILES: CC(C)(C)Oc1ccc(Oc2ccc(CNC(=O)C3(NC(=O)c4cncnc4)CC3)cc2)cc1] |
| (73) | 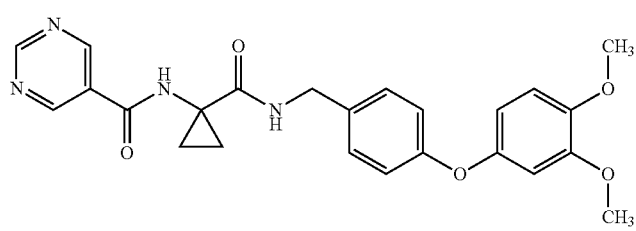 |
| (74) | 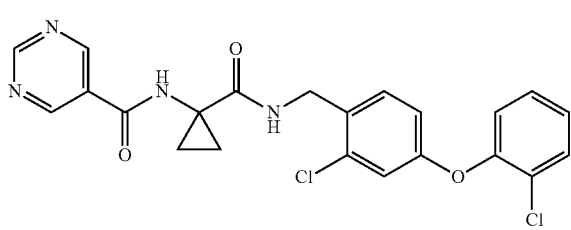 [SMILES: O=C(NC1(C(=O)NCc2ccc(Oc3ccccc3Cl)cc2Cl)CC1)c1cncnc1] |

-continued

| No. | Structure |
|---|---|
| (75) | 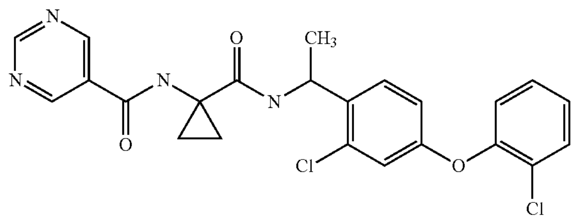 [SMILES: CC(NC(=O)C1(NC(=O)c2cncnc2)CC1)c1ccc(Oc2ccccc2Cl)cc1Cl] |
| (76) | 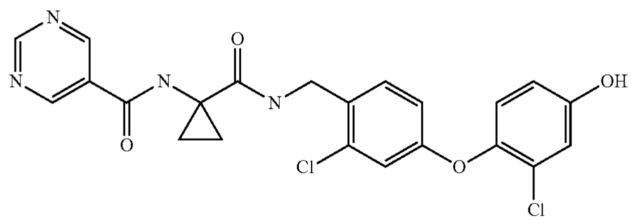 [SMILES: O=C(NC1(C(=O)NCc2ccc(Oc3ccc(O)cc3Cl)cc2Cl)CC1)c1cncnc1] |
| (77) | 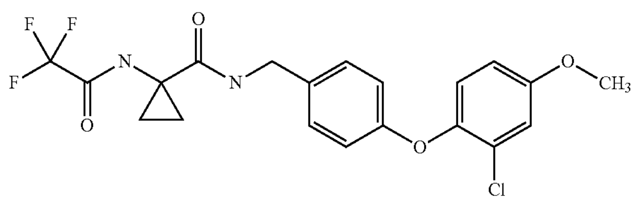 [SMILES: COc1ccc(Oc2ccc(CNC(=O)C3(NC(=O)C(F)(F)F)CC3)cc2)c(Cl)c1] |
| (78) | 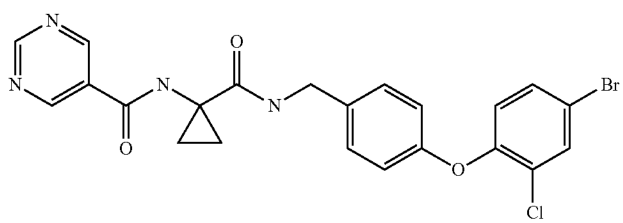 [SMILES: O=C(NC1(C(=O)NCc2ccc(Oc3ccc(Br)cc3Cl)cc2)CC1)c1cncnc1] |
| (79) | 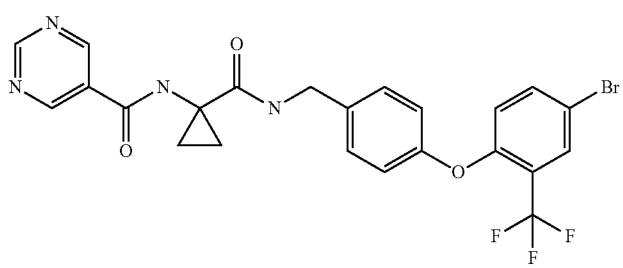 [SMILES: O=C(NC1(C(=O)NCc2ccc(Oc3ccc(Br)cc3C(F)(F)F)cc2)CC1)c1cncnc1] |
| (80) | 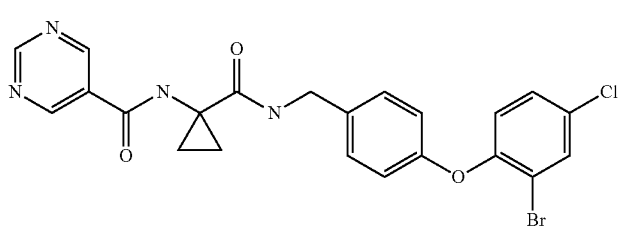 [SMILES: O=C(NC1(C(=O)NCc2ccc(Oc3ccc(Cl)cc3Br)cc2)CC1)c1cncnc1] |
| (81) | 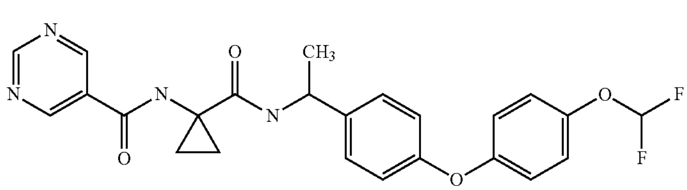 [SMILES: CC(NC(=O)C1(NC(=O)c2cncnc2)CC1)c1ccc(Oc2ccc(OC(F)F)cc2)cc1] |

-continued
| No. | Structure |
|---|---|
| (82) | 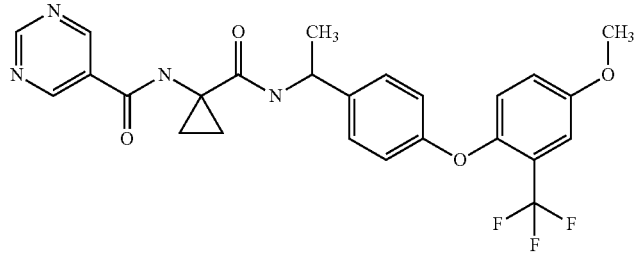 [SMILES: COc1ccc(Oc2ccc(C(C)NC(=O)C3(NC(=O)c4cncnc4)CC3)cc2)c(C(F)(F)F)c1] |
| (83) | 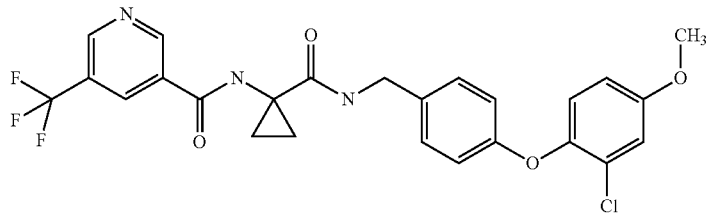 [SMILES: COc1ccc(Oc2ccc(CNC(=O)C3(NC(=O)c4cncc(C(F)(F)F)c4)CC3)cc2)c(Cl)c1] |
| (84) | 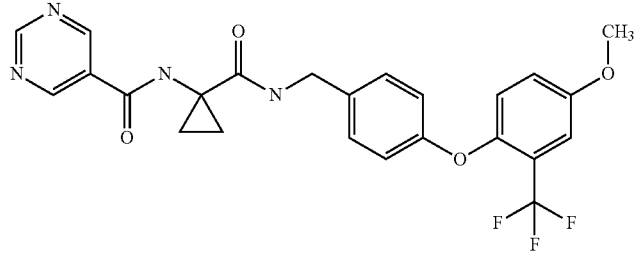 [SMILES: COc1ccc(Oc2ccc(CNC(=O)C3(NC(=O)c4cncnc4)CC3)cc2)c(C(F)(F)F)c1] |
| (85) | 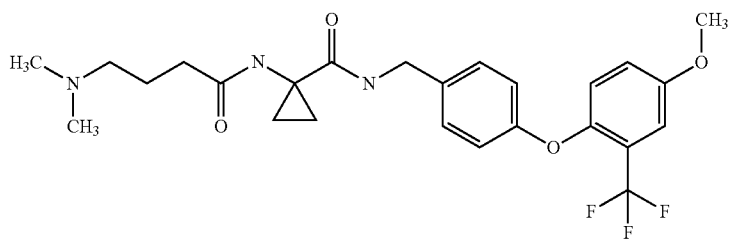 |
| (86) | 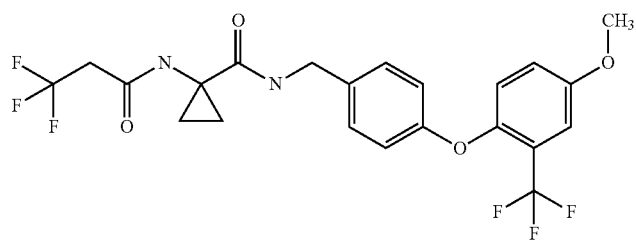 [SMILES: COc1ccc(Oc2ccc(CNC(=O)C3(NC(=O)CC(F)(F)F)CC3)cc2)c(C(F)(F)F)c1] |
| (87) | 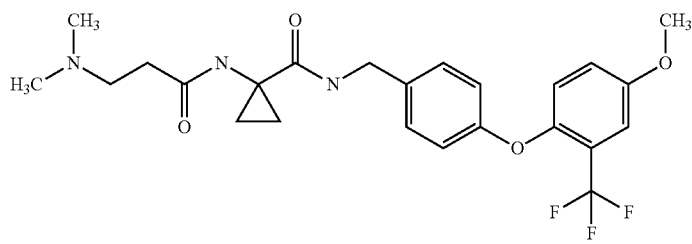 |

| No. | Structure |
|---|---|
| (88) | 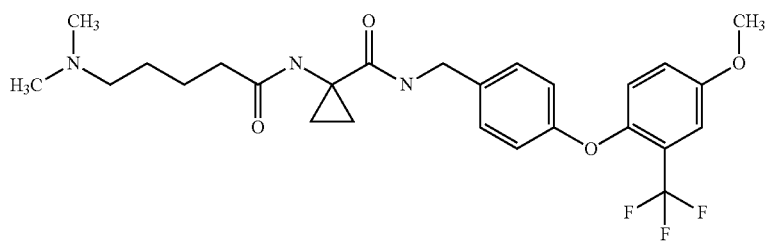 |
| (89) | 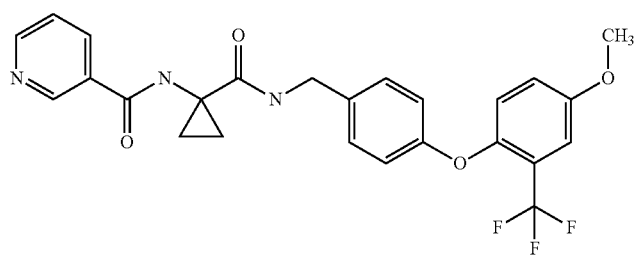 [SMILES: COc1ccc(Oc2ccc(CNC(=O)C3(NC(=O)c4cccnc4)CC3)cc2)c(C(F)(F)F)c1] |
| (90) | 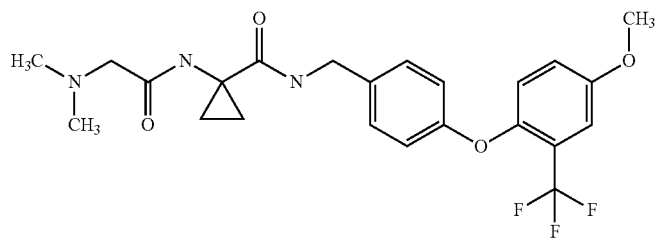 |
| (91) | 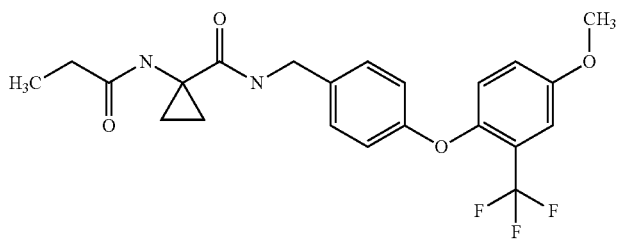 [SMILES: CCC(=O)NC1(C(=O)NCc2ccc(Oc3ccc(OC)cc3C(F)(F)F)cc2)CC1] |
| (92) | 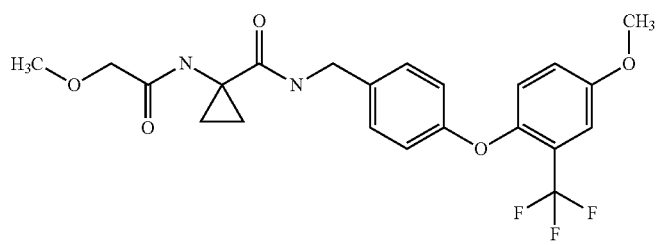 |
| (93) | 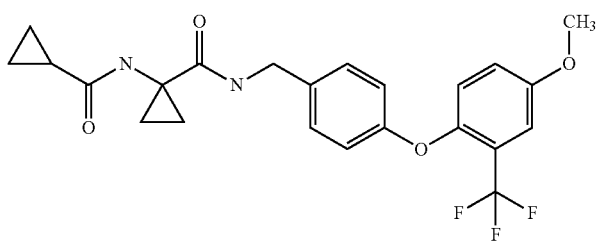 [SMILES: COc1ccc(Oc2ccc(CNC(=O)C3(NC(=O)C4CC4)CC3)cc2)c(C(F)(F)F)c1] |

| No. | Structure |
|---|---|
| (94) | 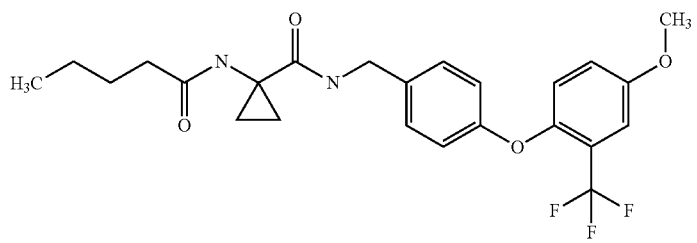 [SMILES: CCCCC(=O)NC1(C(=O)NCc2ccc(Oc3ccc(OC)cc3C(F)(F)F)cc2)CC1] |
| (95) | 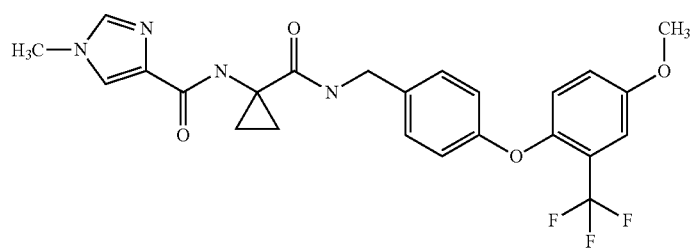 |
| (96) | 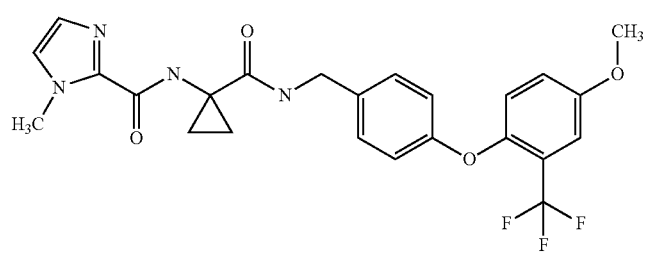 [SMILES: COc1ccc(Oc2ccc(CNC(=O)C3(NC(=O)c4nccn4C)CC3)cc2)c(C(F)(F)F)c1] |
| (97) | 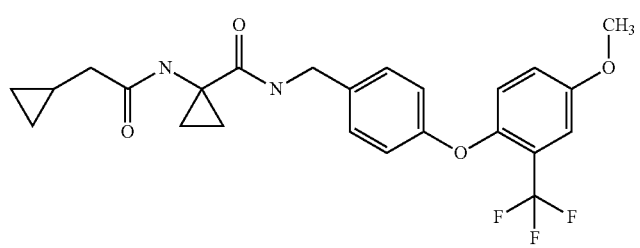 [SMILES: COc1ccc(Oc2ccc(CNC(=O)C3(NC(=O)CC4CC4)CC3)cc2)c(C(F)(F)F)c1] |
| (98) | 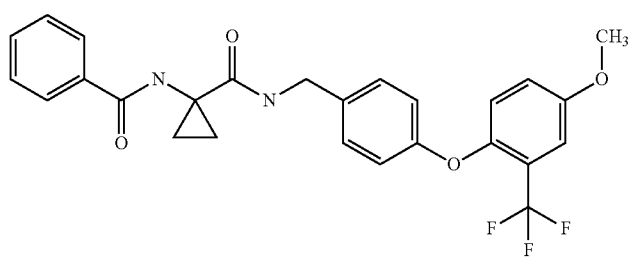 [SMILES: COc1ccc(Oc2ccc(CNC(=O)C3(NC(=O)c4ccccc4)CC3)cc2)c(C(F)(F)F)c1] |
| (99) | 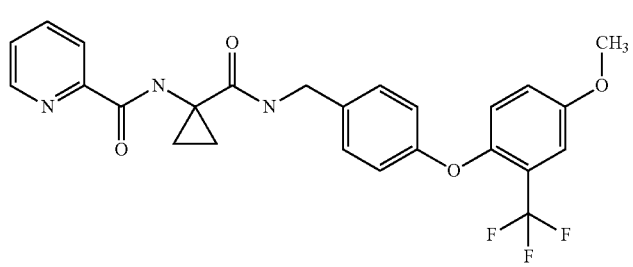 [SMILES: COc1ccc(Oc2ccc(CNC(=O)C3(NC(=O)c4ccccn4)CC3)cc2)c(C(F)(F)F)c1] |

-continued
| No. | Structure |
|---|---|
| (100) | 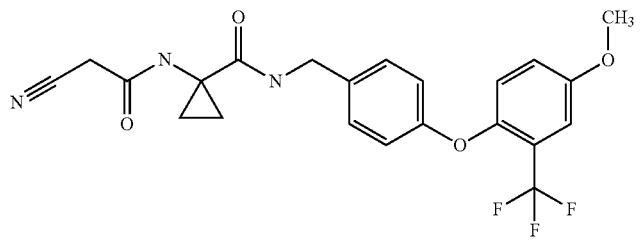 [SMILES: COc1ccc(Oc2ccc(CNC(=O)C3(NC(=O)CC#N)CC3)cc2)c(C(F)(F)F)c1] |
| (101) | 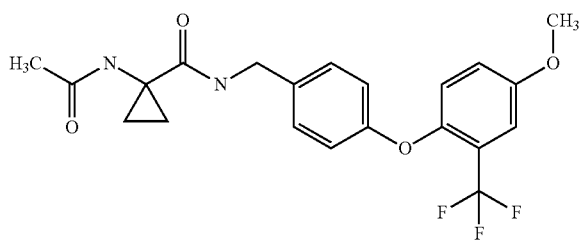 [SMILES: COc1ccc(Oc2ccc(CNC(=O)C3(NC(C)=O)CC3)cc2)c(C(F)(F)F)c1] |
| (102) | 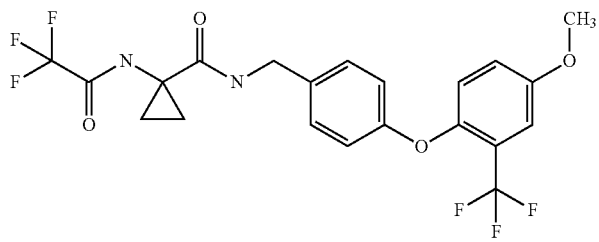 [SMILES: COc1ccc(Oc2ccc(CNC(=O)C3(NC(=O)C(F)(F)F)CC3)cc2)c(C(F)(F)F)c1] |
| (103) | 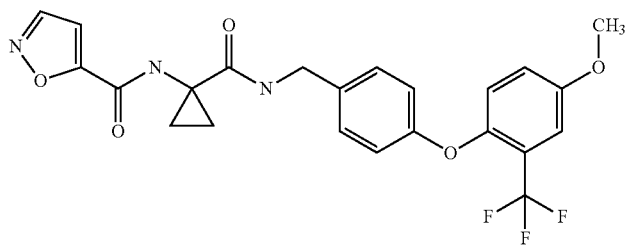 [SMILES: COc1ccc(Oc2ccc(CNC(=O)C3(NC(=O)c4ccno4)CC3)cc2)c(C(F)(F)F)c1] |
| (104) | 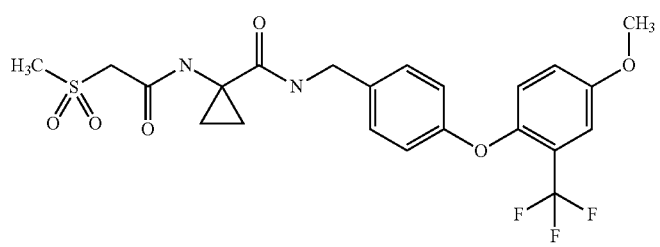 |
| (105) | 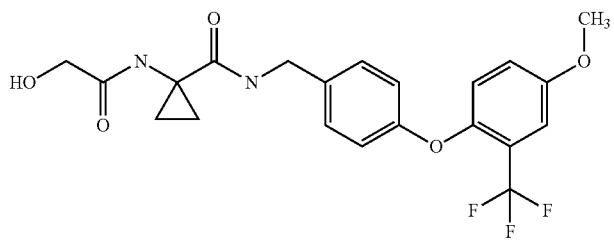 [SMILES: COc1ccc(Oc2ccc(CNC(=O)C3(NC(=O)CO)CC3)cc2)c(C(F)(F)F)c1] |

| No. | Structure |
|---|---|
| (106) | 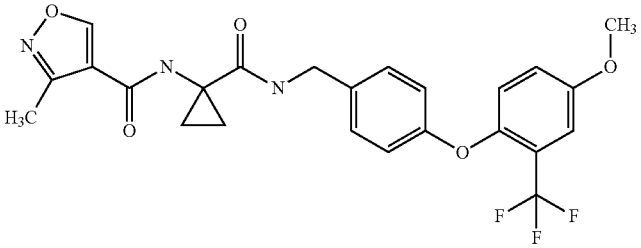 [SMILES: COc1ccc(Oc2ccc(CNC(=O)C3(NC(=O)c4conc4C)CC3)cc2)c(C(F)(F)F)c1] |
| (107) | 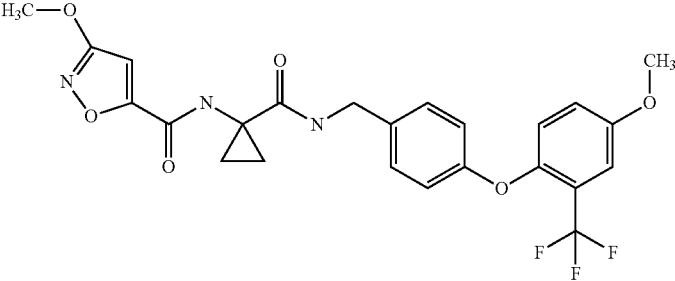 |
| (108) | 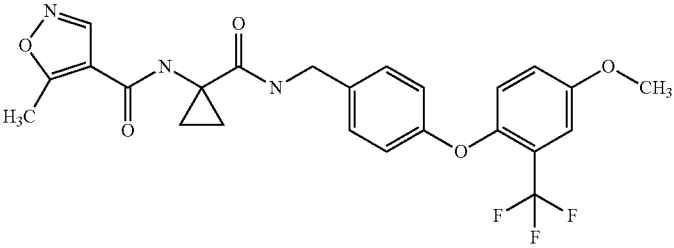 [SMILES: COc1ccc(Oc2ccc(CNC(=O)C3(NC(=O)c4cnoc4C)CC3)cc2)c(C(F)(F)F)c1] |
| (109) | 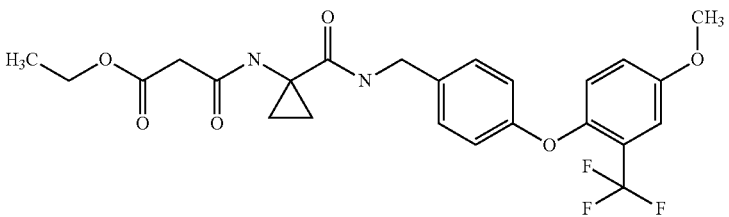 [SMILES: CCOC(=O)CC(=O)NC1(C(=O)NCc2ccc(Oc3ccc(OC)cc3C(F)(F)F)cc2)CC1] |
| (110) | 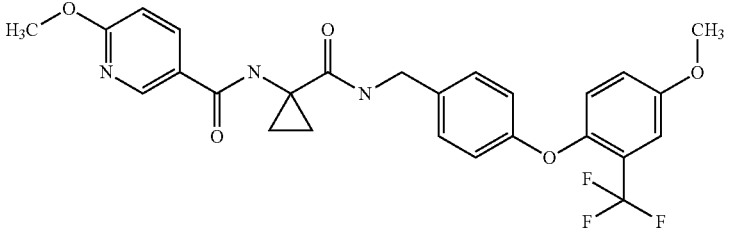 |
| (111) | 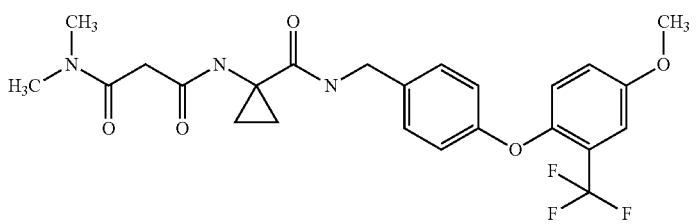 |

-continued

| No. | Structure |
|---|---|
| (112) | 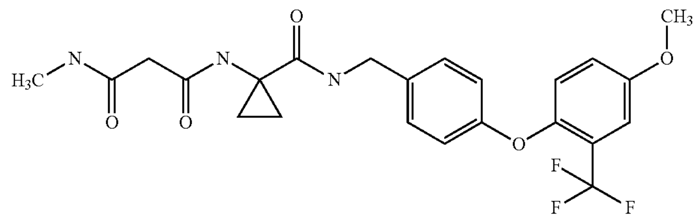 |
| (113) | 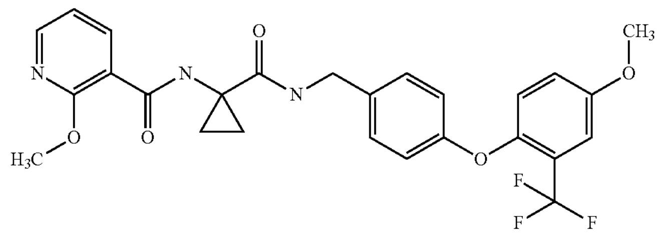 [SMILES: COc1ccc(Oc2ccc(CNC(=O)C3(NC(=O)c4cccnc4OC)CC3)cc2)c(C(F)(F)F)c1] |
| (114) | 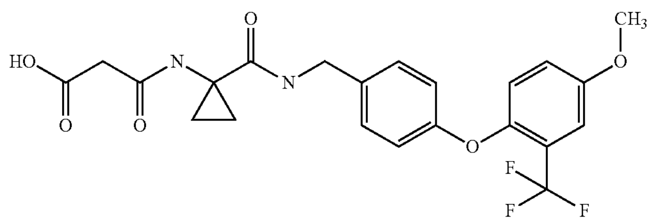 [SMILES: COc1ccc(Oc2ccc(CNC(=O)C3(NC(=O)CC(=O)O)CC3)cc2)c(C(F)(F)F)c1] |
| (115) | 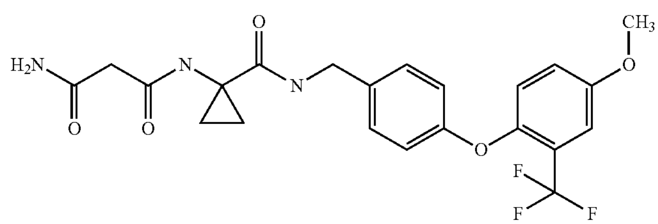 [SMILES: COc1ccc(Oc2ccc(CNC(=O)C3(NC(=O)CC(N)=O)CC3)cc2)c(C(F)(F)F)c1] |
| (116) | 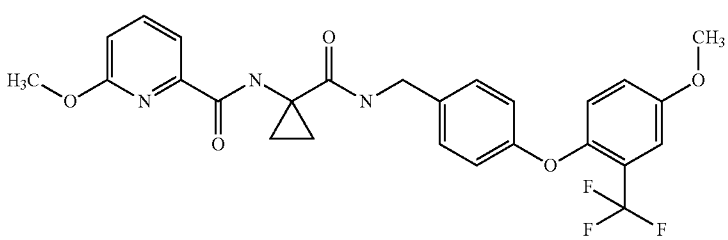 |
| (117) | 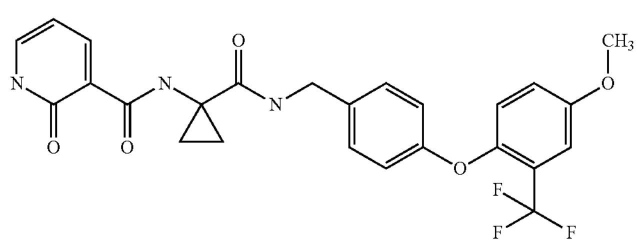 [SMILES: COc1ccc(Oc2ccc(CNC(=O)C3(NC(=O)c4ccc[nH]c4=O)CC3)cc2)c(C(F)(F)F)c1] |

| No. | Structure |
|---|---|
| (118) | 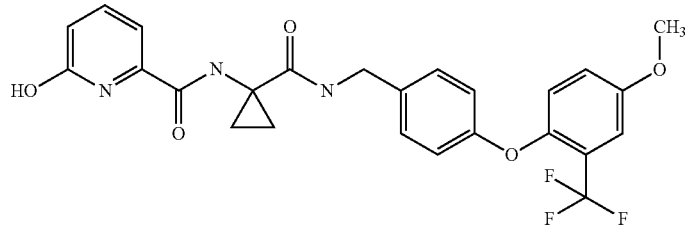 [SMILES: COc1ccc(Oc2ccc(CNC(=O)C3(NC(=O)c4cccc(O)n4)CC3)cc2)c(C(F)(F)F)c1] |
| (119) | 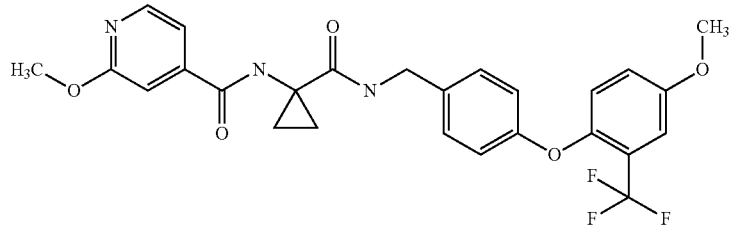 |
| (120) | 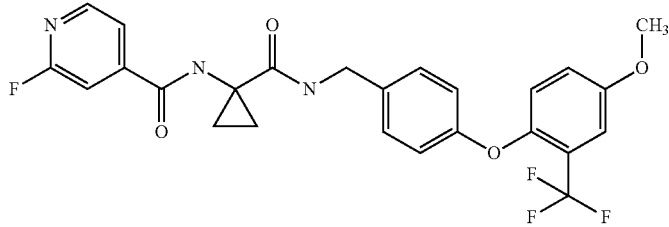 [SMILES: COc1ccc(Oc2ccc(CNC(=O)C3(NC(=O)c4ccnc(F)c4)CC3)cc2)c(C(F)(F)F)c1] |
| (121) | 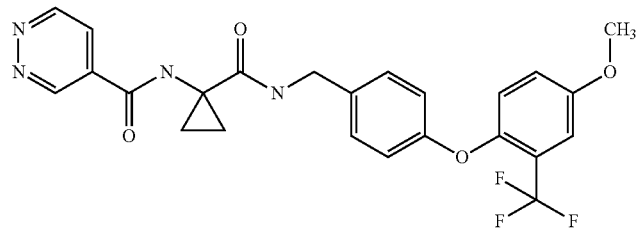 [SMILES: COc1ccc(Oc2ccc(CNC(=O)C3(NC(=O)c4ccnnc4)CC3)cc2)c(C(F)(F)F)c1] |
| (122) | 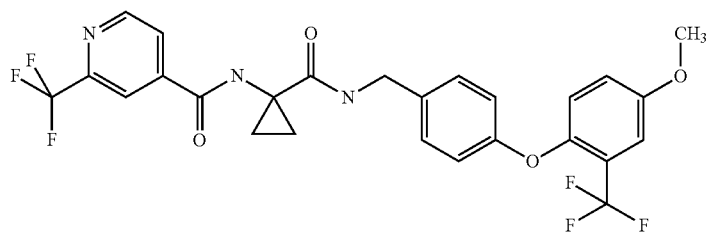 [SMILES: COc1ccc(Oc2ccc(CNC(=O)C3(NC(=O)c4ccnc(C(F)(F)F)c4)CC3)cc2)c(C(F)(F)F)c1] |
| (123) | 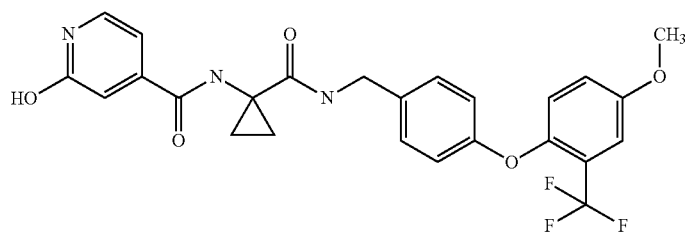 [SMILES: COc1ccc(Oc2ccc(CNC(=O)C3(NC(=O)c4ccnc(O)c4)CC3)cc2)c(C(F)(F)F)c1] |

| No. | Structure |
|---|---|
| (124) | 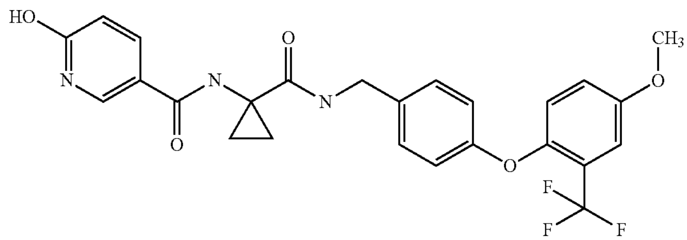 [SMILES: COc1ccc(Oc2ccc(CNC(=O)C3(NC(=O)c4ccc(O)nc4)CC3)cc2)c(C(F)(F)F)c1] |
| (125) | 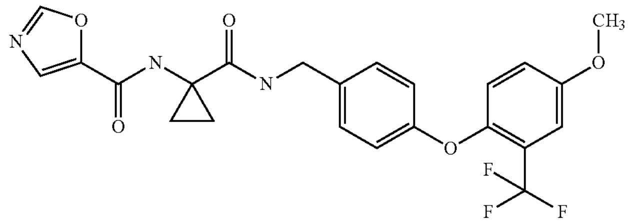 [SMILES: COc1ccc(Oc2ccc(CNC(=O)C3(NC(=O)c4cnco4)CC3)cc2)c(C(F)(F)F)c1] |
| (126) | 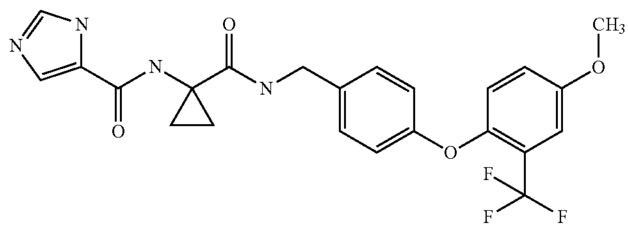 [SMILES: COc1ccc(Oc2ccc(CNC(=O)C3(NC(=O)c4cnc[nH]4)CC3)cc2)c(C(F)(F)F)c1] |
| (127) | 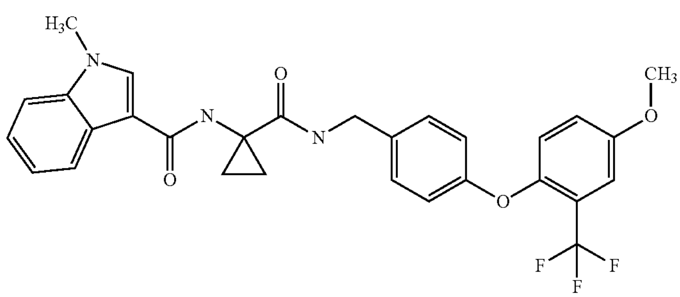 [SMILES: COc1ccc(Oc2ccc(CNC(=O)C3(NC(=O)c4cn(C)c5ccccc45)CC3)cc2)c(C(F)(F)F)c1] |
| (128) | 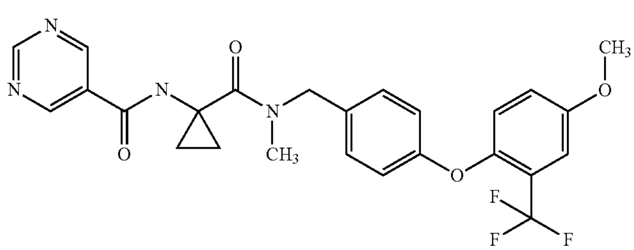 [SMILES: COc1ccc(Oc2ccc(CN(C)C(=O)C3(NC(=O)c4cncnc4)CC3)cc2)c(C(F)(F)F)c1] |
| (129) | 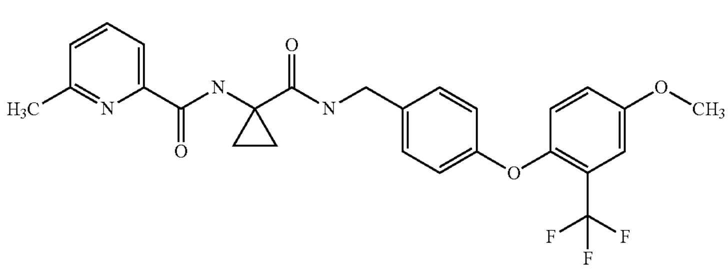 |

| No. | Structure |
|---|---|
| (130) | 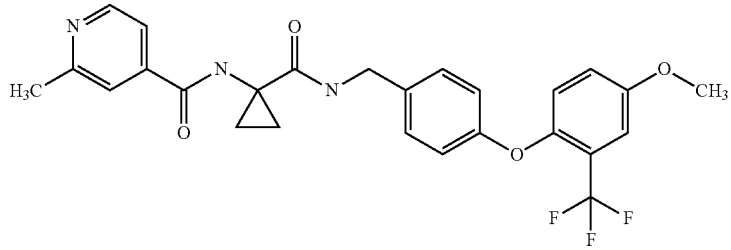 |
| (131) | 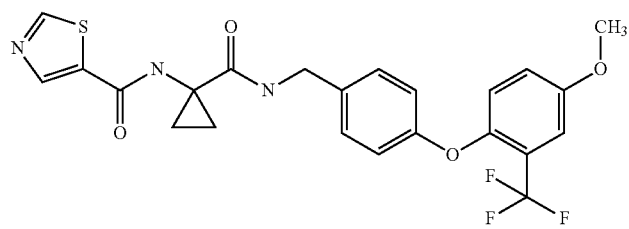 |
| (132) | 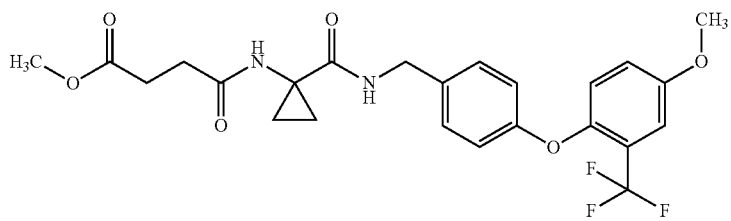 |
| (133) | 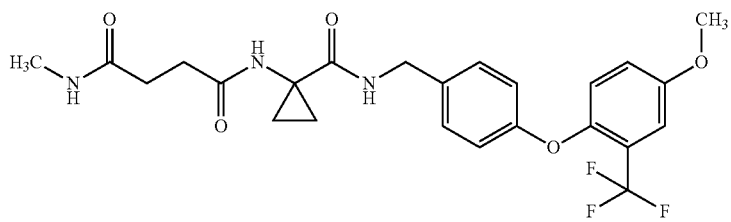 |
| (134) | 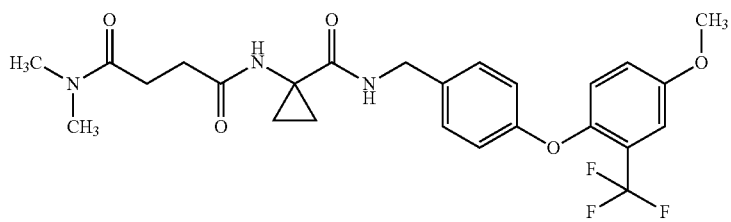 |
| (135) | 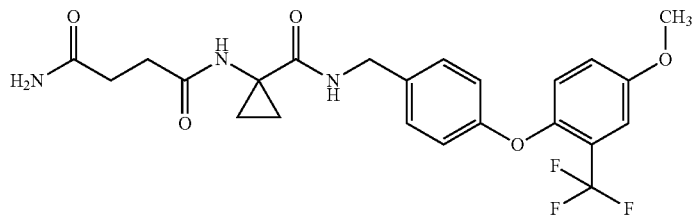 [SMILES: COc1ccc(Oc2ccc(CNC(=O)C3(NC(=O)CCC(N)=O)CC3)cc2)c(C(F)(F)F)c1] |

| No. | Structure |
|---|---|
| (136) | Thiazole-2-carbonyl-NH-C(cyclopropane)(C(=O)NH-CH2-[4-(4-methoxy-2-trifluoromethylphenoxy)phenyl]) |
| (137) | 2-Chloropyridine-4-carbonyl-NH-C(cyclopropane)(C(=O)NH-CH2-[4-(4-methoxy-2-trifluoromethylphenoxy)phenyl]) |
| (138) | 6-Chloropyridine-2-carbonyl-NH-C(cyclopropane)(C(=O)NH-CH2-[4-(4-methoxy-2-trifluoromethylphenoxy)phenyl]) |
| (139) | HOOC-CH2-CH2-C(=O)-NH-C(cyclopropane)(C(=O)NH-CH2-[4-(4-methoxy-2-trifluoromethylphenoxy)phenyl]) |
| (140) | Pyrimidine-5-carbonyl-NH-C(cyclopropane)(C(=O)NH-CH2-[4-(4-cyano-2-trifluoromethylphenoxy)phenyl]) |
| (141) | Pyrimidine-5-carbonyl-NH-C(cyclopropane)(C(=O)NH-CH2-[4-(4-methoxy-2-methylphenoxy)phenyl]) |

| No. | Structure |
|---|---|
| (142) | *Structure of compound 142: 2-aminopyrimidine-5-carboxamide linked to 1-aminocyclopropane-1-carboxamide, connected via NH-CH2 to a 4-(4-methoxy-2-(trifluoromethyl)phenoxy)phenyl group* |
| (143) | *Structure of compound 143: 4-methoxypyridine-2-carboxamide linked to 1-aminocyclopropane-1-carboxamide, connected via NH-CH2 to a 4-(4-methoxy-2-(trifluoromethyl)phenoxy)phenyl group* |
| (144) | *Structure of compound 144: 2-(methylthio)pyrimidine-5-carboxamide linked to 1-aminocyclopropane-1-carboxamide, connected via NH-CH2 to a 4-(4-methoxy-2-(trifluoromethyl)phenoxy)phenyl group* |
| (145) | *Structure of compound 145: pyrimidine-5-carboxamide linked to 1-aminocyclopropane-1-carboxamide, connected via NH-CH2 to a 4-(2-bromophenoxy)phenyl group* |
| (146) | *Structure of compound 146: pyrimidine-5-carboxamide linked to 1-aminocyclopropane-1-carboxamide, connected via NH-CH2 to a 4-(2-cyanophenoxy)phenyl group* |
| (147) | *Structure of compound 147: pyrimidine-5-carboxamide linked to 1-aminocyclopropane-1-carboxamide, connected via NH-CH2 to a 4-(2-cyano-4-methoxyphenoxy)phenyl group* |

| No. | Structure |
|---|---|
| (148) | 2-(methylsulfinyl)pyrimidine-5-carboxamide linked to 1-[(4-(4-methoxy-2-(trifluoromethyl)phenoxy)benzyl)carbamoyl]cyclopropane |
| (149) | 2-(methylsulfonyl)pyrimidine-5-carboxamide linked to 1-[(4-(4-methoxy-2-(trifluoromethyl)phenoxy)benzyl)carbamoyl]cyclopropane |
| (150) | 4-hydroxypyridine-2-carboxamide linked to 1-[(4-(4-methoxy-2-(trifluoromethyl)phenoxy)benzyl)carbamoyl]cyclopropane |
| (151) | pyrimidine-5-carboxamide linked to 1-{[1-(4-(4-methoxy-2-(trifluoromethyl)phenoxy)phenyl)propyl]carbamoyl}cyclopropane |
| (152) | 2-cyanopyrimidine-5-carboxamide linked to 1-[(4-(4-methoxy-2-(trifluoromethyl)phenoxy)benzyl)carbamoyl]cyclopropane |

| No. | Structure |
|---|---|
| (153) | 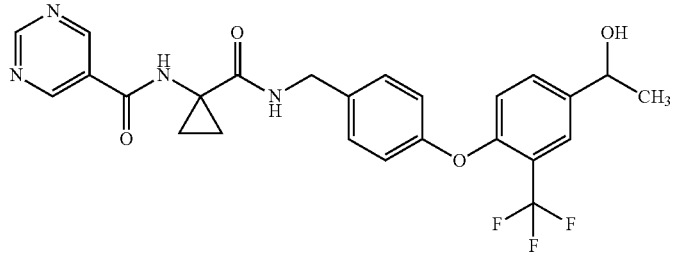 [SMILES: CC(O)c1ccc(Oc2ccc(CNC(=O)C3(NC(=O)c4cncnc4)CC3)cc2)c(C(F)(F)F)c1] |
| (154) | 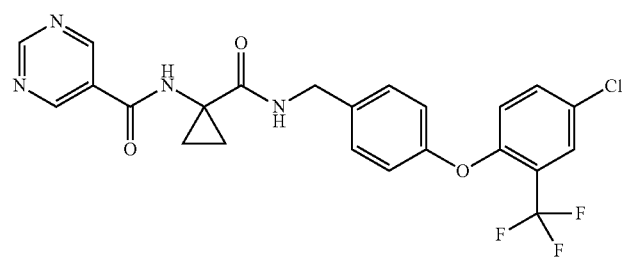 [SMILES: O=C(NC1(C(=O)NCc2ccc(Oc3ccc(Cl)cc3C(F)(F)F)cc2)CC1)c1cncnc1] |
| (155) | 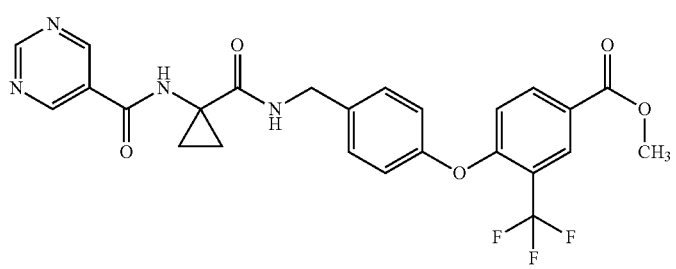 [SMILES: COC(=O)c1ccc(Oc2ccc(CNC(=O)C3(NC(=O)c4cncnc4)CC3)cc2)c(C(F)(F)F)c1] |
| (156) | 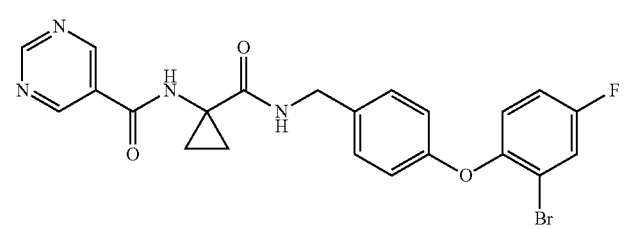 |
| (157) | 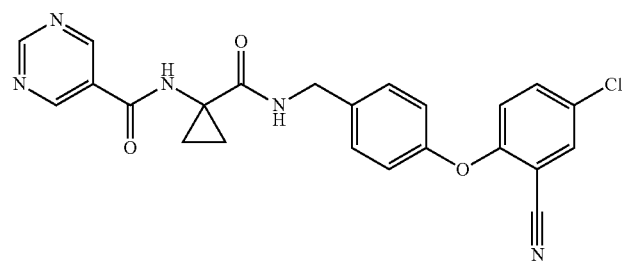 |
| (158) | 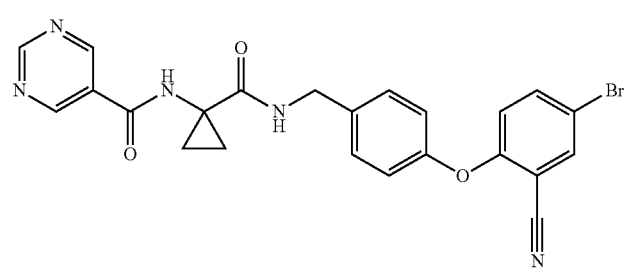 |

-continued

| No. | Structure |
|---|---|
| (159) | 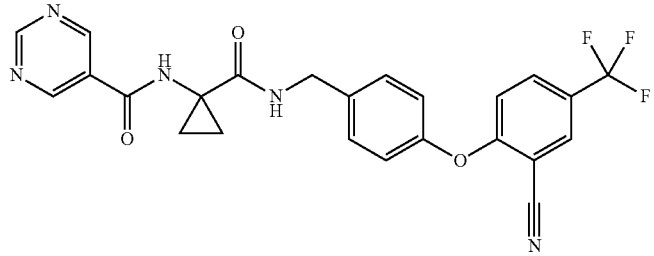 [SMILES: N#Cc1cc(C(F)(F)F)ccc1Oc1ccc(CNC(=O)C2(NC(=O)c3cncnc3)CC2)cc1] |
| (160) | 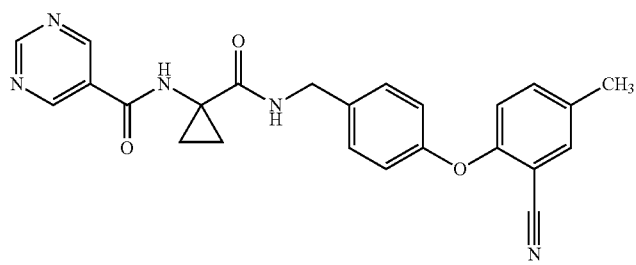 [SMILES: Cc1ccc(Oc2ccc(CNC(=O)C3(NC(=O)c4cncnc4)CC3)cc2)c(C#N)c1] |
| (161) | 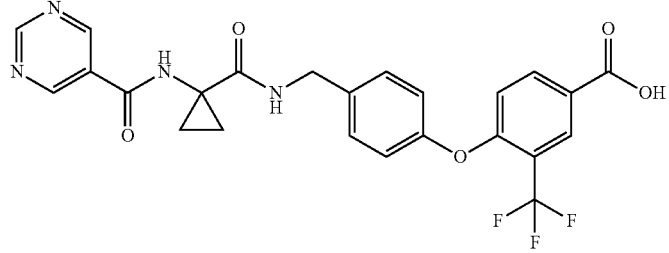 [SMILES: O=C(O)c1ccc(Oc2ccc(CNC(=O)C3(NC(=O)c4cncnc4)CC3)cc2)c(C(F)(F)F)c1] |
| (162) | 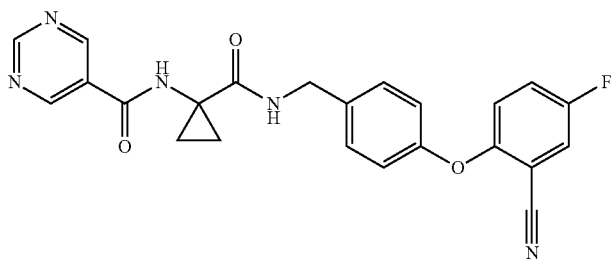 [SMILES: N#Cc1cc(F)ccc1Oc1ccc(CNC(=O)C2(NC(=O)c3cncnc3)CC2)cc1] |
| (163) | 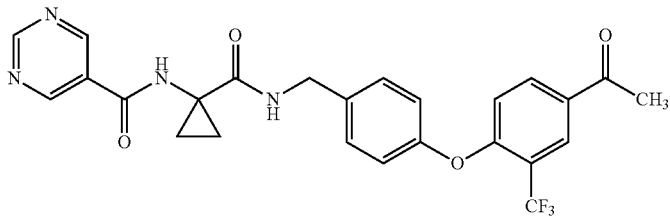 | the enantiomers, the diastereomers, the mixtures thereof and the salts thereof, particularly the physiologically acceptable salts thereof with organic or inorganic acids or bases.

Terms and Definitions Used

Unless otherwise stated, all the substituents are independent of one another. If for example there are a plurality of $C_{1-6}$-alkyl groups as substituents in one group, in the case of three $C_{1-6}$-alkyl substituents, independently of one another, one may represent methyl, one n-propyl and one tert-butyl.

Within the scope of this application, in the definition of possible substituents, these may also be represented in the form of a structural formula. If present, an asterisk (*) in the structural formula of the substituent is to be understood as being the linking point to the rest of the molecule.

The subject-matter of this invention also includes the compounds according to the invention, including the salts thereof, wherein one or more hydrogen atoms, for example one, two, three, four or five hydrogen atoms, are replaced by deuterium.

By the term "$C_{1-3}$-alkyl" (including those which are part of other groups) are meant alkyl groups with 1 to 3 carbon atoms, by the term "$C_{1-4}$-alkyl" are meant branched and unbranched alkyl groups with 1 to 4 carbon atoms, by the term "$C_{1-6}$-alkyl" are meant branched and unbranched alkyl groups with 1 to 6 carbon atoms and by the term "$C_{1-8}$-alkyl" are meant branched and unbranched alkyl groups with 1 to 8 carbon atoms. Examples of these include: methyl, ethyl, n-propyl, iso-propyl, n-butyl, iso-butyl, sec-butyl, tert-butyl, n-pentyl, neopentyl, n-hexyl, n-heptyl and n-octyl. The abbreviations Me, Et, n-Pr, i-Pr, n-Bu, i-Bu, t-Bu, etc. may optionally also be used for the groups mentioned above. Unless stated otherwise, the definitions propyl and butyl include all the possible isomeric forms of the groups in question. Thus, for example, propyl includes n-propyl and iso-propyl, butyl includes iso-butyl, sec-butyl and tert-butyl.

Moreover the terms mentioned above also include those groups wherein each methylene group may be substituted by up to two fluorine atoms and each methyl group may be substituted by up to three fluorine atoms.

By the term "$C_{0-2}$-alkylene" are meant branched and unbranched alkylene groups with 0 to 2 carbon atoms, while a $C_0$-alkylene group denotes a bond. Examples of these include: methylene, ethylene and ethane-1,1-diyl.

Moreover the terms mentioned above also include those groups wherein each methylene group may be substituted by up to two fluorine atoms.

By the term "$C_{3-7}$-cycloalkyl" (including those which are part of other groups) are meant cyclic alkyl groups with 3 to 7 carbon atoms and by the term "$C_{3-6}$-cycloalkyl" are meant cyclic alkyl groups with 3 to 6 carbon atoms. Examples of these include: cyclopropyl, cyclobutyl, cyclopentyl, cyclohexyl or cycloheptyl.

Unless otherwise stated, the cyclic alkyl groups may be substituted by one or more groups selected from among methyl, ethyl, iso-propyl, tert-butyl, hydroxy, fluorine, chlorine, bromine and iodine.

By the term "$C_{2-6}$-alkenyl" (including those which are part of other groups) are meant branched and unbranched alkenyl groups with 2 to 6 carbon atoms, provided that they have at least one double bond. Alkenyl groups with 2 to 4 carbon atoms are preferred. Examples of these include: ethenyl or vinyl, propenyl, butenyl, pentenyl, or hexenyl. Unless stated otherwise, the definitions propenyl, butenyl, pentenyl and hexenyl include all the possible isomeric forms of the groups in question. Thus, for example, propenyl includes 1-propenyl and 2-propenyl, butenyl includes 1-butenyl, 2-butenyl and 3-butenyl, 1-methyl-1-propenyl, 1-methyl-2-propenyl etc.

By the term "$C_{2-6}$-alkynyl" (including those which are part of other groups) are meant branched and unbranched alkynyl groups with 2 to 6 carbon atoms, provided that they have at least one triple bond. Alkynyl groups with 2 to 4 carbon atoms are preferred. Examples of these include: ethynyl, propynyl, butynyl, pentynyl or hexynyl. Unless stated otherwise, the definitions propynyl, butynyl, pentynyl and hexynyl include all the possible isomeric forms of the groups in question. Thus, for example, propynyl includes 1-propynyl and 2-propynyl, butynyl includes 1-butynyl, 2-butynyl and 3-butynyl, 1-methyl-1-propynyl, 1-methyl-2-propynyl etc.

"Halogen" within the scope of the present invention denotes fluorine, chlorine, bromine or iodine. Unless stated otherwise, fluorine, chlorine and bromine are regarded as preferred halogens.

By the term "heterocyclic rings" are meant stable 4-, 5- or 6-membered monocyclic heterocyclic ring systems which may be both saturated and monounsaturated and besides carbon atoms may carry one or two heteroatoms which are selected from among nitrogen, oxygen and sulphur. Both nitrogen and sulphur heteroatoms may optionally be oxidised. The previously mentioned heterocycles may be linked to the rest of the molecule via a carbon atom or a nitrogen atom. The following compounds are mentioned by way of example:

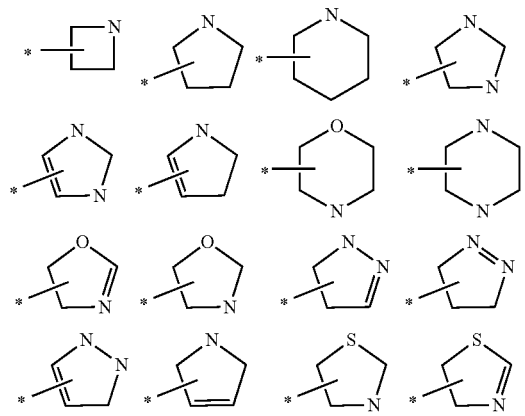

"Cyclic imides" include for example succinimide, maleimide and phthalimide.

By the term "aryl" (including those which are part of other groups) are meant aromatic ring systems with 6 or 10 carbon atoms. Examples of these include phenyl, 1-naphthyl or 2-naphthyl; the preferred aryl group is phenyl. Unless otherwise stated, the aromatic groups may be substituted by one or more groups selected from among methyl, ethyl, n-propyl, iso-propyl, tert-butyl, hydroxy, methoxy, trifluoromethoxy, fluorine, chlorine, bromine and iodine, while the groups may be identical or different.

By the term "heteroaryl" are meant five- or six-membered heterocyclic aromatic groups which may contain one, two, three or four heteroatoms, selected from among oxygen, sulphur and nitrogen, and which additionally contain sufficient conjugated double bonds to form an aromatic system. These heteroaryls may additionally be benzo-fused to a phenyl ring, so that nine- or ten-membered bicyclic heteroaryls are formed.

The following are examples of five- or six-membered heterocyclic aromatic groups:

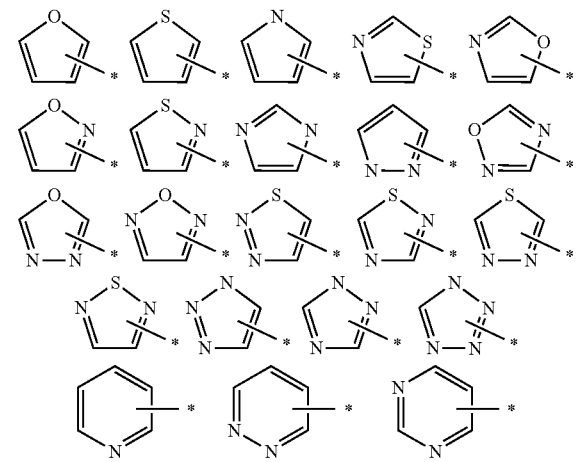

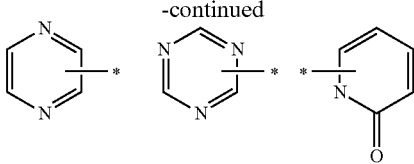

The following are examples of nine- or ten-membered heterocyclic aromatic groups:

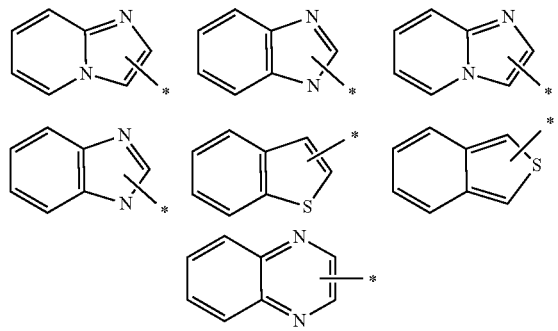

Unless otherwise stated, the heteroaryls mentioned previously may be substituted by one or more groups selected from among methyl, ethyl, n-propyl, iso-propyl, tert-butyl, hydroxy, methoxy, trifluoromethoxy, fluorine, chlorine, bromine and iodine, while the groups may be identical or different. In addition, a nitrogen atom present in the heteroaryl group may be oxidised, thus forming an N-oxide.

By the term "oxo group" is meant an oxygen substituent at a carbon atom, which leads to the formation of a carbonyl group —C(O)—. The introduction of an oxo group as substituent at a non-aromatic carbon atom leads to the conversion of a —CH$_2$ group into a —C(O) group. The introduction of an oxo group at an aromatic carbon atom leads to the conversion of a —CH group into a —C(O) group and result in the loss of aromaticity.

If they contain suitable basic functions, for example amino groups, compounds of general formula I may be converted, particularly for pharmaceutical use, into the physiologically acceptable salts thereof with inorganic or organic acids. Examples of inorganic acids for this purpose include hydrobromic acid, phosphoric acid, nitric acid, hydrochloric acid, sulphuric acid, methanesulphonic acid, ethanesulphonic acid, benzenesulphonic acid or p-toluenesulphonic acid, while organic acids that may be used include malic acid, succinic acid, acetic acid, fumaric acid, maleic acid, mandelic acid, lactic acid, tartaric acid or citric acid.

In addition, the compounds of general formula I, if they contain suitable carboxylic acid functions, may if desired be converted into the addition salts thereof with inorganic or organic bases. Examples of inorganic bases include alkali or alkaline earth metal hydroxides, e.g. sodium hydroxide or potassium hydroxide, or carbonates, ammonia, zinc or ammonium hydroxides; examples of organic amines include diethylamine, triethylamine, ethanolamine, diethanolamine, triethanolamine, cyclohexylamine or dicyclohexylamine.

The compounds according to the invention may be present as racemates, provided that they have only one chiral element, but may also be obtained as pure enantiomers, i.e. in the (R) or (S) form.

However, the application also includes the individual diastereomeric pairs of antipodes or mixtures thereof, which are obtained if there is more than one chiral element in the compounds of general formula I, as well as the individual optically active enantiomers of which the above-mentioned racemates are made up.

Methods of Preparation

According to the invention the compounds of general formula I are obtained by methods known per se to those skilled in the art, for example by the following methods:

(A) amide coupling:

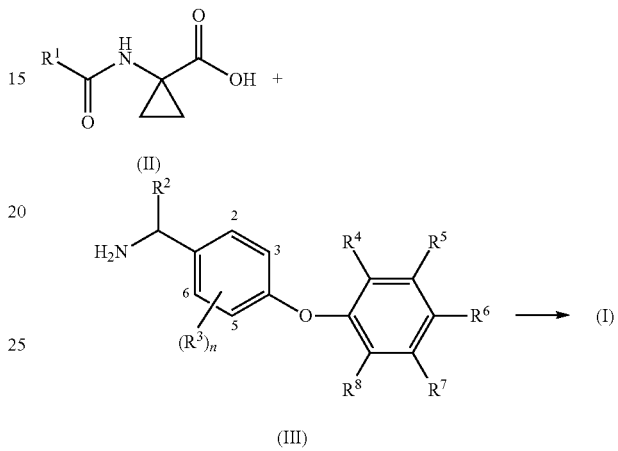

(B) amide coupling:

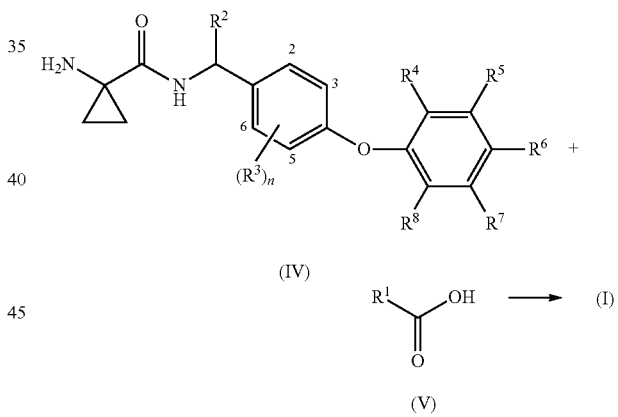

(C) reductive amination of the aldehydes or ketones; reduction of the oximes previously formed from the aldehydes or ketones:

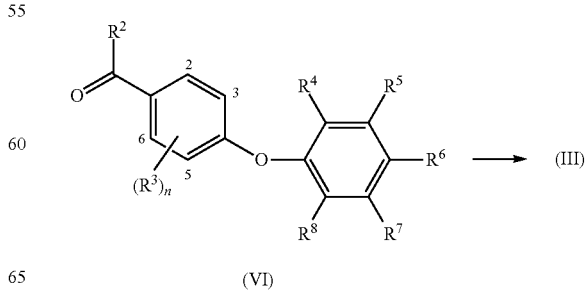

(D) nucleophilic substitution at 4-fluoro-aldehydes or ketones:

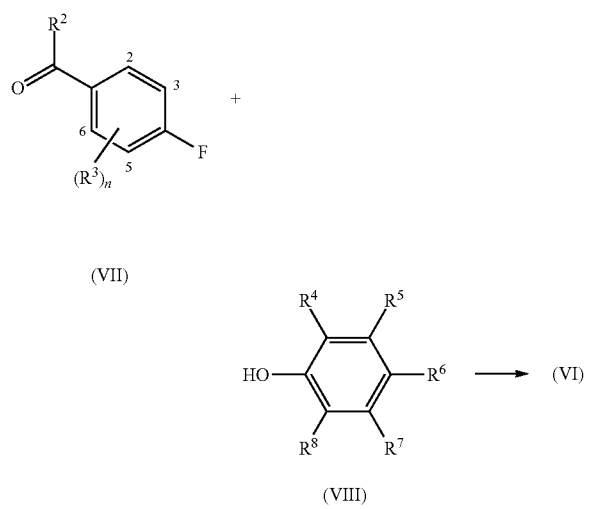

(E) reduction of the nitrile arouo:

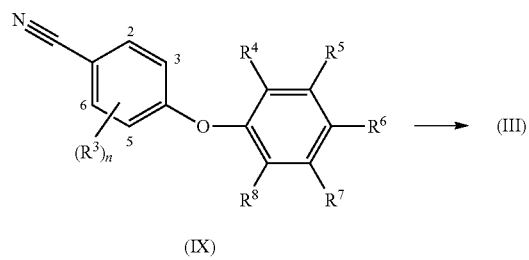

(F) nucleophilic substitution at 4-fluoro-benzonitriles:

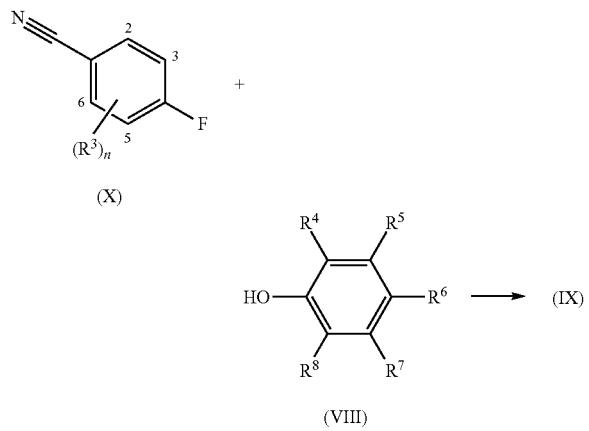

Description of the Method of hBK1 Receptor Binding

CHO cells expressing the hBK1 receptor are cultivated in Dulbecco's modified medium. The medium from confluent cultures is removed and the cells are washed with PBS buffer, scraped off and isolated by centrifugation. The cells are then homogenized in suspension and the homogenate is centrifuged and resuspended. The protein content is determined and the membrane preparation obtained in this manner is then frozen at −80° C.

After thawing, 200 μl of the homogenate (50 to 100 μg of proteins/assay) are incubated at room temperature with 0.5 to 1.0 nM of kallidin (DesArg10, Leu9), [3,4-prolyl-3,43H(N)] and increasing concentrations of the test substance in a total volume of 250 μl for 60 minutes. The incubation is terminated by rapid filtration through GF/B glass fibre filters which had been pretreated with polyethyleneimine (0.3%). The protein-bound radioactivity is measured in a TopCount NXT. Non-specific binding is defined as radioactivity bound in the presence of 1.0 μM of kallidin (DesArg10, Leu9), [3,4-prolyl-3, 43H(N)]. The concentration/binding curve is analysed using a computer-assisted nonlinear curve fitting. The $K_i$ which corresponds to the test substance is determined using the data obtained in this manner.

Indications

By virtue of their pharmacological properties, the novel compounds and their physiologically acceptable salts are suitable for treating diseases and symptoms of diseases caused at least to some extent by stimulation of bradykinin-B1 receptors.

In view of their pharmacological effect the substances are suitable for the treatment of (a) acute pain such as e.g. toothache, peri- and postoperative pain, traumatic pain, muscle pain, the pain caused by burns, sunburn, trigeminal neuralgia, pain caused by colic, as well as spasms of the gastro-intestinal tract or uterus;

(b) visceral pain such as e.g. chronic pelvic pain, gynaecological pain, pain before and during menstruation, pain caused by pancreatitis, peptic ulcers, interstitial cystitis, renal colic, angina pectoris, pain caused by irritable bowel, non-ulcerative dyspepsia and gastritis, non-cardiac thoracic pain and pain caused by myocardial ischaemia and cardiac infarct;

(c) neuropathic pain such as e.g. painful neuropathies, pain of diabetic neuropathy, AIDS-associated neuropathic pain, pain of lumbago, non-herpes-associated neuralgia, post-zoster neuralgia, nerve damage, cerebro-cranial trauma, pain of nerve damage caused by toxins or chemotherapy, phantom pain, pain of multiple sclerosis, nerve root tears and painful traumatically-caused damage to individual nerves;

(d) inflammatory/pain receptor-mediated pain in connection with diseases such as osteoarthritis, rheumatoid arthritis, rheumatic fever, tendo-synovitis, tendonitis, gout, vulvodynia, damage to and diseases of the muscles and fascia (muscle injury, fibromyalgia), osteoarthritis, juvenile arthritis, spondylitis, gout-arthritis, psoriasis-arthritis, fibromyalgia, myositis, migraine, dental disease, influenza and other virus infections such as colds, systemic lupus erythematodes, (e) tumour pain associated with cancers such as lymphatid or myeloid leukaemia, Hodgkin's disease, non-Hodgkin's lymphomas, lymphogranulomatosis, lymphosarcomas, solid malignant tumours and extensive metastases;

(f) headache diseases such as e.g. headache of various origins, cluster headaches, migraine (with or without aura) and tension headaches.

The compounds are also suitable for treating (g) inflammatory changes connected with diseases of the airways such as bronchial asthma, including allergic asthma (atopic and non-atopic) as well as bronchospasm on exertion, occupationally induced asthma, viral or bacterial exacerbation of an existing asthma and other non-allergically induced asthmatic diseases;

chronic obstructive pulmonary disease (COPD) including pulmonary emphysema, acute adult respiratory distress syndrome (ARDS), bronchitis, lung inflammation, allergic rhinitis (seasonal and all year round), vasomotor rhinitis and diseases caused by dust in the lungs such as aluminosis, anthracosis, asbestosis, chalicosis, siderosis, silicosis, tabacosis and byssinosis;

(h) inflammatory phenomena caused by sunburn and burns, oedema after burns trauma, cerebral oedema and angiooedema, intestinal complaints including Crohn's diseases and ulcerative colitis, irritable bowel syndrome, pancreatitis, nephritis, cystitis (interstitial cystitis), uveitis; inflammatory skin diseases (such as e.g. psoriasis and eczema), vascular diseases of the connective tissue, lupus, sprains and fractures;

(i) diabetes mellitus and its effects (such as e.g. diabetic vasculopathy, diabetic neuropathy, diabetic retinopathy) and diabetic symptoms in insulitis (e.g. hyperglycaemia, diuresis, proteinuria and increased renal excretion of nitrite and kallikrein);

(j) neurodegenerative diseases such as Parkinson's disease and Alzheimer's disease;

(k) sepsis and septic shock after bacterial infections or after trauma;

(l) syndromes that cause itching and allergic skin reactions;

(m) osteoporosis;

(n) epilepsy;

(o) damage to the central nervous system;

(p) wounds and tissue damage;

(q) inflammation of the gums;

(r) benign prostatic hyperplasia and hyperactive bladder;

(s) pruritus;

(t) vitiligo;

(u) disorders of the motility of respiratory, genito-urinary, gastro-intestinal or vascular regions and (v) post-operative fever.

By the term "treatment" or "therapy" is meant a therapeutic treatment of patients with manifest, acute or chronic indications, this term including on the one hand symptomatic (palliative) treatment for relieving the symptoms of the disease and on the other hand the causal or curative treatment of the indication with the aim of bringing an end to the pathological condition, reducing the severity of the pathological condition or delaying the progress of the pathological condition, irrespective of the nature or gravity of the indication.

In another aspect the present invention relates to the use of a compound of general formula I for preparing a pharmaceutical composition for the acute and prophylactic treatment of acute pain, visceral pain, neuropathic pain, inflammatory pain or pain mediated by pain receptors, cancer pain and headache diseases.

The use is characterised in that it comprises administering an effective amount of a compound of general formula I or a physiologically acceptable salt thereof to a patient requiring such treatment.

In addition to being suitable as human therapeutic agents, these substances are also useful in the veterinary treatment of domestic animals, exotic animals and farm animals.

Combinations

For treating pain, it may be advantageous to combine the compounds according to the invention with stimulating substances such as caffeine or other pain-alleviating active compounds. If active compounds suitable for treating the cause of the pain are available, these can be combined with the compounds according to the invention. If, independently of the pain treatment, other medical treatments are also indicated, for example for high blood pressure or diabetes, the active compounds required can be combined with the compounds according to the invention.

The following compounds may be used for combination therapy, for example:

Non-steroidal antirheumatics (NSAR): COX-2 inhibitors such as propionic acid derivatives (alminoprofen, benoxaprofen, bucloxic acid, carprofen, fenhufen, fenoprofen, fiuprofen, fiulbiprofen, ibuprofen, indoprofen, ketoprofen, miroprofen, naproxen, oxaprozin, pirprofen, pranoprofen, suprofen, tiaprofenic acid, tioxaprofen), acetic acid derivatives (indomethacin, acemetacin, alcofenac, isoxepac, oxpinax, sulindac, tiopinac, tolmetin, zidometacin, zomepirac) fenamic derivatives (meclofenamic acid, mefenamic acid, tolfenamic acid), biphenyl-carboxylic acid derivatives, oxicams (isoxicam, meloxicam, piroxicam, sudoxicam and tenoxicam), salicylic acid derivatives (acetylsalicylic acid, sulphasalazin, why not also mesalazin, olsalazin, and pyrazolone (apazone, bezpiperylone, feprazone, mofebutazone, oxyphenbutazone, phenylbutazone, why not also propyphenazone and metamizol, and coxibs (celecoxib, valecoxib, rofecoxib, etoricoxib).

Opiate receptor agonists such as e.g. morphine, propoxyphen (Darvon), tramadol, buprenorphine.

Cannabinoid agonists such as e.g. GW-1000, KDS-2000, SAB-378, SP-104, NVP001-GW-843166, GW-842166X, PRS-211375.

Sodium channel blockers such as e.g. carbamazepine, mexiletin, lamotrigin, pregabalin, tectin, NW-1029, CGX-1002.

N-type calcium channel blockers such as e.g. ziconitide, NMED-160, SP1-860. Serotonergic and noradrenergic modulators such as e.g. SR-57746, paroxetine, duloxetine, clonidine, amitriptyline, citalopram.

Corticosteroids such as e.g. betamethasone, budesonide, cortisone, dexamethasone, hydrocortisone, methylprednisolone, prednisolone, prednisone and triamcinolone.

Histamine H1-receptor antagonists such as e.g. bromopheniramine, chlorpheniramine, dexchlorpheniramine, triprolidine, clemastine, diphenhydramine, diphenylpyraline, tripelennamine, hydroxyzine, methdilazine, promethazine, trimeprazine azatadine, cyproheptadine, antazoline, pheniramine, pyrilamine, astemizole, terfenadine, loratadine, cetirizine, desloratadine, fexofenadine, levocetirizine.

Histamine H2-receptor antagonists such as e.g. cimetidine, famotidine, and ranitidine.

Proton pump inhibitors such as e.g. omeprazole, pantoprazole, esomeprazole.

Leukotriene antagonists and 5-lipoxygenasehemmer such as e.g. zafirlukast, montelukast, pranlukast and zileuton.

Local anaesthetics such as e.g. Ambroxol, lidocaine.

VR1 agonists and antagonists such as e.g. NGX-4010, WL-1002, ALGRX-4975, WL-10001, AMG-517.

Nicotine receptor agonists such as e.g. ABT-202, A-366833, ABT-594, BTG-102, A-85380, CGX1204.

P2X3-receptor antagonists such as e.g. A-317491, ISIS-13920, AZD-9056.

NGF agonists and antagonists such as e.g. RI-724, RI-1024, AMG-819, AMG-403, PPH 207.

NK1 and NK2 antagonists such as e.g. DA-5018, R-116301, CP-728663, ZD-2249.

NMDA antagonists such as e.g. NER-MD-11, CNS-5161, EAA-090, AZ-756, CNP-3381.

potassium channel modulators such as e.g. CL-888, ICA-69673, retigabin.

GABA modulators such as e.g. lacosamide.

Serotonergic and noradrenergic modulators such as e.g. SR-57746, paroxetine, duloxetine, clonidine, amitriptyline, citalopram, flibanserine.

Anti-migraine drugs such as e.g. sumatriptan, zolmitriptan, naratriptan, eletriptan.

The dosage necessary for obtaining a pain-alleviating effect is, in the case of intravenous administration, expediently from 0.01 to 3 mg/kg of body weight, preferably from 0.1 to 1 mg/kg, and, in the case of oral administration, from 0.1 to 8 mg/kg of body weight, preferably from 0.5 to 3 mg/kg, in each case 1 to 3 times per day. The compounds prepared according to the invention can be administered intravenously, subcutaneously, intramuscularly, intrarectally, intranasally, by inhalation, transdermally or orally, aerosol formulations being particularly suitable for inhalation. They can be incorporated into customary pharmaceutical preparations, such as tablets, coated tablets, capsules, powders, suspensions, solutions, metered-dose aerosols or suppositories, if appropriate together with one or more customary inert carriers and/or diluents, for example with maize starch, lactose, cane sugar, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances, such as hardened fat, or suitable mixtures thereof.

Experimental Section

Generally, there are mass spectra and/or $^1$H NMR spectra for the compounds that were prepared. The ratios given for the eluants are in volume units of the solvents in question. For ammonia, the given volume units are based on a concentrated solution of ammonia in water.

Unless indicated otherwise, the acid, base and salt solutions used for working up the reaction solutions are aqueous systems having the stated concentrations. For chromatographic purification, silica gel from Millipore (MATREX™, 35 to 70 µm) or Alox (E. Merck, Darmstadt, Alumina 90 standardized, 63 to 200 µm, article No. 1.01097.9050) are used.

In the descriptions of the experiments, the following abbreviations are used:

TLC thin layer chromatogram
DIPEA diisopropylethylamine
DMA N,N-dimethylacetamide
DMAP 4-dimethylaminopyridine
DMF N,N-dimethylformamide
DMSO dimethylsulphoxide
HATU O-(7-azabenzotriazol-1-yl)-N,N,N',N'-tetramethyluronium hexafluorophosphate
tert tertiary
TBTU 2-(1H-benzotriazol-1-yl)-1,1,3,3-tetramethyluronium-tetrafluoroborate
THF tetrahydrofuran The following analytical HPLC methods were used:

Method 1: Column: XTerra™ MS C18, 2.5 µM, 4.6×30 mm
Detection: 210-420 nm
Eluant A: water/0.1% formic acid
Eluant B: acetonitrile/0.1% formic acid
Gradient:

| time in min | % A | % B | flow rate in mL/min |
|---|---|---|---|
| 0.0 | 95.0 | 5.0 | 1.0 |
| 0.1 | 95.0 | 5.0 | 1.0 |
| 3.1 | 2.0 | 98.0 | 1.0 |
| 4.5 | 2.0 | 98.0 | 1.0 |
| 5.0 | 95.0 | 5.0 | 1.0 |

Method 2: Column: Microsorb C18, 3 µM, 4.6×50 mm
Detection: 220-320 nm
Eluant A: water/0.1% TFA
Eluant B: acetonitrile/0.1% TFA
Gradient:

| time in min | % A | % B | flow rate in mL/min |
|---|---|---|---|
| 0.0 | 95.0 | 5.0 | 1.5 |
| 0.5 | 95.0 | 5.0 | 1.5 |
| 3.8 | 2.0 | 98.0 | 1.5 |
| 4.3 | 2.0 | 98.0 | 1.5 |
| 4.35 | 95.0 | 5.0 | 1.5 |
| 4.6 | 95.0 | 5.0 | 1.5 |

Method 3: Column: XTerra™ MS C18, 3.5 µM, 4.6×50 mm
Detection: 210-420 nm
Eluant A: water/0.1% formic acid
Eluant B: acetonitrile/0.1% formic acid
Gradient:

| time in min | % A | % B | flow rate in mL/min |
|---|---|---|---|
| 0.0 | 95.0 | 5.0 | 1.0 |
| 0.1 | 95.0 | 5.0 | 1.0 |
| 7.1 | 2.0 | 98.0 | 1.0 |
| 7.9 | 2.0 | 98.0 | 1.0 |
| 8.0 | 95.0 | 5.0 | 1.0 |

Method 4: Column: Zorbax Stable Bond C18, 3.5 µM, 4.6×75 mm
Detection: 230-360 nm
Eluant A: water/0.1% formic acid
Eluant B: acetonitrile/0.1% formic acid
Gradient:

| time in min | % A | % B | flow rate in mL/min |
|---|---|---|---|
| 0.0 | 95.0 | 5.0 | 1.6 |
| 0.1 | 95.0 | 5.0 | 1.6 |
| 4.5 | 10.0 | 90.0 | 1.6 |
| 5.09 | 10.0 | 90.0 | 1.6 |
| 5.5 | 90.0 | 10.0 | 1.6 |

Method 5: Column: Interchim Strategy C18, 5 µM, 4.6×50 mm
Detection: 220-320 nm
Eluant A: water/0.1% TFA
Eluant B: acetonitrile
Gradient:

| time in min | % A | % B | flow rate in mL/min |
|---|---|---|---|
| 0.0 | 95.0 | 5.0 | 3.0 |
| 0.3 | 95.0 | 5.0 | 3.0 |

-continued

| time in min | % A | % B | flow rate in mL/min |
|---|---|---|---|
| 2.0 | 2.0 | 98.0 | 3.0 |
| 2.4 | 2.0 | 98.0 | 3.0 |
| 2.45 | 95.0 | 5.0 | 3.0 |
| 2.8 | 95.0 | 5.0 | 3.0 |

Method 6: Column: Merck Cromolith Speed ROD RP18e, 4.6×50 mm
Detection: 190-400 nm
Eluant A: water/0.1% formic acid
Eluant B: acetonitrile/0.1% formic acid
Gradient:

| time in min | % A | % B | flow rate in mL/min |
|---|---|---|---|
| 0.0 | 90.0 | 10.0 | 1.5 |
| 4.5 | 10.0 | 90.0 | 1.5 |
| 5.0 | 10.0 | 90.0 | 1.5 |
| 5.5 | 90.0 | 10.0 | 1.5 |

The following preparative methods were used for the reversed-phase chromatography:

Method 1: Column: AXIA Gemini C18 10 μM, 100×30 mm
Detection: 210-500 nm
Eluant A: water/0.1% trifluoroacetic acid
Eluant B: acetonitrile
Gradient:

| time in min | % A | % B | flow rate in mL/min |
|---|---|---|---|
| 0.0 | 90.0 | 10.0 | 50 |
| 0.6 | 90.0 | 10.0 | 50 |
| 1.5 | 90.0 | 10.0 | 50 |
| 8.0 | 5.0 | 95.0 | 50 |
| 9.0 | 5.0 | 95.0 | 50 |
| 9.2 | 90.0 | 10.0 | 50 |
| 10.0 | 90.0 | 10.0 | 50 |

Method 2: Column: Atlantis C18 5 μM, 100×30 mm
Detection: 210-500 nm
Eluant A: water/0.1% trifluoroacetic acid
Eluant B: acetonitrile
Gradient:

| time in min | % A | % B | flow rate in mL/min |
|---|---|---|---|
| 0.0 | 95.0 | 5.0 | 5 |
| 0.5 | 95.0 | 5.0 | 50 |
| 8.0 | 5.0 | 95.0 | 50 |
| 9.0 | 5.0 | 95.0 | 50 |
| 9.5 | 95.0 | 5.0 | 50 |
| 10.0 | 95.0 | 5.0 | 50 |
| 10.1 | 95.0 | 5.0 | 5 |

The following microwave apparatus was used: Biotage EmrysOptimizer™, OEM Explorer™, CEM Discover™

EXAMPLE 1

Pyrimidine-5-carboxylic acid{1-[4-(4-chloro-2-fluoro-phenoxy)-3-fluoro-benzylcarbamoyl]-cyclopropyl}-amide

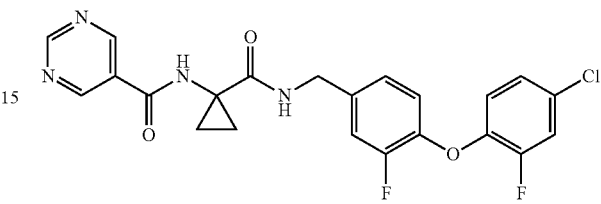

1a) ethyl 1-[(pyrimidine-5-carbonyl)-amino]-cyclopropanecarboxylate

A solution of 6.80 g (54.8 mmol) of pyrimidine-5-carboxylic acid, 18.82 mL (135 mmol) of triethylamine and 19.27 g (60 mmol) of TBTU in 200 mL THF was stirred for 30 minutes at ambient temperature. Then 9.11 g (55 mmol) of ethyl 1-amino-cyclopropanecarboxylate hydrochloride were added and the mixture was stirred further overnight. Then the mixture was evaporated down, the residue was stirred with 200 mL water and the crude product was extracted with ethyl acetate. The intermediate product was purified by column chromatography (silica gel, dichloromethane+0-4% methanol).
Yield: 88% of theory
$C_{11}H_{13}N_3O_3$ (235.24)
Mass spectrum: $[M+H]^+=236$ 1b) 1-[(pyrimidine-5-carbonyl)-amino]-cyclopropanecarboxylic acid 65 mL of a 2N sodium hydroxide solution were added to a solution of 11.0 g (46.76 mmol) of ethyl 1-[(pyrimidine-5-carbonyl)amino]-cyclopropanecarboxylate in 200 mL methanol and the mixture was stirred for one hour at 50° C. Then it was neutralised with concentrated acetic acid and evaporated to dryness in vacuo. The crude product thus obtained was purified by chromatography.
Yield: 52% of theory
$C_9H_9N_3O_3$ (207.19)
Mass spectrum: $[M+H]^+=208$
$[M-H]^-=206$ 1c) 4-(4-chloro-2-fluoro-phenoxy)-3-fluoro-benzonitrile A solution of 1.6 mL (15 mmol) of 4-chloro-2-fluorophenol and 1.68 g (15 mmol) of potassium tert. butoxide in 10 mL DMSO was stirred for one hour at ambient temperature. Then 2.1 g (15 mmol) of 3,4-difluoro-benzonitrile were added and the mixture was stirred overnight at 60° C. The mixture was then combined with approx. 50 mL water, then extracted three times with 30 ml of ethyl acetate. The organic extracts were washed with sodium chloride solution, dried on sodium sulphate and evaporated down. The product thus obtained was reacted further without any further purification.

Yield: 98% of theory.
C$_{13}$H$_6$ClF$_2$NO (265.64)
R$_f$=0.90 thin layer chromatography (silica gel, dichloromethane+ethanol 50:1):

1d) 4-(4-chloro-2-fluoro-phenoxy)-3-fluoro-benzylamine 1.0 g (3.76 mmol) of 4-(4-chloro-2-fluoro-phenoxy)-3-fluoro-benzonitrile were hydrogenated in 30 mL methanolic ammonia solution with the addition of Raney nickel at 50° C. under a hydrogen pressure of 50 psi. Then the catalyst was filtered off and the filtrate was evaporated to dryness. The crude product thus obtained was reacted further without any further purification.
Yield: 99% of theory
C$_{13}$H$_{10}$ClF$_2$NO (269.67)
Mass spectrum: [M+H]$^+$=270/72

1e) Pyrimidine-5-carboxylic acid-{1-[4-(4-chloro-2-fluoro-phenoxy)-3-fluoro-benzylcarbamoyl]-cyclopropyl}-amide hydrochloride 0.5 mL (3.6 mmol) of triethylamine, 0.433 g (1.35 mmol) of TBTU and 325.5 mg (1.2 mmol) of 4-(4-chloro-2-fluoro-phenoxy)-3-fluoro-benzylamine were added to a solution of 250 mg (1.2 mmol) of 1-[(pyrimidine-5-carbonyl)-amino]-cyclopropanecarboxylic acid (from 1b) in 15 mL tetrahydrofuran and the mixture was stirred overnight at ambient temperature. Then the mixture was evaporated to dryness and the crude product thus obtained was purified by chromatography. The purified product was dissolved in approx. 4 mL ethyl acetate and the dropwise addition of ethereal hydrochloric acid solution caused the hydrochloride to precipitate out, which was then filtered off and dried.
Yield: 56% of theory
C$_{22}$H$_{17}$ClF$_2$N$_4$O$_3$×HCl (496.31)
Mass spectrum: [M−H]$^-$=457/59
Thin layer chromatography (silica gel, dichloromethane+ethanol 9:1): R$_f$=0.48

EXAMPLE 2

Pyrimidine-5-carboxylic acid-(1-{1-[4-(4-chloro-2-fluoro-phenoxy)-phenyl]-ethylcarbamoyl}-cyclopropyl)-amide

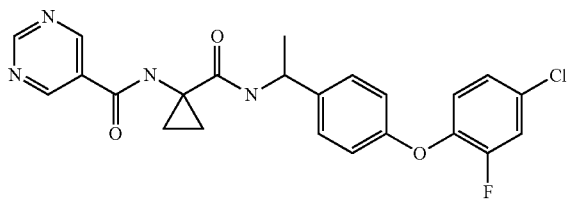 [SMILES: CC(NC(=O)C1(NC(=O)c2cncnc2)CC1)c1ccc(Oc2ccc(Cl)cc2F)cc1]

2a) 1-[4-(4-chloro-2-fluoro-phenoxy)-phenyl]-ethanone

A solution of 2.45 g (17.7 mmol) of 4-fluoro-acetophenone and 2.60 g (17.7 mmol) of 4-chloro-2-fluorophenol in 40 mL DMSO was combined with 8.0 g (57.9 mmol) of potassium carbonate and the mixture was stirred for 32 hours at 120° C. Then it was evaporated to dryness in vacuo, the residue was combined with approx. 50 mL water and extracted three times with 40 mL methyl acetate. The extracts were washed with 2N potassium carbonate solution, dried on sodium sulphate and evaporated down. The crude product thus obtained was purified by column chromatography (silica gel, dichloromethane).
Yield: 72% of theory
C$_{14}$H$_{10}$ClFC$_2$ (264.68)
Mass spectrum: [M+H]$^+$=265
R$_f$=0.18 thin layer chromatography (aluminium oxide, petroleum ether+dichloromethane 4:1)

2b) 1-[4-(4-chloro-2-fluoro-phenoxy)-phenyl]-ethanone-oxime

A mixture of 3.4 g (12.8 mmol) of 1-[4-(4-chloro-2-fluoro-phenoxy)-phenyl]-ethanone and 3.0 mL hydroxylamine solution (50% in water) in 100 mL ethanol was refluxed for five hours. Then the mixture was evaporated to dryness, the residue was combined with approx. 15 mL water and extracted three times with 10 mL ethyl acetate. The extracts were washed with saturated sodium chloride solution, dried and evaporated down. The product thus obtained was reacted further without any further purification.
Yield: 72% of theory
C$_{14}$H$_{11}$ClFNO$_2$ (279.69)
Mass spectrum: [M+H]$^+$=280
R$_f$=0.55 thin layer chromatography (silica gel, dichloromethane+methanol 50:1)

2c) 1-[4-(4-chloro-2-fluoro-phenoxy)-phenyl]-ethylamine 2.60 g (9.3 mmol) of 1-[4-(4-chloro-2-fluoro-phenoxy)-phenyl]-ethanone-oxime were dissolved in 20 mL methanol, then combined with 30 mL 7N methanolic ammonia solution and after the addition of 0.2 g Raney nickel hydrogenated at ambient temperature and 50 psi hydrogen pressure. Then the catalyst was filtered off and the filtrate was evaporated down. The crude product thus obtained was reacted further without any further purification.
Yield: 89% of theory
C$_{14}$H$_{13}$ClFNO (265.71)
Mass spectrum: [M−NH$_2$]$^+$=249/51
R$_f$=0.36 thin layer chromatography (silica gel, dichloromethane+methanol 9:1)

2d) pyrimidine-5-carboxylic acid-(1-{1-[4-(4-chloro-2-fluoro-phenoxy)-phenyl]-ethylcarbamoyl}-cyclopropyl)-amide Analogously to Example (1e) the title compound was prepared from 1-[(pyrimidine-5-carbonyl)-amino]-cyclopropanecarboxylic acid and 1-[4-(4-chloro-2-fluoro-phenoxy)-phenyl]-ethylamine.
Yield: 29% of theory
C$_{23}$H$_{20}$ClFN$_4$O$_3$ (454.88)
Mass spectrum: [M+H]$^+$=455/57

$R_f$=0.44 thin layer chromatography (silica gel, dichloromethane+methanol 9:1)

EXAMPLE 7

Pyrimidine-5-carboxylic acid{1-[3-fluoro-4-(4-methoxy-phenoxy)-benzylcarbamoyl]-cyclopropyl}-amide

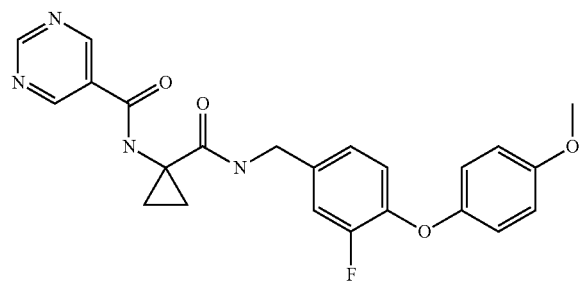 [SMILES: COc1ccc(Oc2ccc(CNC(=O)C3(NC(=O)c4cncnc4)CC3)cc2F)cc1]

7a) 3-fluoro-4-(4-methoxy-phenoxy)-benzaldehyde 4.9 g (40 mmol) of 4-methoxy-phenol and 4.4 ml (40 mmol) of 3,4-difluorobenzaldehyde were dissolved in 40 ml DMA and stirred in a microwave (CEM Explorer) for 15 minutes at 110° C., then filtered through basic Alox, washed with DMF and concentrated by rotary evaporation. The residue was separated through a KG column with a gradient (cyclohexane+10-25% ethyl acetate) and concentrated by rotary evaporation.

Yield: 57% of theory
$C_{14}H_{11}FO_3$ (246.24)
Mass spectrum: $[M+H]^+$=247

7b) 3-fluoro-4-(4-methoxy-phenoxy)-benzylamine 73.9 mg (0.3 mmol) of 3-fluoro-4-(4-methoxy-phenoxy)-benzaldehyde are dissolved in 5 ml of methanolic ammonia, combined with Ra—Ni and shaken for about 9 hours at 35° C. and 3 bar $H_2$ pressure.

The catalyst was removed by suction filtering and the solution was evaporated down in vacuo, dissolved in 3 ml DMF and purified by chromatography.

Yield: 67% of theory
$C_{14}H_{14}FNO_2$ (247.27)
Mass spectrum: $[M-NH_2]^+$=231

7c) pyrimidine-5-carboxylic acid-{1-[3-fluoro-4-(4-methoxy-phenoxy)-benzylcarbamoyl]-cyclopropyl}-amide 24.7 mg (0.1 mmol) of 3-fluoro-4-(4-methoxy-phenoxy)-benzylamine were dissolved in 1 ml DMF. 20.7 mg (0.1 mmol) of 1-[(pyrimidine-5-carbonyl)-amino]-cyclopropanecarboxylic acid (prepared in 1b) were also dissolved in DMF and 35.3 mg (0.11 mmol) and 21 µl triethylamine (0.15 mmol) were added. Shaken overnight at ambient temperature and purified by reversed-phase chromatography.

Yield: 65% of theory
$C_{23}H_{21}FN_4O_4$ (436.44)
Mass spectrum: $[M+H]^+$=437

EXAMPLE 9

Pyrimidine-5-carboxylic acid{1-[4-(4-carbamoyl-phenoxy)-benzylcarbamoyl]-cyclopropyl}-amide

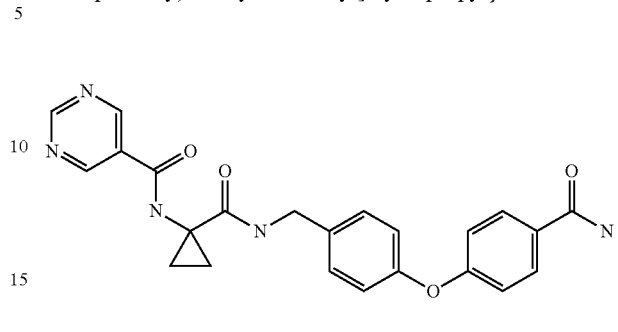

9a) 4-(4-formyl-phenoxy)-benzamide 3.1 g (23 mmol) of 4-hydroxybenzamide and 2.8 g (23 mmol) of 4-fluorobenzaldehyde were dissolved in DMSO, combined with 4.4 g (32 mmol) of $K_2CO_3$ and stirred overnight at 140° C., filtered through basic Alox, washed with DMF, concentrated by rotary evaporation and purified by chromatography (silica gel column, dichloromethane with a gradient of 10-20% methanol). As there was still some DMF present, the mixture was triturated with water, suction filtered and dried Yield: 57% of theory
$C_{14}H_{11}NO_3$ (241.25)
Mass spectrum (EI):$M^+$=241

9b) 4-(4-aminomethyl-phenoxy)-benzamide

Analogously to Example (7b) 4-(4-formyl-phenoxy)-benzamide was used as starting material.
$C_{14}H_{14}N_2O_2$ (242.28)
Mass spectrum: $[M-NH_2]^+$=226

9c) pyrimidine-5-carboxylic acid-{1-[4-(4-carbamoyl-phenoxy)-benzylcarbamoyl]-cyclopropyl}-amide Analogously to Example (7c) the title compound was prepared starting from 4-(4-aminomethyl-phenoxy)-benzamide.
Yield: 69% of theory
$C_{23}H_{21}N_5O_4$ (431.54)
Mass spectrum: $[M+H]^+$=432

EXAMPLE 10

Pyrimidine-5-carboxylic acid[1-(2,6-dimethyl-4-phenoxy-benzylcarbamoyl)-cyclopropyl]-amide

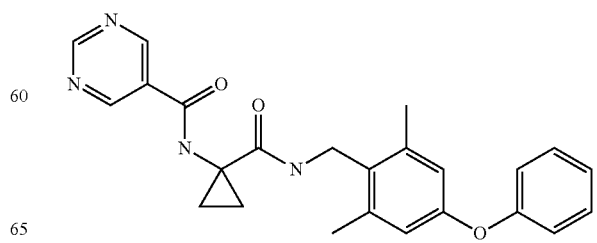

10a) 2,6-dimethyl-4-phenoxy-benzaldehyde 2.3 g (25 mmol) of phenol and 3.8 g (25 mmol) of 2,6-dimethyl-4-fluorobenzaldehyde were dissolved in 60 ml DMA, combined with 4.8 g (35 mmol) of $K_2CO_3$ and stirred at 150° C. for 5 min in a microwave (OEM Discoverer), filtered through basic Alox, washed with DMF and concentrated by rotary evaporation. Taken up in a mixture of acetonitrile/water. The substance crystallised, was filtered off and dried.
Yield: 83% of theory
$C_{15}H_{14}O_2$ (226.28)
Mass spectrum: $[M+H]^+=227$

10b) 2,6-dimethyl-4-phenoxy-benzylamine

Analogously to Example (7b) 2,6-dimethyl-4-phenoxy-benzaldehyde was used as starting material.
$C_{15}H_{17}NO$ (227.31)
Mass spectrum: $[M-NH_2]^+=211$

10c) pyrimidine-5-carboxylic acid[1-(2,6-dimethyl-4-phenoxy-benzylcarbamoyl)-cyclopropyl]-amide Analogously to Example (7c) the title compound was prepared starting from 2,6-dimethyl-4-phenoxy-benzylamine.
Yield: 53% of theory
$C_{24}H_{24}N_4O_3$ (416.48)
Mass spectrum: $[M+H]^+=417$

EXAMPLE 14

Pyrimidine-5-carboxylic acid(1-{4-[3-(pyrrolidine-1-carbonyl)-phenoxy]-benzylcarbamoyl}-cyclopropyl)-amide

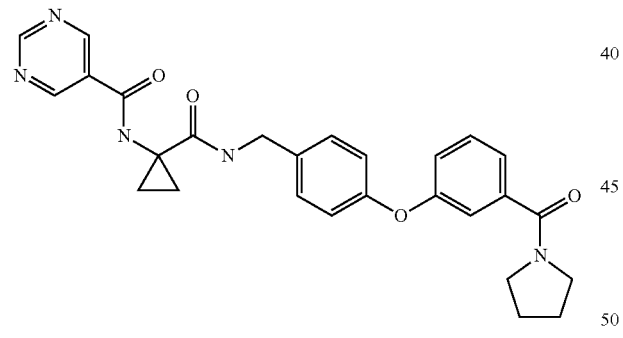

14a) 3-(4-formyl-phenoxy)-benzoic acid 5.3 g (35 mmol) of methyl 3-hydroxy-benzoate and 4.3 g (35 mmol) of 4-fluorobenzaldehyde were dissolved in DMSO and 5.8 g (42 mmol) of $K_2CO_3$ were added and tm stirred for 6 h at 80° C. Then it was filtered through basic Alox with Celite, concentrated by rotary evaporation and purified by chromatography (silica gel column, cyclohexane with gradient of 5-30% ethyl acetate).
This was then combined with 50 ml of methanol and 24 ml of 2M NaOH, the mixture was stirred for 2 hours at ambient temperature and the methanol was eliminated. The residue was diluted with water and combined with 44 ml of 1M hydrochloric acid, during which time the product was precipitated. Washed with water and dried.

Yield: 63% of theory
$C_{14}H_{10}O_4$ (242.23)
Mass spectrum: $[M-H]^-=241$

14b) 4-[3-(pyrrolidine-1-carbonyl)-phenoxy]-benzaldehyde 1 g (4.1 mmol) of 3-(4-formyl-phenoxy)-benzoic acid were dissolved in 25 ml DMF and combined with 0.86 ml (4.95 mmol) of DIPEA and 1.32 g (4.1 mmol) of TBTU, stirred for 5 min at ambient temperature and then 0.29 g (4.1 mmol) of pyrrolidine were added. The mixture was stirred at ambient temperature, filtered through basic Alox, concentrated by rotary evaporation and purified by chromatography (silica gel column, dichloromethane with gradient of 0-10% methanol).
Yield: 41% of theory.
$C_{18}H_{17}NO_3$ (295.34)
Mass spectrum: $[M+H]^+=296$

14c) [3-(4-aminomethyl-phenoxy)-phenyl]-pyrrolidin-1-yl-methanone

Analogously to Example (9b) 4-[3-(pyrrolidine-1-carbonyl)-phenoxy]-benzaldehyde was used as starting material.
$C_{18}H_{20}N_2O_2$ (296.37)
Mass spectrum: $[M-NH_2]^+=280$

14d) pyrimidine-5-carboxylic acid(1-{4-[3-(pyrrolidine-1-carbonyl)-phenoxy]-benzylcarbamoyl}-cyclopropyl)-amide Analogously to Example (7c) the title compound was prepared starting from [3-(4-aminomethyl-phenoxy)-phenyl]-pyrrolidin-1-yl-methanone.
Yield: 77% of theory
$C_{27}H_{27}N_5O_4$ (485.54)
Mass spectrum: $[M+H]^+=486$

EXAMPLE 39

Pyrimidine-5-carboxylic acid-(1-{1-[4-(4-methoxy-phenoxy)-phenyl]-ethylcarbamoyl}-cyclopropyl)-amide

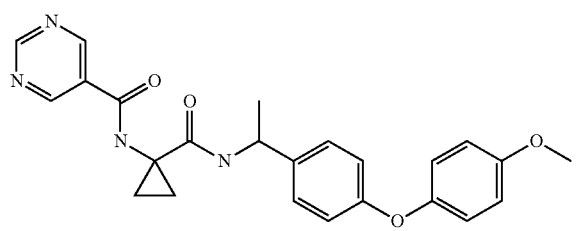 [SMILES: COc1ccc(Oc2ccc(C(C)NC(=O)C3(NC(=O)c4cncnc4)CC3)cc2)cc1]

39a) 1-[4-(4-methoxy-phenoxy)-phenyl]-ethanone 138 mg (1 mmol) of 4-fluoroacetophenone were taken and 124 mg (1 mmol) of 4-methoxyphenol were dissolved in DMSO and added thereto, then 200 mg (1.45 mmol) of $K_2CO_3$ were added and the mixture was stirred for 8 h at 80° C., then for 6 h at 100° C., then for 3 h at 120° C. and for 3 h at 140° C. The reaction mixture was filtered through basic Alox, washed with DMF/methanol=9/1 and concentrated by rotary evaporation. The substance was purified by reversed-phase chromatography.
Yield: 32% of theory
$C_{15}H_{14}O_3$ (242.27)
Mass spectrum: $[M+H]^+=243$ 39b) 1-[4-(4-methoxy-phenoxy)-phenyl]-ethylamine 78 mg (0.32 mmol) of 1-[4-(4-methoxy-phenoxy)-phenyl]-ethanone were dissolved in 10 ml of 7M methanolic ammonia and combined with 50 mg of Raney nickel. The mixture was shaken for 6 h at 50° C. and 3 bar hydrogen pressure. Raney nickel was added twice more and hydrogenation was continued for 2 h and 6 h under the same conditions. The catalyst was removed by suction filtering and the residue was evaporated down.
Yield: 73% of theory
$C_{15}H_{17}NO_2$ (243.31)
Mass spectrum: $[M-NH_2]^+=227$ 39c) pyrimidine-5-carboxylic acid-(1-{1-[4-(4-methoxy-phenoxy)-phenyl]-ethylcarbamoyl}-cyclopropyl)-amide Analogously to Example (7c) the title compound was prepared starting from 1-[4-(4-methoxy-phenoxy)-phenyl]-ethylamine.
Yield: 32% of theory
$C_{24}H_{24}N_4O_4$ (432.48)
Mass spectrum: $[M+H]^+=433$

EXAMPLE 40

Pyrimidine-5-carboxylic acid-{1-[4-(2-chloro-phenoxy)-2-fluoro-benzylcarbamoyl]-cyclopropyl}-amide

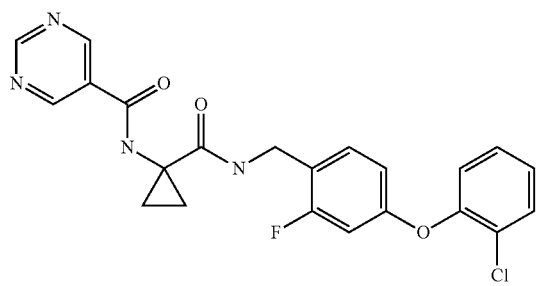 [SMILES: O=C(NC1(C(=O)NCc2ccc(Oc3ccccc3Cl)cc2F)CC1)c1cncnc1]

40a) 4-(2-chlorophenoxy)-2-fluorobenzaldehyde 142 mg (1 mmol) of 2,4-difluorobenzaldehyde were dissolved in 5 ml DMSO and taken and combined with 200 mg (1.45 mmol) of $K_2CO_3$. 128 mg (1 mmol) of 2-chlorophenol were dissolved in 10 ml DMSO and added and stirred for 2 days at ambient temperature. The reaction mixture was filtered through basic Alox, washed with DMF and concentrated by rotary evaporation. The substance was purified by reversed-phase chromatography.
Yield: 48% of theory
$C_{13}H_8ClFO_2$ (250.66)
Mass spectrum: $[M+H]^+=251/253$ 40b) 4-(2-chlorophenoxy)-2-fluorobenzylamine 148 mg (0.59 mmol) of 4-(2-chlorophenoxy)-2-fluorobenzaldehyde were dissolved in 10 ml of 7M methanolic ammonia and 50 mg Raney nickel were added. The mixture was shaken for 4 h at 35° C. and 3 bar hydrogen pressure. The catalyst was removed by suction filtering, the residue was evaporated down and purified by reversed-phase chromatography.
Yield: 43% of theory
$C_{13}H_{11}ClFNO$ (251.69)
Mass spectrum: $[M+H]^+=252/254$ 40c) pyrimidine-5-carboxylic acid-{1-[4-(2-chlorophenoxy)-2-fluoro-benzylcarbamoyl]-cyclopropyl}-amide Analogously to Example (7c) the title compound was prepared starting from 4-(2-chlorophenoxy)-2-fluorobenzylamine.
Yield: 67% of theory
$C_{22}H_{18}ClFN_4O_3$ (440.86)
Mass spectrum: $[M+H]^+=441/443$

EXAMPLE 43

Pyrimidine-5-carboxylic acid-{1-[2-fluoro-4-(4-methoxy-phenoxy)-benzylcarbamoyl]-cyclopropyl}-amide

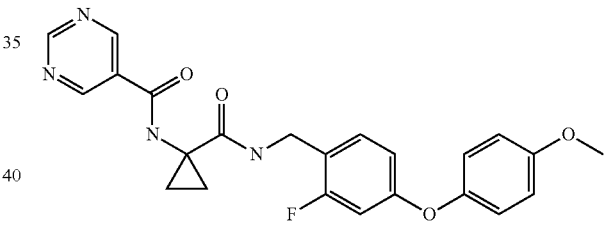

43a) 2-fluoro-4-(4-methoxy-phenoxy)-benzaldehyde

Analogously to Example (40a) 2,4-difluorobenzaldehyde and 4-methoxyphenol were used as starting material.
Yield: 47% of theory
$C_{14}H_{11}FO_3$ (246.24)
Mass spectrum: $[M+H]^+=247$ 43b) 2-fluoro-4-(4-methoxy-phenoxy)-benzylamine 180 mg (0.73 mmol) of 2-fluoro-4-(4-methoxy-phenoxy)-benzaldehyde were stirred with 180 µl (3 mmol) of hydroxylamine solution (50% in water) in 5 ml DMF at 100° C. for 1 h and then stirred overnight at ambient temperature. The mixture was evaporated down, dissolved in 10 ml of 7M methanolic ammonia and combined with 50 mg Raney nickel. It was then shaken for 4 h at ambient temperature and 3 bar hydrogen pressure. The catalyst was removed by suction filtering, the residue was evaporated down and purified by reversed-phase chromatography.
Yield: 52% of theory
$C_{14}H_{14}FNO_2$ (247.27)
Mass spectrum: $[M-NH_2]^+=231$

43c) pyrimidine-5-carboxylic acid-{1-[2-fluoro-4-(4-methoxy-phenoxy)-benzylcarbamoyl]-cyclopropyl}-amide Analogously to Example (7c) the title compound was prepared starting from 2-fluoro-4-(4-methoxy-phenoxy)-benzylamine.
Yield: 64% of theory
$C_{23}H_{21}FN_4O_4$ (436.45)
Mass spectrum: $[M+H]^+=437$

EXAMPLE 44

Pyrimidine-5-carboxylic acid(1-{1-[4-(2-chloro-phenoxy)-2-fluoro-phenyl]-ethylcarbamoyl}-cyclopropyl)-amide

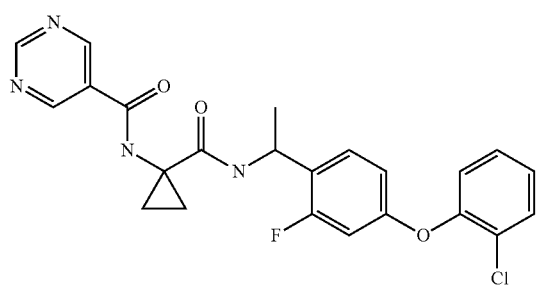 [SMILES: CC(NC(=O)C1(NC(=O)c2cncnc2)CC1)c1ccc(Oc2ccccc2Cl)cc1F]

44a) 1-[4-(2-chloro-phenoxy)-2-fluoro-phenyl]-ethanone 156 mg (1 mmol) of 2,4-difluoracetophenone were dissolved in 5 ml DMSO, taken and combined with 200 mg (1.45 mmol) of $K_2CO_3$. 128 mg (1 mmol) of 2-chlorophenol were dissolved in 5 ml DMSO and added thereto and the mixture was stirred for 2 days at ambient temperature. The reaction mixture was filtered through basic Alox, washed with DMF and concentrated by rotary evaporation. The substance was purified by reversed-phase chromatography.
Yield: 35% of theory
$C_{14}H_{10}ClFO_2$ (264.69)
Mass spectrum: $[M+H]^+=265/267$

44b) 1-[4-(2-chloro-phenoxy)-2-fluoro-phenyl]-ethylamine

Analogously to Example (43b) 1-[4-(2-chloro-phenoxy)-2-fluoro-phenyl]-ethanone was used as starting material.
Yield: 49% of theory
$C_{14}H_{13}ClFNO$ (265.72)
Mass spectrum: $[M-NH_2]^+=249/251$

44c) pyrimidine-5-carboxylic acid(1-{1-[4-(2-chloro-phenoxy)-2-fluoro-phenyl]-ethylcarbamoyl}-cyclopropyl)-amide Analogously to Example (7c) the title compound was prepared starting from 1-[4-(2-chloro-phenoxy)-2-fluoro-phenyl]-ethylamine.
Yield: 56% of theory
$C_{23}H_{20}ClFN_4O_3$ (454.89)
Mass spectrum: $[M+H]^+=455/457$

EXAMPLE 49

Pyrimidine-5-carboxylic acid-{1-[4-(2-isopropyl-phenoxy)-benzylcarbamoyl]-cyclopropyl}-amide

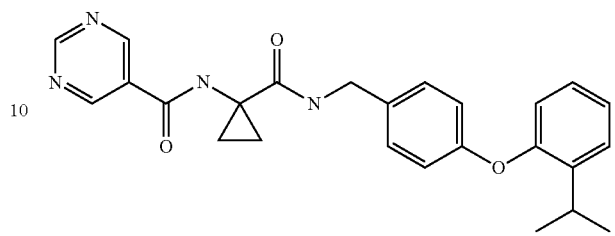

49a) 4-(2-isopropyl-phenoxy)-benzylamine 27 mg (0.2 mmol) of 2-isopropyl-phenol were dissolved in 2 ml DMSO. Then 41.4 mg (0.3 mmol) of $K_2CO_3$ and 1 ml of a 0.2 M solution of 4-fluoro-benzaldehyde in DMSO were added and the mixture was shaken overnight at 100° C. It was then filtered through basic Alox, washed with DMF and concentrated by rotary evaporation. The residue was dissolved in 2 ml of methanol and 7 ml of 7M methanolic ammonia were added, Ra—Ni was added and the mixture was shaken for 7 hours at 55° C. and 3.5 bar $H_2$ pressure. The catalyst was removed by suction filtering, washed with methanol and the solution was evaporated down in vacuo, dissolved in 2 ml DMF and purified by chromatography.
Yield: 14% according to UV chromatography in the LCMS
$C_{16}H_{19}NO$ (241.34)
Mass spectrum: $[M-NH_2]^+=225$

49b) pyrimidine-5-carboxylic acid-{1-[4-(2-isopropyl-phenoxy)-benzylcarbamoyl]-cyclopropyl}-amide Analogously to Example (7c) the title compound was prepared from 1-[(pyrimidine-5-carbonyl)-amino]-cyclopropanecarboxylic acid and 4-(2-isopropyl-phenoxy)-benzylamine.
Yield: 89% of theory
$C_{25}H_{26}N_4O_3$ (430.51)
Mass spectrum: $[M+H]^+=431$

EXAMPLE 74

Pyrimidine-5-carboxylic acid{1-[2-chloro-4-(2-chloro-phenoxy)-benzyl-carbamoyl]-cyclopropyl}-amide

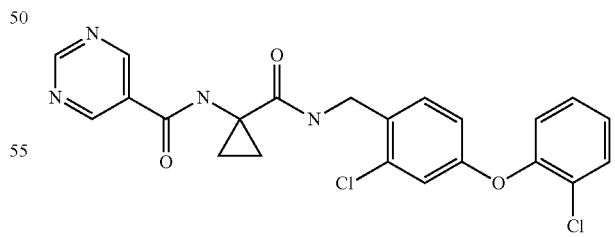

74a) 2-chloro-4-(2-chloro-phenoxy)-benzonitrile

A solution of 1.17 g (7.54 mmol) of 2-chloro-4-fluorobenzonitrile and 0.97 g (7.54 mmol) of 2-chlorophenol in 40 mL DMSO was combined with 3.2 g (23.16 mmol) of potassium carbonate and stirred overnight at 120° C. Then the mixture was evaporated to dryness in vacuo, the residue was mixed with water and extracted with ethyl acetate. The extracts were washed with water and saturated sodium chloride solution, dried and evaporated down. The crude product thus obtained was purified by column chromatography (silica gel, dichloromethane).
Yield: 60% of theory
$C_{13}H_7Cl_2NO$ (264.106)
Mass spectrum: $[M+NH_4]^+=281/3/5$

74b) 2-chloro-4-(2-chloro-phenoxy)-benzylamine 1.2 g (4.54 mmol) of 2-chloro-4-(2-chloro-phenoxy)-benzonitrile were dissolved in 30 mL methanol and 30 ml 7M methanolic ammonia were added, then 150 mg Raney nickel were added to the mixture. It was shaken at 50° C. under 50 psi hydrogen pressure. The catalyst was separated off by suction filtering and the filtrate was evaporated down.
Yield: 98% of theory
$C_{13}H_{11}Cl_2NO$ (268.14)
Mass spectrum: $[M+H]^+=268/70/2$

74c) Pyrimidine-5-carboxylic acid{1-[2-chloro-4-(2-chloro-phenoxy)-benzyl-carbamoyl]-cyclopropyl}-amide 85 mg (0.84 mmol) of triethylamine, 130 mg (0.40 mmol) of TBTU and 100 mg (0.37 mmol) of 2-chloro-4-(2-chloro-phenoxy)-benzylamine were added to a solution of 80 mg (0.38 mmol) of 1-[(pyrimidin-5-carbonyl)-amino]-cyclopropanecarboxylic acid (from 1 b) in 30 mL tetrahydrofuran and 5 mL DMF and the mixture was stirred overnight at ambient temperature. Then the mixture was evaporated to dryness and the residue was combined with 2 M potassium carbonate solution. It was extracted with ethyl acetate and the organic phase was washed with water and saturated sodium chloride solution, dried and evaporated down. The crude product thus obtained was purified by reversed-phase chromatography. The fractions were evaporated down to the aqueous phase, made basic with ammonia and extracted with ethyl acetate. The organic phase was washed with saturated sodium chloride solution, dried and evaporated down. The residue was evaporated out with ether and dried.
Yield: 29% of theory
$C_{22}H_{18}Cl_2N_4O_3$ (457.31)
Mass spectrum: $[M+H]^+=457/9/61$
$R_f=0.7$ thin layer chromatography (silica gel, dichloromethane+methanol 9:1)

EXAMPLE 75

Pyrimidine-5-carboxylic acid(1-{1-[2-chloro-4-(2-chloro-phenoxy)-phenyl]-ethylcarbamoyl}-cyclopropyl)-amide

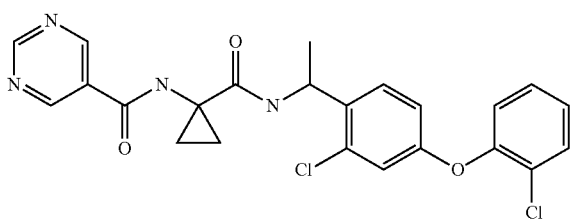 [SMILES: CC(NC(=O)C1(NC(=O)c2cncnc2)CC1)c1ccc(Oc2ccccc2Cl)cc1Cl]

75a) 1-[2-chloro-4-(2-chloro-phenoxy)-phenyl]-ethanone

Obtained analogously to Example 74a) starting from 2-chloro-4-fluoracetophenone and 2-chlorophenol.

Yield: 77% of theory
$C_{14}H_{10}Cl_2O_2$ (281.13)
Mass spectrum: $[M+H]^+=281/3/5$

75b) 1-[2-chloro-4-(2-chloro-phenoxy)-phenyl]-ethanone-oxime

A mixture of 2.4 g (8.54 mmol) of 1-[2-chloro-4-(2-chloro-phenoxy)-phenyl]-ethanone and 0.76 mL hydroxylamine solution (50% in water) in 60 mL ethanol was refluxed for 24 hours. Then the mixture was evaporated to dryness and the residue was purified by chromatography (silica gel column, methylene chloride).
Yield: 73% of theory
$C_{14}H_{11}Cl_2NO_2$ (296.15)
Mass spectrum: $[M+H]^+=296/8/300$

75c) 1-[2-chloro-4-(2-chloro-phenoxy)-phenyl]-ethylamine 1.8 g (6.08 mmol) of 1-[2-chloro-4-(2-chloro-phenoxy)-phenyl]-ethanone-oxime was dissolved in 50 mL methanol and 50 mL 7M methanolic ammonia were added, followed by 400 mg Raney nickel. The mixture was shaken at RT and 50 psi hydrogen pressure. The catalyst was suction filtered and the filtrate was evaporated down. The residue was purified by chromatography (silica gel column, dichloromethane:methanol=50:1 to 9:1)
Yield: 42% of theory
$C_{14}H_{13}Cl_2NO$ (282.16)
Mass spectrum: $[M+H]^+=282/4/6$

75d) Pyrimidine-5-carboxylic acid(1-{1-[2-chloro-4-(2-chloro-phenoxy)-phenyl]-ethylcarbamoyl}-cyclopropyl)-amide Analogously to Example (74c) the title compound was prepared starting from 1-[2-chloro-4-(2-chloro-phenoxy)-phenyl]-ethylamine.
Yield: 35% of theory
$C_{23}H_{20}Cl_2N_4O_3$ (471.34)
Mass spectrum: $[M+H]^+=471/473/475$
$R_f=0.15$ thin layer chromatography (silica gel, dichloromethane+methanol 19:1)

EXAMPLE 76

Pyrimidine-5-carboxylic acid{1-[2-chloro-4-(2-chloro-4-hydroxy-phenoxy)-benzylcarbamoyl]-cyclopropyl}-amide

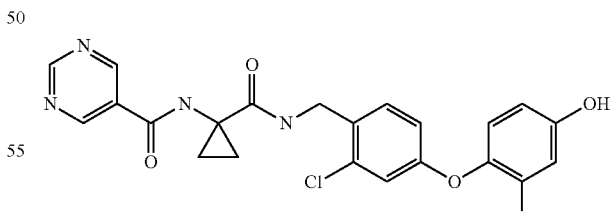

76a) 2-chloro-4-(2-chloro-4-methoxy-phenoxy)-benzonitrile

A solution of 3.0 g (19.28 mmol) of 2-chloro-4-fluorobenzonitrile and 3.06 g (19.28 mmol) of 2-chloro-4-methoxyphenol in 77 mL DMSO was combined with 5.32 g (38.57 mmol) of potassium carbonate and stirred for 2 h at 120° C. Then the mixture was evaporated to dryness in vacuo, the residue was taken up in dichloromethane and washed once with semisaturated potassium carbonate solution and twice with water. The organic phase was dried on sodium sulphate and evaporated down.

Yield: 100% of theory $C_{14}H_9Cl_2NO_2$ (294.13)

Mass spectrum: $[M-H]^-=292/4/6$

76b) 2-chloro-4-(2-chloro-4-hydroxy-phenoxy)-benzonitrile 0.5 g (1.7 mmol) of 2-chloro-4-(2-chloro-4-methoxy-phenoxy)-benzonitrile and 2.21 mL (2.21 mmol) of boron tribromide 1M in dichloromethane were stirred in 5.5 mL dichloromethane for 5 days at RT. The mixture was carefully combined with methanol and then water and dichloromethane were added. The phases were separated and the aqueous phase was extracted twice more with dichloromethane. The organic phase was dried on sodium sulphate and evaporated down.

Yield: 100% of theory $C_{13}H_7Cl_2NO_2$ (280.11)

Mass spectrum: $[M-H]^-=278/80/2$

76c) 4-(4-aminomethyl-3-chloro-phenoxy)-3-chloro-phenol-trifluoroacetic acid salt 74 mg (1.96 mmol) of lithium aluminium hydride were taken and at 0° C. 3 mL of THF were added dropwise. Then 498 mg (1.78 mmol) of 2-chloro-4-(2-chloro-4-hydroxy-phenoxy)-benzonitrile in 3 mL THF was slowly added dropwise at 0° C. The reaction mixture was stirred overnight at RT, then combined with 2M sodium hydroxide solution at 0° C. and filtered through Celite. The mixture was washed with THF and the filtrate was dried on sodium sulphate and evaporated down. The residue was purified by chromatography (reversed phase).

Yield: 21% of theory $C_{13}H_{11}Cl_2NO_2$ (284.14)

Mass spectrum: $[M-NH_2]^+=267/9/71$

76d) Pyrimidine-5-carboxylic acid{1-[2-chloro-4-(2-chloro-4-hydroxy-phenoxy)-benzylcarbamoyl]-cyclopropyl}-amide 269 µl (1.93 mmol) of triethylamine and 166 mg (0.52 mmol) of TBTU were added to a solution of 100 mg (0.48 mmol) of 1-[(pyrimidin-5-carbonyl)-amino]-cyclopropanecarboxylic acid (from 1b) in 5 mL DMF and the mixture was stirred for 10 min at RT. Then 147 mg (0.37 mmol) of 4-(4-aminomethyl-3-chloro-phenoxy)-3-chloro-phenol-trifluoroacetic acid salt dissolved in 30 mL THF was added. The reaction mixture was stirred for 2 h at RT and evaporated to dryness. The residue was purified by chromatography (reversed phase).

Yield: 43% of theory $C_{22}H_{18}Cl_2N_4O_4$ (473.31)

Mass spectrum: $[M+H]^+=473/5/7$

EXAMPLE 77

1-(2,2,2-trifluoro-acetylamin)-cyclopropanecarboxylic acid 4-(2-chloro-4-methoxy-phenoxy)-benzylamide

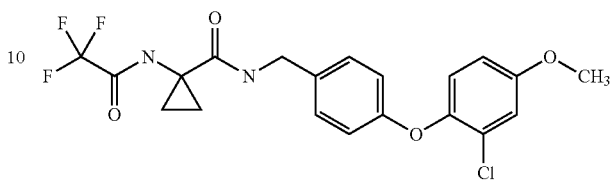

77a) 1-(2,2,2-trifluoro-acetylamin)-cyclopropanecarboxylic acid 4-(2-chloro-4-methoxyphenoxy)-benzylamide 150 mg (0.43 mmol) of 1-amino-cyclopropanecarboxylic acid 4-(2-chloro-4-methoxy-phenoxy)-benzylamide was dissolved in 15 mL dichloromethane, and 90 µL (0.65 mmol) of triethylamine and 72 µL (0.52 mmol) of trifluoroacetic acid were added. The reaction mixture was stirred for 2 h at RT and then mixed with water and evaporated down. The residue was dissolved in DMF and purified by chromatography (reversed phase).

Yield: 29% of theory $C_{20}H_{18}ClF_3N_2O_4$ (442.82)

Mass spectrum: $[M-H]^-=441/3$

EXAMPLE 78

Pyrimidine-5-carboxylic acid{1-[4-(4-bromo-2-chloro-phenoxy)-benzylcarbamoyl]-cyclopropyl}-amide

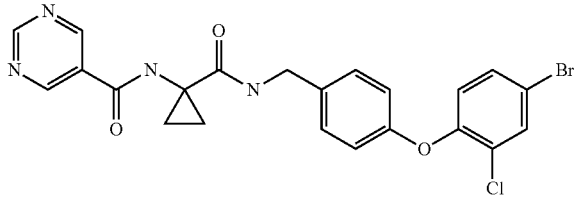

78a) 4-(4-bromo-2-chloro-phenoxy)-benzaldehyde

A solution of 50 mg (0.40 mmol) of 4-fluorobenzaldehyde and 83.6 mg (0.40 mmol) of 4-bromo-2-chlorophenol in 2 mL DMSO was combined with 80 mg (0.58 mmol) of potassium carbonate and stirred overnight at 120° C. The reaction mixture was filtered through Alox B, washed with dichloromethane and evaporated down. The residue was purified by chromatography (reversed phase).

Yield: 16% of theory $C_{13}H_8BrClO_2$ (311.56)

Mass spectrum: $[M+H]^+=311/3/5$

78b) 4-(4-bromo-2-chloro-phenoxy)-benzaldehyde-oxime 20 mg (0.06 mmol) of 4-(4-bromo-2-chloro-phenoxy)-benzaldehyde were stirred with 20 µL (0.33 mmol) of hydroxylamine solution (50% in water) in 2 mL f DMF at 80° C. for 1 h. The reaction mixture was purified by chromatography (reversed phase).

Yield: 86% of theory
$C_{13}H_9BrClNO_2$ (326.57)
Mass spectrum: $[M+H]^+$=326/8/30

78c) 4-(4-bromo-2-chloro-phenoxy)-benzylamine 18 mg (0.06 mmol) of 4-(4-bromo-2-chloro-phenoxy)-benzaldehyde-oxime was dissolved in 2 mL methanol, then 37 mg (0.15 mmol) of nickel(II)chloride hexahydrate and 21 mg (0.56 mmol) of sodium borohydride were slowly added. The reaction mixture was stirred overnight at RT and then purified by chromatography (reversed phase).

Yield: 46% of theory
$C_{13}H_{11}BrClNO$ (312.59)
Mass spectrum: $[M+H]^+$=295/7/9

78d) Pyrimidine-5-carboxylic acid{1-[4-(4-bromo-2-chloro-phenoxy)-benzylcarbamoyl]-cyclopropyl}-amide 7 µL (0.05 mmol) of triethylamine and 8.4 mg (0.03 mmol) of TBTU were added to a solution of 5.4 mg (0.03 mmol) of 1-[(pyrimidin-5-carbonyl)-amino]-cyclo-propanecarboxylic acid (from 1b) in 1 mL DMF and stirred for 5 min at RT. Then 8 mg (0.03 mmol) of 4-(4-bromo-2-chloro-phenoxy)-benzylamine was added and the mixture was stirred overnight at ambient temperature. The reaction mixture was purified by chromatography (reversed phase).

Yield: 84% of theory
$C_{22}H_{18}BrClN_4O_3$ (501.76)
Mass spectrum: $[M-H]^-$=499/501/3

EXAMPLE 79

Pyrimidine-5-carboxylic acid{1-[4-(4-bromo-2-trifluoromethyl-phenoxy)-benzylcarbamoyl]-cyclopropyl}-amide

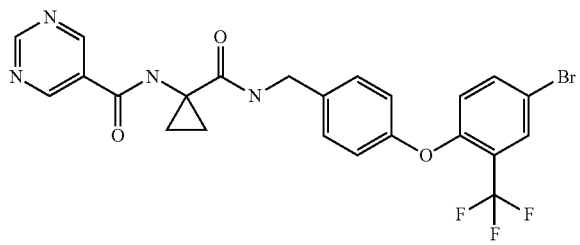

79a) 4-(4-bromo-2-trifluoromethyl-phenoxy)-benzaldehyde

Prepared analogously to Example 78a) starting from 4-fluorobenzaldehyde and 4-bromo-2-(trifluoromethyl)-benzenol.

Yield: 30% of theory
$C_{14}H_8BrF_3O_2$ (345.11)
Mass spectrum: $[M+H]^+$=345/7

79b) 4-(4-bromo-2-trifluoromethyl-phenoxy)-benzaldehyde-oxime

Prepared analogously to 78b) starting from 4-(4-bromo-2-trifluoromethyl-phenoxy)-benzaldehyde, it was further reacted directly without chromatographic purification.

Yield: 100% of theory
$C_{14}H_9BrF_3NO_2$ (360.13)
Mass spectrum: $[M+H]^+$=360/2

79c) 4-(4-bromo-2-trifluoromethyl-phenoxy)-benzylamine-trifluoroacetic acid salt Prepared analogously to 78c) starting from 4-(4-bromo-2-trifluoromethyl-phenoxy)-benzaldehyde-oximebut with a reaction time of only 10 min.

Yield: 52% of theory
$C_{14}H_{11}BrF_3NO$ (346.15)
Mass spectrum: $[M+H]^+$=346/8

79d) Pyrimidine-5-carboxylic acid{1-[4-(4-bromo-2-trifluoromethyl-phenoxy)-benzylcarbamoyl]-cyclopropyl}-amide Analogously to Example (78d) the title compound was prepared starting from 4-(4-bromo-2-trifluoromethyl-phenoxy)-benzylamine-trifluoroacetic acid salt.

Yield: 80% of theory
$C_{23}H_{18}BrF_3N_4O_3$ (535.32)
Mass spectrum: $[M+H]^+$=535/7

EXAMPLE 81

Pyrimidine-5-carboxylic acid(1-{1-[4-(4-difluoromethoxy-phenoxy)-phenyl]-ethylcarbamoyl}-cyclopropyl)-amide

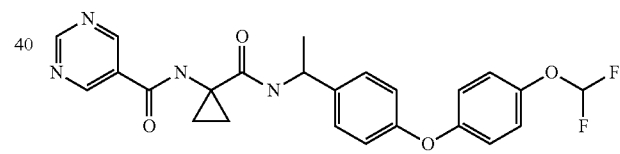

81 a) 1-[4-(4-difluoromethoxy-phenoxy)-phenyl]-ethanone

A solution of 666 µL (5.52 mmol) of 4-fluoroacetophenone and 883 mg (5.52 mmol) of 4-(difluoromethoxy)phenol in 10 mL DMSO was combined with 1.91 g (13.78 mmol) of potassium carbonate and stirred overnight at 100° C. The reaction mixture was poured onto 250 mL semisaturated sodium chloride solution and extracted twice with tert-butylmethylether. The organic phase was dried and evaporated down. The residue was purified by chromatography (silica gel, petroleum ether/ethyl acetate).

Yield: 89% of theory
$C_{15}H_{12}F_2O_3$ (278.25)
Mass spectrum: $[M+H]^+$=279

81b) 1-[4-(4-difluoromethoxy-phenoxy)-phenyl]-ethanone-oxime

A mixture of 1.37 g (4.92 mmol) of 1-[4-(4-difluoromethoxy-phenoxy)-phenyl]-ethanone and 1.16 mL hydroxylamine solution (50% in water) in 5 mL ethanol was refluxed for 3 hours. Then the mixture was concentrated and evaporated down several times with ethanol, and the residue was purified by chromatography (silica gel column, petroleum ether/ethyl acetate).
Yield: 94% of theory
$C_{15}H_{13}F_2NO_3$ (293.27)
Mass spectrum: $[M+H]^+=294$

81c) 1-[4-(4-difluoromethoxy-phenoxy)-phenyl]-ethylamine 1.35 g (4.60 mmol) of 1-[4-(4-difluoromethoxy-phenoxy)-phenyl]-ethanone-oxime were dissolved in 50 ml of 7M methanolic ammonia, then combined with 100 mg Raney nickel. The mixture was shaken overnight at RT and 50 psi hydrogen pressure. The catalyst was removed by suction filtering and the filtrate was evaporated down.
Yield: 99% of theory
$C_{15}H_{15}F_2NO_2$ (279.28)
Mass spectrum: $[M-NH_2]^+=263$

81d) Pyrimidine-5-carboxylic acid(1-{1-[4-(4-difluoromethoxy-phenoxy)-phenyl]-ethylcarbamoyl}-cyclopropyl)-amide 376 µL (2.70 mmol) of triethylamine and 0.52 g (1.62 mmol) of TBTU were added to a solution of 0.28 g (1.35 mmol) of 1-[(pyrimidin-5-carbonyl)-amino]-cyclo-propanecarboxylic acid (from 1b) in 5 mL DMF and the mixture was stirred for 5 min at RT. Then 0.42 g (1.50 mmol) of 1-[4-(4-difluoromethoxy-phenoxy)-phenyl]-ethylamine was added and the mixture was stirred for 30 min at ambient temperature. The reaction mixture was purified by chromatography (reversed phase). The acetonitrile was distilled off, the aqueous phase was made basic with ammonia and extracted with dichloromethane. The organic phase was dried and evaporated down.
Yield: 66% of theory
$C_{24}H_{22}F_2N_4O_4$ (468.45)
Mass spectrum: $[M-H]^-=467$

EXAMPLE 82

Pyrimidine-5-carboxylic acid(1-{1-[4-(4-methoxy-2-trifluoromethyl-phenoxy)-phenyl]-ethylcarbamoyl}-cyclopropyl)-amide

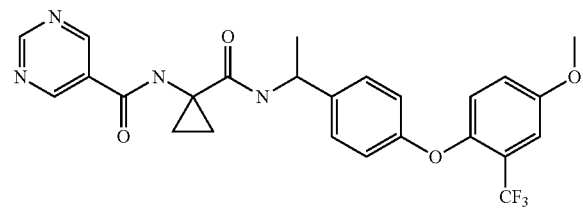 [SMILES: COc1ccc(Oc2ccc(C(C)NC(=O)C3(NC(=O)c4cncnc4)CC3)cc2)c(C(F)(F)F)c1]

82a) 1-benzyloxy-4-methoxy-2-trifluoromethyl-benzene 18 g (166.67 mmol) of benzylalcohol was slowly added to a solution of 6.7 g (167.50 mmol) of sodium hydride in 148 mL NMP. The reaction mixture was stirred for 30 min at RT, then a solution of 27 g (139.09 mmol) of 1-fluoro-4-methoxy-2-trifluoromethyl-benzene in 515 mL NMP was added, and this was stirred for 30 min at RT and for 2 h at 100° C. After cooling to RT the mixture was diluted with water and extracted with ethyl acetate, the organic phase was washed with saturated sodium chloride solution, dried on sodium sulphate and evaporated down. The residue was purified by chromatography (silica gel, petroleum ether/ethyl acetate).
Yield: 76% of theory
$C_{15}H_{13}F_3O_2$ (282.26)
Mass spectrum: $[M+]=282$
$R_f=0.4$ thin layer chromatography (silica gel, ethyl acetate/petroleum ether 7:93)

82b) 4-methoxy-2-trifluoromethyl-phenol 30 g (106.28 mmol) of 1-benzyloxy-4-methoxy-2-trifluoromethyl-benzene were dissolved in 60 mL ethyl acetate and then combined with 3 g palladium/C 10%. The mixture was shaken at RT and 50 psi hydrogen pressure for 4 h. The reaction mixture was suction filtered through Celite and the filtrate was evaporated down. The residue was purified by chromatography (silica gel, petroleum ether/ethyl acetate).
Yield: 97% of theory
$C_8H_7F_3O_2$ (192.14)
Mass spectrum: $[M-H]^-=191$
$R_f=0.2$ thin layer chromatography (silica gel, ethyl acetate/petroleum ether 1:10)

82c) 4-(4-methoxy-2-trifluoromethyl-phenoxy)-benzonitrile

A solution of 4 g (20.82 mmol) of 4-methoxy-2-trifluoromethyl-phenol and 2.52 g (20.82 mmol) of 4-fluorobenzonitrile in 60 mL DMSO was combined with 5.75 g (41.64 mmol) of potassium carbonate and stirred for 3 h at 120° C. The reaction mixture was diluted with water, and extracted three times with dichloromethane. The organic phase was washed twice with water, dried on sodium sulphate and evaporated down. The residue was purified by chromatography (reversed phase).
Yield: 52% of theory
$C_{18}H_{10}F_3NO_2$ (293.24)
Mass spectrum: $[M-H]^-=292$

82d) 1-[4-(4-methoxy-2-trifluoromethyl-phenoxy)-phenyl]-ethanone 4.87 mL (6.82 mmol) of methylmagnesium bromide (1.4 M in THF) was placed under a nitrogen atmosphere and cooled to −20° C., then 0.5 g (1.71 mmol) of 4-(4-methoxy-2-trifluoromethyl-phenoxy)-benzonitrile in 2.5 mL diethyl ether was added dropwise. After this addition the mixture was stirred for a further 15 min at −20° C. and then allowed to come up to RT. The reaction mixture was slowly added to an ice/ammonium chloride refrigerant mixture and then extracted with diethyl ether. The organic phase was dried and evaporated down. The residue was purified by chromatography (silica gel, petroleum ether/acetic acid ethyl ester).
Yield: 62% of theory
$C_{16}H_{13}F_3O_3$ (310.27)
Mass spectrum: $[M+H]^+=311$

82e) 1-[4-(4-methoxy-2-trifluoromethyl-phenoxy)-phenyl]-ethanone-oxime

Prepared analogously to Example 81b) starting from 1-[4-(4-methoxy-2-trifluoromethyl-phenoxy)-phenyl]-ethanone.

Yield: 95% of theory
C$_{16}$H$_{14}$F$_3$NO$_3$ (325.28)
Mass spectrum: [M+H]$^+$=326

82f) 1-[4-(4-methoxy-2-trifluoromethyl-phenoxy)-phenyl]-ethylamine

Prepared analogously to Example 2c) starting from 1-[4-(4-methoxy-2-trifluoromethyl-phenoxy)-phenyl]-ethanone-oxime.
Yield: 100% of theory
C$_{16}$H$_{16}$F$_3$NO$_2$ (311.30)
Mass spectrum (EI): [M*+]=311

82g) Pyrimidine-5-carboxylic acid(1-{1-[4-(4-methoxy-2-trifluoromethyl-phenoxy)-phenyl]-ethylcarbamoyl}-cyclopropyl)-amide Prepared analogously to Example 76d) starting from 1-[4-(4-methoxy-2-trifluoromethyl-phenoxy)-phenyl]-ethylamine.
Yield: 53% of theory
C$_{25}$H$_{23}$F$_3$N$_4$O$_4$ (500.47)
Mass spectrum: [M+H]$^+$=501

EXAMPLE 83

N-{1-[4-(2-chloro-4-methoxy-phenoxy)-benzylcarbamoyl]-cyclopropyl}-5-trifluoromethyl-nicotinamide

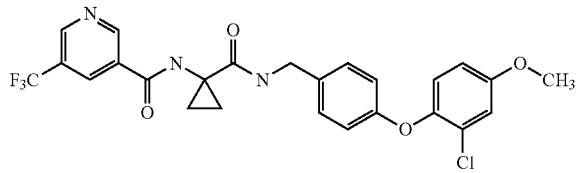 [SMILES: COc1ccc(Oc2ccc(CNC(=O)C3(NC(=O)c4cncc(C(F)(F)F)c4)CC3)cc2)c(Cl)c1]

83a) N-{1-[4-(2-chloro-4-methoxy-phenoxy)-benzylcarbamoyl]-cyclopropyl}-5-trifluoromethyl-nicotinamide 102 µL (0.73 mmol) of triethylamine and 117 mg (0.36 mmol) of TBTU were added to a solution of 73.7 mg (0.37 mmol) of 1-tert-butoxycarbonylamino-cyclopropanecarboxylic acid in 6 mL DMF and the mixture was stirred for 5 min at RT. Then 96.6 mg (0.37 mmol) of 4-(2-chloro-4-methoxy-phenoxy)-benzylamine was added and the mixture was stirred overnight at ambient temperature. The reaction mixture was filtered through Alox B, washed with DMF and the filtrate was evaporated down. 10 ml of dichloromethane/trifluoroacetic acid=1/1 were added to the residue and this was shaken for 1 h at RT. The reaction mixture was evaporated down and the residue was purified by chromatography (reversed phase). The corresponding fractions were freeze-dried. 35 mg (0.18 mmol) of 5-(trifluoromethyl)nicotinic acid was dissolved in 2 ml DMF and combined with 52 µL (0.37 mmol) of triethylamine and 59 mg (0.18 mmol) of TBTU and stirred for 10 min at RT. Then the freeze-dried 1-amino-cyclopropanecarboxylic acid-4-(2-chloro-4-methoxy-phenoxy)-benzylamide was added and the mixture was stirred overnight at RT. The reaction mixture was purified directly by chromatography (reversed phase).
Yield: 21% of theory
C$_{25}$H$_{21}$ClF$_3$N$_3$O$_4$ (519.90)
Mass spectrum: [M+H]$^+$=520

EXAMPLE 84

Pyrimidine-5-carboxylic acid{1-[4-(4-methoxy-2-trifluoromethyl-phenoxy)-benzylcarbamoyl]-cyclopropyl}-amide

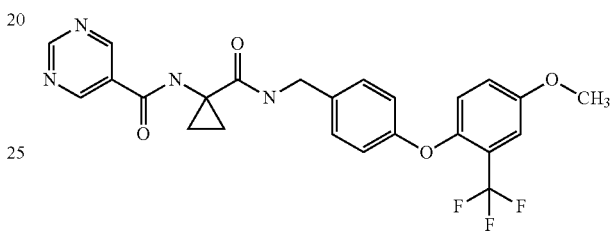

84a) 4-(4-methoxy-2-trifluoromethyl-phenoxy)-benzylamine 2.53 g (8.63 mmol) of 4-(4-methoxy-2-trifluoromethyl-phenoxy)-benzonitrile (from 82c) were dissolved in 100 ml 7M methanolic ammonia, then combined with 250 mg Raney nickel. The mixture was shaken at RT and 50 psi hydrogen pressure for 3 h. The catalyst was removed by suction filtering and the filtrate was evaporated down.
Yield: 90% of theory
C$_{15}$H$_{14}$F$_3$NO$_2$ (297.27)
Mass spectrum: [M–NH2]$^+$=281

84b) Pyrimidine-5-carboxylic acid{1-[4-(4-methoxy-2-trifluoromethyl-phenoxy)-benzylcarbamoyl]-cyclopropyl}-amide Prepared analogously to Example 78d) starting from 4-(4-methoxy-2-trifluoromethyl-phenoxy)-benzylamine.
C$_{24}$H$_{21}$F$_3$N$_4$O$_4$ (486.44)
Mass spectrum: [M+H]$^+$=487

EXAMPLE 85

1-(4-dimethylamino-butyrylamino)-cyclopropanecarboxylic acid 4-(4-methoxy-2-trifluoromethyl-phenoxy)-benzylamide

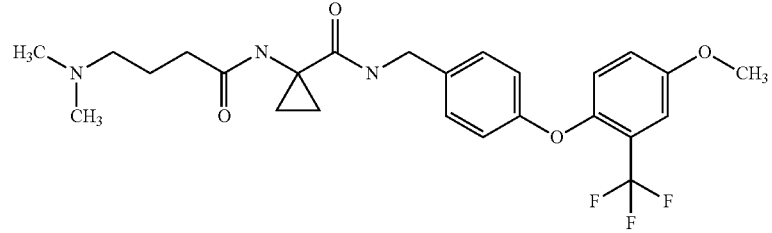

85a) 1-amino-cyclopropanecarboxylic acid 4-(4-methoxy-2-trifluoromethyl-phenoxy)-benzylamide 540 μL (3.85 mmol) of triethylamine and 864 mg (2.69 mmol) of TBTU were added to a solution of 541.5 mg (2.69 mmol) of 1-tert-butoxycarbonylamino-cyclopropanecarboxylic acid in 45 mL DMF and the mixture was stirred for 5 min at RT. Then 800 mg (2.69 mmol) of 4-(4-methoxy-2-trifluoromethyl-phenoxy)-benzylamine (from 84a) was added and the mixture was stirred for 2 h at ambient temperature. The reaction mixture was filtered through Alox B, washed with DMF/MeOH=9/1 and the filtrate was evaporated down. 20 ml dichloromethane/trifluoroacetic acid/water=50/45/5 were added to the residue and the mixture was stirred for 1 h at RT. The reaction mixture was evaporated down, the residue was dissolved in dichloromethane and extracted with 10 mL of 1 M sodium hydroxide solution. The dichloromethane phase was separated off and evaporated down.

Yield: 79% of theory
$C_{19}H_{19}F_3N_2O_3$ (380.36)
Mass spectrum: $[M+H]^+=381$

85b) 1-(4-dimethylamino-butyrylamino)-cyclopropanecarboxylic acid 4-(4-methoxy-2-trifluoromethyl-phenoxy)-benzylamide 1.44 mg (11 μMol) 4-dimethylamino-butyric acid was dissolved in 100 μL DMF, 3.5 μL (24.95 μMol) triethylamine and 3.37 mg (10.5 μMol) TBTU in 100 μL DMF were added and the mixture was stirred for 10 min at RT. Then 3.80 mg (10 μMol) 1-amino-cyclopropanecarboxylic acid 4-(4-methoxy-2-trifluoromethyl-phenoxy)-benzylamide in 100 μL DMF was added and the mixture was shaken for 3 days at ambient temperature. Filtered through Alox B, washed with DMF/MeOH=9/1 and the filtrate was evaporated down.

Yield: 73% of theory
$C_{25}H_{30}F_3N_3$ (493.53)
Mass spectrum: $[M+H]^+=494$

EXAMPLE 100

1-(2-cyano-acetylamino)-cyclopropanecarboxylic acid 4-(4-methoxy-2-tri-fluoromethyl-phenoxy)-benzylamide

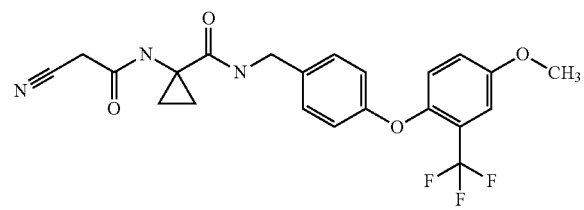 [SMILES: COc1ccc(Oc2ccc(CNC(=O)C3(NC(=O)CC#N)CC3)cc2)c(C(F)(F)F)c1]

100a) 1-(2-cyano-acetylamino)-cyclopropanecarboxylic acid 4-(4-methoxy-2-trifluoromethyl-phenoxy)-benzylamide Prepared analogously to Example 85b) starting from cyanoacetic acid and 1-amino-cyclopropanecarboxylic acid 4-(4-methoxy-2-trifluoromethyl-phenoxy)-benzylamide (from 85a). In addition, the residue was finally purified by chromatography (reversed phase).

Yield: 25% of theory
$C_{22}H_{20}F_3N_3$ (447.42)
Mass spectrum: $[M+H]^+=448$

EXAMPLE 106

3-methyl-isoxazole-4-carboxylic acid{1-[4-(4-methoxy-2-trifluoromethyl-phenoxy)-benzylcarbamoyl]-cyclopropyl}-amide

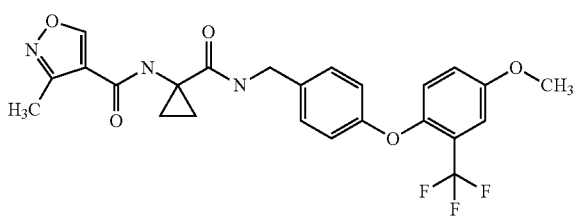 [SMILES: COc1ccc(Oc2ccc(CNC(=O)C3(NC(=O)c4conc4C)CC3)cc2)c(C(F)(F)F)c1]

106a) 3-methyl-isoxazole-4-carboxylic acid{1-[4-(4-methoxy-2-trifluoromethyl-phenoxy)-benzylcarbamoyl]-cyclopropyl}-amide 37 μL (0.26 mmol) of triethylamine and 84.4 mg (0.26 mmol) of TBTU were added to a solution of 33.4 mg (0.26 mmol) of 3-methylisoxazole-4-carboxylic acid in 5 mL DMF and the mixture was stirred for 10 min at RT. Then 100 mg (0.26 mmol) of 1-amino-cyclopropanecarboxylic acid 4-(4-methoxy-2-trifluoromethyl-phenoxy)-benzylamide (from 85a) was added and the mixture was stirred for 4 h at ambient temperature and overnight at 40° C. The reaction mixture was purified by chromatography (reversed phase).

Yield: 12% of theory
$C_{24}H_{22}F_3N_3O_5$ (489.44)
Mass spectrum: $[M+H]^+=490$

EXAMPLE 107

3-methoxy-isoxazole-5-carboxylic acid{1-[4-(4-methoxy-2-trifluoromethyl-phenoxy)-benzylcarbamoyl]-cyclopropyl}-amide

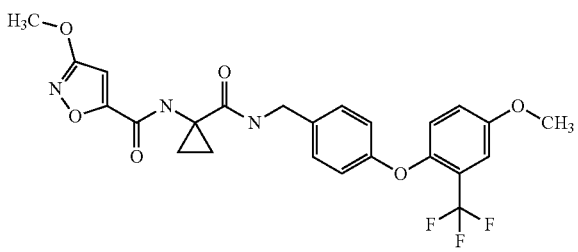

107a) 3-methoxy-isoxazole-5-carboxylic acid{1-[4-(4-methoxy-2-trifluoromethyl-phenoxy)-benzylcarbamoyl]-cyclopropyl}-amide Prepared analogously to Example 106a) starting from 3-methoxy-isoxazole-5-carboxylic acid. The reaction time was 4 h at RT.

Yield: 25% of theory
$C_{24}H_{22}F_3N_3O_6$ (505.44)
Mass spectrum: $[M+H]^+=506$

EXAMPLE 108

5-methyl-isoxazole-4-carboxylic acid{1-[4-(4-methoxy-2-trifluoromethyl-phenoxy)-benzylcarbamoyl]-cyclopropyl}amide

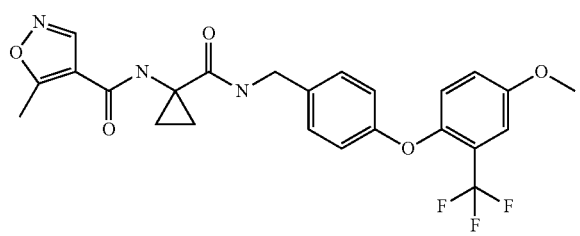 [SMILES: COc1ccc(Oc2ccc(CNC(=O)C3(NC(=O)c4cnoc4C)CC3)cc2)c(C(F)(F)F)c1]

108a) 5-methyl-isoxazole-4-carboxylic acid{1-[4-(4-methoxy-2-trifluoromethyl-phenoxy)-benzylcarbamoyl]-cyclopropyl}amide Prepared analogously to Example 106a) starting from 3-methyl-isoxazole-4-carboxylic acid. The reaction was carried out overnight at RT.
Yield: 45% of theory
$C_{24}H_{22}F_3N_3O_5$ (489.44)
Mass spectrum: $[M+H]^+=490$

EXAMPLE 109

N-{1-[4-(4-methoxy-2-trifluoromethyl-phenoxy)-benzylcarbamoyl]-cyclopropyl}-malonic acid monoamide monoethylester

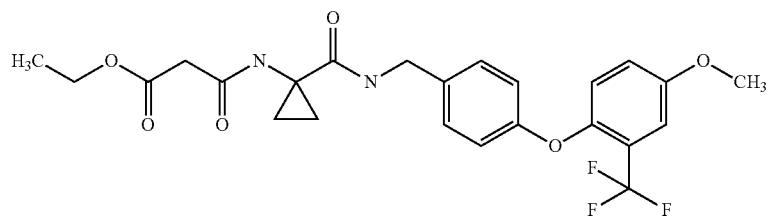 [SMILES: CCOC(=O)CC(=O)NC1(C(=O)NCc2ccc(Oc3ccc(OC)cc3C(F)(F)F)cc2)CC1]

109a) N-{1-[4-(4-methoxy-2-trifluoromethyl-phenoxy)-benzylcarbamoyl]-cyclopropyl}-malonic acid monoamide monoethylester 87 µL (0.50 mmol) of DIPEA and 80.9 mg (0.25 mmol) of TBTU were added to a solution of 33.27 mg (0.25 mmol) of monoethylmalonate in 100 µL DMF and the mixture was stirred for 5 min at RT. Then 83 mg (0.17 mmol) of 1-aminocyclopropanecarboxylic acid 4-(4-methoxy-2-trifluoromethyl-phenoxy)-benzylamide-trifluoroacetic acid salt (from 85a) was added and the mixture was stirred for 1.5 h at ambient temperature. The reaction mixture was purified by chromatography (reversed phase).
Yield: 76% of theory
$C_{24}H_{25}F_3N_2O_6$ (494.46)
Mass spectrum: $[M+H]^+=495$

EXAMPLE 113

2-methoxy-N-{1-[4-(4-methoxy-2-trifluoromethyl-phenoxy)-benzylcarbamoyl]-cyclopropyl}-nicotinamide

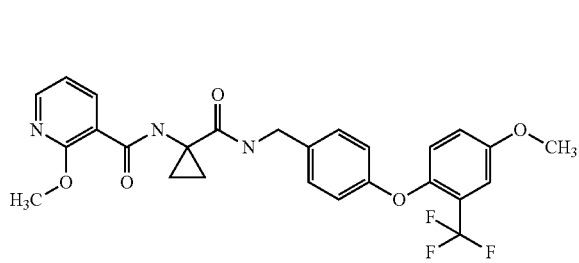 [SMILES: COc1ccc(Oc2ccc(CNC(=O)C3(NC(=O)c4cccnc4OC)CC3)cc2)c(C(F)(F)F)c1]

113a) 2-methoxy-N-{1-[4-(4-methoxy-2-trifluoromethyl-phenoxy)-benzylcarbamoyl]-cyclopropyl}-nicotinamide Prepared analogously to Example 109a) starting from 2-methoxynicotinic acid. The reaction time was 24 h at RT.
Yield: 61% of theory
$C_{26}H_{24}F_3N_3O_5$ (515.48)
Mass spectrum: $[M+H]^+=516$

EXAMPLE 114

N-{1-[4-(4-methoxy-2-trifluoromethyl-phenoxy)-benzylcarbamoyl]-cyclopropyl}-malonic acid monoamide

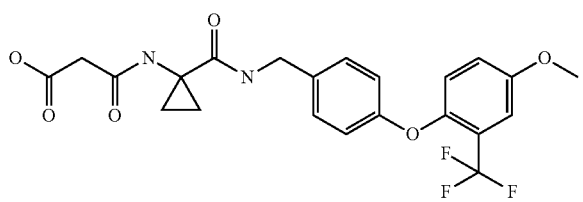 [SMILES: COc1ccc(Oc2ccc(CNC(=O)C3(NC(=O)CC(=O)O)CC3)cc2)c(C(F)(F)F)c1]

114a) N-{1-[4-(4-methoxy-2-trifluoromethyl-phenoxy)-benzylcarbamoyl]-cyclopropyl}malonic acid monoamide 33 mg (0.067 mmol) of N-{1-[4-(4-methoxy-2-trifluoromethyl-phenoxy)-benzylcarbamoyl]-cyclopropyl}-malonic acid monoamide monoethylester (from 109a) was stirred for 1 h at RT together with 1 mL sodium hydroxide solution 1M in 20 mL THF. The reaction mixture was evaporated down and the residue was purified by chromatography (reversed phase).
Yield: 26% of theory
$C_{22}H_{21}F_3N_2O_6$ (466.41)
Mass spectrum: $[M+H]^+=467$

EXAMPLE 116

6-methoxy-pyridine-2-carboxylic acid{1-[4-(4-methoxy-2-trifluoromethyl-phenoxy)-benzylcarbamoyl]-cyclopropyl}-amide

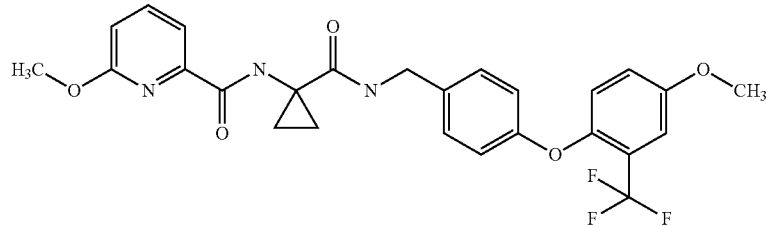

116a) 6-methoxy-pyridine-2-carboxylic acid{1-[4-(4-methoxy-2-trifluoromethyl-phenoxy)-benzylcarbamoyl]-cyclopropyl}-amide Prepared analogously to Example 109a) starting from 6-methoxy-2-pyridincarboxylic acid. The reaction was carried out overnight at RT.
Yield: 53% of theory
$C_{26}H_{24}F_3N_3O_5$ (515.48)
Mass spectrum: $[M+H]^+=516$

EXAMPLE 118

6-hydroxy-pyridine-2-carboxylic acid{1-[4-(4-methoxy-2-trifluoromethyl-phenoxy)-benzylcarbamoyl]-cyclopropyl}-amide

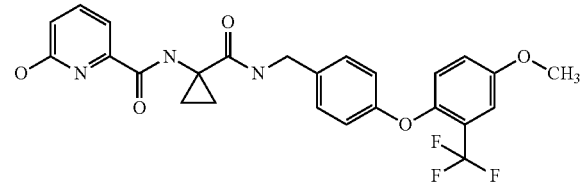 [SMILES: COc1ccc(Oc2ccc(CNC(=O)C3(NC(=O)c4cccc(O)n4)CC3)cc2)c(C(F)(F)F)c1]

118a) 6-hydroxy-pyridine-2-carboxylic acid{1-[4-(4-methoxy-2-trifluoromethyl-phenoxy)-benzylcarbamoyl]-cyclopropyl}-amide 74 µL (0.43 mmol) of DIPEA and 57.7 mg (0.18 mmol) of TBTU were added to a solution of 20 mg (0.14 mmol) of 6-hydroxypicolinic acid in 100 µL DMF and the mixture was stirred for 5 min at RT. Then 71 mg (0.14 mmol) of 1-amino-cyclopropanecarboxylic acid 4-(4-methoxy-2-trifluoromethyl-phenoxy)-benzylamide-trifluoroacetic acid salt (from 84a) was added and the mixture was stirred for 3 days at ambient temperature. The reaction mixture was purified by chromatography (reversed phase).
Yield: 52% of theory
$C_{25}H_{22}F_3N_3O_5$ (501.46)
Mass spectrum: $[M+H]^+=502$

EXAMPLE 119

2-methoxy-N-{1-[4-(4-methoxy-2-trifluoromethyl-phenoxy)-benzylcarbamoyl]-cyclopropyl}-isonicotinamide

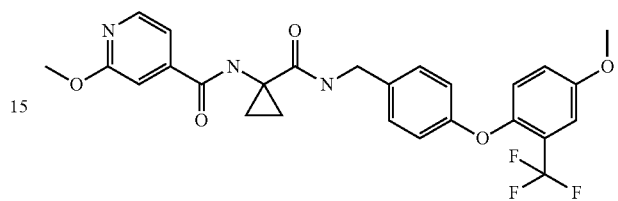

119a) 2-methoxy-N-{1-[4-(4-methoxy-2-trifluoromethyl-phenoxy)-benzylcarbamoyl]-cyclopropyl}-isonicotinamide Prepared analogously to Example 118a) from 2-methoxy-4-pyridinecarboxylic acid. The reaction time was 2 h at RT.
Yield: 51% of theory
$C_{26}H_{24}F_3N_3O_5$ (515.48)
Mass spectrum: $[M+H]^+=516$

EXAMPLE 120

2-fluoro-N-{1-[4-(4-methoxy-2-trifluoromethyl-phenoxy)-benzylcarbamoyl]-cyclopropyl}-isonicotinamide

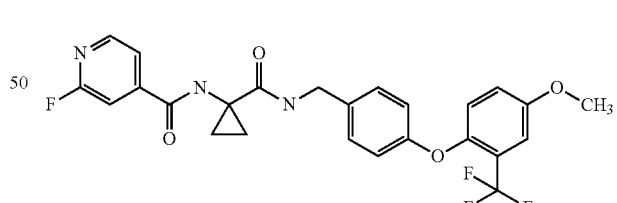

120a) 2-fluoro-N-{1-[4-(4-methoxy-2-trifluoromethyl-phenoxy)-benzylcarbamoyl]-cyclopropyl}-isonicotinamide 68 µL (0.48 mmol) of TEA and 57 mg (0.19 mmol) of TBTU were added to a solution of 23 mg (0.16 mmol) of 6-fluoro-nicotinic acid in 2 mL DMF and the mixture was stirred for 5 min at RT. Then 80 mg (0.16 mmol) of 1-amino-cyclopropanecarboxylic acid 4-(4-methoxy-2-trifluoromethyl-phenoxy)-benzylamide-trifluoroacetic acid salt (from 85a) was added and the mixture was stirred for 2 h at ambient temperature. A further 57 mg (0.19 mmol) of TBTU, 68 μL (0.48 mmol) of TEA and 23 mg (0.16 mmol) of 6-fluoronicotinic acid were added and the mixture was stirred overnight at RT. The reaction mixture was purified by chromatography (reversed phase).
Yield: 33% of theory
$C_{25}H_{21}F_4N_3O_4$ (503.46)
Mass spectrum: $[M+H]^+=504$

EXAMPLE 125

Oxazole-5-carboxylic acid{1-[4-(4-methoxy-2-trifluoromethyl-phenoxy)-benzylcarbamoyl]-cyclopropyl}-amide

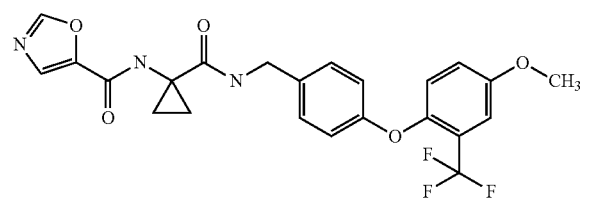 [SMILES: COc1ccc(Oc2ccc(CNC(=O)C3(NC(=O)c4cnco4)CC3)cc2)c(C(F)(F)F)c1]

125a) oxazole-5-carboxylic acid{1-[4-(4-methoxy-2-trifluoromethyl-phenoxy)-benzylcarbamoyl]-cyclopropyl}-amide 57.5 μL (0.41 mmol) of TEA and 48 mg (0.15 mmol) of TBTU were added to a solution of 15.4 mg (0.14 mmol) of oxazole-5-carboxylic acid in 1.5 mL DMF and the mixture was stirred for 5 min at RT. Then 67.5 mg (0.14 mmol) of 1-amino-cyclopropanecarboxylic acid 4-(4-methoxy-2-trifluoromethyl-phenoxy)-benzylamide-trifluoroacetic acid salt (from 85a) were added and the mixture was stirred for 2 h at ambient temperature. The reaction mixture was purified by chromatography (reversed phase).
Yield: 25% of theory
$C_{23}H_{20}F_3N_3O_5$ (475.42)
Mass spectrum: $[M+H]^+=476$

EXAMPLE 129

6-methyl-pyridine-2-carboxylic acid{1-[4-(4-methoxy-2-trifluoromethyl-phenoxy)-benzylcarbamoyl]-cyclopropyl}-amide

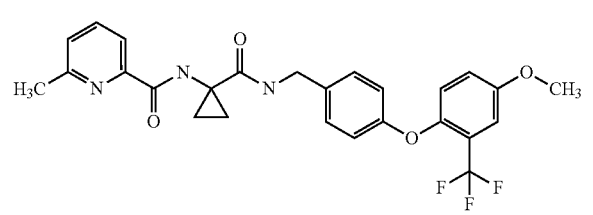

129a) 6-methyl-pyridine-2-carboxylic acid{1-[4-(4-methoxy-2-trifluoromethyl-phenoxy)-benzylcarbamoyl]-cyclopropyl}amide 28 μL (0.20 mmol) of TEA and 118.8 mg (0.30 mmol) of HATU were added to a solution of 27.7 mg (0.20 mmol) of 6-methylpicolinic acid in 5 mL DMF and the mixture was stirred for 5 min at RT. Then 112 μL (0.81 mmol) of TEA and 100 mg (0.20 mmol) of 1-amino-cyclopropanecarboxylic acid 4-(4-methoxy-2-trifluoromethyl-phenoxy)-benzylamide-trifluoroacetic acid salt (from 85a) were added and the mixture was stirred overnight at RT. The reaction mixture was purified by chromatography (reversed phase).
Yield: 80% of theory
$C_{26}H_{24}F_3N_3O_4$ (499.48)
Mass spectrum: $[M+H]^+=500$

EXAMPLE 139

N-{1-[4-(4-methoxy-2-trifluoromethyl-phenoxy)-benzylcarbamoyl]-cyclopropyl}-succinic acid-monoamid

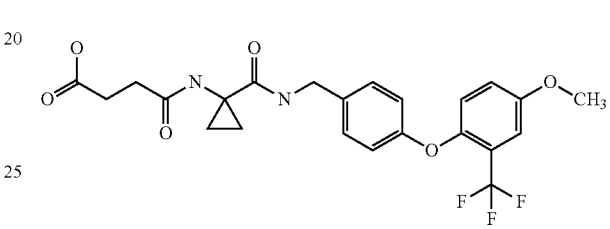

A solution of 82 mg (0.166 mmol) of N-{1-[4-(4-methoxy-2-trifluoromethyl-phenoxy)-benzylcarbamoyl]-cyclopropyl}-succinic acid-monoamide-methylester (product from Example 132) and 2 mL sodium hydroxide solution (1 N) in 10 mL THF was stirred for two hours at ambient temperature, then neutralised with 0.1 N hydrochloric acid and evaporated down. The solid residue was stirred in approx. 3 mL dichloromethane, filtered off and evaporated down again.
Yield: 98% of theory
$C_{23}H_{23}F_3N_2O_6$ (480.43)
Mass spectrum: $[M+H]^+=481$

EXAMPLE 140

Pyrimidine-5-carboxylic acid{1-[4-(4-cyano-2-trifluoromethyl-phenoxy)-benzylcarbamoyl]-cyclopropyl}-amide

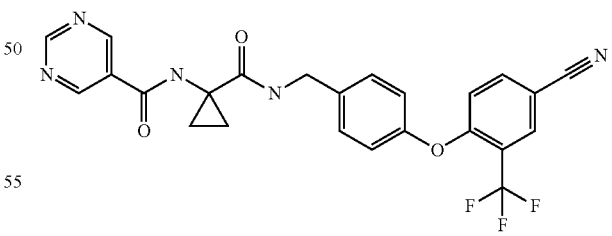

A solution of 100 mg (0.32 mmol) of pyrimidin-5-carboxylic acid[1-(4-hydroxy-benzylcarbamoyl)-cyclopropyl]-amide, 60.5 mg (0.32 mmol) of 4-fluoro-3-trifluoromethyl-benzonitrile and 110 mg (0.8 mmol) of potassium carbonate in 5 mL DMF was stirred for two hours at 110° C. After cooling the mixture was diluted with approx. 3 mL acetone, filtered and evaporated down. The crude product thus obtained was purified by column chromatography (reversed phase).

Yield: 82% of theory
C$_{24}$H$_{18}$F$_3$N$_6$O$_3$ (481.43)
Mass spectrum: [M+H]$^+$=481

EXAMPLE 148

2-methanesulphinyl-pyrimidine-5-carboxylic acid{1-[4-(4-methoxy-2-trifluoromethyl-phenoxy)-benzyl-carbamoyl]-cyclopropyl}-amide

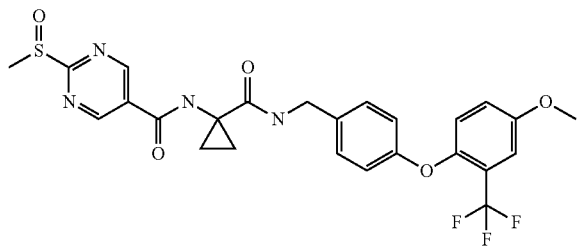

186 mg (1.08 mmol) of 3-chloroperbenzoic acid were added at approx. 5° C. to a solution of 575 mg (1.08 mmol) of 2-methylthio-pyrimidine-5-carboxylic acid{1-[4-(4-methoxy-2-trifluoromethyl-phenoxy)-benzylcarbamoyl]-cyclopropyl}-amide (product from Example 144) in 10 mL dichloromethane. Then the cooling was removed and the reaction mixture stirred for a further three hours at ambient temperature. Half the solution was evaporated down and the crude product thus obtained was purified by chromatography (reversed phase HPLC).

Yield: 6% of theory
C$_{25}$H$_{23}$F$_3$N$_4$O$_5$S (548.54)
Mass spectrum: [M+H]$^+$=549

EXAMPLE 149

2-methanesulphonyl-pyrimidine-5-carboxylic acid{1-[4-(4-methoxy-2-trifluoromethyl-phenoxy)-benzylcarbamoyl]-cyclopropyl}-amide

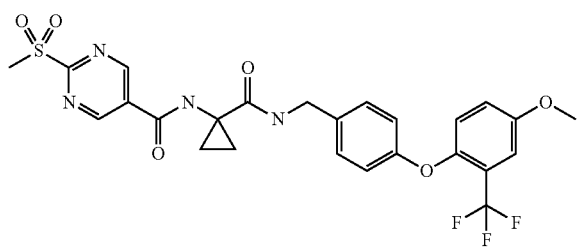

Half the crude product mixture from Example 148 was combined with a further 186 mg 3-chloroperbenzoic acid and stirred for two hours at ambient temperature. After the solution had been evaporated down the crude product thus obtained was purified by chromatography (reversed phase HPLC).

Yield: 47% of theory
C$_{25}$H$_{23}$F$_3$N$_4$O$_6$S (564.54)
Mass spectrum: [M+H]$^+$=565

EXAMPLE 152

2-Cyano-pyrimidine-5-carboxylic acid{1-[4-(4-methoxy-2-trifluoromethyl-phenoxy)-benzylcarbamoyl]-cyclopropyl}-amide

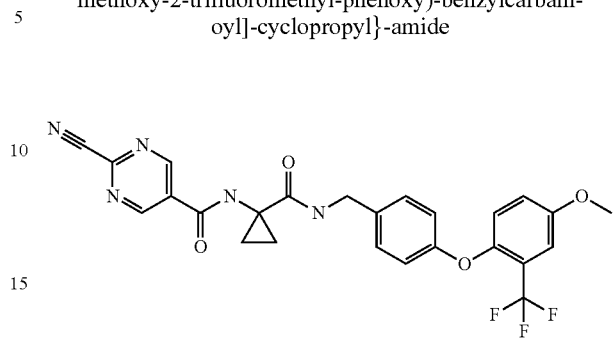

A solution of 50 mg (0.089 mmol) of 2-methanesulphonyl-pyrimidine-5-carboxylic acid{1-[4-(4-methoxy-2-trifluoromethyl-phenoxy)-benzylcarbamoyl]-cyclopropyl}-amide (product from Example 149) in 2 mL DMF was combined with 9 mg (0.13 mmol) of potassium cyanide and then heated to 100° C. for 10 minutes in a microwave apparatus. The mixture was then combined with 2 mL concentrated ammonia solution and extracted with dichloromethane. The crude product obtained after evaporation was purified by chromatography (reversed phase HPLC).

Yield: 51% of theory
C$_{25}$H$_{20}$F$_3$N$_5$O$_4$ (511.45)
Mass spectrum: [M+H]$^+$=512

EXAMPLE 163

Pyrimidine-5-carboxylic acid{1-[4-(4-acetyl-2-trifluoromethyl-phenoxy)-benzylcarbamoyl]-cyclopropyl}-amide

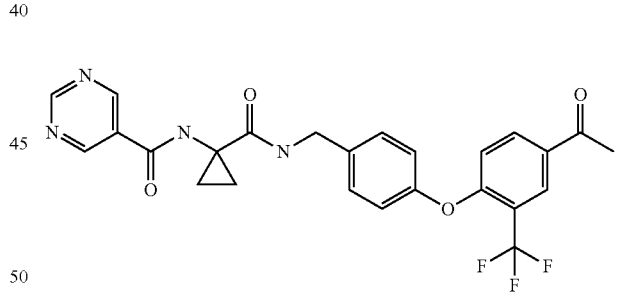

A solution of 70 mg (0.14 mmol) of pyrimidine-5-carboxylic acid(1-{4-[4-(1-hydroxyethyl)-2-trifluoromethyl-phenoxy]-benzylcarbamoyl}-cyclopropyl)amide (product from Example 153) in 10 mL dichloromethane was combined with 300 mg (3.5 mmol) of manganese dioxide and stirred for three days at ambient temperature. The mixture was then filtered and evaporated down. The crude product thus obtained was purified by chromatography (reversed phase HPLC).

Yield: 21% of theory
C$_{25}$H$_{21}$F$_3$N$_4$O$_4$ (498.45)
Mass spectrum: [M+H]$^+$=499

The remaining compounds are prepared analogously to the foregoing Examples.

Table of End Compounds:

| No. | Structure | Educt (benzylamine) | Method of manufacture | LCMS |
|---|---|---|---|---|
| (1) | 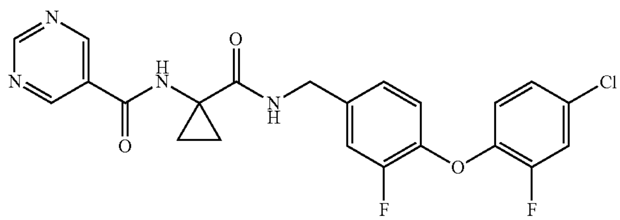 [SMILES: O=C(NC1(C(=O)NCc2ccc(Oc3ccc(Cl)cc3F)c(F)c2)CC1)c1cncnc1] | 1d) | 1e) | [M − H]− = 457/459 |
| (2) | 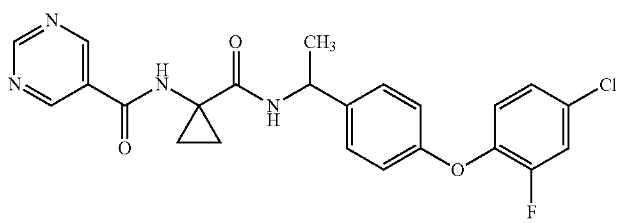 [SMILES: CC(NC(=O)C1(NC(=O)c2cncnc2)CC1)c1ccc(Oc2ccc(Cl)cc2F)cc1] | 2c) | analogously to 1e) | [M + H]+ = 455/457 |
| (3) | 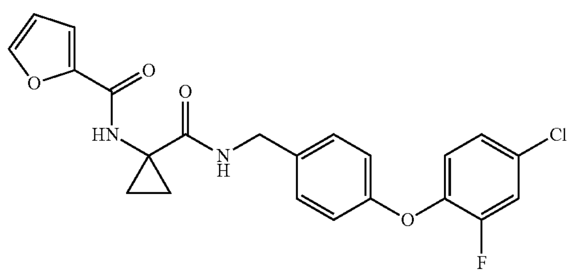 [SMILES: O=C(NC1(C(=O)NCc2ccc(Oc3ccc(Cl)cc3F)cc2)CC1)c1ccco1] | 3b) | analogously to 1e) | [M + H]+ = 429/431 |
| (4) | 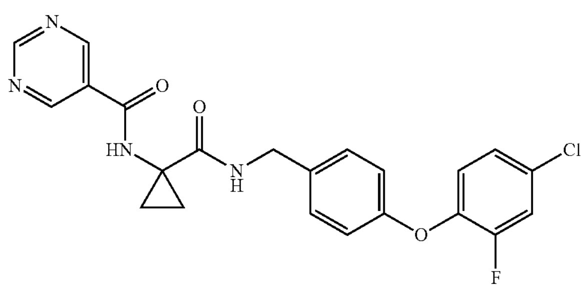 [SMILES: O=C(NC1(C(=O)NCc2ccc(Oc3ccc(Cl)cc3F)cc2)CC1)c1cncnc1] | 3b) | analogously to 1e) | [M + H]+ = 441/443 |
| (5) | 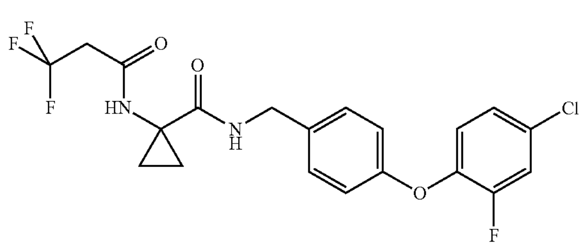 [SMILES: O=C(CC(F)(F)F)NC1(C(=O)NCc2ccc(Oc3ccc(Cl)cc3F)cc2)CC1] | 3b) | analogously to 1e) | [M + H]+ = 445/447 |
| (6) | 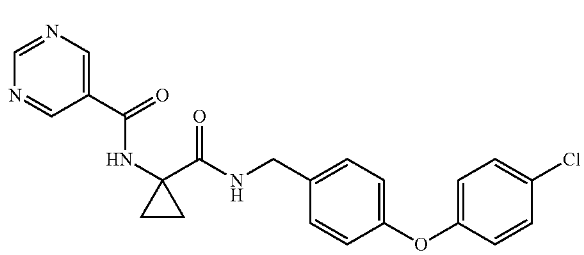 [SMILES: O=C(NC1(C(=O)NCc2ccc(Oc3ccc(Cl)cc3)cc2)CC1)c1cncnc1] | 6b) | analogously to 1e) | [M + H]+ = 423/425 |

-continued

| No. | Structure | Educt (benzylamine) | Method of manufacture | LCMS |
|---|---|---|---|---|
| (7) | 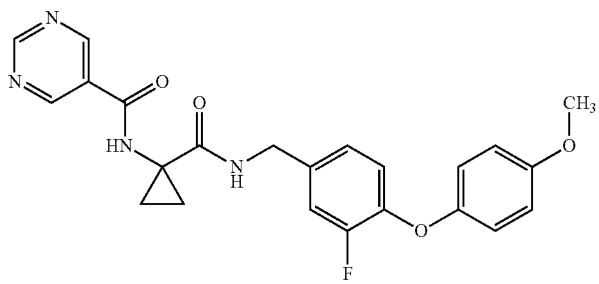 [SMILES: COc1ccc(Oc2ccc(CNC(=O)C3(NC(=O)c4cncnc4)CC3)cc2F)cc1] | 7b) | 7c) | [M + H]+ = 437 |
| (8) | 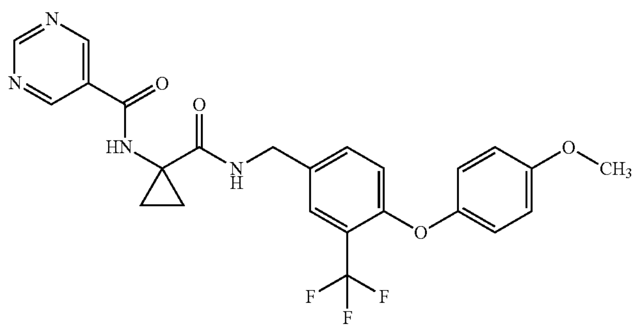 [SMILES: COc1ccc(Oc2ccc(CNC(=O)C3(NC(=O)c4cncnc4)CC3)cc2C(F)(F)F)cc1] | 8b) | analogously to 7c) | [M + H]+ = 487 |
| (9) | 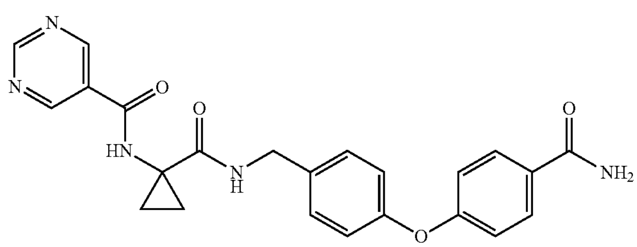 [SMILES: NC(=O)c1ccc(Oc2ccc(CNC(=O)C3(NC(=O)c4cncnc4)CC3)cc2)cc1] | 9b) | analogously to 7c) | [M + H]+ = 432 |
| (10) | 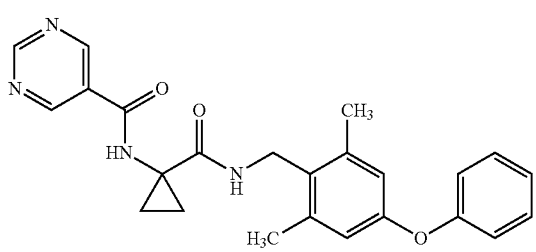 [SMILES: Cc1cc(Oc2ccccc2)cc(C)c1CNC(=O)C1(NC(=O)c2cncnc2)CC1] | 10b) | analogously to 7c) | [M + H]+ = 417 |
| (11) | 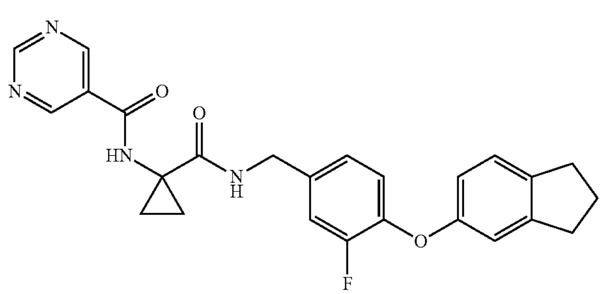 [SMILES: O=C(NC1(C(=O)NCc2ccc(Oc3ccc4c(c3)CCC4)c(F)c2)CC1)c1cncnc1] | 11b) | analogously to 7c) | [M + H]+ = 447 |

-continued

| No. | Structure | Educt (benzylamine) | Method of manufacture | LCMS |
|---|---|---|---|---|
| (12) | 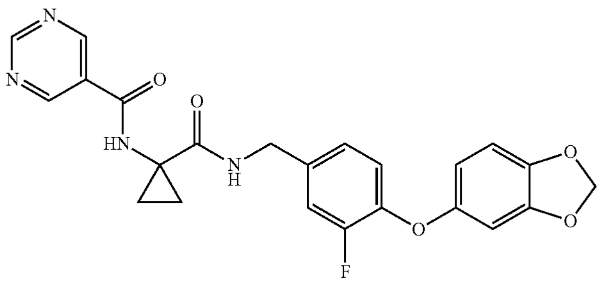 [SMILES: O=C(NC1(C(=O)NCc2ccc(Oc3ccc4c(c3)OCO4)c(F)c2)CC1)c1cncnc1] | 12b) | analogously to 7c) | [M + H]+ = 451 |
| (13) | 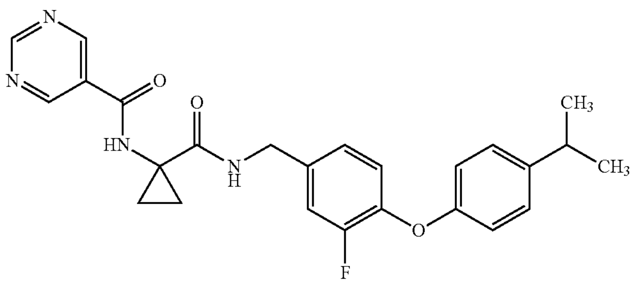 [SMILES: CC(C)c1ccc(Oc2ccc(CNC(=O)C3(NC(=O)c4cncnc4)CC3)cc2F)cc1] | 13b) | analogously to 7c) | [M + H]+ = 449 |
| (14) | 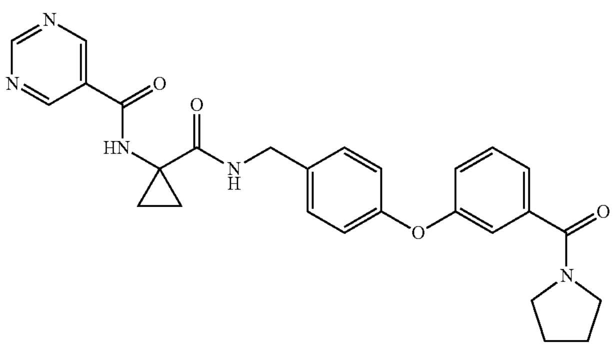 [SMILES: O=C(NC1(C(=O)NCc2ccc(Oc3cccc(C(=O)N4CCCC4)c3)cc2)CC1)c1cncnc1] | 14c) | analogously to 7c) | [M + H]+ = 486 |
| (15) | 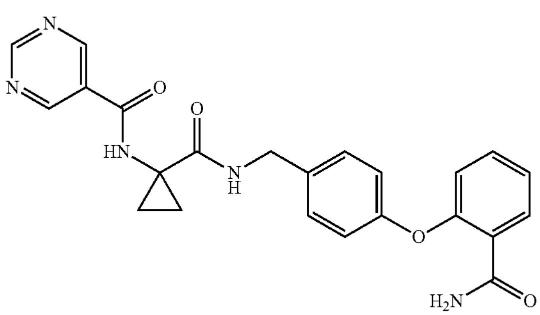 [SMILES: NC(=O)c1ccccc1Oc1ccc(CNC(=O)C2(NC(=O)c3cncnc3)CC2)cc1] | 15c) | analogously to 7c) | [M + H]+ = 432 |
| (16) | 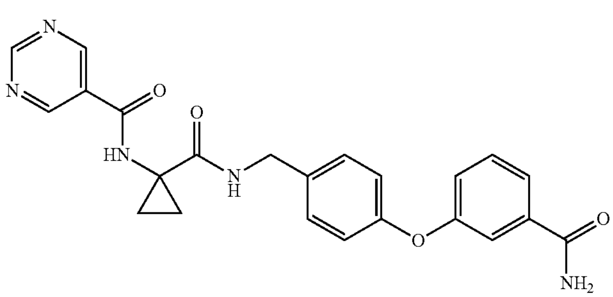 [SMILES: NC(=O)c1cccc(Oc2ccc(CNC(=O)C3(NC(=O)c4cncnc4)CC3)cc2)c1] | 16c) | analogously to 7c) | [M + H]+ = 432 |

-continued

| No. | Structure | Edruct (benzylamine) | Method of manufacture | LCMS |
|---|---|---|---|---|
| (17) | 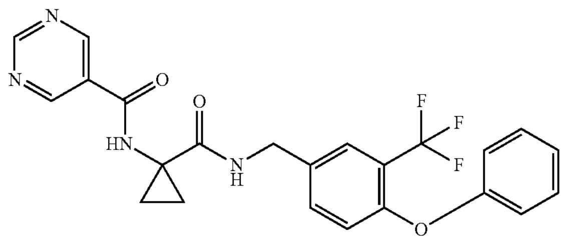 [SMILES: O=C(NC1(C(=O)NCc2ccc(Oc3ccccc3)c(C(F)(F)F)c2)CC1)c1cncnc1] | 17b) | analogously to 7c) | [M + H]+ = 457 |
| (18) | 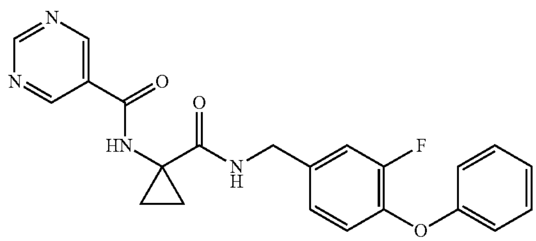 [SMILES: O=C(NC1(C(=O)NCc2ccc(Oc3ccccc3)c(F)c2)CC1)c1cncnc1] | 18b) | analogously to 7c) | [M + H]+ = 407 |
| (19) | 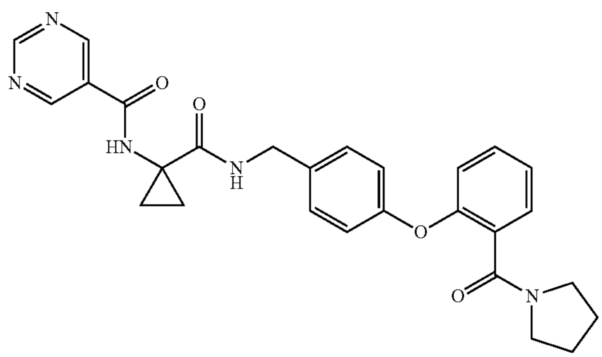 [SMILES: O=C(NC1(C(=O)NCc2ccc(Oc3ccccc3C(=O)N3CCCC3)cc2)CC1)c1cncnc1] | 19c) | analogously to 7c) | [M + H]+ = 486 |
| (20) | 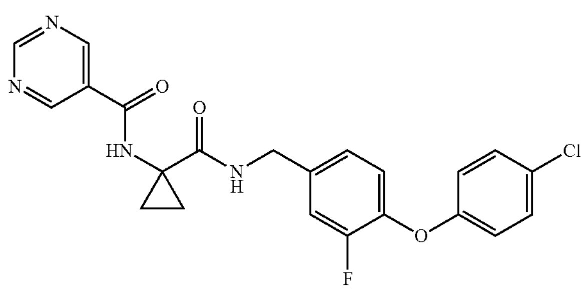 [SMILES: O=C(NC1(C(=O)NCc2ccc(Oc3ccc(Cl)cc3)c(F)c2)CC1)c1cncnc1] | 20b) | analogously to 7c) | [M + H]+ = 441/443 |
| (21) | 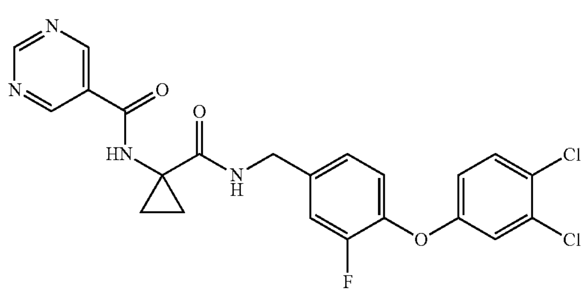 [SMILES: O=C(NC1(C(=O)NCc2ccc(Oc3ccc(Cl)c(Cl)c3)c(F)c2)CC1)c1cncnc1] | 21b) | analogously to 7c) | [M + H]+ = 475/477/479 |

-continued

| No. | Structure | Educt (benzylamine) | Method of manufacture | LCMS |
|---|---|---|---|---|
| (22) | 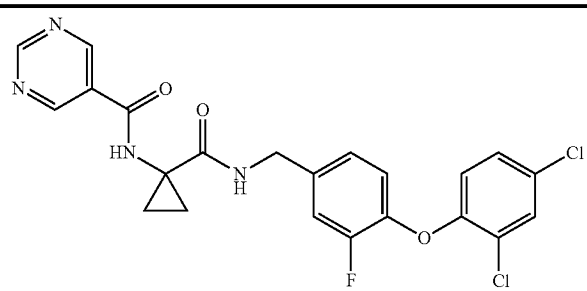 | 22b) | analogously to 7c) | [M + H]+ = 475/477/479 |
| (23) | 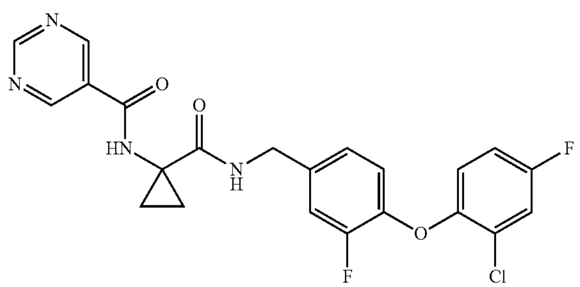 [SMILES: O=C(NC1(C(=O)NCc2ccc(Oc3ccc(F)cc3Cl)c(F)c2)CC1)c1cncnc1] | 23b) | analogously to 7c) | [M + H]+ = 459/461 |
| (24) | 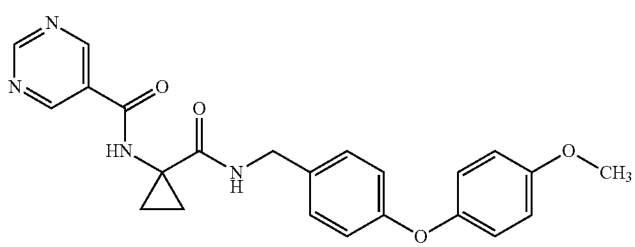 [SMILES: COc1ccc(Oc2ccc(CNC(=O)C3(NC(=O)c4cncnc4)CC3)cc2)cc1] | commercially obtainable | analogously to 7c) | [M + H]+ = 419 |
| (25) | 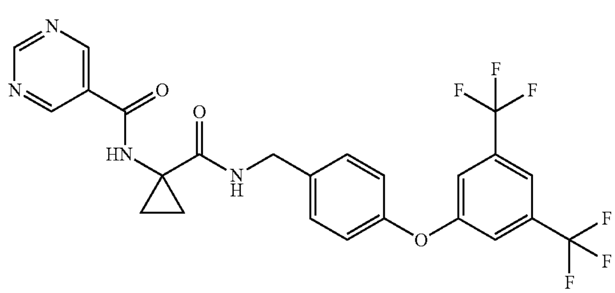 [SMILES: O=C(NC1(C(=O)NCc2ccc(Oc3cc(C(F)(F)F)cc(C(F)(F)F)c3)cc2)CC1)c1cncnc1] | commercially obtainable | analogously to 7c) | [M + H]+ = 525 |
| (26) | 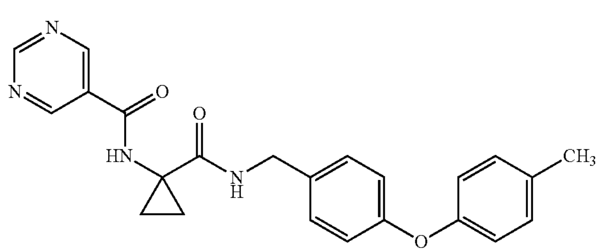 [SMILES: Cc1ccc(Oc2ccc(CNC(=O)C3(NC(=O)c4cncnc4)CC3)cc2)cc1] | commercially obtainable | analogously to 7c) | [M + H]+ = 403 |

-continued

| No. | Structure | Educt (benzylamine) | Method of manufacture | LCMS |
|---|---|---|---|---|
| (27) | 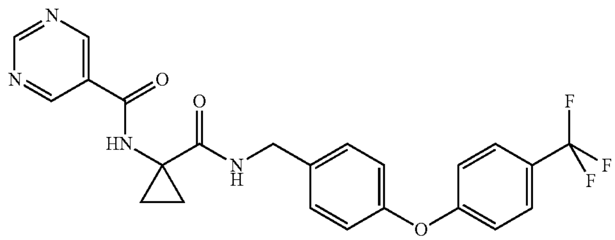 [SMILES: O=C(NC1(C(=O)NCc2ccc(Oc3ccc(C(F)(F)F)cc3)cc2)CC1)c1cncnc1] | commercially obtainable | analogously to 7c) | [M + H]+ = 457 |
| (28) | 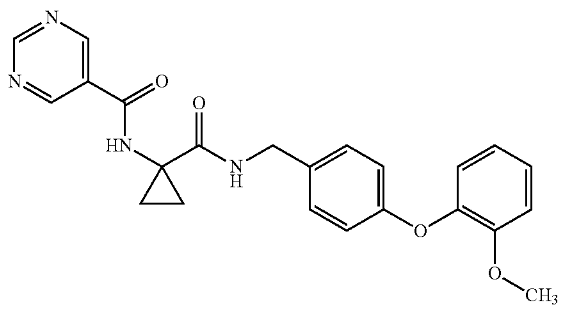 [SMILES: COc1ccccc1Oc1ccc(CNC(=O)C2(NC(=O)c3cncnc3)CC2)cc1] | commercially obtainable | analogously to 7c) | [M + H]+ = 419 |
| (29) | 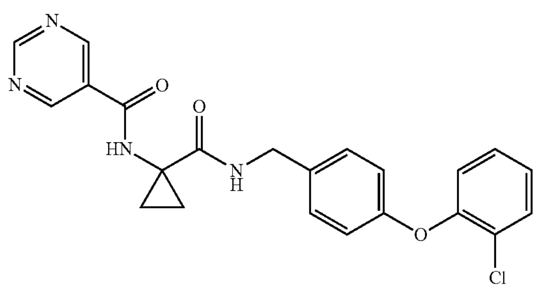 [SMILES: O=C(NC1(C(=O)NCc2ccc(Oc3ccccc3Cl)cc2)CC1)c1cncnc1] | commercially obtainable | analogously to 7c) | [M + H]+ = 423/425 |
| (30) | 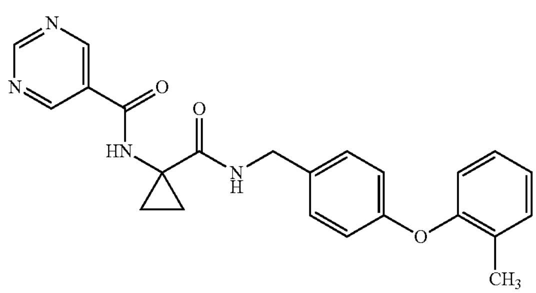 [SMILES: Cc1ccccc1Oc1ccc(CNC(=O)C2(NC(=O)c3cncnc3)CC2)cc1] | commercially obtainable | analogously to 7c) | [M + H]+ = 403 |
| (31) | 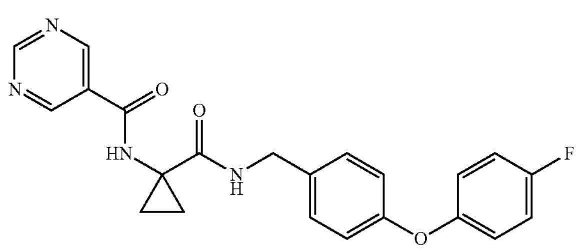 [SMILES: O=C(NC1(C(=O)NCc2ccc(Oc3ccc(F)cc3)cc2)CC1)c1cncnc1] | commercially obtainable | analogously to 7c) | [M + H]+ = 407 |

-continued

| No. | Structure | Educt (benzylamine) | Method of manufacture | LCMS |
|---|---|---|---|---|
| (32) | 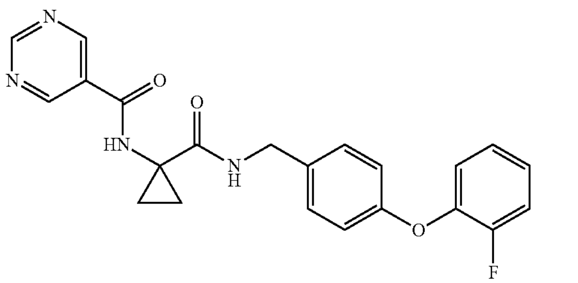 [SMILES: O=C(NC1(C(=O)NCc2ccc(Oc3ccccc3F)cc2)CC1)c1cncnc1] | commercially obtainable | analogously to 7c) | [M + H]+ = 407 |
| (33) | 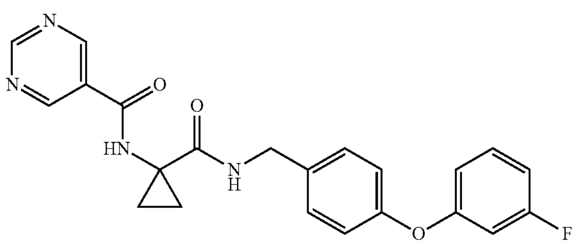 [SMILES: O=C(NC1(C(=O)NCc2ccc(Oc3cccc(F)c3)cc2)CC1)c1cncnc1] | commercially obtainable | analogously to 7c) | [M + H]+ = 407 |
| (34) | 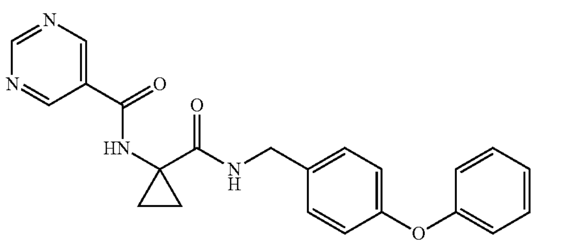 [SMILES: O=C(NC1(C(=O)NCc2ccc(Oc3ccccc3)cc2)CC1)c1cncnc1] | commercially obtainable | analogously to 7c) | [M − H]− = 387 |
| (35) | 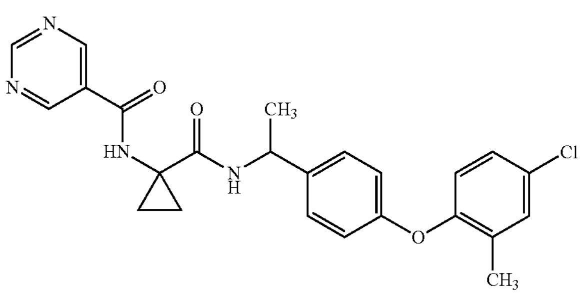 | commercially obtainable | analogously to 7a, b, c) | [M + H]+ = 451 |
| (36) | 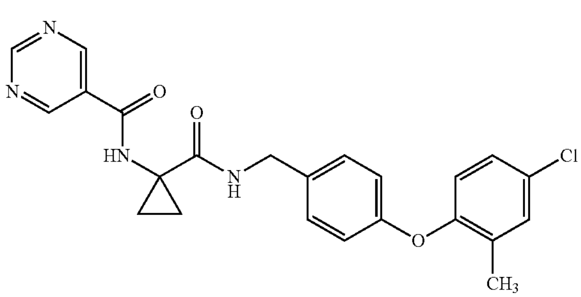 [SMILES: Cc1cc(Cl)ccc1Oc1ccc(CNC(=O)C2(NC(=O)c3cncnc3)CC2)cc1] | commercially obtainable | analogously to 7a, b, c) | [M + H]+ = 437 |

-continued

| No. | Structure | Educt (benzylamine) | Method of manufacture | LCMS |
|---|---|---|---|---|
| (37) | 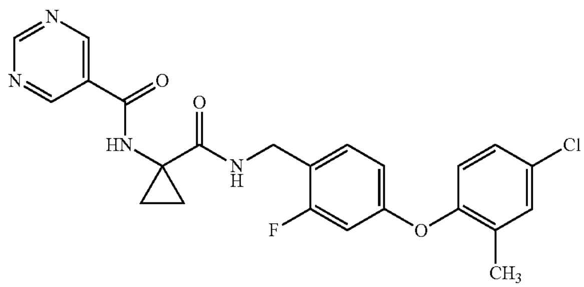 | commercially obtainable | analogously to 7a, b, c) | [M + H]+ = 455/457 |
| (38) | 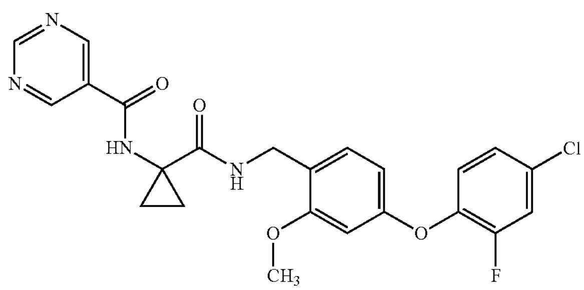 [SMILES: COc1cc(Oc2ccc(Cl)cc2F)ccc1CNC(=O)C1(NC(=O)c2cncnc2)CC1] | commercially obtainable | analogously to 7a, b, c) | [M + H]+ = 471/473 |
| (39) | 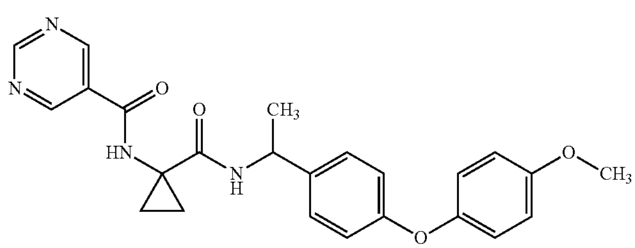 [SMILES: COc1ccc(Oc2ccc(C(C)NC(=O)C3(NC(=O)c4cncnc4)CC3)cc2)cc1] | 39b) | analogously to 7c) | [M + H]+ = 433 |
| (40) | 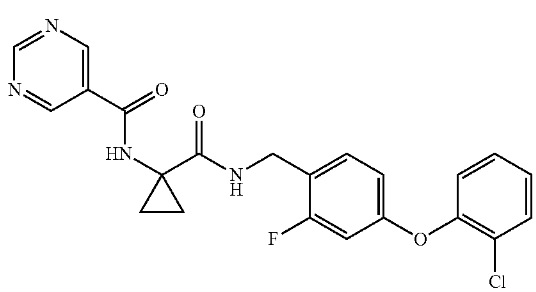 [SMILES: O=C(NC1(C(=O)NCc2ccc(Oc3ccccc3Cl)cc2F)CC1)c1cncnc1] | 40b) | analogously to 7c) | [M + H]+ = 441/443 |
| (41) | 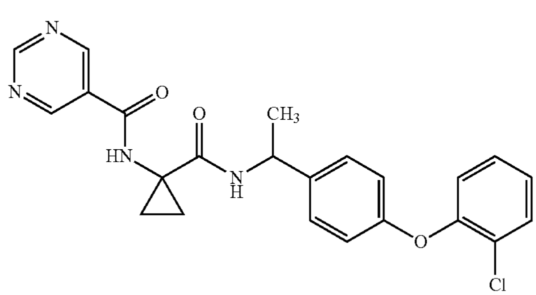 [SMILES: CC(NC(=O)C1(NC(=O)c2cncnc2)CC1)c1ccc(Oc2ccccc2Cl)cc1] | 41b) | analogously to 7c) | [M + H]+ = 437/439 |

-continued

| No. | Structure | Educt (benzylamine) | Method of manufacture | LCMS |
|---|---|---|---|---|
| (42) | 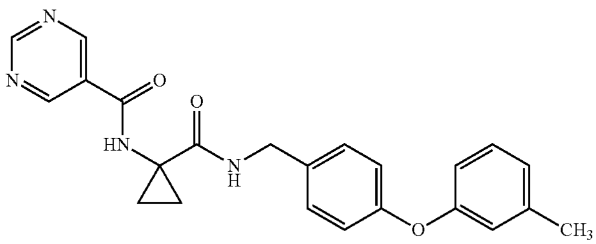 [SMILES: Cc1cccc(Oc2ccc(CNC(=O)C3(NC(=O)c4cncnc4)CC3)cc2)c1] | commercially obtainable | analogously to 7c) | [M + H]+ = 403 |
| (43) | 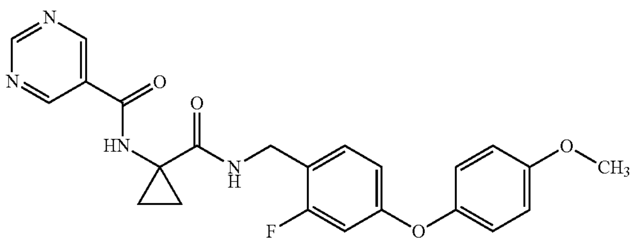 [SMILES: COc1ccc(Oc2ccc(CNC(=O)C3(NC(=O)c4cncnc4)CC3)c(F)c2)cc1] | 43b) | analogously to 7c) | [M + H]+ = 437 |
| (44) | 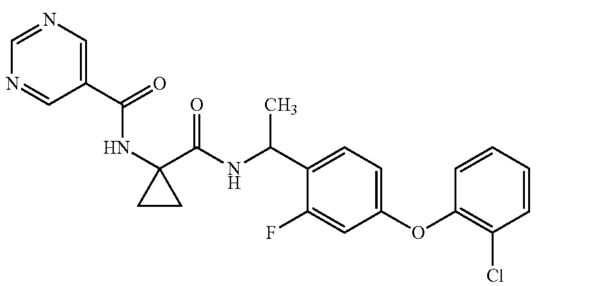 [SMILES: CC(NC(=O)C1(NC(=O)c2cncnc2)CC1)c1ccc(Oc2ccccc2Cl)cc1F] | 44b) | analogously to 7c) | [M + H]+ = 455/457 |
| (45) | 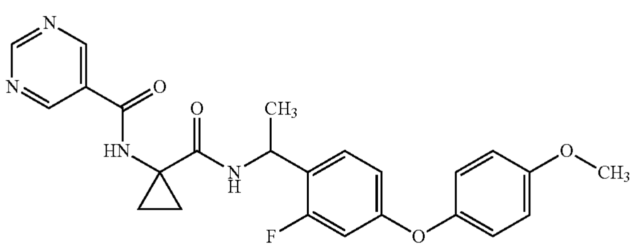 [SMILES: COc1ccc(Oc2ccc(C(C)NC(=O)C3(NC(=O)c4cncnc4)CC3)c(F)c2)cc1] | 45b) | analogously to 7c) | [M + H]+ = 451 |
| (46) | 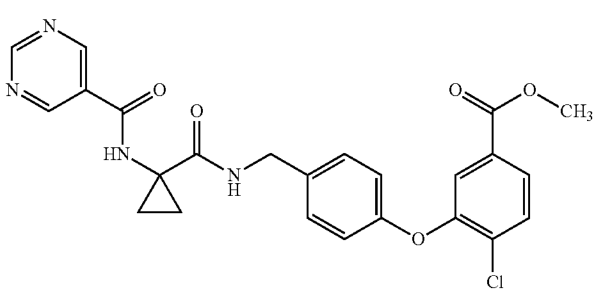 [SMILES: COC(=O)c1ccc(Cl)c(Oc2ccc(CNC(=O)C3(NC(=O)c4cncnc4)CC3)cc2)c1] | 46b) | analogously to 1e) | [M + H]+ = 481/483 |

-continued

| No. | Structure | Educt (benzylamine) | Method of manufacture | LCMS |
|---|---|---|---|---|
| (47) | 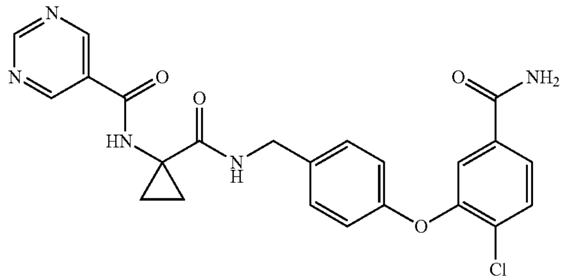 [SMILES: NC(=O)c1ccc(Cl)c(Oc2ccc(CNC(=O)C3(NC(=O)c4cncnc4)CC3)cc2)c1] | 47b) | analogously to 1e) | [M + H]+ = 466/468 |
| (48) | 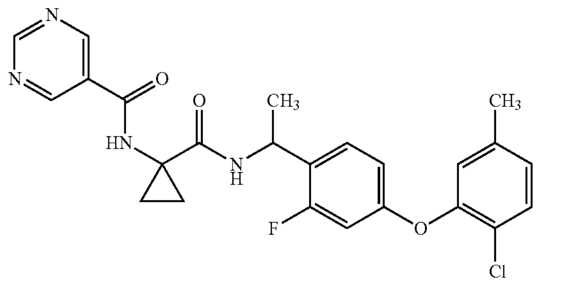 [SMILES: Cc1ccc(Cl)c(Oc2ccc(C(C)NC(=O)C3(NC(=O)c4cncnc4)CC3)c(F)c2)c1] | 48b) | analogously to 1e) | [M + H]+ = 467/469 |
| (49) | 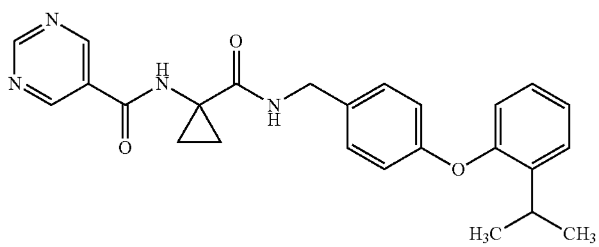 [SMILES: CC(C)c1ccccc1Oc1ccc(CNC(=O)C2(NC(=O)c3cncnc3)CC2)cc1] | 49a) | analogously to 7c) | [M + H]+ = 431 |
| (50) | 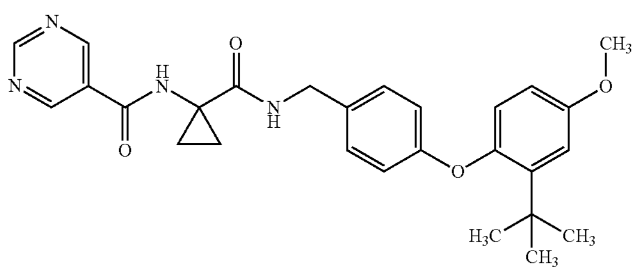 [SMILES: COc1ccc(Oc2ccc(CNC(=O)C3(NC(=O)c4cncnc4)CC3)cc2)c(C(C)(C)C)c1] | 50a) | analogously to 7c) | [M + H]+ = 475 |
| (51) | 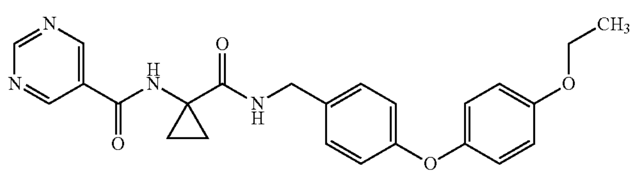 [SMILES: CCOc1ccc(Oc2ccc(CNC(=O)C3(NC(=O)c4cncnc4)CC3)cc2)cc1] | 51a) | analogously to 7c) | [M + H]+ = 433 |
| (52) | 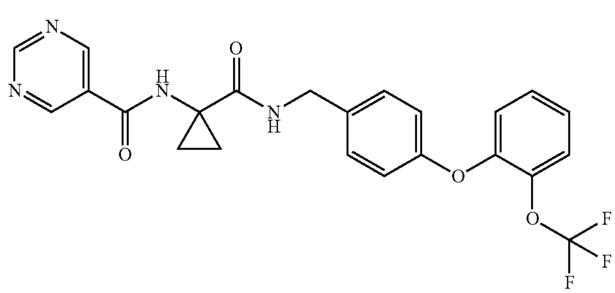 [SMILES: O=C(NC1(C(=O)NCc2ccc(Oc3ccccc3OC(F)(F)F)cc2)CC1)c1cncnc1] | 52a) | analogously to 7c) | [M + H]+ = 473 |

-continued
| No. | Structure | Educt (benzylamine) | Method of manufacture | LCMS |
|---|---|---|---|---|
| (53) | 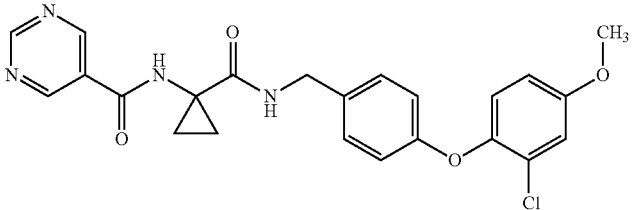 | 53a) | analogously to 7c) | [M + H]+ = 453/455 |
| (54) | 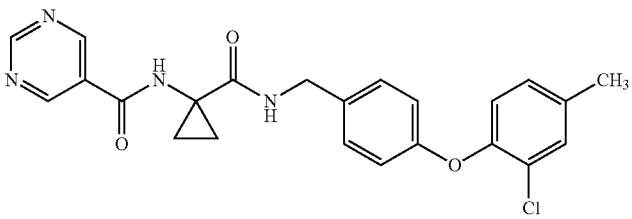 [SMILES: Cc1ccc(Oc2ccc(CNC(=O)C3(NC(=O)c4cncnc4)CC3)cc2)c(Cl)c1] | 54a) | analogously to 7c) | [M + H]+ = 437/439 |
| (55) | 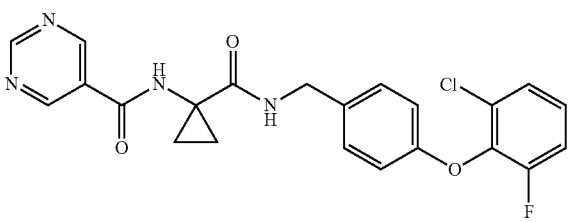 [SMILES: O=C(NC1(C(=O)NCc2ccc(Oc3c(F)cccc3Cl)cc2)CC1)c1cncnc1] | 55a) | analogously to 7c) | [M + H]+ = 441/443 |
| (56) | 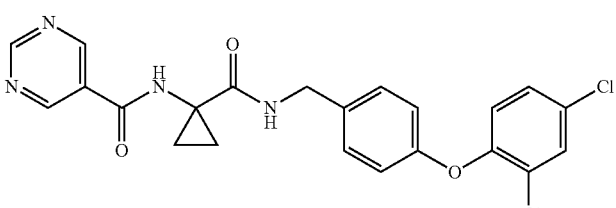 | 56a) | analogously to 7c) | [M + H]+ = 457/459/461 |
| (57) | 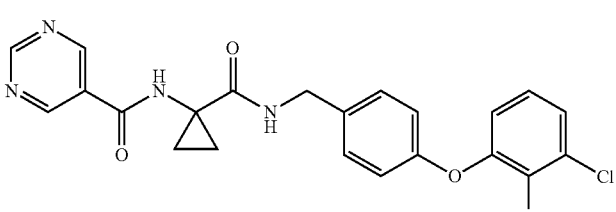 | 57a) | analogously to 7c) | [M + H]+ = 457/459/461 |
| (58) | 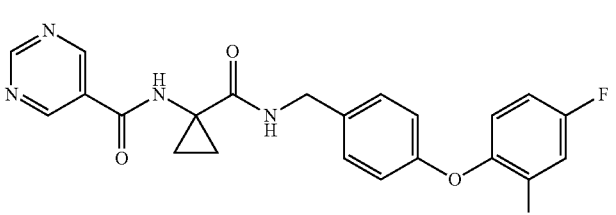 | 58a) | analogously to 7c) | [M + H]+ = 441/443 |

-continued

| No. | Structure | Educt (benzylamine) | Method of manufacture | LCMS |
|---|---|---|---|---|
| (59) | 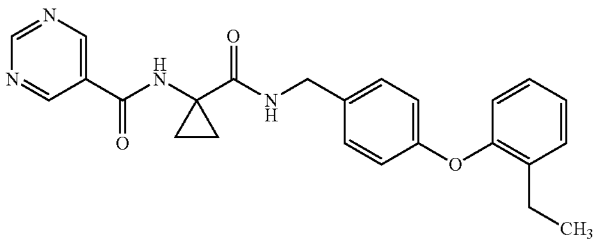 [SMILES: CCc1ccccc1Oc1ccc(CNC(=O)C2(NC(=O)c3cncnc3)CC2)cc1] | 59a) | analogously to 7c) | [M + H]+ = 417 |
| (60) | 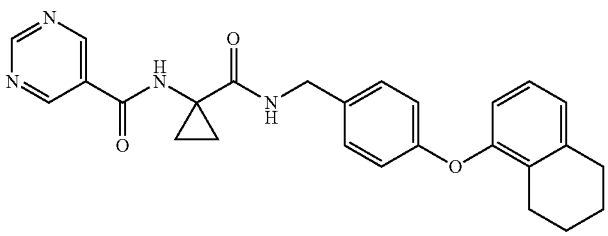 [SMILES: O=C(NC1(C(=O)NCc2ccc(Oc3cccc4c3CCCC4)cc2)CC1)c1cncnc1] | 60a) | analogously to 7c) | [M + H]+ = 443 |
| (61) | 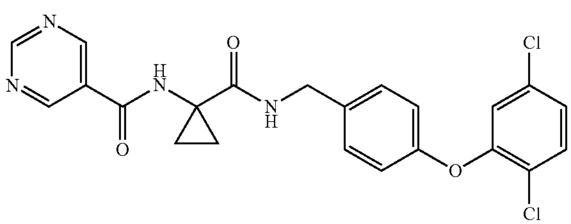 [SMILES: O=C(NC1(C(=O)NCc2ccc(Oc3cc(Cl)ccc3Cl)cc2)CC1)c1cncnc1] | 61a) | analogously to 7c) | [M + H]+ = 457/459/461 |
| (62) | 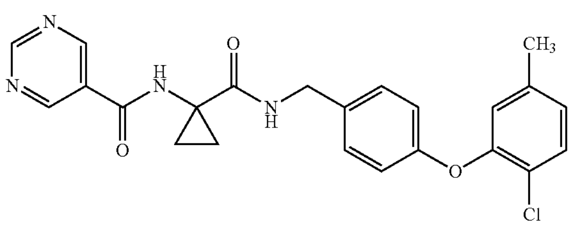 | 62a) | analogously to 7c) | [M + H]+ = 437/439 |
| (63) | 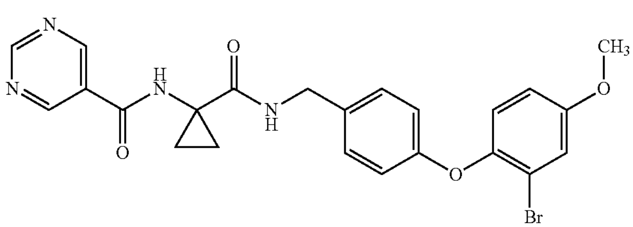 [SMILES: COc1ccc(Oc2ccc(CNC(=O)C3(NC(=O)c4cncnc4)CC3)cc2)c(Br)c1] | 63a) | analogously to 7c) | [M + H]+ = 497/499 |
| (64) | 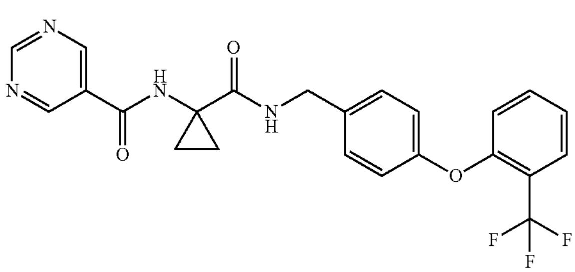 [SMILES: O=C(NC1(C(=O)NCc2ccc(Oc3ccccc3C(F)(F)F)cc2)CC1)c1cncnc1] | 64a) | analogously to 7c) | [M + H]+ = 457 |

-continued

| No. | Structure | Educt (benzylamine) | Method of manufacture | LCMS |
|---|---|---|---|---|
| (65) | 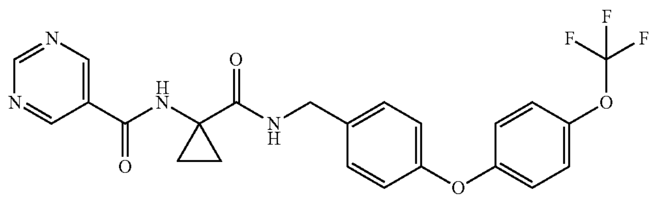 [SMILES: O=C(NC1(C(=O)NCc2ccc(Oc3ccc(OC(F)(F)F)cc3)cc2)CC1)c1cncnc1] | 65a) | analogously to 7c) | [M + H]+ = 473 |
| (66) | 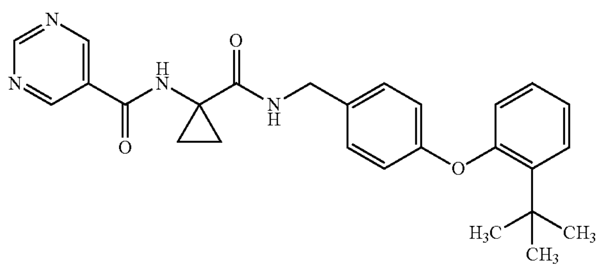 [SMILES: CC(C)(C)c1ccccc1Oc1ccc(CNC(=O)C2(NC(=O)c3cncnc3)CC2)cc1] | 66a) | analogously to 7c) | [M + H]+ = 445 |
| (67) | 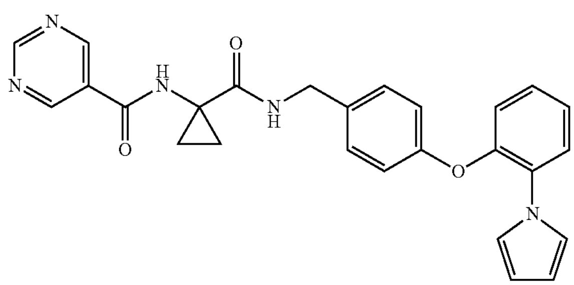 [SMILES: O=C(NC1(C(=O)NCc2ccc(Oc3ccccc3-n3cccc3)cc2)CC1)c1cncnc1] | 67a) | analogously to 7c) | [M + H]+ = 454 |
| (68) | 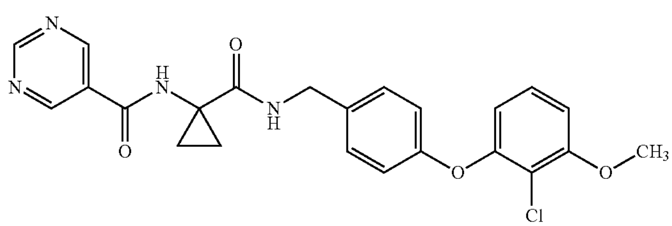 [SMILES: COc1cccc(Oc2ccc(CNC(=O)C3(NC(=O)c4cncnc4)CC3)cc2)c1Cl] | 68a) | analogously to 7c) | [M + H]+ = 453/455 |
| (69) | 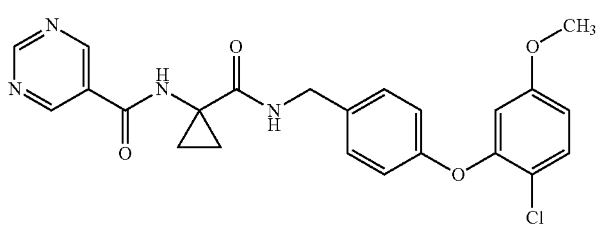 [SMILES: COc1ccc(Cl)c(Oc2ccc(CNC(=O)C3(NC(=O)c4cncnc4)CC3)cc2)c1] | 69a) | analogously to 7c) | [M + H]+ = 453/455 |
| (70) | 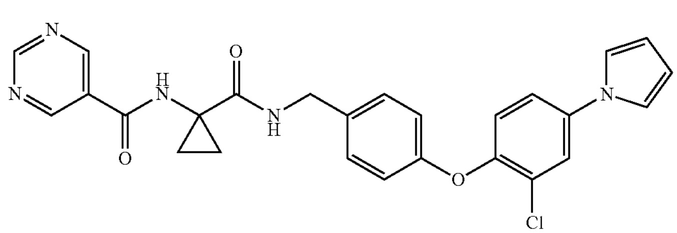 [SMILES: O=C(NC1(C(=O)NCc2ccc(Oc3ccc(-n4cccc4)cc3Cl)cc2)CC1)c1cncnc1] | 70a) | analogously to 7c) | [M + H]+ = 488/490 |

-continued

| No. | Structure | Educt (benzylamine) | Method of manufacture | LCMS |
|---|---|---|---|---|
| (71) | 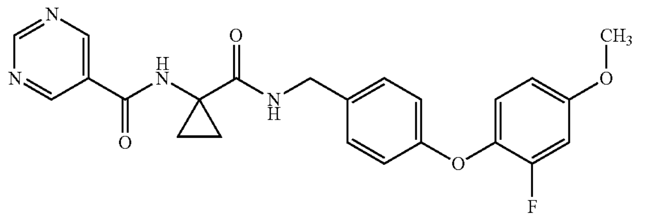 | 71a) | analogously to 7c) | [M + H]+ = 437/439 |
| (72) | 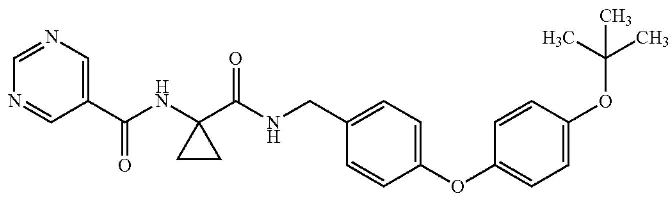 [SMILES: CC(C)(C)Oc1ccc(Oc2ccc(CNC(=O)C3(NC(=O)c4cncnc4)CC3)cc2)cc1] | 72a) | analogously to 7c) | [M + H]+ = 461 |
| (73) | 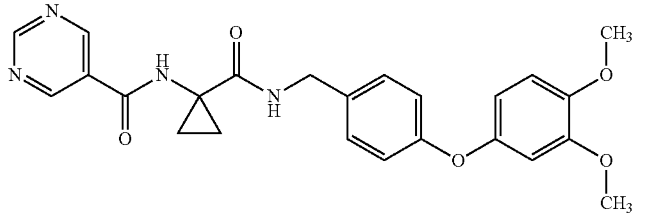 [SMILES: COc1ccc(Oc2ccc(CNC(=O)C3(NC(=O)c4cncnc4)CC3)cc2)cc1OC] | 73a) | analogously to 7c) | [M + H]+ = 449 |
| (74) | 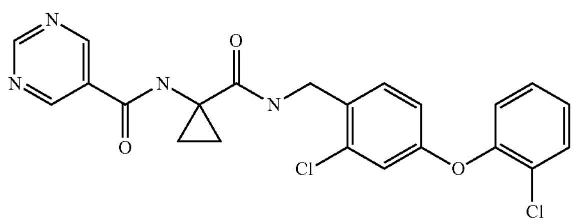 [SMILES: O=C(NC1(C(=O)NCc2ccc(Oc3ccccc3Cl)cc2Cl)CC1)c1cncnc1] | 74b) | 74c) | [M + H]+ = 457/9/61 |
| (75) | 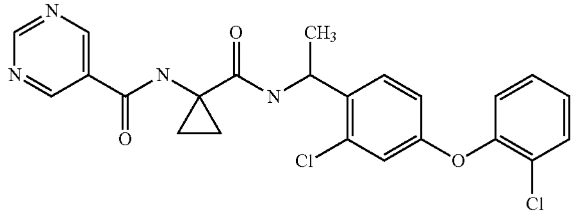 [SMILES: CC(NC(=O)C1(NC(=O)c2cncnc2)CC1)c1ccc(Oc2ccccc2Cl)cc1Cl] | 75c) | analogously to 74c) | [M + H]+ = 471/3/5 |
| (76) | 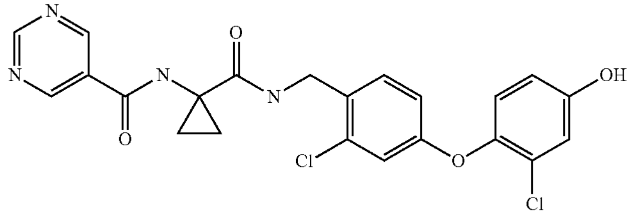 [SMILES: O=C(NC1(C(=O)NCc2ccc(Oc3ccc(O)cc3Cl)cc2Cl)CC1)c1cncnc1] | 76c) | 76d) | [M + H]+ = 473/5/7 |
| (77) | 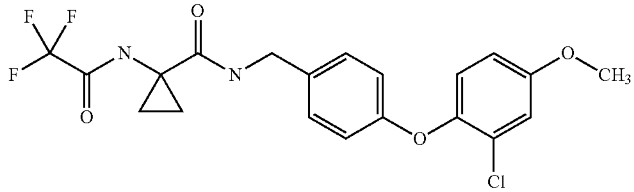 [SMILES: COc1ccc(Oc2ccc(CNC(=O)C3(NC(=O)C(F)(F)F)CC3)cc2)c(Cl)c1] | 53a) | 77a) | [M − H]− = 441/443 |

-continued

| No. | Structure | Educt (benzylamine) | Method of manufacture | LCMS |
|---|---|---|---|---|
| (78) | 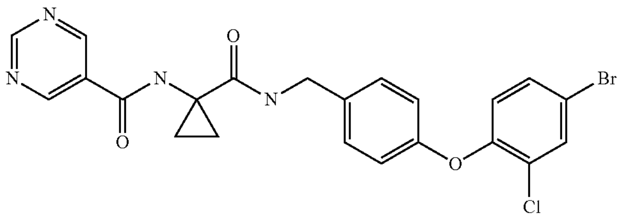 [SMILES: O=C(NC1(C(=O)NCc2ccc(Oc3ccc(Br)cc3Cl)cc2)CC1)c1cncnc1] | 78c) | 78d) | [M − H]− = 499/501/3 |
| (79) | 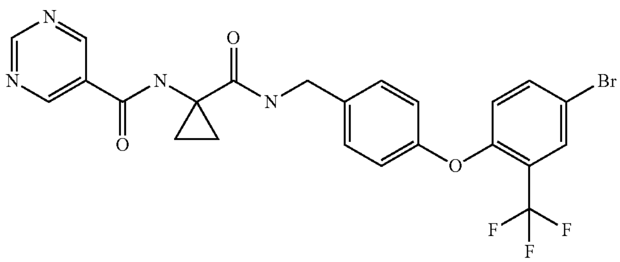 [SMILES: O=C(NC1(C(=O)NCc2ccc(Oc3ccc(Br)cc3C(F)(F)F)cc2)CC1)c1cncnc1] | 79c) | analogously to 78d) | [M + H]+ = 535/7 |
| (80) | 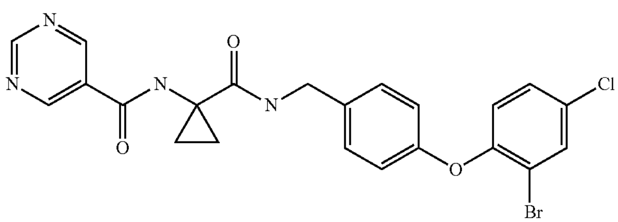 [SMILES: O=C(NC1(C(=O)NCc2ccc(Oc3ccc(Cl)cc3Br)cc2)CC1)c1cncnc1] | 80c) | analogously to 78d) | [M + H]+ = 501/3/5 |
| (81) | 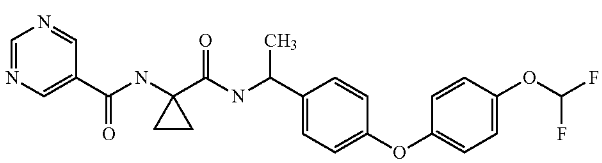 [SMILES: CC(NC(=O)C1(NC(=O)c2cncnc2)CC1)c1ccc(Oc2ccc(OC(F)F)cc2)cc1] | 81c) | 81d) | [M − H]− = 467 |
| (82) | 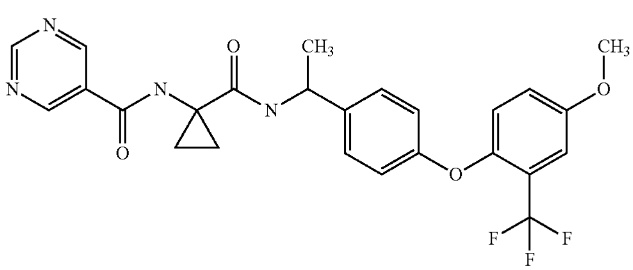 [SMILES: COc1ccc(Oc2ccc(C(C)NC(=O)C3(NC(=O)c4cncnc4)CC3)cc2)c(C(F)(F)F)c1] | 82f) | analogously to 76d) | [M + H]+ = 501 |
| (83) | 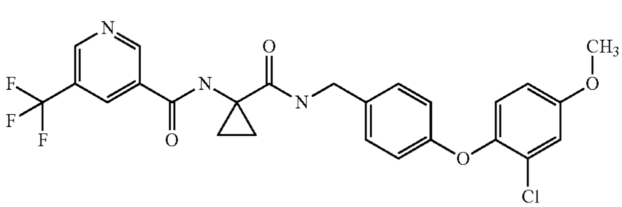 [SMILES: COc1ccc(Oc2ccc(CNC(=O)C3(NC(=O)c4cncc(C(F)(F)F)c4)CC3)cc2)c(Cl)c1] | 53a) | 83a) | [M + H]+ = 520 |

-continued
| No. | Structure | Educt (benzylamine) | Method of manufacture | LCMS |
|---|---|---|---|---|
| (84) | 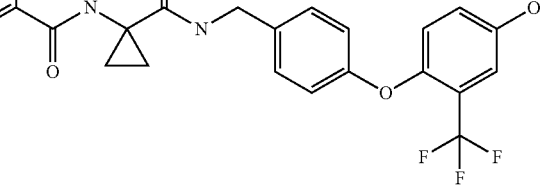 | 84a) | 84b) | [M + H]+ = 487 |
| (85) | 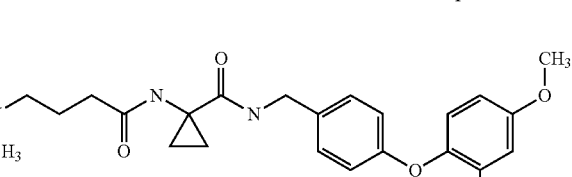 | 84a) | 85b) | [M + H]+ = 494 |
| (86) | 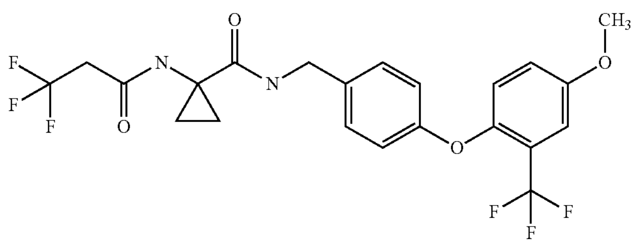 [SMILES: COc1ccc(Oc2ccc(CNC(=O)C3(NC(=O)CC(F)(F)F)CC3)cc2)c(C(F)(F)F)c1] | 84a) | analogously to 85b) | [M + H]+ = 491 |
| (87) | 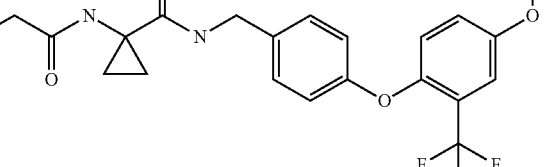 | 84a) | analogously to 85b) | [M + H]+ = 480 |
| (88) | 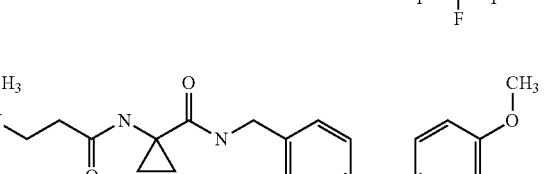 | 84a) | analogously to 85b) | [M + H]+ = 508 |
| (89) | 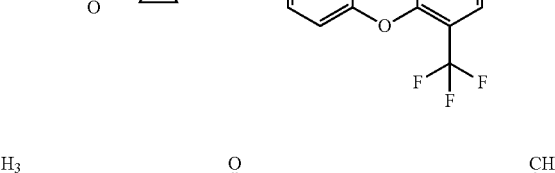 | 84a) | analogously to 85b) | [M + H]+ = 486 |

-continued
| No. | Structure | Educt (benzylamine) | Method of manufacture | LCMS |
|---|---|---|---|---|
| (90) | 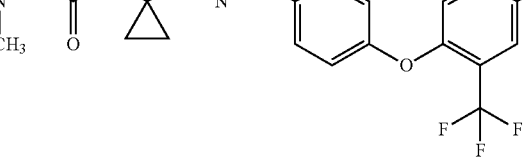 | 84a) | analogously to 85b) | [M + H]+ = 466 |
| (91) | 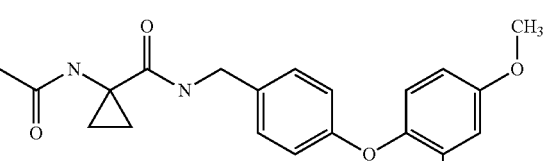 | 84a) | analogously to 85b) | [M + H]+ = 437 |
| (92) | 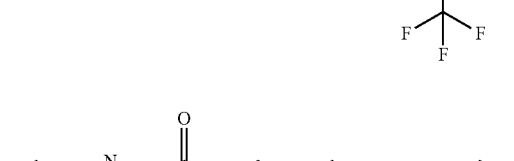 | 84a) | analogously to 85b) | [M + H]+ = 453 |
| (93) | 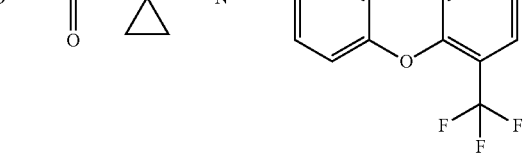 | 84a) | analogously to 85b) | [M + H]+ = 449 |
| (94) | 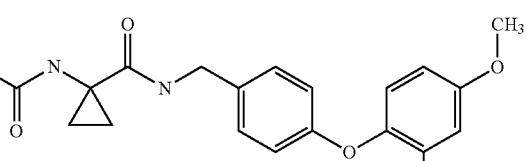 | 84a) | analogously to 85b) | [M + H]+ = 465 |
| (95) | 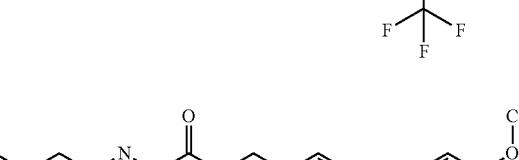 | 84a) | analogously to 85b) | [M + H]+ = 489 |

-continued

| No. | Structure | Educt (benzylamine) | Method of manufacture | LCMS |
|---|---|---|---|---|
| (96) | 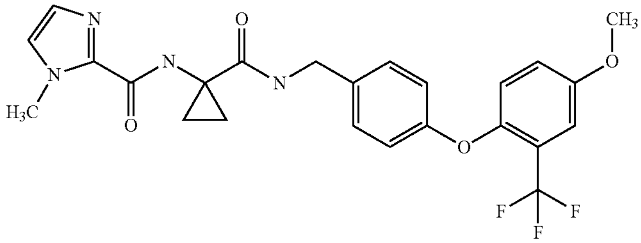 [SMILES: COc1ccc(Oc2ccc(CNC(=O)C3(NC(=O)c4nccn4C)CC3)cc2)c(C(F)(F)F)c1] | 84a) | analogously to 85b) | [M + H]+ = 489 |
| (97) | 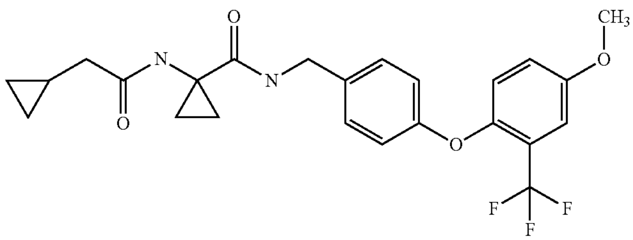 [SMILES: COc1ccc(Oc2ccc(CNC(=O)C3(NC(=O)CC4CC4)CC3)cc2)c(C(F)(F)F)c1] | 84a) | analogously to 85b) | [M + H]+ = 463 |
| (98) | 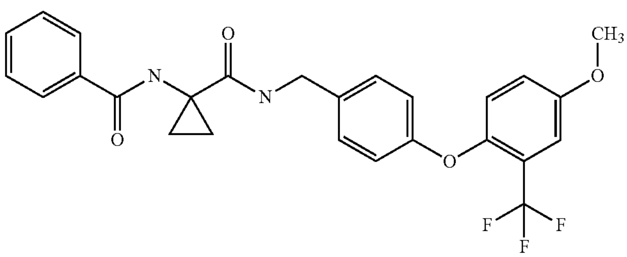 [SMILES: COc1ccc(Oc2ccc(CNC(=O)C3(NC(=O)c4ccccc4)CC3)cc2)c(C(F)(F)F)c1] | 84a) | analogously to 85b) | [M + H]+ = 485 |
| (99) | 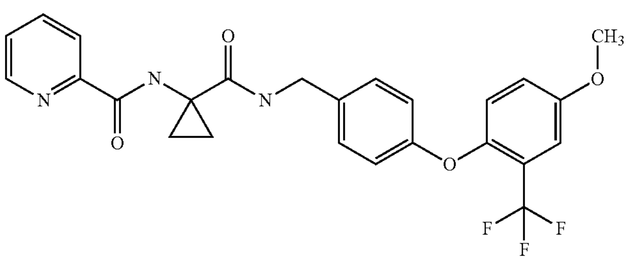 [SMILES: COc1ccc(Oc2ccc(CNC(=O)C3(NC(=O)c4ccccn4)CC3)cc2)c(C(F)(F)F)c1] | 84a) | analogously to 85b) | [M + H]+ = 486 |
| (100) | 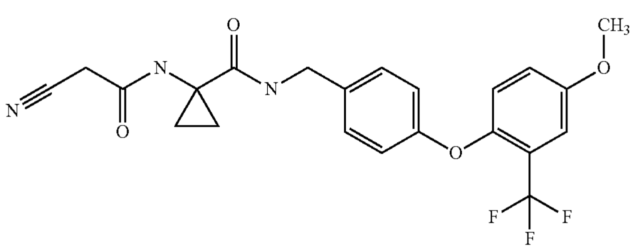 [SMILES: COc1ccc(Oc2ccc(CNC(=O)C3(NC(=O)CC#N)CC3)cc2)c(C(F)(F)F)c1] | 84a) | 100a) | [M + H]+ = 448 |
| (101) | 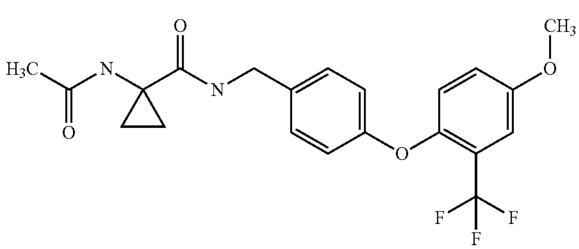 [SMILES: COc1ccc(Oc2ccc(CNC(=O)C3(NC(C)=O)CC3)cc2)c(C(F)(F)F)c1] | 84a) | analogously to 100a) | [M + H]+ = 423 |

-continued

| No. | Structure | Educt (benzylamine) | Method of manufacture | LCMS |
|---|---|---|---|---|
| (102) | 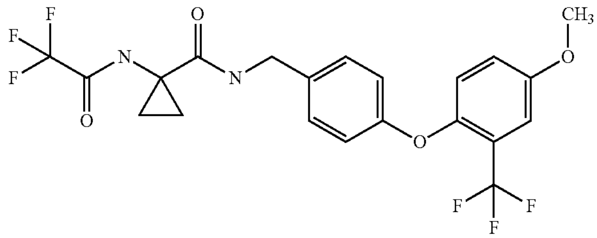 [SMILES: COc1ccc(Oc2ccc(CNC(=O)C3(NC(=O)C(F)(F)F)CC3)cc2)c(C(F)(F)F)c1] | 84a) | analogously to 100a) | [M + H]+ = 477 |
| (103) | 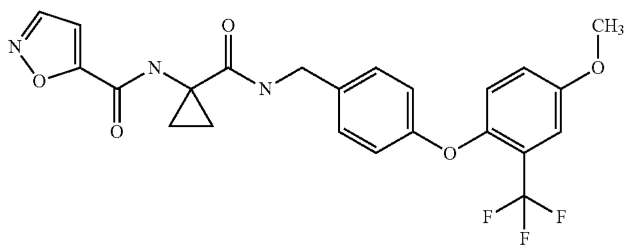 [SMILES: COc1ccc(Oc2ccc(CNC(=O)C3(NC(=O)c4ccno4)CC3)cc2)c(C(F)(F)F)c1] | 84a) | analogously to 100a) | [M + H]+ = 476 |
| (104) | 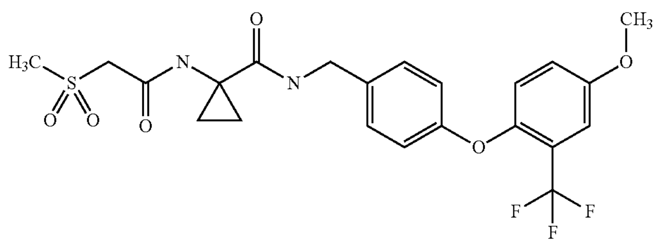 | 84a) | analogously to 78d) | [M + H]+ = 501 |
| (105) | 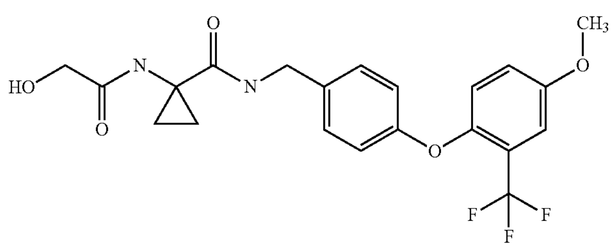 [SMILES: COc1ccc(Oc2ccc(CNC(=O)C3(NC(=O)CO)CC3)cc2)c(C(F)(F)F)c1] | 84a) | analogously to 78d) | [M + H]+ = 439 |
| (106) | 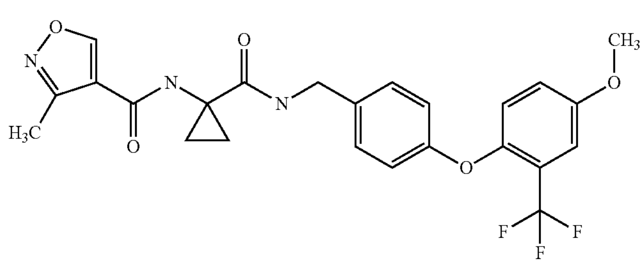 [SMILES: COc1ccc(Oc2ccc(CNC(=O)C3(NC(=O)c4conc4C)CC3)cc2)c(C(F)(F)F)c1] | 84a) | 106a) | [M + H]+ = 490 |
| (107) | 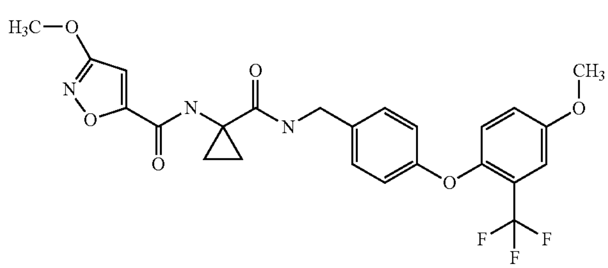 | 84a) | 107a), analogously to 106a) | [M + H]+ = 506 |

-continued

| No. | Structure | Educt (benzylamine) | Method of manufacture | LCMS |
|---|---|---|---|---|
| (108) | 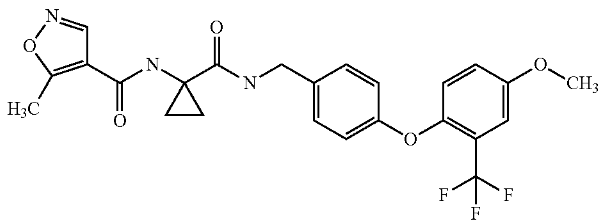 [SMILES: COc1ccc(Oc2ccc(CNC(=O)C3(NC(=O)c4cnoc4C)CC3)cc2)c(C(F)(F)F)c1] | 84a) | 108a), analogously to 106a) | [M + H]+ = 490 |
| (109) | 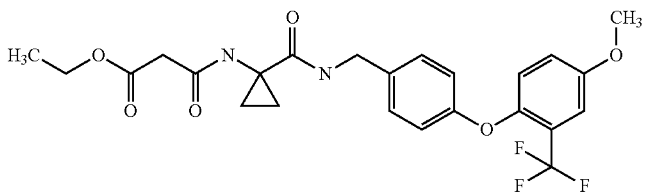 [SMILES: CCOC(=O)CC(=O)NC1(C(=O)NCc2ccc(Oc3ccc(OC)cc3C(F)(F)F)cc2)CC1] | 84a) | 109a) | [M + H]+ = 495 |
| (110) | 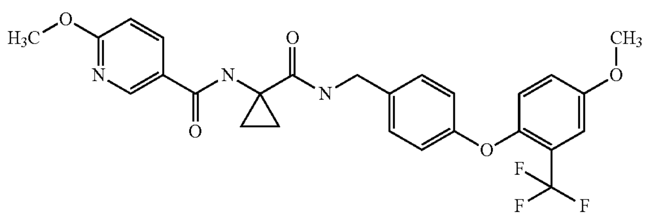 | 84a) | analogously to 109a) | [M + H]+ = 516 |
| (111) | 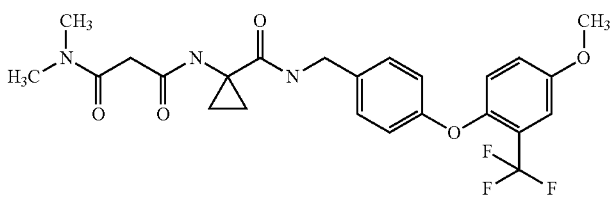 | 84a) | analogously to 109a) | [M + H]+ = 494 |
| (112) | 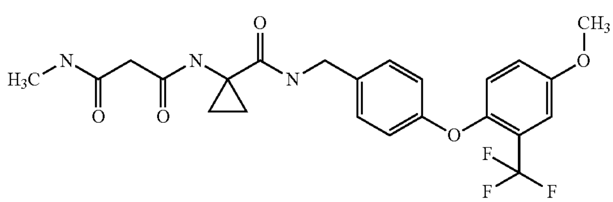 | 84a) | analogously to 109a) | [M + H]+ = 480 |
| (113) | 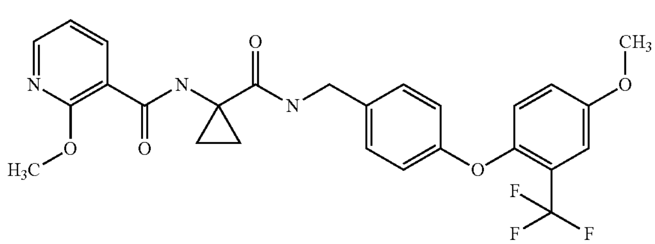 [SMILES: COc1ccc(Oc2ccc(CNC(=O)C3(NC(=O)c4cccnc4OC)CC3)cc2)c(C(F)(F)F)c1] | 84a) | 113a) | [M + H]+ = 516 |
| (114) | 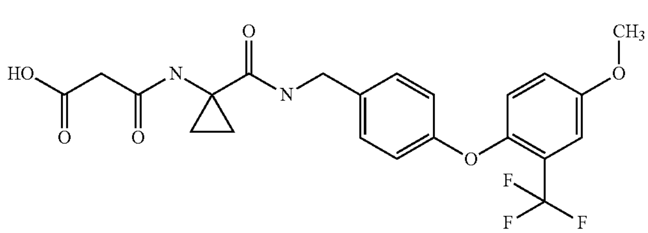 [SMILES: COc1ccc(Oc2ccc(CNC(=O)C3(NC(=O)CC(=O)O)CC3)cc2)c(C(F)(F)F)c1] | 84a) | 114a) | [M + H]+ = 467 |

-continued

| No. | Structure | Educt (benzylamine) | Method of manufacture | LCMS |
|---|---|---|---|---|
| (115) | 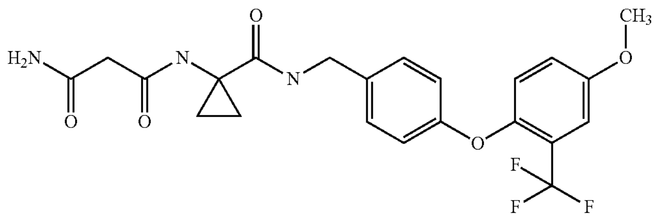 [SMILES: COc1ccc(Oc2ccc(CNC(=O)C3(NC(=O)CC(N)=O)CC3)cc2)c(C(F)(F)F)c1] | 84a) | analogously to 109a) | [M + H]+ = 466 |
| (116) | 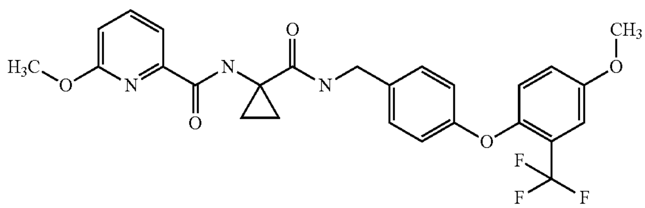 | 84a) | 116a), analogously to 109a) | [M + H]+ = 516 |
| (117) | 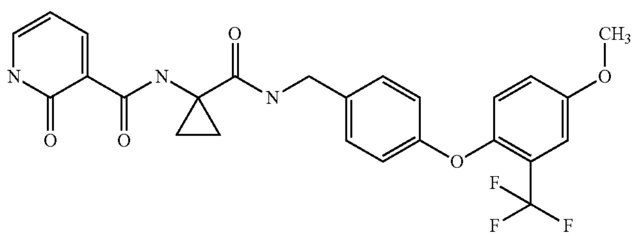 [SMILES: COc1ccc(Oc2ccc(CNC(=O)C3(NC(=O)c4ccc[nH]c4=O)CC3)cc2)c(C(F)(F)F)c1] | 84a) | analogously to 107a) | [M + H]+ = 502 |
| (118) | 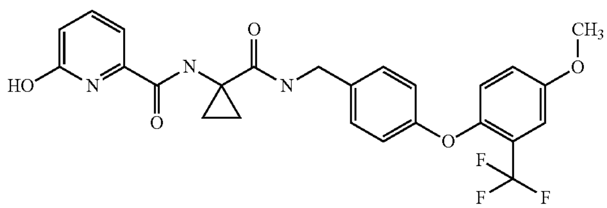 [SMILES: COc1ccc(Oc2ccc(CNC(=O)C3(NC(=O)c4cccc(O)n4)CC3)cc2)c(C(F)(F)F)c1] | 84a) | 118a) | [M + H]+ = 502 |
| (119) | 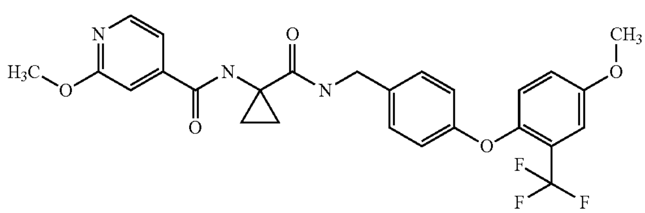 | 84a) | 119a), analogously to 118a) | [M + H]+ = 516 |
| (120) | 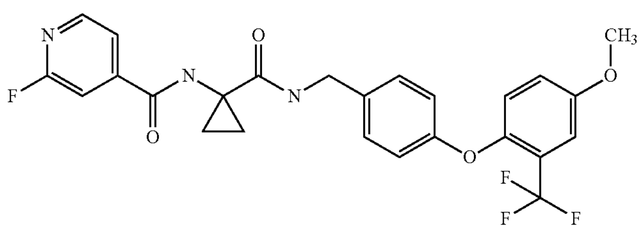 [SMILES: COc1ccc(Oc2ccc(CNC(=O)C3(NC(=O)c4ccnc(F)c4)CC3)cc2)c(C(F)(F)F)c1] | 84a) | 120a) | [M + H]+ = 504 |
| (121) | 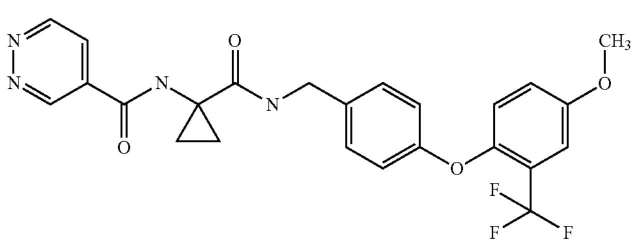 [SMILES: COc1ccc(Oc2ccc(CNC(=O)C3(NC(=O)c4ccnnc4)CC3)cc2)c(C(F)(F)F)c1] | 84a) | analogously to 120a) | [M + H]+ = 487 |

-continued

| No. | Structure | Educt (benzylamine) | Method of manufacture | LCMS |
|---|---|---|---|---|
| (122) | 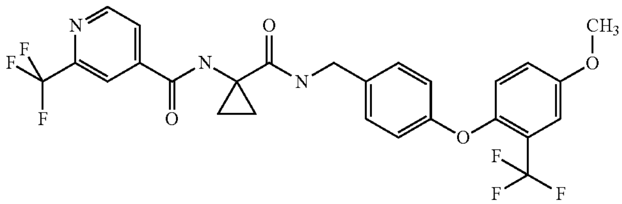 [SMILES: COc1ccc(Oc2ccc(CNC(=O)C3(NC(=O)c4ccnc(C(F)(F)F)c4)CC3)cc2)c(C(F)(F)F)c1] | 84a) | analogously to 120a) | [M + H]+ = 554 |
| (123) | 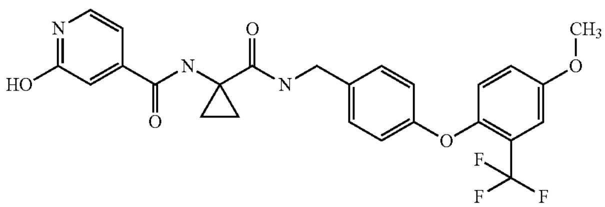 [SMILES: COc1ccc(Oc2ccc(CNC(=O)C3(NC(=O)c4ccnc(O)c4)CC3)cc2)c(C(F)(F)F)c1] | 84a) | analogously to 78d) | [M + H]+ = 502 |
| (124) | 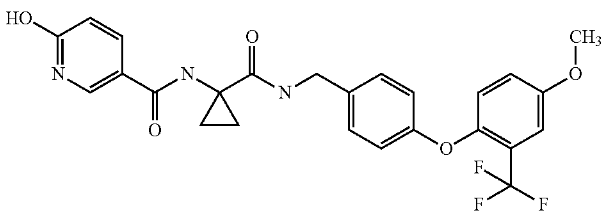 [SMILES: COc1ccc(Oc2ccc(CNC(=O)C3(NC(=O)c4ccc(O)nc4)CC3)cc2)c(C(F)(F)F)c1] | 84a) | analogously to 78d) | [M + H]+ = 502 |
| (125) | 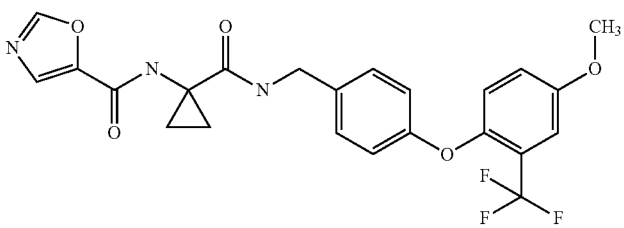 | 84a) | 125a) | [M + H]+ = 476 |
| (126) | 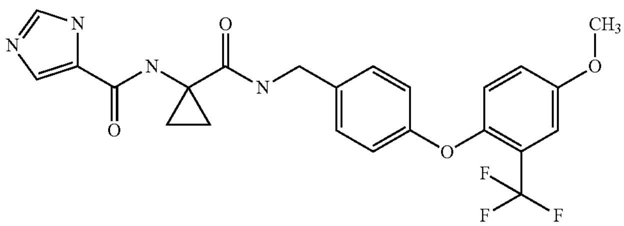 [SMILES: COc1ccc(Oc2ccc(CNC(=O)C3(NC(=O)c4cnc[nH]4)CC3)cc2)c(C(F)(F)F)c1] | 84a) | analogously to 120a) | [M + H]+ = 475 |
| (127) | 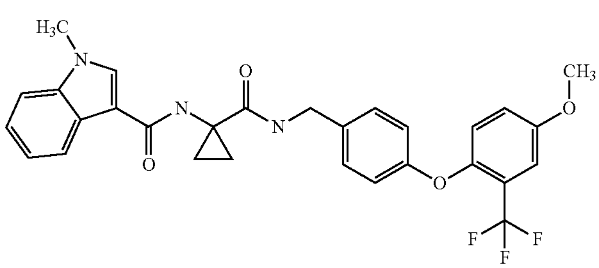 [SMILES: COc1ccc(Oc2ccc(CNC(=O)C3(NC(=O)c4cn(C)c5ccccc45)CC3)cc2)c(C(F)(F)F)c1] | 84a) | analogously to 78d) | [M + H]+ = 538 |

-continued

| No. | Structure | Educt (benzylamine) | Method of manufacture | LCMS |
|---|---|---|---|---|
| (128) | 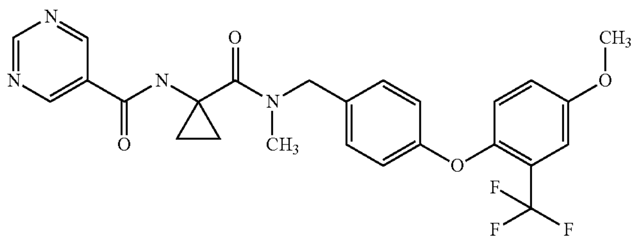 [SMILES: COc1ccc(Oc2ccc(CN(C)C(=O)C3(NC(=O)c4cncnc4)CC3)cc2)c(C(F)(F)F)c1] | 84a) | analogously to 78d) | [M + H]+ = 501 |
| (129) | 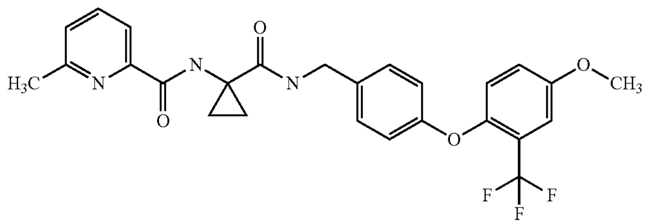 | 84a) | 129a) | [M + H]+ = 500 |
| (130) | 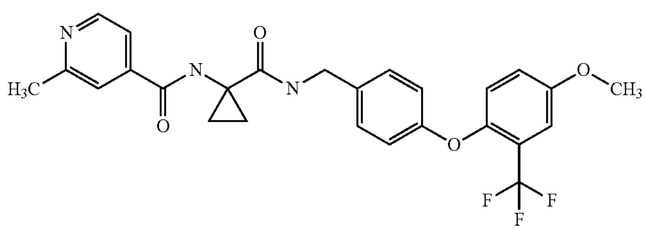 | 84a) | analogously to 129a) | [M + H]+ = 500 |
| (131) | 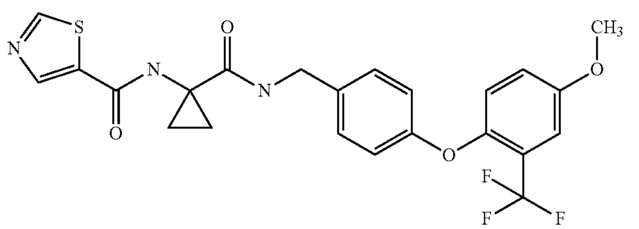 | 84a) | analogously to 125a) | [M + H]+ = 492 |
| (132) | 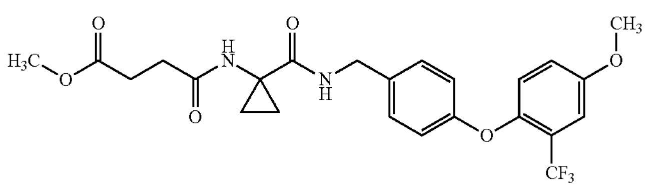 | 84a) | analogously to 109 | [M + H]+ = 495 |
| (133) | 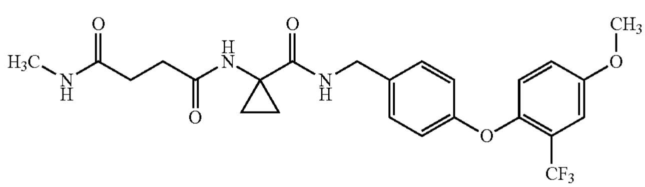 | 84a) | analogously to 109 | [M + H]+ = 494 |
| (134) | 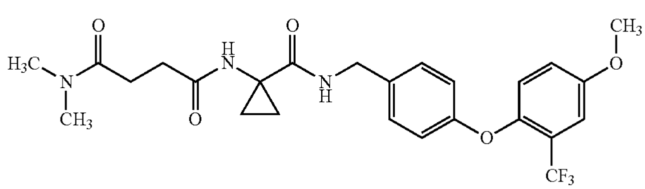 | 84a) | analogously to 109 | [M + H]+ = 508 |

-continued

| No. | Structure | Educt (benzylamine) | Method of manufacture | LCMS |
|---|---|---|---|---|
| (135) | 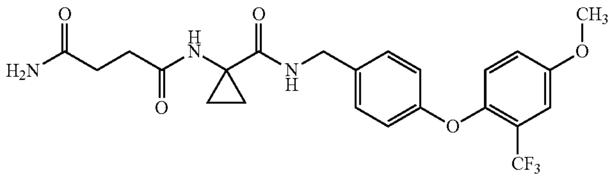 [SMILES: COc1ccc(Oc2ccc(CNC(=O)C3(NC(=O)CCC(N)=O)CC3)cc2)c(C(F)(F)F)c1] | 84a) | analogously to 109 | [M + H]+ = 480 |
| (136) | 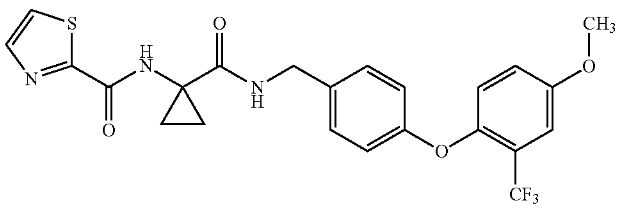 [SMILES: COc1ccc(Oc2ccc(CNC(=O)C3(NC(=O)c4nccs4)CC3)cc2)c(C(F)(F)F)c1] | 84a) | analogously to 129 | [M + H]+ = 492 |
| (137) | 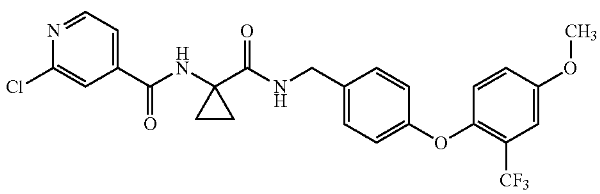 | 84a) | analogously to 129 | [M + H]+ = 520 |
| (138) | 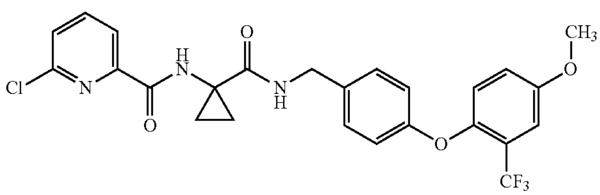 [SMILES: COc1ccc(Oc2ccc(CNC(=O)C3(NC(=O)c4cccc(Cl)n4)CC3)cc2)c(C(F)(F)F)c1] | 84a) | analogously to 129 | [M + H]+ = 520 |
| (139) | 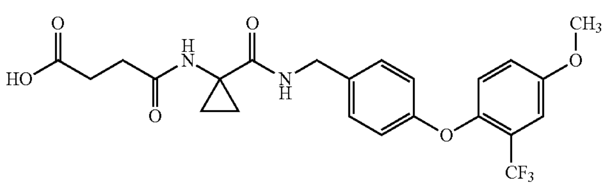 [SMILES: COc1ccc(Oc2ccc(CNC(=O)C3(NC(=O)CCC(=O)O)CC3)cc2)c(C(F)(F)F)c1] | | | [M + H]+ = 481 |
| (140) | 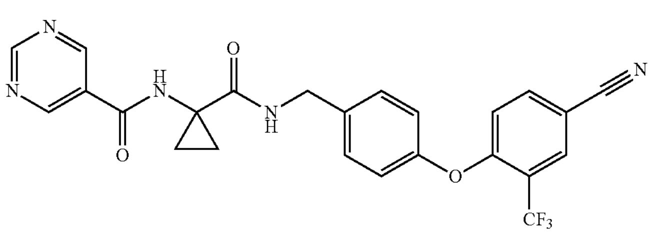 [SMILES: N#Cc1ccc(Oc2ccc(CNC(=O)C3(NC(=O)c4cncnc4)CC3)cc2)c(C(F)(F)F)c1] | | | [M + H]+ = 482 |
| (141) | 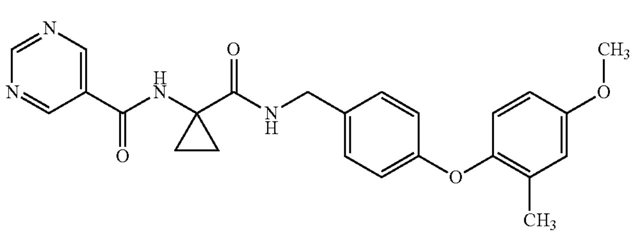 [SMILES: COc1ccc(Oc2ccc(CNC(=O)C3(NC(=O)c4cncnc4)CC3)cc2)c(C)c1] | 85 | analogously to 1e) | [M + H]+ = 433 |

-continued

| No. | Structure | Educt (benzylamine) | Method of manufacture | LCMS |
|---|---|---|---|---|
| (142) | [structure: 2-aminopyrimidine-5-carbonyl-NH-cyclopropyl(C=O)-NH-CH2-C6H4-O-C6H3(CF3)-OCH3] | 84a) | analogously to 129 | [M + H]+ = 502 |
| (143) | [structure: 4-methoxypyridine-2-carbonyl-NH-cyclopropyl(C=O)-NH-CH2-C6H4-O-C6H3(CF3)-OCH3] | 84a) | analogously to 129 | [M + H]+ = 516 |
| (144) | [structure: 2-(methylthio)pyrimidine-5-carbonyl-NH-cyclopropyl(C=O)-NH-CH2-C6H4-O-C6H3(CF3)-OCH3] | 84a) | analogously to 129 | [M + H]+ = 533 |
| (145) | [structure: pyrimidine-5-carbonyl-NH-cyclopropyl(C=O)-NH-CH2-C6H4-O-C6H4-Br] | 86 | analogously to 1e) | [M + H]+ = 467 |
| (146) | [structure: pyrimidine-5-carbonyl-NH-cyclopropyl(C=O)-NH-CH2-C6H4-O-C6H4-CN] | | analogously to 140 | [M + H]+ = 414<br>[M − H]− = 412 |
| (147) | [structure: pyrimidine-5-carbonyl-NH-cyclopropyl(C=O)-NH-CH2-C6H4-O-C6H3(CN)-OCH3] | | analogously to 140 | [M + H]+ = 444<br>[M − H]− = 442 |

-continued

| No. | Structure | Educt (benzylamine) | Method of manufacture | LCMS |
|---|---|---|---|---|
| (148) | 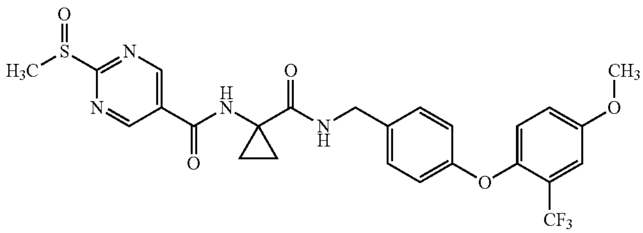 | | | [M + H]+ = 549 |
| (149) | 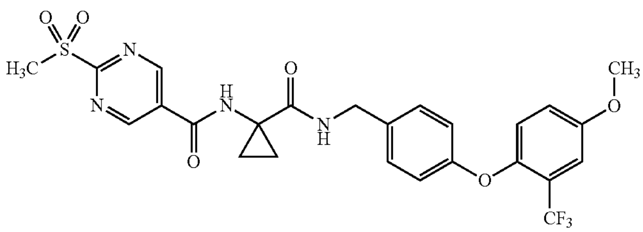 | | | [M + H]+ = 565 |
| (150) | 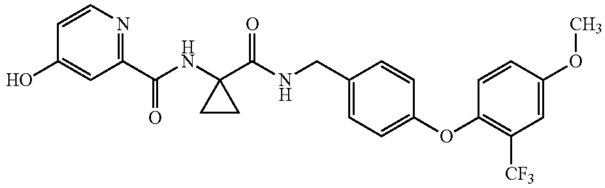 [SMILES: COc1ccc(Oc2ccc(CNC(=O)C3(NC(=O)c4cc(O)ccn4)CC3)cc2)c(C(F)(F)F)c1] | 84a) | analogously to 129 | [M + H]+ = 502 |
| (151) | 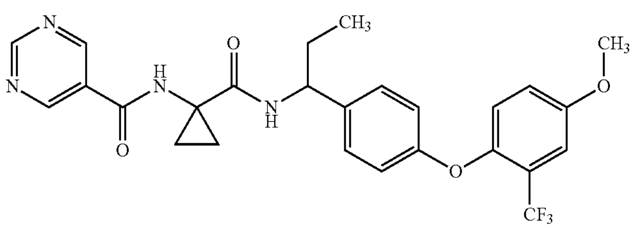 [SMILES: CCC(NC(=O)C1(NC(=O)c2cncnc2)CC1)c1ccc(Oc2ccc(OC)cc2C(F)(F)F)cc1] | 87 | analogously to 1e) | [M + H]+ = 515 |
| (152) | 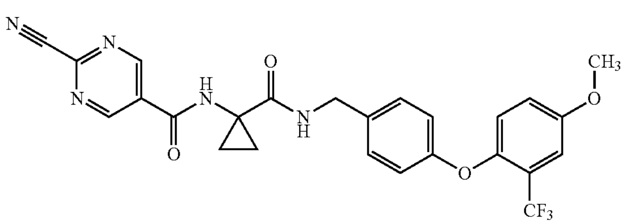 [SMILES: COc1ccc(Oc2ccc(CNC(=O)C3(NC(=O)c4cnc(C#N)nc4)CC3)cc2)c(C(F)(F)F)c1] | | | [M + H]+ = 512 |
| (153) | 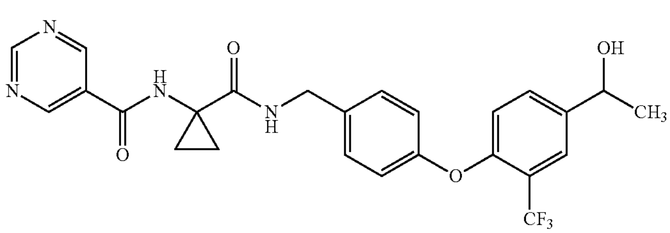 [SMILES: CC(O)c1ccc(Oc2ccc(CNC(=O)C3(NC(=O)c4cncnc4)CC3)cc2)c(C(F)(F)F)c1] | 88 | analogously to 1e) | [M + H]+ = 501 |
| (154) | 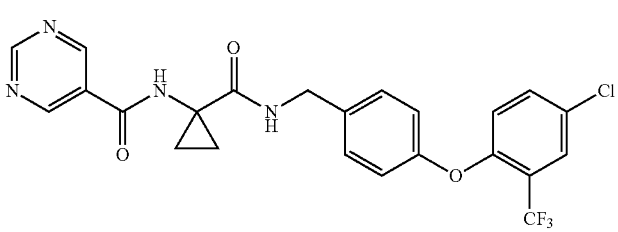 [SMILES: O=C(NC1(C(=O)NCc2ccc(Oc3ccc(Cl)cc3C(F)(F)F)cc2)CC1)c1cncnc1] | 89 | analogously to 1e) | [M + H]+ = 491 |

-continued

| No. | Structure | Educt (benzylamine) | Method of manufacture | LCMS |
|---|---|---|---|---|
| (155) | 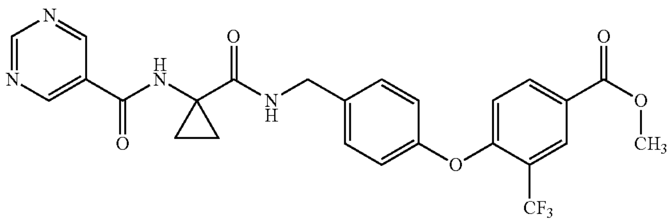 [SMILES: COC(=O)c1ccc(Oc2ccc(CNC(=O)C3(NC(=O)c4cncnc4)CC3)cc2)c(C(F)(F)F)c1] | 90 | analogously to 1e) | [M + H]+ = 515 |
| (156) | 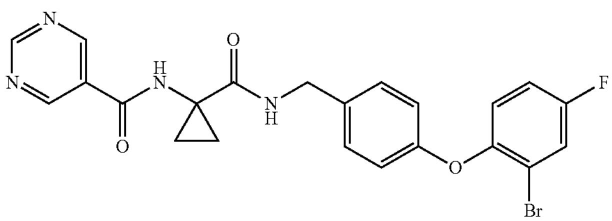 [SMILES: O=C(NC1(C(=O)NCc2ccc(Oc3ccc(F)cc3Br)cc2)CC1)c1cncnc1] | 91 | analogously to 1e) | [M + H]+ = 485<br>[M − H]− = 483 |
| (157) | 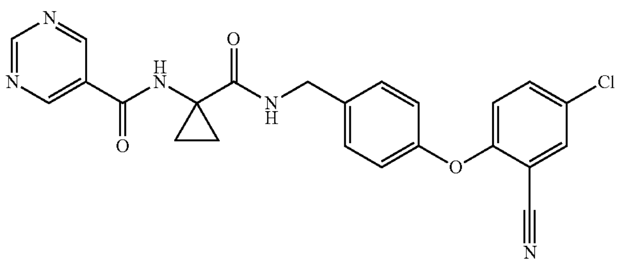 [SMILES: N#Cc1cc(Cl)ccc1Oc1ccc(CNC(=O)C2(NC(=O)c3cncnc3)CC2)cc1] | | analogously to 140 | [M + H]+ = 448 |
| (158) | 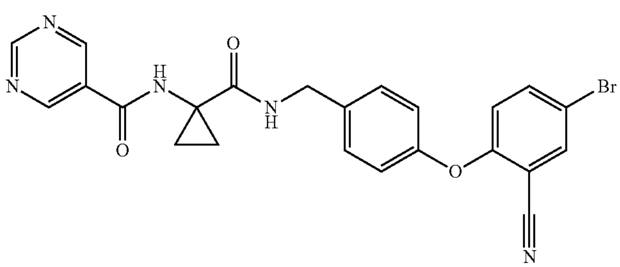 [SMILES: N#Cc1cc(Br)ccc1Oc1ccc(CNC(=O)C2(NC(=O)c3cncnc3)CC2)cc1] | | analogously to 140 | [M + H]+ = 492/94 |
| (159) | 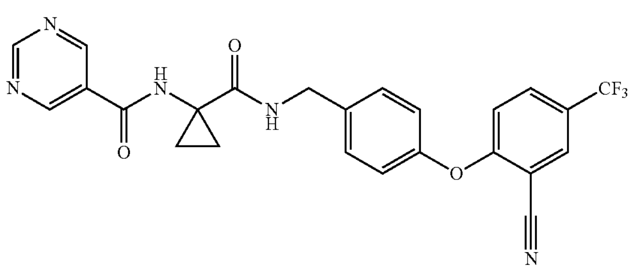 [SMILES: N#Cc1cc(C(F)(F)F)ccc1Oc1ccc(CNC(=O)C2(NC(=O)c3cncnc3)CC2)cc1] | | analogously to 140 | [M + H]+ = 482 |
| (160) | 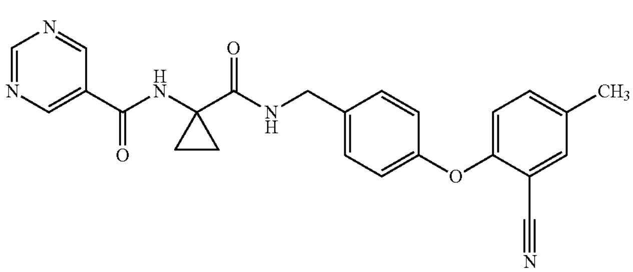 [SMILES: Cc1ccc(Oc2ccc(CNC(=O)C3(NC(=O)c4cncnc4)CC3)cc2)c(C#N)c1] | | analogously to 140 | [M + H]+ = 428 |

-continued
| No. | Structure | Educt (benzylamine) | Method of manufacture | LCMS |
|---|---|---|---|---|
| (161) | 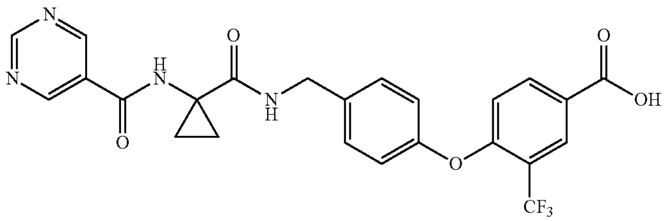 [SMILES: O=C(O)c1ccc(Oc2ccc(CNC(=O)C3(NC(=O)c4cncnc4)CC3)cc2)c(C(F)(F)F)c1] | | analogously to 139 | [M + H]+ = 501<br>[M − H]− = 499 |
| (162) | 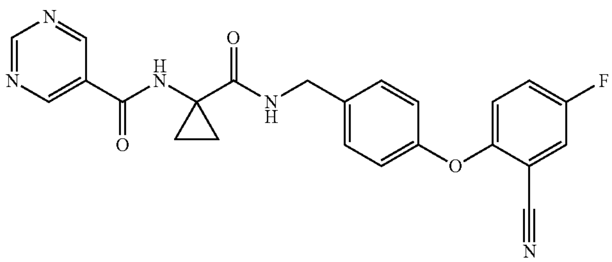 [SMILES: N#Cc1cc(F)ccc1Oc1ccc(CNC(=O)C2(NC(=O)c3cncnc3)CC2)cc1] | | analogously to 140 | [M + H]+ = 432<br>[M − H]− = 430 |
| (163) | 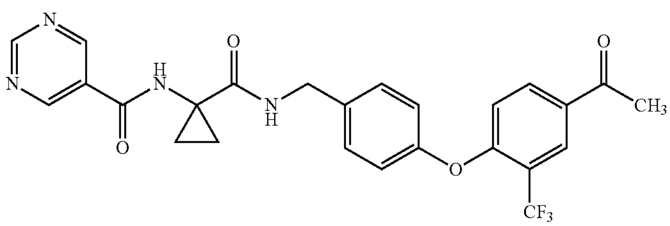 [SMILES: CC(=O)c1ccc(Oc2ccc(CNC(=O)C3(NC(=O)c4cncnc4)CC3)cc2)c(C(F)(F)F)c1] | | | [M + H]+ = 499 |
Table of Intermediate Compounds III
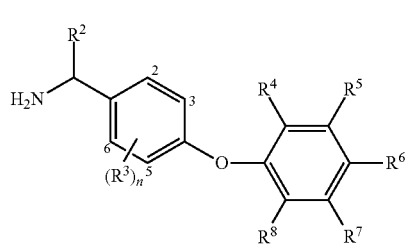
(III)
| No. | Structure | Method of manufacture | LCMS |
|---|---|---|---|
| (1d) | 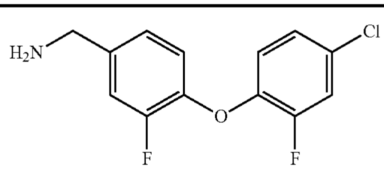 | (1d) | [M + H]+ = 270/272 |
| (2c) | 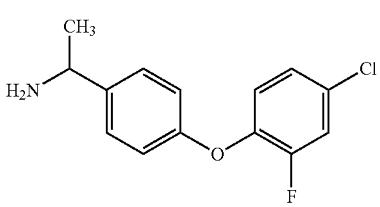 [SMILES: CC(N)c1ccc(Oc2ccc(Cl)cc2F)cc1] | (2c) | [M − NH2]− = 249/251 |

-continued
(III)
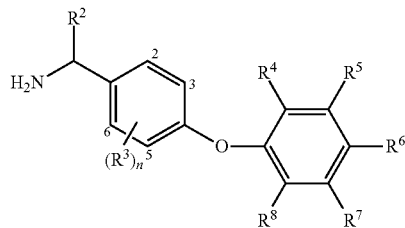
| No. | Structure | Method of manufacture | LCMS |
|---|---|---|---|
| (3b) | 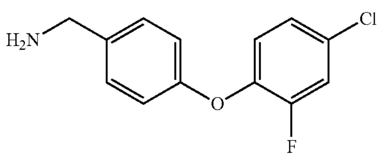 [SMILES: NCc1ccc(Oc2ccc(Cl)cc2F)cc1] | analogously to (1d) | [M + H]+ = 252/254 |
| (7b) | 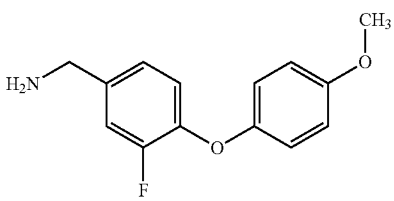 [SMILES: COc1ccc(Oc2ccc(CN)cc2F)cc1] | (7a, b) | [M − NH2]+ = 231 |
| (8b) | 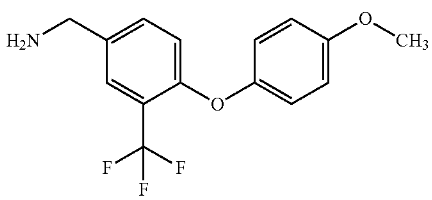 [SMILES: COc1ccc(Oc2ccc(CN)cc2C(F)(F)F)cc1] | analogously to (7a, b) | [M − NH2]+ = 281 |
| (9b) | 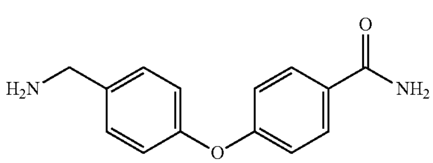 [SMILES: NCc1ccc(Oc2ccc(C(N)=O)cc2)cc1] | (9a, b) | [M − NH2]+ = 226 |
| (10b) | 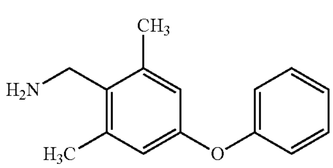 [SMILES: Cc1cc(Oc2ccccc2)cc(C)c1CN] | (10a, b) | [M − NH2]+ = 211 |
| (11b) | 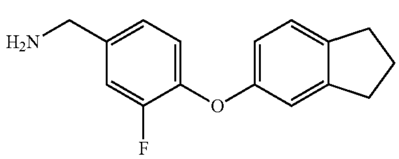 [SMILES: NCc1ccc(Oc2ccc3c(c2)CCC3)c(F)c1] | analogously to (7a, b) | [M − NH2]+ = 241 |
| (12b) | 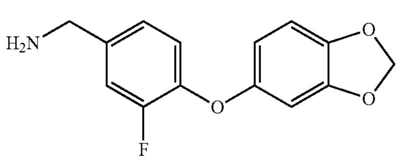 [SMILES: NCc1ccc(Oc2ccc3c(c2)OCO3)c(F)c1] | analogously to (7a, b) | [M − NH2]+ = 245 |

-continued
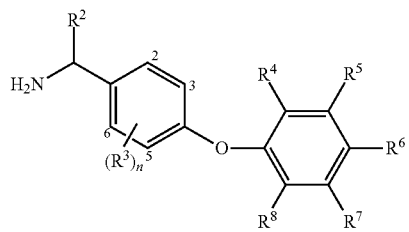
(III)
| No. | Structure | Method of manufacture | LCMS |
|---|---|---|---|
| (13b) | 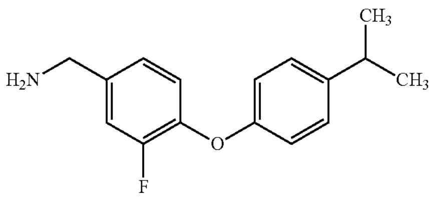 [SMILES: CC(C)c1ccc(Oc2ccc(CN)cc2F)cc1] | analogously to (7a, b) | [M − NH2]+ = 243 |
| (14c) | 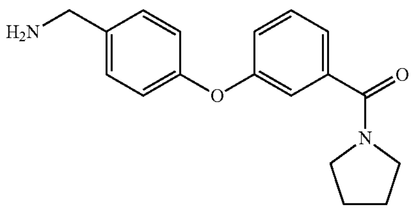 [SMILES: NCc1ccc(Oc2cccc(C(=O)N3CCCC3)c2)cc1] | analogously to (9a, b) | [M − NH2]+ = 280 |
| (15c) | 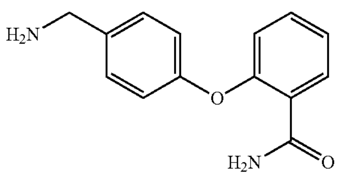 [SMILES: NCc1ccc(Oc2ccccc2C(N)=O)cc1] | analogously to (9a, b) | [M − NH2]+ = 226 |
| (16c) | 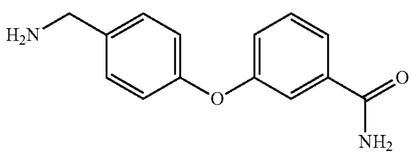 | analogously to (9a, b) | [M − NH2]+ = 226 |
| (17b) | 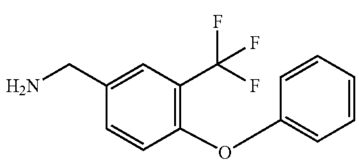 [SMILES: NCc1ccc(Oc2ccccc2)c(C(F)(F)F)c1] | analogously to (8a, b) | [M − NH2]+ = 251 |
| (18b) | 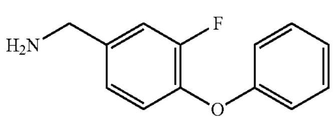 [SMILES: NCc1ccc(Oc2ccccc2)c(F)c1] | analogously to (7a, b) | [M − NH2]+ = 201 |
| (19c) | 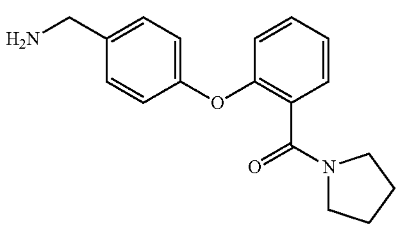 [SMILES: NCc1ccc(Oc2ccccc2C(=O)N2CCCC2)cc1] | analogously to (9a, b) | [M − NH2]+ = 280 |

-continued

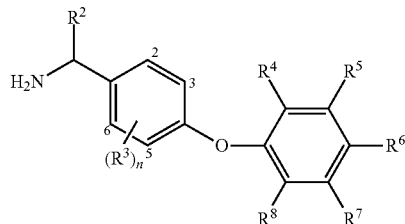
(III)

| No. | Structure | Method of manufacture | LCMS |
|---|---|---|---|
| (20b) | H₂N–C₆H₃(F)–O–C₆H₄–Cl | analogously to (7a, b) | [M − NH2]+ = 235 |
| (21b) | H₂N–C₆H₃(F)–O–C₆H₃(Cl)(Cl) | analogously to (7a, b) | [M + H]+ = 286/288/290 |
| (22b) | H₂N–C₆H₃(F)–O–C₆H₃(Cl)(Cl) | analogously to (7a, b) | [M − NH2]+ = 269/71/73 |
| (23b) | H₂N–C₆H₃(F)–O–C₆H₃(Cl)(F) | analogously to (7a, b) | [M + H]+ = 270/272 |
| (39b) | CH₃–CH(NH₂)–C₆H₄–O–C₆H₄–OCH₃ | (39a, b) | [M − NH2]+ = 269/71/73 |
| (40b) | H₂N–CH₂–C₆H₃(F)–O–C₆H₄–Cl | (40a, b) | [M + H]+ = 252/254 |
| (41b) | CH₃–CH(NH₂)–C₆H₄–O–C₆H₄–Cl | analogously to (39a, b) | [M − NH2]+ = 231/233 |
| (43b) | H₂N–CH₂–C₆H₃(F)–O–C₆H₄–OCH₃ | (43a, b) | [M − NH2]+ = 231 |

-continued
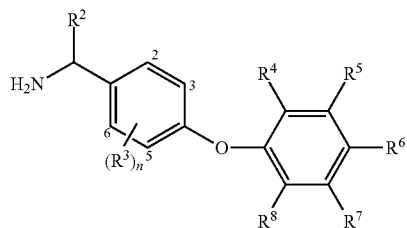
(III)
| No. | Structure | Method of manufacture | LCMS |
|---|---|---|---|
| (44b) | 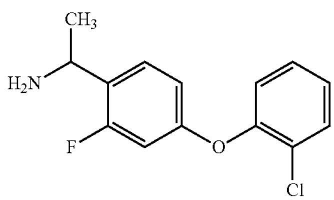 [SMILES: CC(N)c1ccc(Oc2ccccc2Cl)cc1F] | (44a, b) | [M − NH2]+ = 249/251 |
| (45b) | 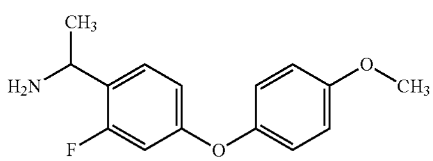 [SMILES: COc1ccc(Oc2ccc(C(C)N)c(F)c2)cc1] | analogously to (44a, b) | [M − NH2]+ = 245 |
| (46b) | 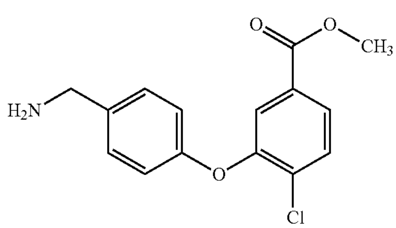 [SMILES: COC(=O)c1ccc(Cl)c(Oc2ccc(CN)cc2)c1] | analogously to (1d) | [M − NH2]+ = 275/277 |
| (49a) | 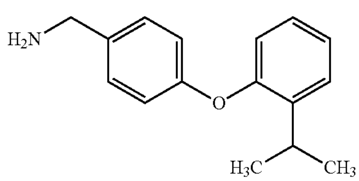 [SMILES: CC(C)c1ccccc1Oc1ccc(CN)cc1] | (49a) | [M − NH2]+ = 225 |
| (50a) | 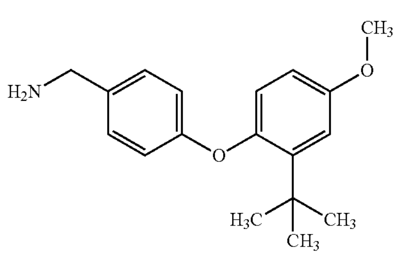 [SMILES: COc1ccc(Oc2ccc(CN)cc2)c(C(C)(C)C)c1] | analogously to (49a) | [M − NH2]+ = 269 |
| (51a) | 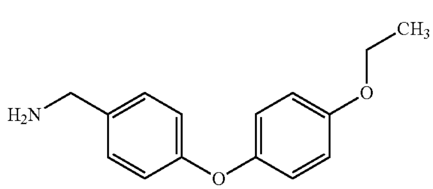 [SMILES: CCOc1ccc(Oc2ccc(CN)cc2)cc1] | analogously to (49a) | [M − NH2]+ = 227 |

-continued
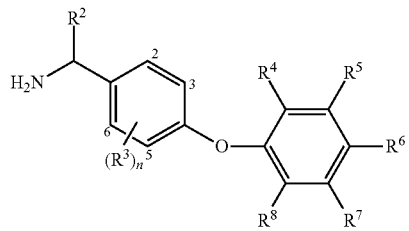
(III)
| No. | Structure | Method of manufacture | LCMS |
|---|---|---|---|
| (52a) | 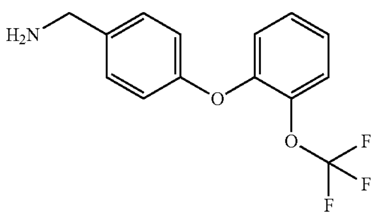 [SMILES: NCc1ccc(Oc2ccccc2OC(F)(F)F)cc1] | analogously to (49a) | [M − NH2]+ = 267 |
| (53a) | 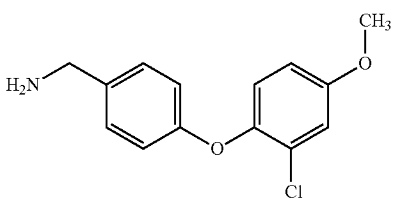 [SMILES: COc1ccc(Oc2ccc(CN)cc2)c(Cl)c1] | analogously to (49a) | [M − NH2]+ = 247 |
| (54a) | 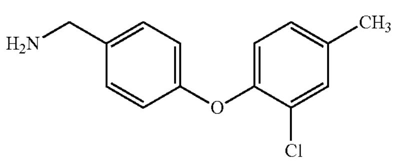 [SMILES: Cc1ccc(Oc2ccc(CN)cc2)c(Cl)c1] | analogously to (49a) | [M − NH2]+ = 231 |
| (55a) | 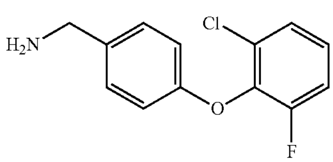 [SMILES: NCc1ccc(Oc2c(F)cccc2Cl)cc1] | analogously to (49a) | [M − NH2]+ = 235 |
| (56a) | 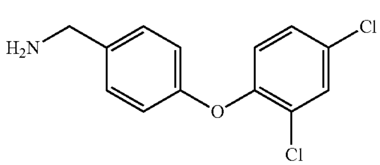 [SMILES: NCc1ccc(Oc2ccc(Cl)cc2Cl)cc1] | analogously to (49a) | [M − NH2]+ = 251/253 |
| (57a) | 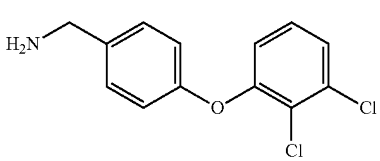 [SMILES: NCc1ccc(Oc2cccc(Cl)c2Cl)cc1] | analogously to (49a) | [M − NH2]+ = 251/253 |
| (58a) | 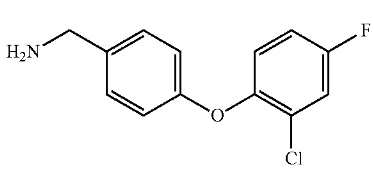 [SMILES: NCc1ccc(Oc2ccc(F)cc2Cl)cc1] | analogously to (49a) | [M − NH2]+ = 235 |

-continued
(III)
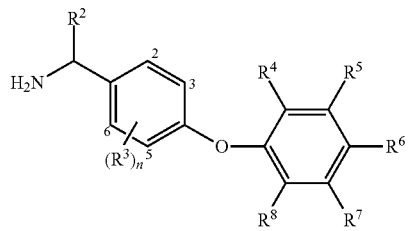
| No. | Structure | Method of manufacture | LCMS |
|---|---|---|---|
| (59a) | 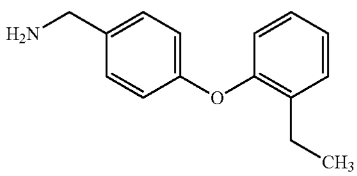 [SMILES: CCc1ccccc1Oc1ccc(CN)cc1] | analogously to (49a) | [M − NH2]+ = 211 |
| (60a) | 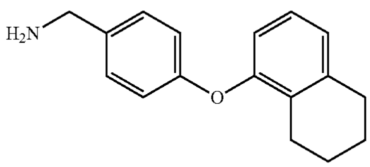 [SMILES: NCc1ccc(Oc2cccc3c2CCCC3)cc1] | analogously to (49a) | [M − NH2]+ = 237 |
| (61a) | 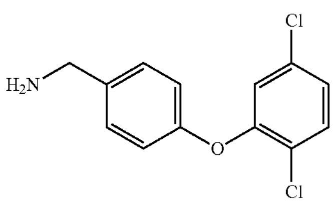 [SMILES: NCc1ccc(Oc2cc(Cl)ccc2Cl)cc1] | analogously to (49a) | [M − NH2]+ = 251/253 |
| (62a) | 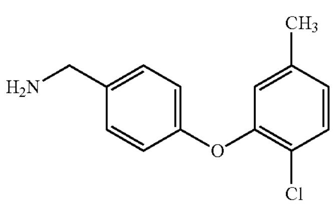 [SMILES: Cc1ccc(Cl)c(Oc2ccc(CN)cc2)c1] | analogously to (49a) | [M − NH2]+ = 231 |
| (63a) | 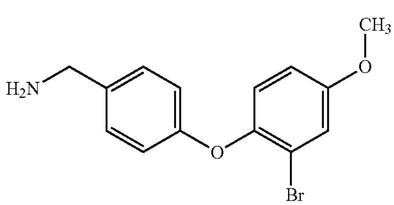 [SMILES: COc1ccc(Oc2ccc(CN)cc2)c(Br)c1] | analogously to (49a) | [M − NH2]+ = 291/293 |
| (64a) | 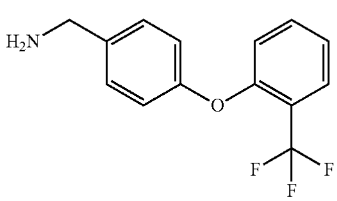 [SMILES: NCc1ccc(Oc2ccccc2C(F)(F)F)cc1] | analogously to (49a) | [M − NH2]+ = 251 |

-continued
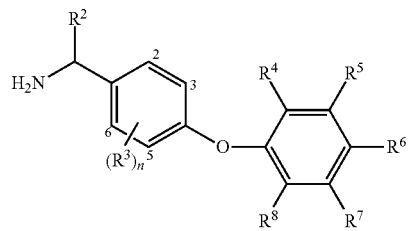
(III)
| No. | Structure | Method of manufacture | LCMS |
|---|---|---|---|
| (65a) | 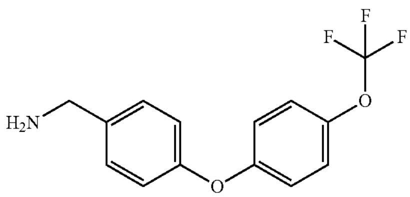 [SMILES: NCc1ccc(Oc2ccc(OC(F)(F)F)cc2)cc1] | analogously to (49a) | [M − NH2]+ = 267 |
| (66a) | 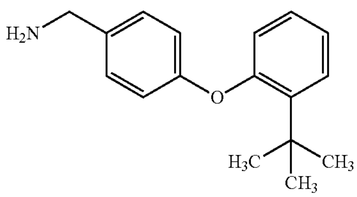 [SMILES: CC(C)(C)c1ccccc1Oc1ccc(CN)cc1] | analogously to (49a) | [M − NH2]+ = 239 |
| (67a) | 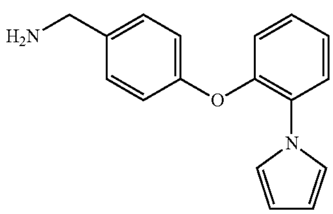 [SMILES: NCc1ccc(Oc2ccccc2-n2cccc2)cc1] | analogously to (49a) | [M − NH2]+ = 248 |
| (68a) | 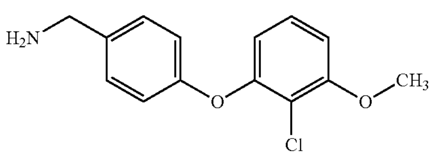 [SMILES: COc1cccc(Oc2ccc(CN)cc2)c1Cl] | analogously to (49a) | [M − NH2]+ = 247 |
| (69a) | 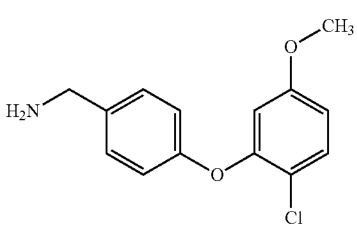 [SMILES: COc1ccc(Cl)c(Oc2ccc(CN)cc2)c1] | analogously to (49a) | [M − NH2]+ = 247 |
| (70a) | 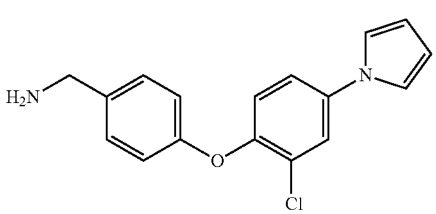 [SMILES: NCc1ccc(Oc2ccc(-n3cccc3)cc2Cl)cc1] | analogously to (49a) | [M − NH2]+ = 282 |

-continued
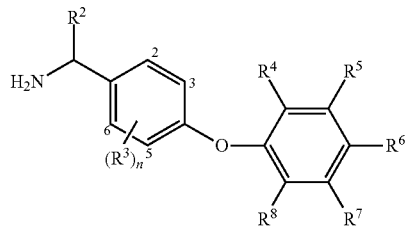
(III)
| No. | Structure | Method of manufacture | LCMS |
|---|---|---|---|
| (71a) | 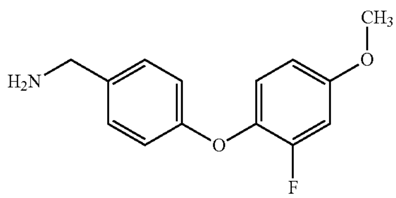 [SMILES: COc1ccc(Oc2ccc(CN)cc2)c(F)c1] | analogously to (49a) | [M − NH2]+ = 231 |
| (72a) | 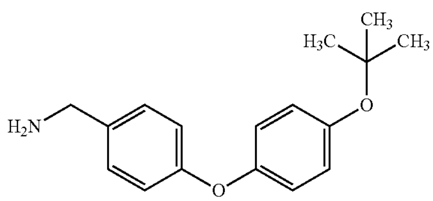 [SMILES: CC(C)(C)Oc1ccc(Oc2ccc(CN)cc2)cc1] | analogously to (49a) | [M − NH2]+ = 255 |
| (73a) | 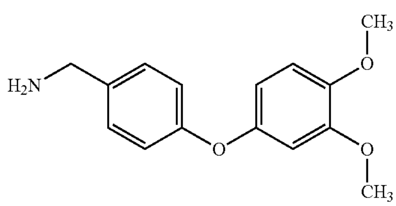 [SMILES: COc1ccc(Oc2ccc(CN)cc2)cc1OC] | analogously to (49a) | [M − NH2]+ = 243 |
| (74b) | 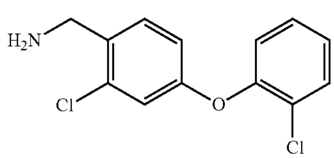 [SMILES: NCc1ccc(Oc2ccccc2Cl)cc1Cl] | (74a, b) | [M + H]+ = 268/70/2 |
| (75c) | 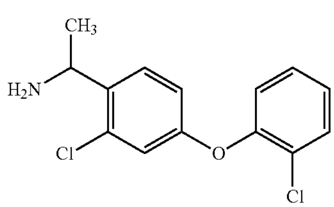 [SMILES: CC(N)c1ccc(Oc2ccccc2Cl)cc1Cl] | (75a, b, c) | [M + H]+ = 282/4/6 |
| (76c) | 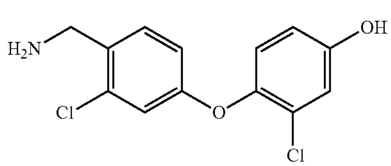 [SMILES: NCc1ccc(Oc2ccc(O)cc2Cl)cc1Cl] | (76a, b, c) | [M − NH4]+ = 267/9/71 |
| (78c) | 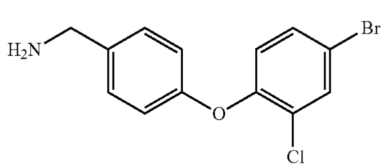 | (78a, b, c) | [M + H]+ = 295/7/9 |

-continued
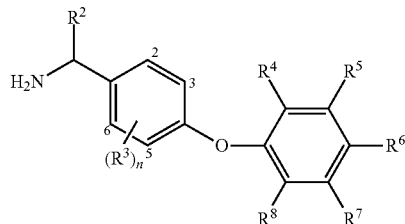
(III)
| No. | Structure | Method of manufacture | LCMS |
|---|---|---|---|
| (79c) | 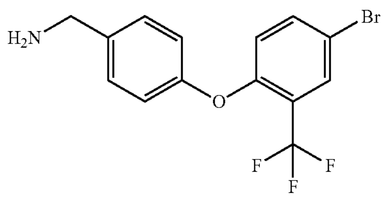 | (79a, b, c) | [M + H]+ = 346/8 |
| (80c) | 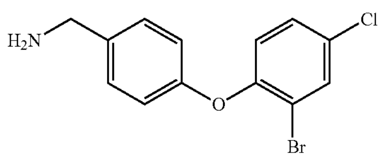 [SMILES: NCc1ccc(Oc2ccc(Br)cc2Cl)cc1] | analogously to (79a, b, c) | [M − NH2]+ = 295/7/9 |
| (81c)) | 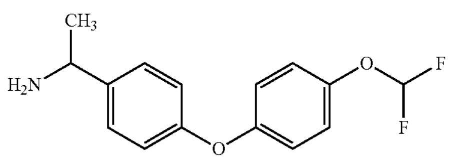 | (81a, b, c) | [M + H − NH3]+ = 263 |
| (82f)) | 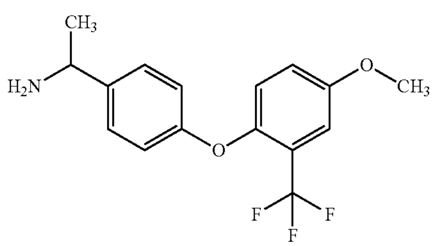 [SMILES: COc1ccc(Oc2ccc(C(C)N)cc2)c(C(F)(F)F)c1] | (82c, d, e, f) | M*+ = 311 |
| (84a)) | 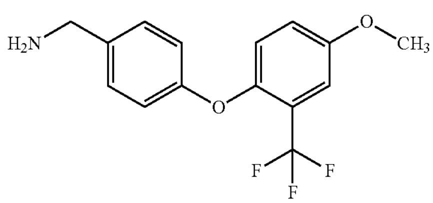 [SMILES: COc1ccc(Oc2ccc(CN)cc2)c(C(F)(F)F)c1] | analogously to (82c) and (84a) | [M − NH2]+ = 281 |
| (85) | 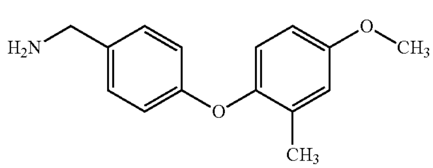 | analogously to (49a) | [M + H − NH3]+ = 227 |
| (86) | 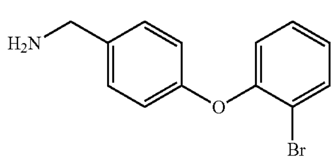 [SMILES: NCc1ccc(Oc2ccccc2Br)cc1] | analogously to (49a) | |

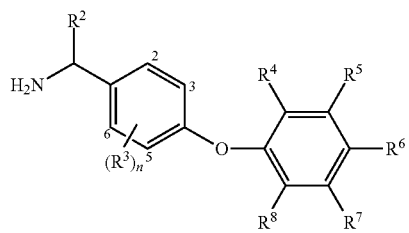
(III)
| No. | Structure | Method of manufacture | LCMS |
|---|---|---|---|
| (87) | 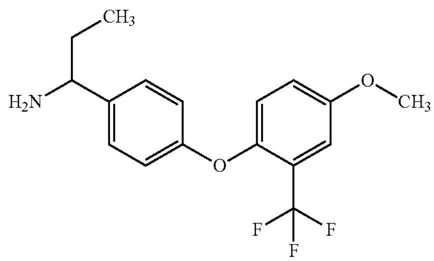 | analogously to (49a) | [M + H − NH3]+ = 309 |
| (88) | 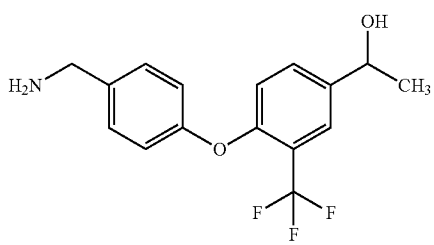 | | [M + H − NH3]+ = 295 |
| (89) | 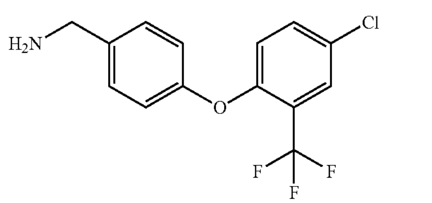 [SMILES: NCc1ccc(Oc2ccc(Cl)cc2C(F)(F)F)cc1] | analogously to (49a) | [M + H − NH3]+ = 285<br>[M + H]+ = 302 |
| (90) | 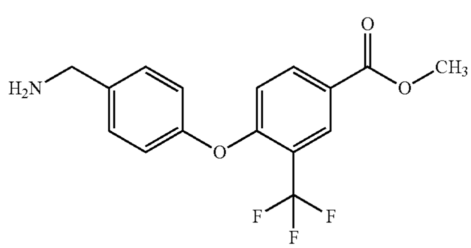 | | [M + H − NH3]+ = 309 |
| (91) | 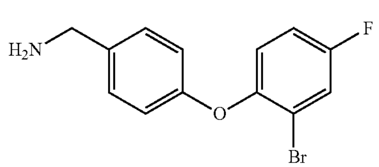 [SMILES: NCc1ccc(Oc2ccc(F)cc2Br)cc1] | analogously to (49a) | [M + H]+ = 296 |
The following Examples describe pharmaceutical formulations which contain as active substance any desired compound of general formula I, but without restricting the scope of the present invention thereto:

EXAMPLE I

Dry Ampoule with 75 mg of Active Compound per 10 ml
Composition:

| Active compound | 75.0 mg |
|---|---|
| Mannitol | 50.0 mg |
| Water for injection | ad 10.0 ml |

Production:
Active compound and mannitol are dissolved in water. The charged ampoules are freeze dried. Water for injection is used to dissolve to give the solution ready for use.

EXAMPLE II

Tablet with 50 mg of Active Compound
Composition:

| (1) Active compound | 50.0 mg |
|---|---|
| (2) Lactose | 98.0 mg |
| (3) Maize starch | 50.0 mg |
| (4) Polyvinylpyrrolidone | 15.0 mg |
| (5) Magnesium stearate | 2.0 mg |
| | 215.0 mg |

Production:
(1), (2) and (3) are mixed and granulated with an aqueous solution of (4). (5) is admixed to the dry granules. Tablets are compressed from this mixture, biplanar with a bevel on both sides and dividing groove on one side.
Diameter of the tablets: 9 mm.

EXAMPLE III

Tablet with 350 mg of Active Compound
Composition:

| (1) Active compound | 350.0 mg |
|---|---|
| (2) Lactose | 136.0 mg |
| (3) Maize starch | 80.0 mg |
| (4) Polyvinylpyrrolidone | 30.0 mg |
| (5) Magnesium stearate | 4.0 mg |
| | 600.0 mg |

Production:
(1), (2) and (3) are mixed and granulated with an aqueous solution of (4). (5) is admixed to the dry granules. Tablets are compressed from this mixture, biplanar with a bevel on both sides and dividing groove on one side.
Diameter of the tablets: 12 mm.

EXAMPLE IV

Capsule with 50 mg of Active Compound
Composition:

| (1) Active compound | 50.0 mg |
|---|---|
| (2) Maize starch dried | 58.0 mg |
| (3) Lactose powdered | 50.0 mg |
| (4) Magnesium stearate | 2.0 mg |
| | 160.0 mg |

Production:
(1) is triturated with (3). This trituration is added to the mixture of (2) and (4) with vigorous mixing.
This powder mixture is packed into hard gelatine two-piece capsules of size 3 in a capsule-filling machine.

EXAMPLE V

Capsules with 350 mg of Active Compound
Composition:

| (1) Active compound | 350.0 mg |
|---|---|
| (2) Maize starch dried | 46.0 mg |
| (3) Lactose powdered | 30.0 mg |
| (4) Magnesium stearate | 4.0 mg |
| | 430.0 mg |

Production:
(1) is triturated with (3). This trituration is added to the mixture of (2) and (4) with vigorous stirring.
This powder mixture is packed into hard gelatine two-piece capsules of size 0 in a capsule-filling machine.

EXAMPLE VI

Suppositories with 100 mg of Active Compound
1 Suppository Comprises:

| Active compound | 100.0 mg |
|---|---|
| Polyethylene glycol (M.W. 1500) | 600.0 mg |
| Polyethylene glycol (M.W. 6000) | 460.0 mg |
| Polyethylene sorbitan monostearate | 840.0 mg |
| | 2000.0 mg |

The invention claimed is:
1. A compound of the formula I wherein
$R^1$ denotes
 (a) a $C_{1-6}$-alkyl group optionally substituted by a group $R^{1.1}$,
 (b) a $C_{1-3}$-alkyl group wherein each methylene group is substituted by up to two fluorine atoms and each methyl group is substituted by up to three fluorine atoms,
 (c) a $C_{3-6}$-cycloalkyl group optionally substituted by a group $R^{1.2}$,
 (d) a $C_{2-6}$-alkenyl group,
 (e) a $C_{2-6}$-alkynyl group,
 (f) an aryl-$C_{1-2}$-alkylene group optionally substituted by 1, 2 or 3 groups $R^{1.3}$,
 (g) a five-membered heteroaryl group optionally substituted by by 1, 2 or 3 groups $R^{1.4}$, which contains at least one N, O or S atom and optionally also contains one, two or three further N atoms and may additionally be benzo-fused,
(h) a six-membered heteroaryl group optionally substituted by a group $R^{1.4}$, which contains one, two or three N atoms and may additionally be benzo-fused,
(i) —O—$R^{1.1.1}$ or
(j) —$NR_{1.1.2}R^{1.1.4}$, $R^{1.1}$ denotes halogen, —$NO_2$, —CN, $C_{3-6}$-cycloalkyl, —$OR^{1.1.1}$, —$SR^{1.1.1}$, —C(O)$R^{1.1.1}$, —S(O)$_2$—$R^{1.1.2}$, —O—S(O)$_2$—$R^{1.1.1}$, —$CO_2R^{1.1.1}$, —O—C(O)—$R^{1.1.1}$, —$NR^{1.1.3}R^{1.1.4}$, —$NR^{1.1.3}$-C(O)—$R^{1.1.1}$, —$NR^{1.1.3}$-C(O)—$R^{1.1.1}$, —$NR^{1.1.3}$-$CO_2$—$R^{1.1.1}$, —C(O)—$NR^{1.1.3}R^{1.1.4}$, $R^{1.1.1}$ denotes
(a) H,
(b) $C_{1-4}$-alkyl,
(c) $C_{1-3}$-alkyl, wherein each methylene group is substituted by up to two fluorine atoms and each methyl group is substituted by up to three fluorine atoms,
(d) a phenyl group optionally substituted by 1, 2 or 3 groups $R^{1.1.1.1}$,
(e) $C_{3-6}$-cycloalkyl,
(f) a pyridyl group optionally substituted by 1, 2 or 3 groups $R^{1.1.1.2}$, $R^{1.1.1.1}$ independently of one another denote
(b) halogen, —$NO_2$, —CN, —OH, —O—$C_{1-4}$-alkyl, $C_{3-6}$-cycloalkyl, $C_{1-4}$-alkyl,
(c) $C_{1-3}$-alkyl, wherein each methylene group is substituted by up to two fluorine atoms and each methyl group is substituted by up to three fluorine atoms, $R^{1.1.1.2}$ independently of one another denote halogen or $C_{1-4}$-alkyl, $R^{1.1.2}$ denotes
(a) $C_{1-4}$-alkyl,
(b) $C_{1-3}$-alkyl, wherein each methylene group is substituted by up to two fluorine atoms and each methyl group is substituted by up to three fluorine atoms,
(c) —O—$C_{1-4}$-alkyl,
(d) a phenyl group optionally substituted by 1, 2 or 3 groups $R^{1.1.1.1}$, $R^{1.1.3}$, $R^{1.1.4}$ independently of one another denote
(a) H,
(b) a $C_{1-4}$-alkyl group optionally substituted by 1, 2 or 3 groups $R^{1.1.4.1}$,
(c) a phenyl group optionally substituted by 1, 2 or 3 groups $R^{1.1.1.1}$,
(d) $C_{3-6}$-cycloalkyl, or $R^{1.1.3}$ and $R^{1.1.4}$ together with the N atom to which they are bound form a 4-, 5- or 6-membered heterocyclic ring, which may additionally contain a further heteroatom selected from N, O and S, or $R^{1.1.3}$ and $R^{1.1.4}$ together with the N atom to which they are bound form a cyclic imide, $R^{1.1.4.1}$ independently of one another denote halogen, —$NH_2$, —NH($C_{1-4}$-alkyl), —N($C_{1-4}$-alkyl)$_2$ or —$SO_2$—$R^{1.1.2}$, $R^{1.2}$ denotes halogen, —$NO_2$, —CN or phenyl, $R^{1.3}$ denotes
(a) halogen, —$NO_2$, —CN, —$OR^{1.1.1}$, —$SR^{1.1.1}$, —$CO_2R^{1.1.1}$, $C_{1-6}$-alkyl,
(b) $C_{1-3}$-alkyl, wherein each methylene group is substituted by up to two fluorine atoms and each methyl group is substituted by up to three fluorine atoms, $R^{1.4}$ independently of one another denote
(a) halogen, —$NO_2$, —CN, —$OR^{1.1.1}$, —$SR^{1.1.1}$, —S(O)—$R^{1.1.2}$, —$NR^{1.1.3}R^{1.1.4}$, $C_{1-6}$-alkyl, (b) $C_{1-3}$-alkyl, wherein each methylene group is substituted by up to two fluorine atoms and each methyl group is substituted by up to three fluorine atoms, or
(c) an oxo group, $R^2$ denotes
(a) H, $C_{1-4}$-alkyl or
(b) $C_{1-3}$-alkyl, wherein each methylene group is substituted by up to two fluorine atoms and each methyl group is substituted by up to three fluorine atoms, $R^3$ independently of one another denote
(a) H, halogen, —CN, —OH, $C_{1-6}$-alkyl, $C_{3-7}$-cycloalkyl, —O—$C_{1-4}$-alkyl, —O—$CF_3$, —O—$C_{3-6}$-cycloalkyl, —N($C_{1-3}$-alkyl)$_2$, —C(O)—$NH_2$, —($SO_2$)$NH_2$, —$SO_2$—$C_{1-3}$-alkyl,
(b) $C_{1-3}$-alkyl, wherein each methylene group is substituted by up to two fluorine atoms and each methyl group is substituted by up to three fluorine atoms, $R^4$, $R^5$, $R^6$, $R^7$, $R^8$ independently of one another denote
(a) H, halogen, —CN, —OH,
(b) $C_{1-6}$-alkyl, wherein two adjacent substituents together may denote a trimethylene or tetramethylene group,
(c) $C_{1-3}$-alkyl, wherein each methylene group is substituted by up to two fluorine atoms and each methyl group is substituted by up to three fluorine atoms,
(d) $C_{3-7}$-cycloalkyl,
(e) —O—$C_{1-6}$-alkyl, wherein two adjacent substituents may denote a methylenedioxy or ethylenedioxy group,
(f) —O—$CF_3$, —O—$C_{3-7}$-cycloalkyl,
(g) —$NH_2$, —NH($C_{1-3}$-alkyl), —N($C_{1-3}$-alkyl)$_2$,
(h) —C(O)—$R^{8.1}$,
(i) —$SO_2$—$R^{8.2}$,
(j) a five-membered heteroaryl group optionally substituted by one or two $C_{1-3}$-alkyl groups which is selected from among pyrrolyl, oxazolyl, isoxazolyl, oxadiazolyl, thiazolyl, isothiazolyl, thiadiazolyl, imidazolyl, pyrazolyl, triazolyl and tetrazolyl,
(k) a six-membered heteroaryl group optionally substituted by one or two $C_{1-3}$-alkyl groups which is selected from among pyridyl, pyrimidinyl, pyrazinyl, pyridazinyl and triazinyl, $R^{8.1}$ denotes —$NH_2$, —NH($C_{1-6}$-alkyl), —N($C_{1-6}$-alkyl)$_2$, N-acetidinyl, N-pyrrolidinyl, N-piperidinyl, N-morpholinyl, —OH, —O—$C_{1-8}$-alkyl, —O—$C_{3-7}$-cycloalkyl, $R^{8.2}$ denotes —$NH_2$, —NH($C_{1-6}$-alkyl), —N($C_{1-6}$-alkyl)$_2$, N-acetidinyl, N-pyrrolidinyl, N-piperidinyl, N-morpholinyl and n denotes one of the numbers 0, 1, 2, 3 or 4,
or a salt thereof.

2. A compound of the formula I according to claim 1, wherein
$R^1$ denotes
(a) a $C_{1-6}$-alkyl group optionally substituted by a group $R^{1.1}$,
(b) a $C_{1-3}$-alkyl group wherein each methylene group is substituted by up to two fluorine atoms and each methyl group is substituted by up to three fluorine atoms,
(c) a $C_{3-6}$-cycloalkyl group optionally substituted by a group $R^{1.2}$,
(e) a five-membered heteroaryl group optionally substituted by a group $R^{1.4}$, which contains at least one N, O or S atom and which optionally additionally contains one, two or three further N atoms, or
(f) a six-membered heteroaryl group optionally substituted by a group $R^{1.4}$, which contains one, two or three N atoms,
$R^{1.1}$ denotes $C_{3-6}$-cycloalkyl, —$OR^{1.1.1}$, —$NR^{1.1.3}R^{1.1.4}$, —C(O)—$NR^{1.1.3}R^{1.1.4}$, —CN, —$CO_2R^{1.1.1}$, —$S(O)_2$—$C_{1-6}$-alkyl or —O—$S(O)_2$—$C_{1-6}$-alkyl,
$R^{1.1.1}$ denotes
  (a) H,
  (b) $C_{1-4}$-alkyl,
  (c) $C_{1-3}$-alkyl, wherein each methylene group is substituted by up to two fluorine atoms and each methyl group is substituted by up to three fluorine atoms, or
  (d) $C_{3-6}$-cycloalkyl,
$R^{1.1.3}$,
$R^{1.1.4}$ independently of one another denote
  (a) H,
  (b) $C_{1-4}$-alkyl or
  (c) $C_{3-6}$-cycloalkyl, and
$R^{1.2}$ denotes halogen, —$NO_2$, —CN or phenyl,
$R^{1.3}$ denotes
  (a) halogen, —$NO_2$, —CN, —$OR^{1.1.1}$, —$SR^{1.1.1}$, —$CO_2R^{1.1.1}$, $C_{1-6}$-alkyl or
  (b) $C_{1-3}$-alkyl, wherein each methylene group is substituted by up to two fluorine atoms and each methyl group is substituted by up to three fluorine atoms, and
$R^{1.4}$ denotes
  (a) halogen, —$NO_2$, —CN, —$OR^{1.1.1}$, —$SR^{1.1.1}$, —$NR^{1.1.3}R^{1.1.4}$, $C_{1-6}$-alkyl,
  (b) $C_{1-3}$-alkyl, wherein each methylene group is substituted by up to two fluorine atoms and each methyl group is substituted by up to three fluorine atoms, or
  (c) an oxo group,
or a salt thereof.

3. A compound of the formula I according to claim 1, wherein
$R^1$ denotes
  (a) a $C_{1-6}$-alkyl group optionally substituted by a group $R^{1.1}$,
  (b) a $C_{1-3}$-alkyl group wherein each methylene group is substituted by up to two fluorine atoms and each methyl group is substituted by up to three fluorine atoms,
  (c) a $C_{3-6}$-cycloalkyl group optionally substituted by a group $R^{1.2}$,
  (e) a five-membered heteroaryl group optionally substituted by a group $R^{1.4}$, which contains at least one N, O or S atom and which optionally additionally contains one, two or three further N atoms, or
  (f) a six-membered heteroaryl group optionally substituted by a group $R^{1.4}$, which contains one, two or three N atoms,
$R^{1.1}$ denotes $C_{3-6}$-cycloalkyl, —$OR^{1.1.1}$, —NR—C(O)—NR —CN, —$CO_2R^{1.1.1}$, —$S(O)_2$—$C_{1-6}$-alkyl or —O—$S(O)_2$—$C_{1-6}$-alkyl,
$R^{1.1.1}$ denotes
  (a) H,
  (b) $C_{1-4}$-alkyl,
  (c) $C_{1-3}$-alkyl, wherein each methylene group is substituted by up to two fluorine atoms and each methyl group is substituted by up to three fluorine atoms, or
  (d) $C_{3-6}$-cycloalkyl,
$R^{1.1.3}$,
$R^{1.1.4}$ independently of one another denote
  (a) H,
  (b) $C_{1-4}$-alkyl or
  (c) $C_{3-6}$-cycloalkyl,
$R^{1.2}$ denotes halogen, —$NO_2$, —CN or phenyl,
$R^{1.3}$ denotes
  (a) halogen, —$NO_2$, —CN, —$OR^{1.1.1}$, —$SR^{1.1.1}$, —$CO_2R^{1.1.1}$, $C_{1-6}$-alkyl or
  (b) $C_{1-3}$-alkyl, wherein each methylene group is substituted by up to two fluorine atoms and each methyl group is substituted by up to three fluorine atoms,
$R^{1.4}$ denotes
  (a) halogen, —$NO_2$, —CN, —$OR^{1.1.1}$, —$SR^{1.1.1}$, —$NR^{1.1.3}R^{1.1.4}$, $C_{1-6}$-alkyl,
  (b) $C_{1-3}$-alkyl, wherein each methylene group is substituted by up to two fluorine atoms and each methyl group is substituted by up to three fluorine atoms, or
  (c) an oxo group
$R^2$ denotes H or $C_{1-3}$-alkyl,
$R^3$ independently of one another denote
  (a) H, halogen, $C_{1-3}$-alkyl, —O—$C_{1-3}$-alkyl or
  (b) $C_{1-3}$-alkyl, wherein each methylene group is substituted by up to two fluorine atoms and each methyl group is substituted by up to three fluorine atoms,
$R^4$ denotes H or halogen,
$R^5$ denotes
  (a) H, halogen,
  (b) $C_{1-3}$-alkyl,
  (c) $C_{1-3}$-alkyl, wherein each methylene group is substituted by up to two fluorine atoms and each methyl group is substituted by up to three fluorine atoms,
  (d) —O—$C_{1-3}$-alkyl,
  (e) —C(O)—O—$C_{1-3}$-alkyl or —C(O)—$NH_2$,
$R^6$ denotes
  (a) H, halogen,
  (b) $C_{1-3}$-alkylene-$R^{6.1}$,
  (c) $C_{1-3}$-alkyl, wherein each methylene group is substituted by up to two fluorine atoms and each methyl group is substituted by up to three fluorine atoms,
  (d) —OH, —O—$C_{1-4}$-alkyl,
  (e) —O—$CHF_2$, —O—$CF_3$,
  (f) —C(O)—O—$R^{6.2}$, —CN, —C(O)—$CH_3$, —C(O)—$NH_2$ or
  (g) pyrrolyl,
$R^{6.1}$ denotes H, —OH,
$R^{6.2}$ denotes H, $C_{1-3}$-alkyl,
$R^7$ denotes
  (a) H, halogen,
  (b) $C_{1-3}$-alkyl,
  (c) $C_{1-3}$-alkyl, wherein each methylene group is substituted by up to two fluorine atoms and each methyl group is substituted by up to three fluorine atoms,
  (d) —O—$C_{1-3}$-alkyl,
  (e) —C(O)—$NH_2$ or —C(O)-pyrrolidinyl, and
$R^8$ denotes
  (a) H, halogen,
  (b) $C_{1-4}$-alkyl,
  (c) $C_{1-3}$-alkyl, wherein each methylene group is substituted by up to two fluorine atoms and each methyl group is substituted by up to three fluorine atoms,
  (d) —O—$C_{1-3}$-alkyl,
  (e) —O—$CF_3$,
  (f) —CN, —C(O)—$NH_2$ or
  (g) pyrrolyl,
or a salt thereof.

4. A compound of the formula formula I according to claim 1, wherein
$R^1$ denotes
  (a) a $C_{1-6}$-alkyl group optionally substituted by a group $R^{1.1}$, (b) a $C_{1-3}$-alkyl group wherein each methylene group is substituted by up to two fluorine atoms and each methyl group is substituted by up to three fluorine atoms, (d) a five-membered heteroaryl group optionally substituted by a group $R^{1.4}$, which is selected from among furanyl, isoxazolyl, isothiazolyl, oxazolyl, thiazolyl, pyrazolyl, thiadiazolyl, oxadiazolyl, triazolyl, tetrazolyl, imidazolyl, indolyl, thienyl, pyrrolyl, benzimidazolyl, benzoxazolyl, benzothiazolyl and benzisoxazinyl, or (e) a six-membered heteroaryl group optionally substituted by a group $R^{1.4}$, which is selected from among pyridyl, pyrimidinyl, pyridazinyl, pyrazinyl, triazinyl, quinazolinyl and quinoxazinyl, $R^{1.1}$ denotes $C_{3-6}$-cycloalkyl, —OR —$NR^{1.1.3}R^{1.1.4}$, —C(O)—$NR^{1.1.3}R^{1.1.4}$, —CN, —$CO_2R^{1.1.1}$, —$S(O)_2$-$C_{1-6}$-alkyl or —O—$S(O)_2$—$C_{1-6}$-alkyl, $R^{1.1.1}$ denotes
  (a) H,
  (b) $C_{1-4}$-alkyl,
  (c) $C_{1-3}$-alkyl, wherein each methylene group is substituted by up to two fluorine atoms and each methyl group is substituted by up to three fluorine atoms, or
  (d) $C_{3-6}$-cycloalkyl, $R^{1.1.3}$, $R^{1.1.4}$ independently of one another denote
  (a) H,
  (b) $C_{1-4}$-alkyl or
  (c) $C_{3-6}$-cycloalkyl, $R^{1.3}$ denotes
  (a) halogen, —$NO_2$, —CN, —$OR^{1.1.1}$, —$SR^{1.1.1}$, —$CO_2R^{1.1.1}$, $C_{1-6}$-alkyl or
  (b) $C_{1-3}$-alkyl, wherein each methylene group is substituted by up to two fluorine atoms and each methyl group is substituted by up to three fluorine atoms, and $R^{1.4}$ denotes
  (a) halogen, —$NO_2$, —CN, —$OR^{1.1.1}$, —$SR^{1.1.1}$, $C_{1-6}$-alkyl,
  (b) $C_{1-3}$-alkyl, wherein each methylene group is substituted by up to two fluorine atoms and each methyl group is substituted by up to three fluorine atoms, or
  (c) an oxo group, or a salt thereof.

5. A compound of the formula I according to claim 1, wherein $R^1$ denotes

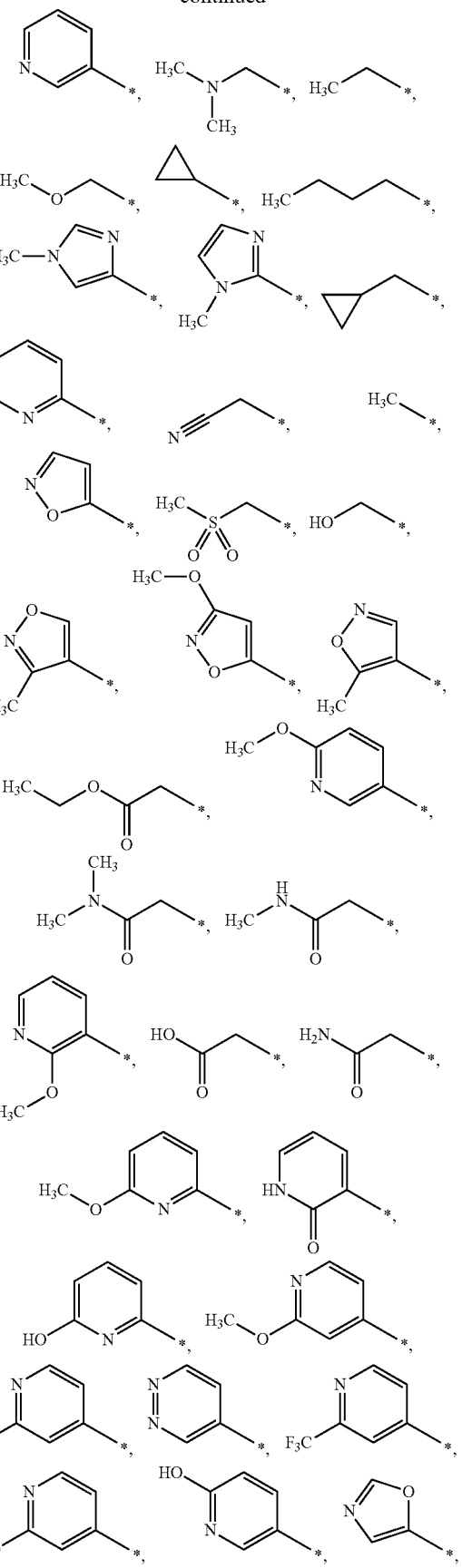

-continued

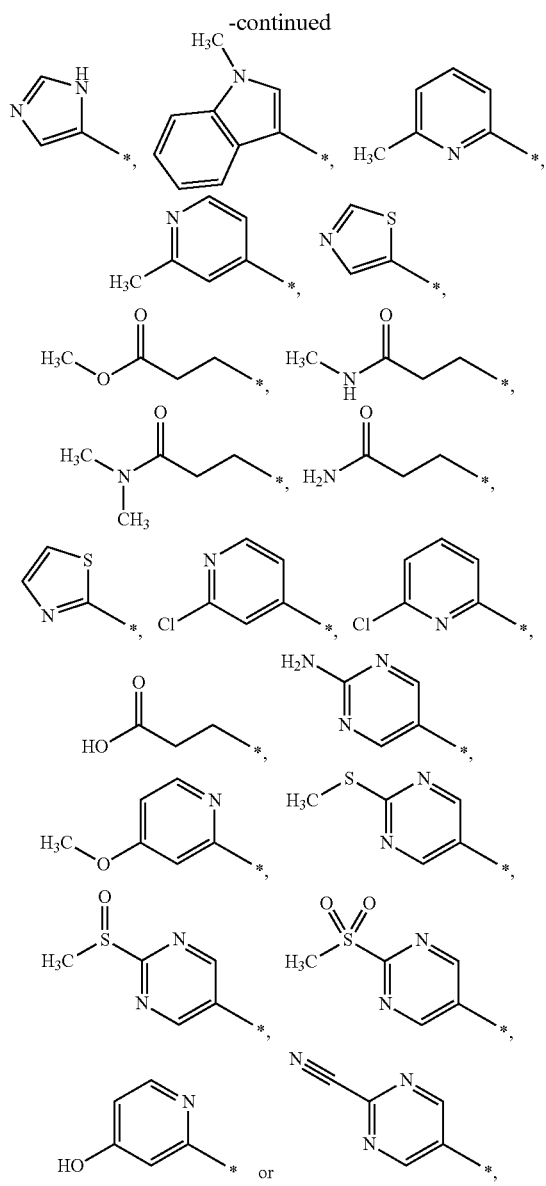

or a salt thereof.

6. A compound of the formula I according to claim 1, wherein
$R^2$ denotes H or $C_{1-3}$-alkyl,
or a salt thereof.

7. A compound of the formula I according to claim 1, wherein
$R^3$ independently of one another denote
(a) H, halogen, $C_{1-3}$-alkyl, —O—$C_{1-3}$-alkyl or
(b) $C_{1-3}$-alkyl, wherein each methylene group is substituted by up to two fluorine atoms and each methyl group is substituted by up to three fluorine atoms,
or a salt thereof.

8. A compound of the formula I according to claim 1, wherein
$R^4$ denotes H or halogen,
or a salt thereof.

9. A compound of the formula I according to claim 1, wherein
$R^5$ denotes
(a) H, halogen,
(b) $C_{1-3}$-alkyl,
(c) $C_{1-3}$-alkyl, wherein each methylene group is substituted by up to two fluorine atoms and each methyl group is substituted by up to three fluorine atoms,
(d) —O—$C_{1-3}$-alkyl,
(e) —C(O)—O—$C_{1-3}$-alkyl or —C(O)—NH$_2$,
or a salt thereof.

10. A compound of the formula I according to claim 1, wherein
$R^6$ denotes
(a) H, halogen,
(b) $C_{1-3}$-alkylene—$R^{6.1}$,
(c) $C_{1-3}$-alkyl, wherein each methylene group is substituted by up to two fluorine atoms and each methyl group is substituted by up to three fluorine atoms,
(d) —OH, —O—$C_{1-4}$-alkyl,
(e) —OCHF$_2$, —O—CF$_3$,
(f) —C(O)—O—$R^{6.2}$, —CN, —C(O)—CH$_3$, —C(O)—NH$_2$ or
(g) pyrrolyl,
$R^{6.1}$ denotes H or —OH and
$R^{6.2}$ denotes H or $C_{1-3}$-alkyl,
or a salt thereof.

11. A compound of the formula I according to claim 1, wherein
$R^7$ denotes
(a) H, halogen,
(b) $C_{1-3}$-alkyl,
(c) $C_{1-3}$-alkyl, wherein each methylene group is substituted by up to two fluorine atoms and each methyl group is substituted by up to three fluorine atoms,
(d) —O—$C_{1-3}$-alkyl,
(e) —C(O)—NH$_2$ or —C(O)-pyrrolidinyl,
or a salt thereof.

12. A compound of the formula I according to claim 1, wherein
$R^8$ denotes
(a) H, halogen,
(b) $C_{1-4}$-alkyl,
(c) $C_{1-3}$-alkyl, wherein each methylene group is substituted by up to two fluorine atoms and each methyl group is substituted by up to three fluorine atoms,
(d) —O—$C_{1-3}$-alkyl,
(e) —O—CF$_3$,
(f) —CN, —C(O)—NH$_2$ or
(g) pyrrolyl,
or a salt thereof.

13. A compound of the formula I according to claim 1, wherein
$R^1$ denotes

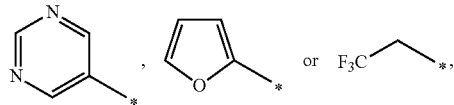

$R^2$ denotes H or —CH$_3$,
$R^3$ denotes H, F, —CF$_3$, —CH$_3$ or —O—CH$_3$,
$R^4$ denotes H or Cl,
$R^5$ denotes H, Cl, $C_{1-3}$-alkyl, —CF$_3$, —O—$C_{1-3}$-alkyl, —C(O)—O—$C_{1-3}$-alkyl or —C(O)—NH$_2$,
$R^6$ denotes H, F, Cl, $C_{1-3}$-alkyl, —CF$_3$, —O—$C_{1-4}$-alkyl, —OCF$_3$, —C(O)—NH$_2$ or pyrrolyl,
$R^7$ denotes H, F, Cl, $C_{1-3}$-alkyl, —CF$_3$, —O—$C_{1-3}$-alkyl, —C(O)—NH$_2$ or —C(O)-pyrrolidinyl, and $R^8$ denotes H, F, Cl, Br, $C_{1-4}$-alkyl, —$CF_3$, —O—$C_{1-3}$-alkyl, —$OCF_3$, —C(O)—$NH_2$, —$OCF_3$ or pyrrolyl,
or a salt thereof.
14. A compound of the formula I according to claim 1, wherein
$R^1$ denotes
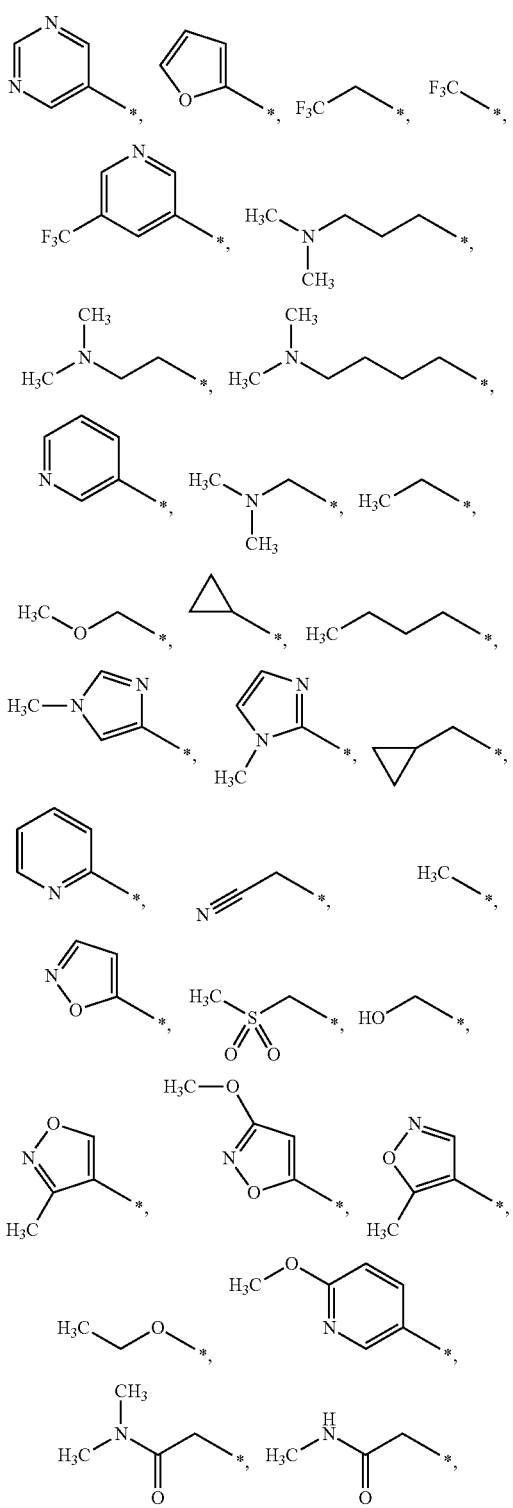
-continued
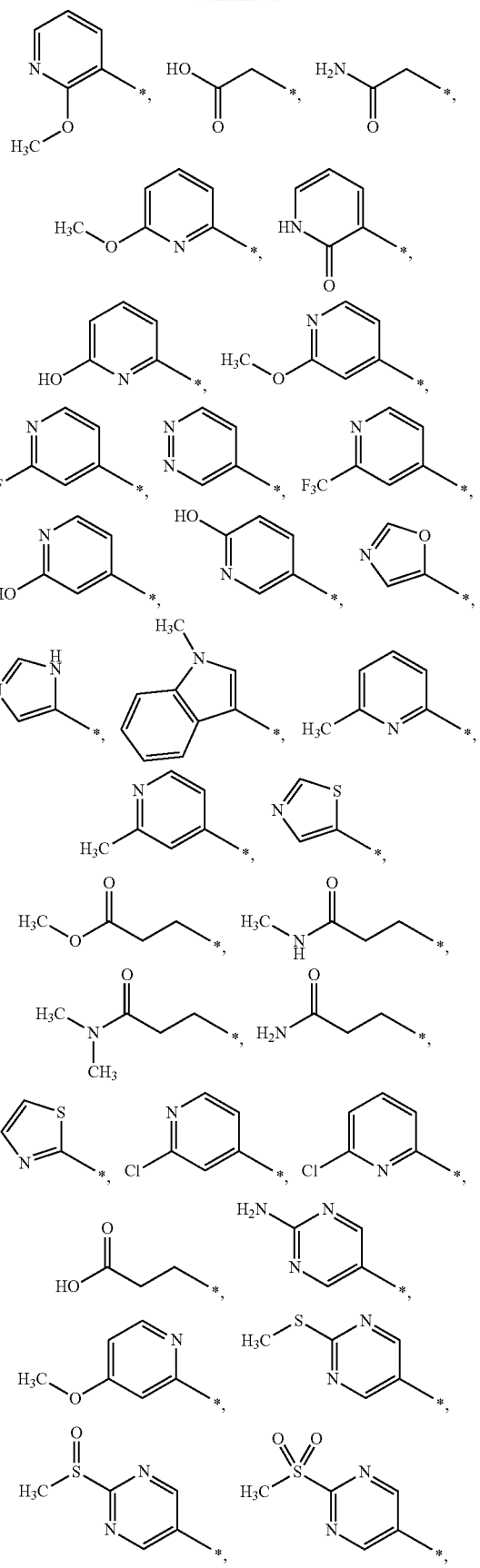

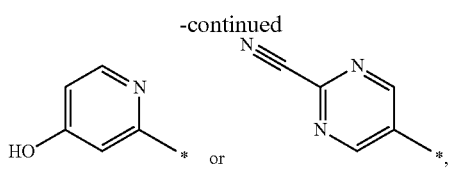

R² denotes H, —CH₃ or —C₂H₅,
R³ denotes H, F, Cl, —CF₃, —CH₃ or —O—CH₃,
R⁴ denotes H or Cl,
R⁵ denotes H, Cl, C$_{1-3}$-alkyl, —CF₃, —O—C$_{1-3}$-alkyl, —C(O)—O—C$_{1-3}$-alkyl or —C(O)—NH₂, R⁶ denotes H, F, Cl, Br, —CN, C$_{1-3}$-alkyl, —CF₃, —COOH, —COO—C$_{1-3}$-alkyl, —CH(OH)CH₃, —OH, —O—C$_{1-4}$-alkyl, —OCF₃, —OCHF₂, —C(O)—CH₃, —C(O)—NH₂ or pyrrolyl,
R⁷ denotes H, F, Cl, C$_{1-3}$-alkyl, —CF₃, —O—C$_{1-3}$-alkyl, —C(O)—NH₂ or —C(O)-pyrrolidinyl and
R⁸ denotes H, F, Cl, Br, —CN, C$_{1-4}$-alkyl, —CF₃, —O—C$_{1-3}$-alkyl, —OCF₃, —C(O)—NH₂, —OCF₃ or pyrrolyl,
or a salt thereof.

15. A compound of the formula I according to claim 1, selected from the group consisting of:

| No. | Structure |
|---|---|
| (1) | 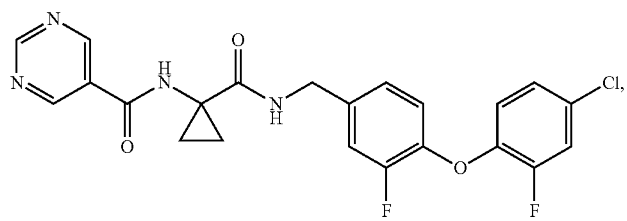 [SMILES: O=C(NC1(C(=O)NCc2ccc(Oc3ccc(Cl)cc3F)c(F)c2)CC1)c1cncnc1] |
| (2) | 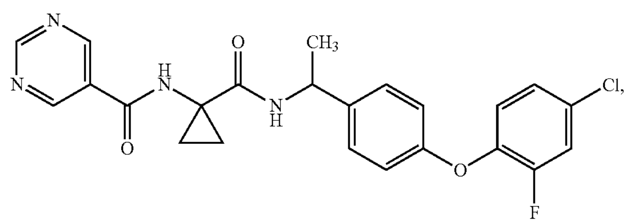 [SMILES: CC(NC(=O)C1(NC(=O)c2cncnc2)CC1)c1ccc(Oc2ccc(Cl)cc2F)cc1] |
| (3) | 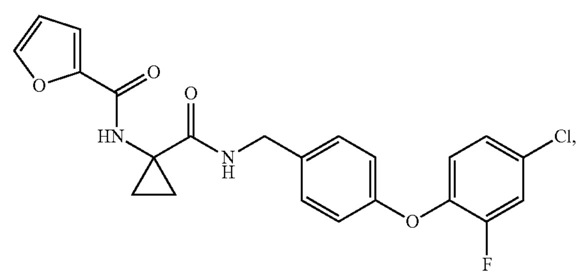 [SMILES: O=C(NC1(C(=O)NCc2ccc(Oc3ccc(Cl)cc3F)cc2)CC1)c1ccco1] |
| (4) | 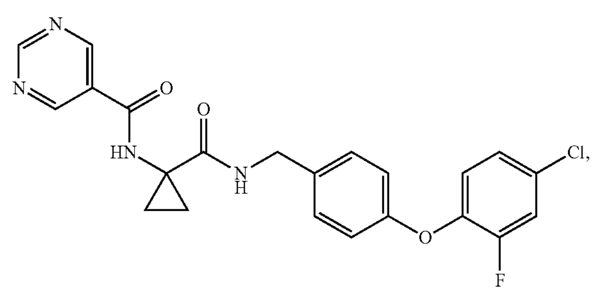 [SMILES: O=C(NC1(C(=O)NCc2ccc(Oc3ccc(Cl)cc3F)cc2)CC1)c1cncnc1] |
| (5) | 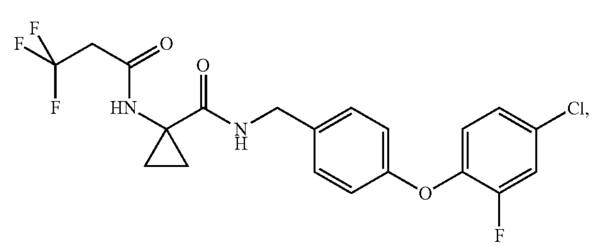 [SMILES: O=C(CC(F)(F)F)NC1(C(=O)NCc2ccc(Oc3ccc(Cl)cc3F)cc2)CC1] |

-continued

| No. | Structure |
|---|---|
| (6) | N-pyrimidin-5-yl-C(=O)-NH-(1-cyclopropyl)-C(=O)-NH-CH₂-(4-phenyl)-O-(4-chlorophenyl) |
| (7) | N-pyrimidin-5-yl-C(=O)-NH-(1-cyclopropyl)-C(=O)-NH-CH₂-(3-fluoro-4-phenyl)-O-(4-methoxyphenyl), OCH₃ |
| (8) | N-pyrimidin-5-yl-C(=O)-NH-(1-cyclopropyl)-C(=O)-NH-CH₂-(3-trifluoromethyl-4-phenyl)-O-(4-methoxyphenyl), OCH₃ |
| (9) | N-pyrimidin-5-yl-C(=O)-NH-(1-cyclopropyl)-C(=O)-NH-CH₂-(4-phenyl)-O-(4-carbamoylphenyl), NH₂ |
| (10) | N-pyrimidin-5-yl-C(=O)-NH-(1-cyclopropyl)-C(=O)-NH-CH₂-(2,6-dimethyl-4-phenoxyphenyl) |

| No. | Structure |
|---|---|
| (11) | 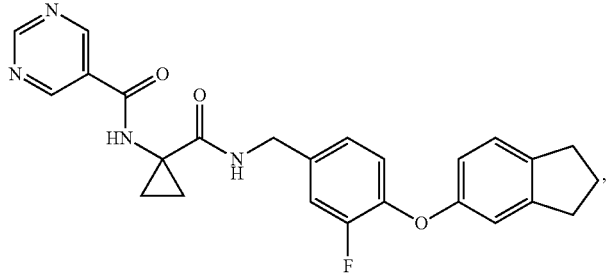 [SMILES: O=C(NC1(C(=O)NCc2ccc(Oc3ccc4c(c3)CCC4)c(F)c2)CC1)c1cncnc1] |
| (12) | 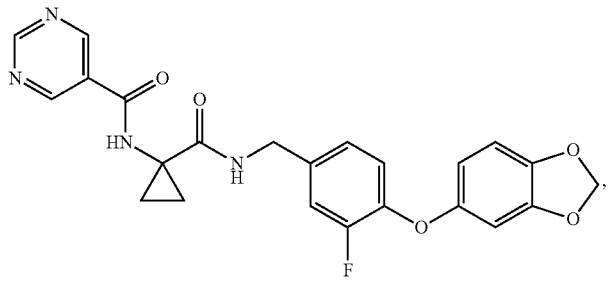 [SMILES: O=C(NC1(C(=O)NCc2ccc(Oc3ccc4c(c3)OCO4)c(F)c2)CC1)c1cncnc1] |
| (13) | 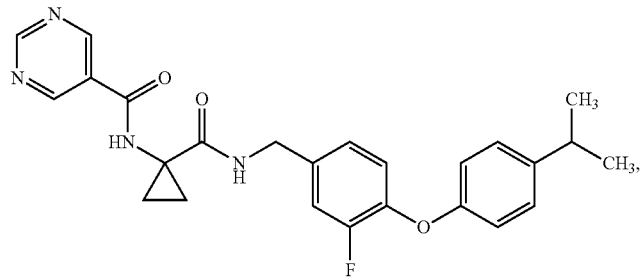 [SMILES: CC(C)c1ccc(Oc2ccc(CNC(=O)C3(NC(=O)c4cncnc4)CC3)cc2F)cc1] |
| (14) | 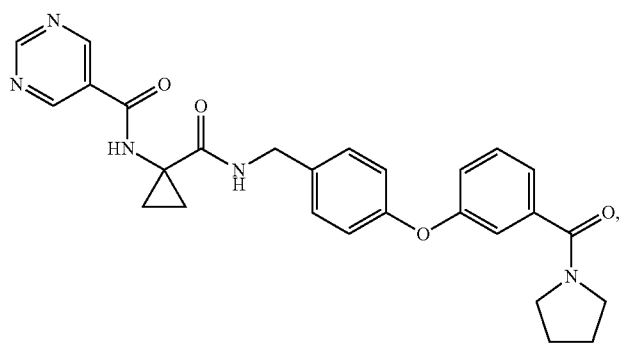 [SMILES: O=C(NC1(C(=O)NCc2ccc(Oc3cccc(C(=O)N4CCCC4)c3)cc2)CC1)c1cncnc1] |
| (15) | 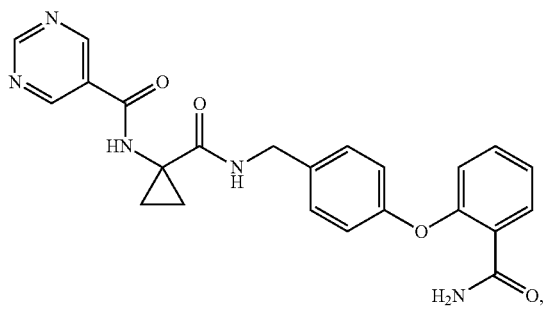 [SMILES: NC(=O)c1ccccc1Oc1ccc(CNC(=O)C2(NC(=O)c3cncnc3)CC2)cc1] |

| No. | Structure |
|---|---|
| (16) | 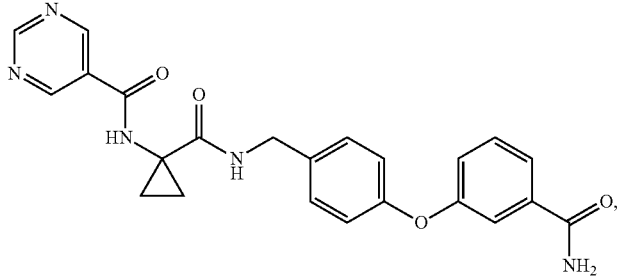 [SMILES: NC(=O)c1cccc(Oc2ccc(CNC(=O)C3(NC(=O)c4cncnc4)CC3)cc2)c1] |
| (17) | 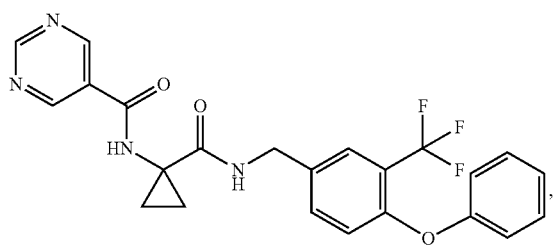 [SMILES: O=C(NC1(C(=O)NCc2ccc(Oc3ccccc3)c(C(F)(F)F)c2)CC1)c1cncnc1] |
| (18) | 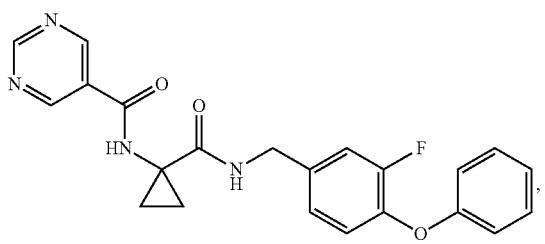 [SMILES: O=C(NC1(C(=O)NCc2ccc(Oc3ccccc3)c(F)c2)CC1)c1cncnc1] |
| (19) | 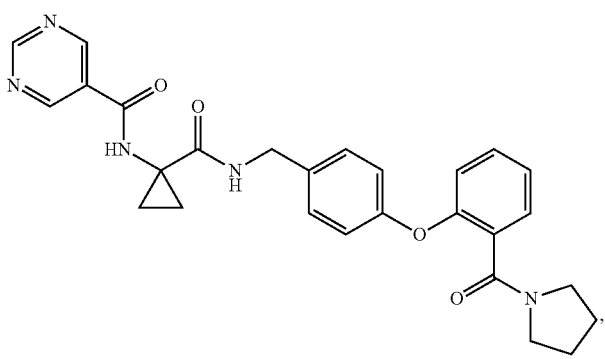 [SMILES: O=C(NC1(C(=O)NCc2ccc(Oc3ccccc3C(=O)N3CCCC3)cc2)CC1)c1cncnc1] |
| (20) | 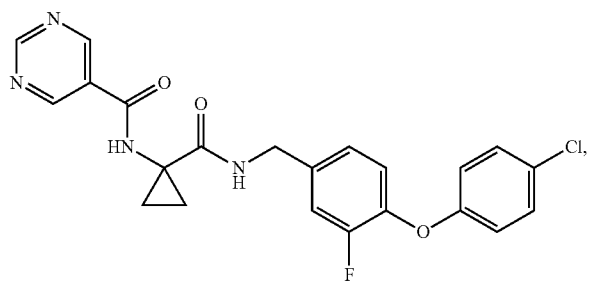 [SMILES: O=C(NC1(C(=O)NCc2ccc(Oc3ccc(Cl)cc3)c(F)c2)CC1)c1cncnc1] |

-continued
| No. | Structure |
|---|---|
| (21) | 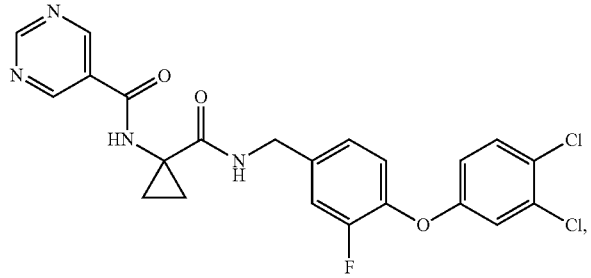 [SMILES: O=C(NC1(C(=O)NCc2ccc(Oc3ccc(Cl)c(Cl)c3)c(F)c2)CC1)c1cncnc1] |
| (22) | 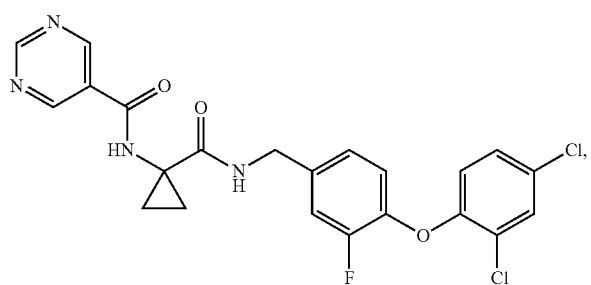 [SMILES: O=C(NC1(C(=O)NCc2ccc(Oc3ccc(Cl)cc3Cl)c(F)c2)CC1)c1cncnc1] |
| (23) | 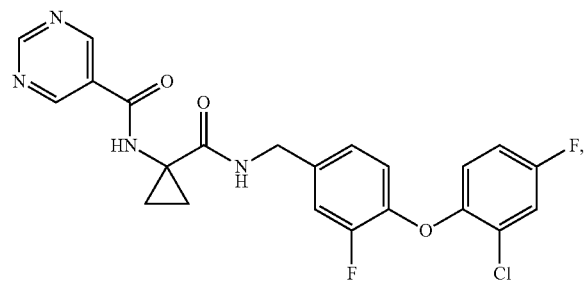 |
| (24) | 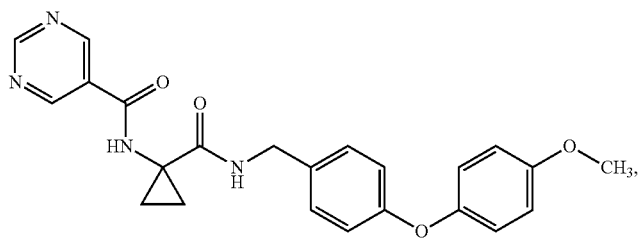 [SMILES: COc1ccc(Oc2ccc(CNC(=O)C3(NC(=O)c4cncnc4)CC3)cc2)cc1] |
| (25) | 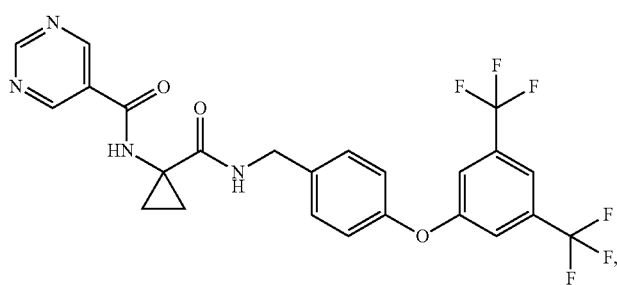 [SMILES: O=C(NC1(C(=O)NCc2ccc(Oc3cc(C(F)(F)F)cc(C(F)(F)F)c3)cc2)CC1)c1cncnc1] |

| No. | Structure |
|---|---|
| (26) | 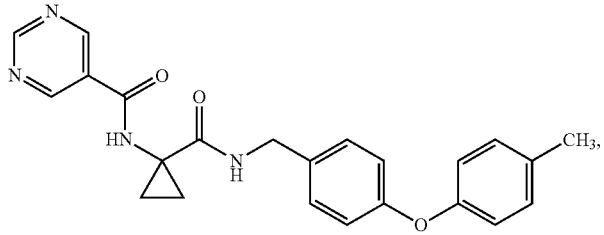 [SMILES: Cc1ccc(Oc2ccc(CNC(=O)C3(NC(=O)c4cncnc4)CC3)cc2)cc1] |
| (27) | 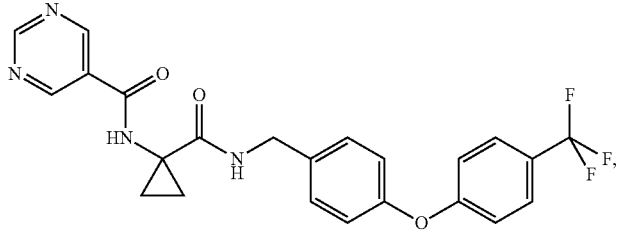 [SMILES: O=C(NC1(C(=O)NCc2ccc(Oc3ccc(C(F)(F)F)cc3)cc2)CC1)c1cncnc1] |
| (28) | 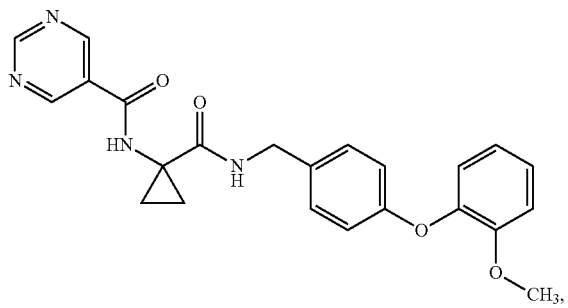 [SMILES: COc1ccccc1Oc1ccc(CNC(=O)C2(NC(=O)c3cncnc3)CC2)cc1] |
| (29) | 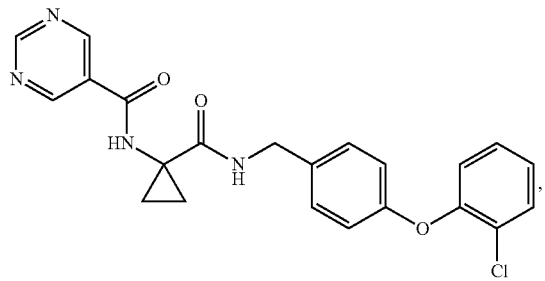 [SMILES: O=C(NC1(C(=O)NCc2ccc(Oc3ccccc3Cl)cc2)CC1)c1cncnc1] |
| (30) | 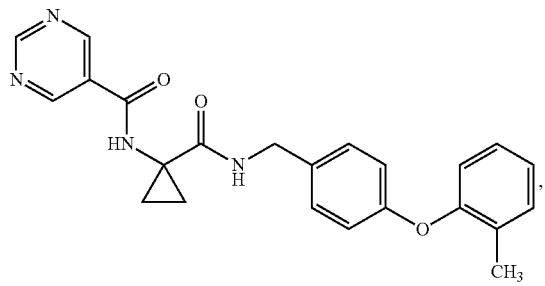 [SMILES: Cc1ccccc1Oc1ccc(CNC(=O)C2(NC(=O)c3cncnc3)CC2)cc1] |

| No. | Structure |
|---|---|
| (31) | 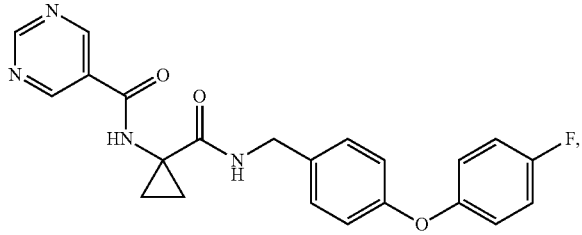 [SMILES: O=C(NC1(C(=O)NCc2ccc(Oc3ccc(F)cc3)cc2)CC1)c1cncnc1] |
| (32) | 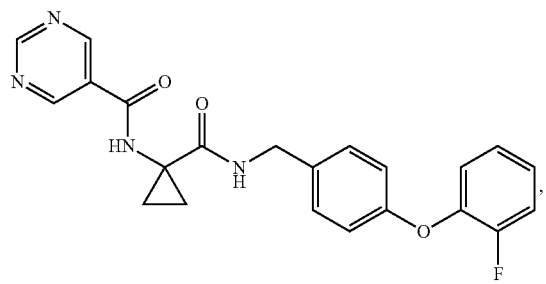 [SMILES: O=C(NC1(C(=O)NCc2ccc(Oc3ccccc3F)cc2)CC1)c1cncnc1] |
| (33) | 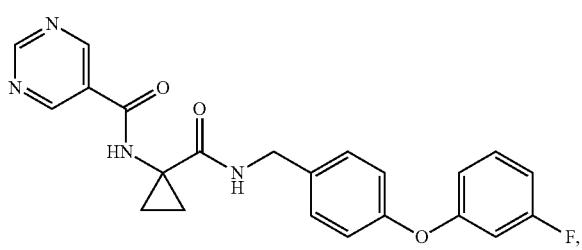 [SMILES: O=C(NC1(C(=O)NCc2ccc(Oc3cccc(F)c3)cc2)CC1)c1cncnc1] |
| (34) | 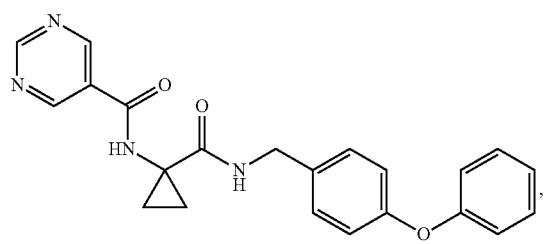 |
| (35) | 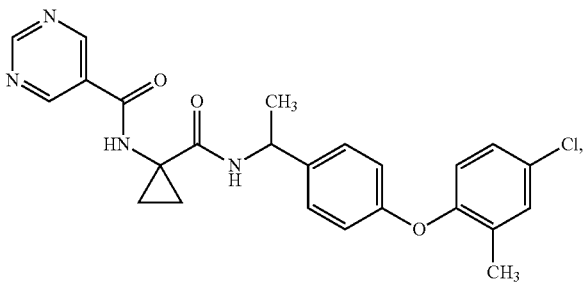 [SMILES: Cc1cc(Cl)ccc1Oc1ccc(C(C)NC(=O)C2(NC(=O)c3cncnc3)CC2)cc1] |
| (36) | 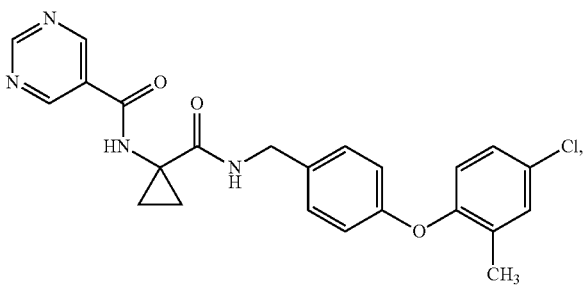 [SMILES: Cc1cc(Cl)ccc1Oc1ccc(CNC(=O)C2(NC(=O)c3cncnc3)CC2)cc1] |

-continued
| No. | Structure |
|---|---|
| (37) | 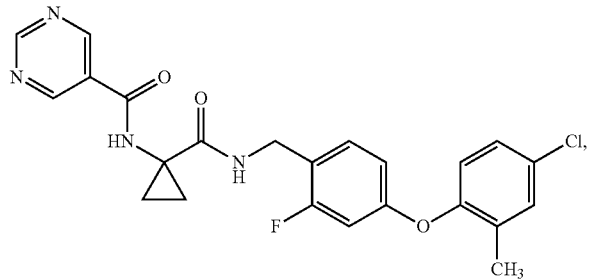 |
| (38) | 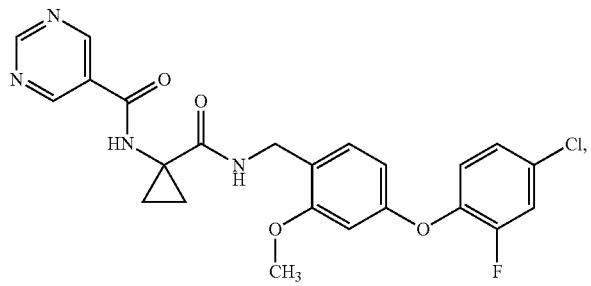 [SMILES: COc1cc(Oc2ccc(Cl)cc2F)ccc1CNC(=O)C1(NC(=O)c2cncnc2)CC1] |
| (39) | 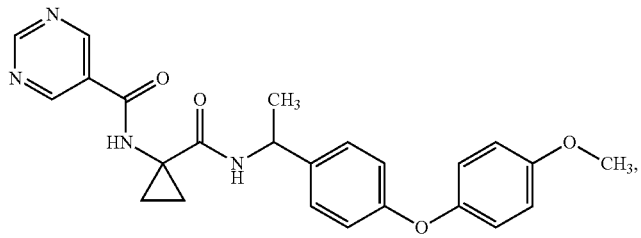 [SMILES: COc1ccc(Oc2ccc(C(C)NC(=O)C3(NC(=O)c4cncnc4)CC3)cc2)cc1] |
| (40) | 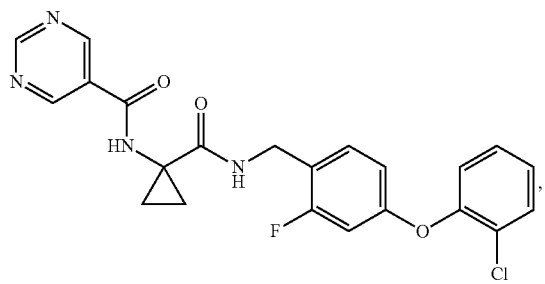 |
| (41) | 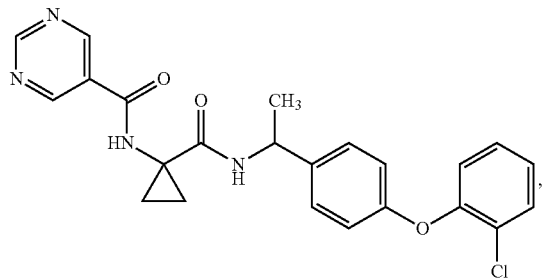 [SMILES: CC(NC(=O)C1(NC(=O)c2cncnc2)CC1)c1ccc(Oc2ccccc2Cl)cc1] |

| No. | Structure |
| --- | --- |
| (42) | 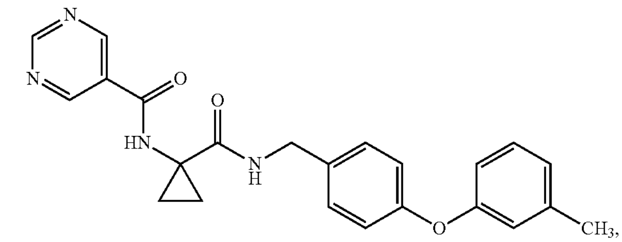 |
| (43) | 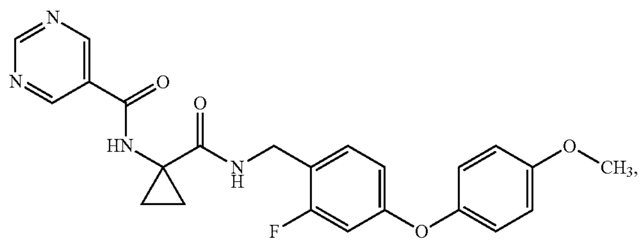 [SMILES: COc1ccc(Oc2ccc(CNC(=O)C3(NC(=O)c4cncnc4)CC3)c(F)c2)cc1] |
| (44) | 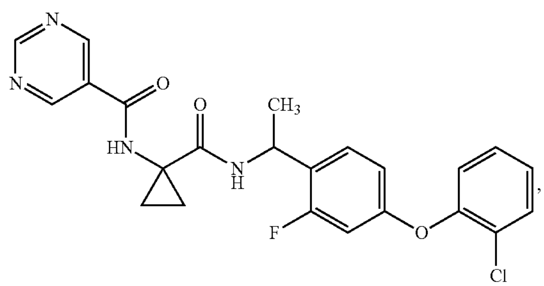 [SMILES: CC(NC(=O)C1(NC(=O)c2cncnc2)CC1)c1ccc(Oc2ccccc2Cl)cc1F] |
| (45) | 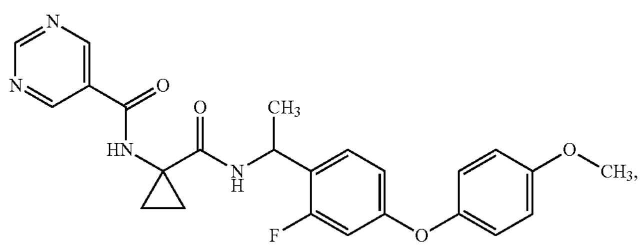 [SMILES: COc1ccc(Oc2ccc(C(C)NC(=O)C3(NC(=O)c4cncnc4)CC3)c(F)c2)cc1] |
| (46) | 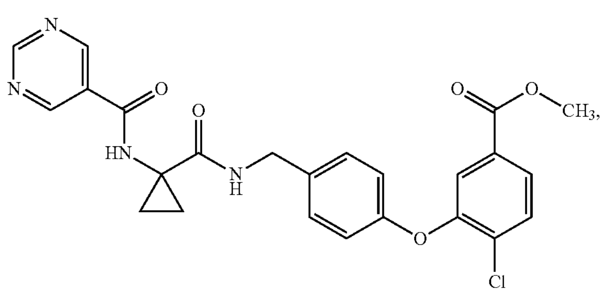 [SMILES: COC(=O)c1ccc(Cl)c(Oc2ccc(CNC(=O)C3(NC(=O)c4cncnc4)CC3)cc2)c1] |
| (47) | 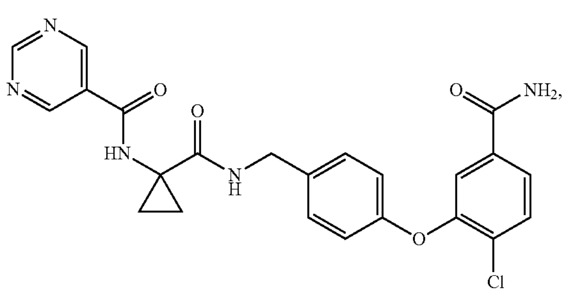 [SMILES: NC(=O)c1ccc(Cl)c(Oc2ccc(CNC(=O)C3(NC(=O)c4cncnc4)CC3)cc2)c1] |

| No. | Structure |
|---|---|
| (48) | 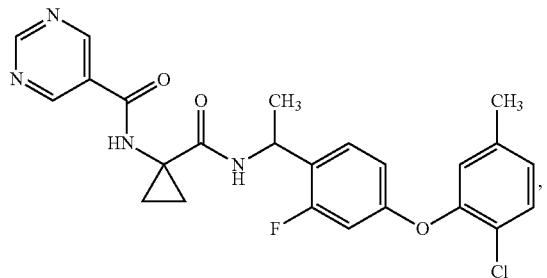 [SMILES: Cc1ccc(Cl)c(Oc2ccc(C(C)NC(=O)C3(NC(=O)c4cncnc4)CC3)c(F)c2)c1] |
| (49) | 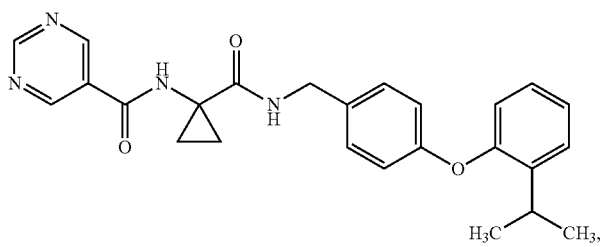 [SMILES: CC(C)c1ccccc1Oc1ccc(CNC(=O)C2(NC(=O)c3cncnc3)CC2)cc1] |
| (50) | 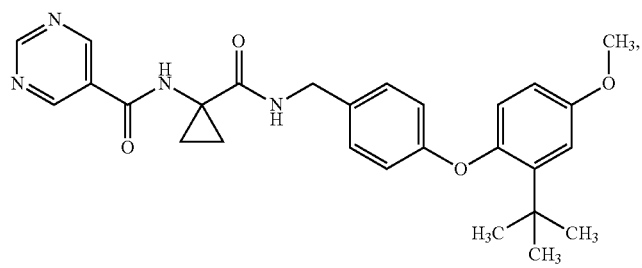 [SMILES: COc1ccc(Oc2ccc(CNC(=O)C3(NC(=O)c4cncnc4)CC3)cc2)c(C(C)(C)C)c1] |
| (51) | 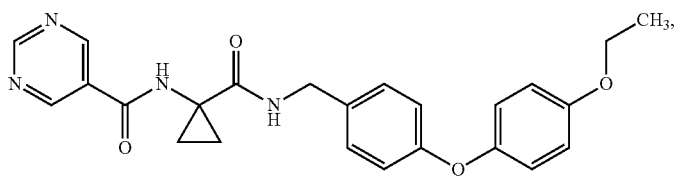 [SMILES: CCOc1ccc(Oc2ccc(CNC(=O)C3(NC(=O)c4cncnc4)CC3)cc2)cc1] |
| (52) | 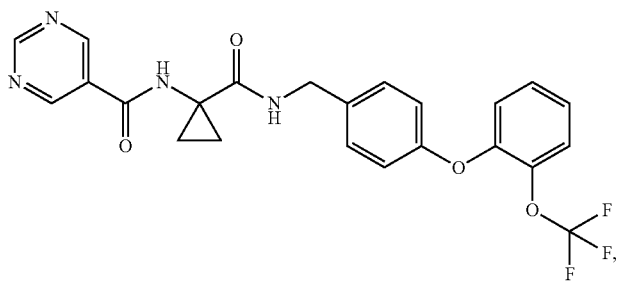 [SMILES: O=C(NC1(C(=O)NCc2ccc(Oc3ccccc3OC(F)(F)F)cc2)CC1)c1cncnc1] |
| (53) | 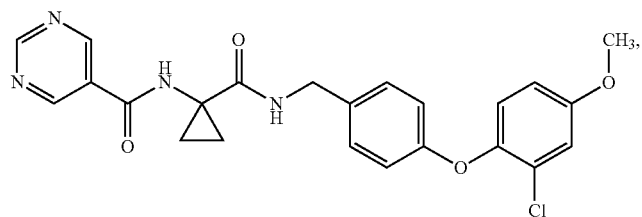 |

| No. | Structure |
|---|---|
| (54) | 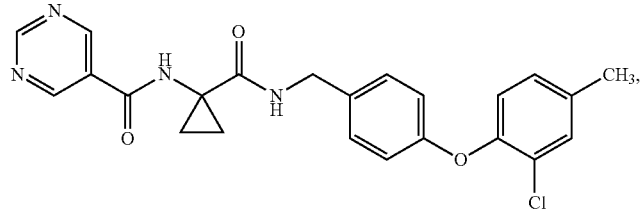 [SMILES: Cc1ccc(Oc2ccc(CNC(=O)C3(NC(=O)c4cncnc4)CC3)cc2)c(Cl)c1] |
| (55) | 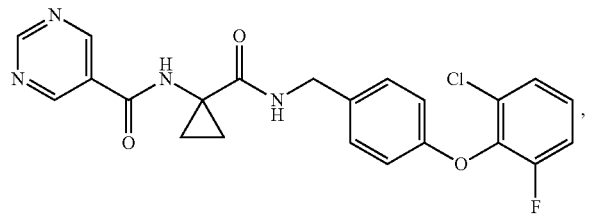 [SMILES: O=C(NC1(C(=O)NCc2ccc(Oc3c(F)cccc3Cl)cc2)CC1)c1cncnc1] |
| (56) | 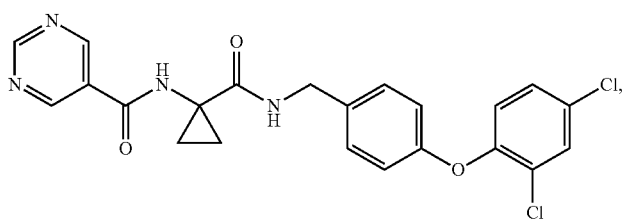 [SMILES: O=C(NC1(C(=O)NCc2ccc(Oc3ccc(Cl)cc3Cl)cc2)CC1)c1cncnc1] |
| (57) | 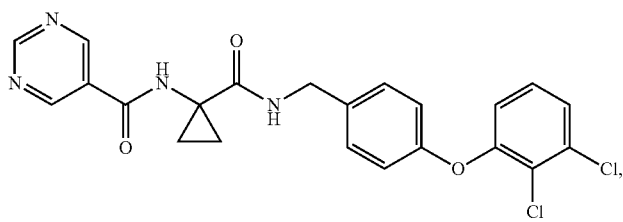 [SMILES: O=C(NC1(C(=O)NCc2ccc(Oc3cccc(Cl)c3Cl)cc2)CC1)c1cncnc1] |
| (58) | 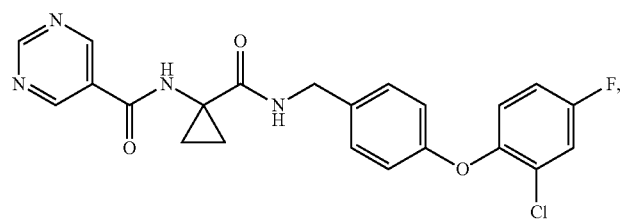 |
| (59) | 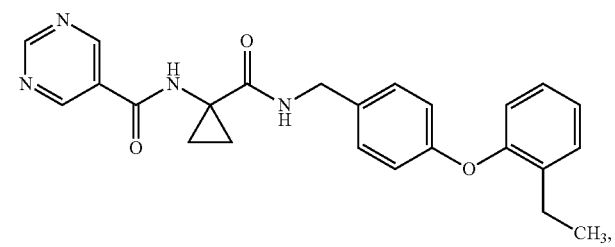 [SMILES: CCc1ccccc1Oc1ccc(CNC(=O)C2(NC(=O)c3cncnc3)CC2)cc1] |
| (60) | 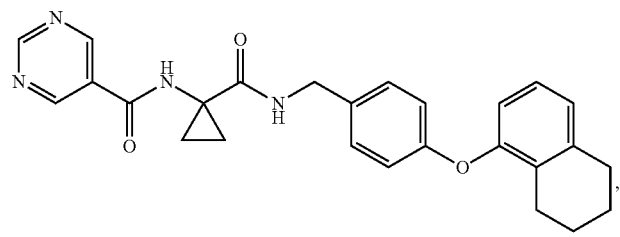 [SMILES: O=C(NC1(C(=O)NCc2ccc(Oc3cccc4c3CCCC4)cc2)CC1)c1cncnc1] |

| No. | Structure |
|---|---|
| (61) | 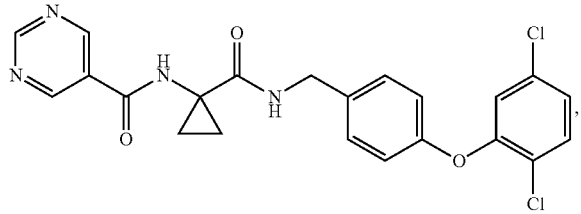 |
| (62) | 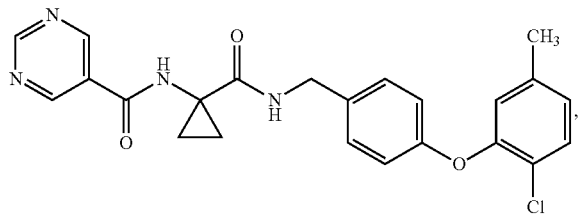 [SMILES: O=C(NC1(C(=O)NCc2ccc(Oc3cc(Cl)ccc3Cl)cc2)CC1)c1cncnc1] |
| (63) | 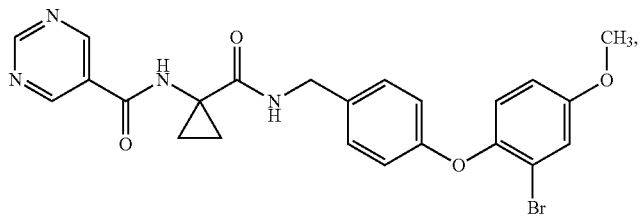 [SMILES: COc1ccc(Oc2ccc(CNC(=O)C3(NC(=O)c4cncnc4)CC3)cc2)c(Br)c1] |
| (64) | 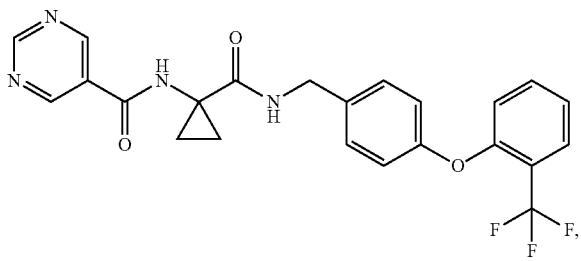 [SMILES: O=C(NC1(C(=O)NCc2ccc(Oc3ccccc3C(F)(F)F)cc2)CC1)c1cncnc1] |
| (65) | 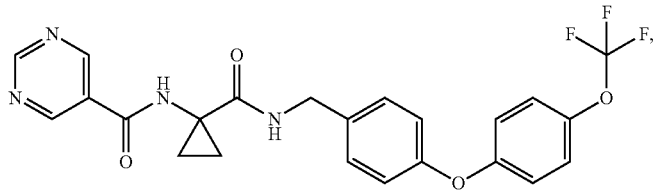 [SMILES: O=C(NC1(C(=O)NCc2ccc(Oc3ccc(OC(F)(F)F)cc3)cc2)CC1)c1cncnc1] |
| (66) | 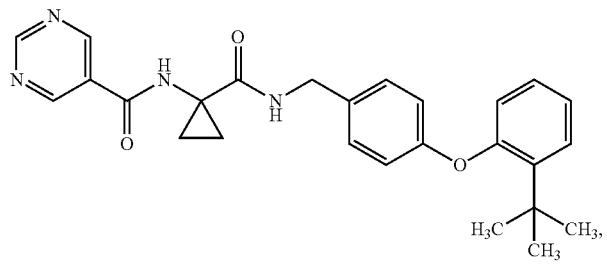 [SMILES: CC(C)(C)c1ccccc1Oc1ccc(CNC(=O)C2(NC(=O)c3cncnc3)CC2)cc1] |

-continued
| No. | Structure |
|---|---|
| (67) | 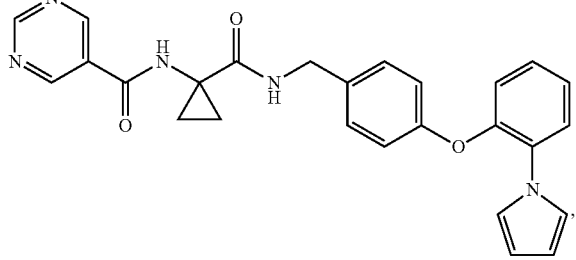 |
| (68) | 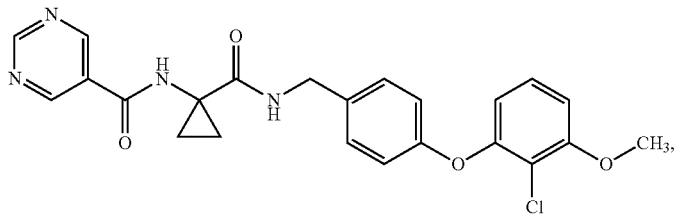 [SMILES: COc1cccc(Oc2ccc(CNC(=O)C3(NC(=O)c4cncnc4)CC3)cc2)c1Cl] |
| (69) | 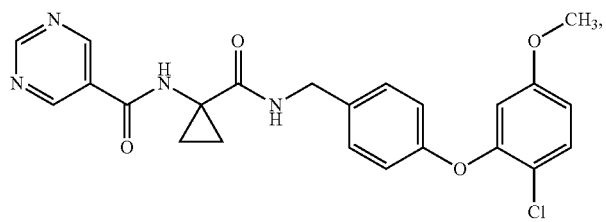 [SMILES: COc1ccc(Cl)c(Oc2ccc(CNC(=O)C3(NC(=O)c4cncnc4)CC3)cc2)c1] |
| (70) | 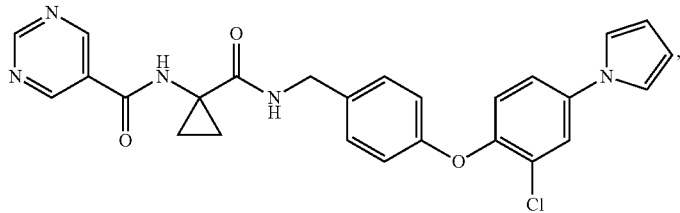 [SMILES: O=C(NC1(C(=O)NCc2ccc(Oc3ccc(-n4cccc4)cc3Cl)cc2)CC1)c1cncnc1] |
| (71) | 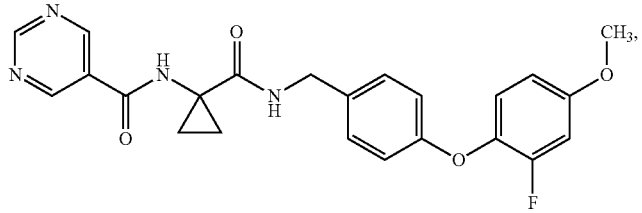 [SMILES: COc1ccc(Oc2ccc(CNC(=O)C3(NC(=O)c4cncnc4)CC3)cc2)c(F)c1] |
| (72) | 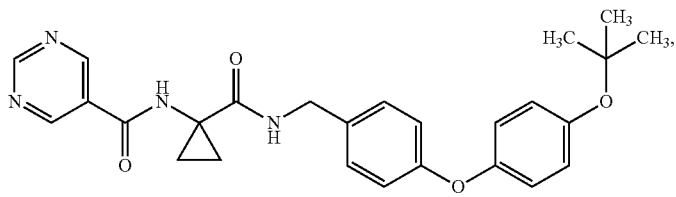 [SMILES: CC(C)(C)Oc1ccc(Oc2ccc(CNC(=O)C3(NC(=O)c4cncnc4)CC3)cc2)cc1] |
| (73) | 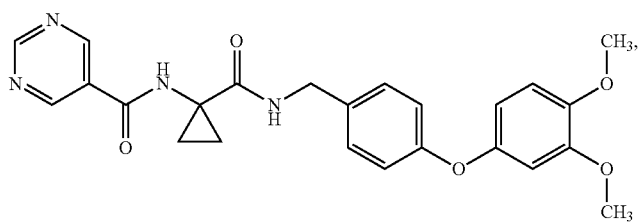 [SMILES: COc1ccc(Oc2ccc(CNC(=O)C3(NC(=O)c4cncnc4)CC3)cc2)cc1OC] |

|No.|Structure|
|---|---|
|(74)|*[chemical structure: pyrimidine-5-carboxamide-N-cyclopropane-C(O)NH-CH2-(2-chlorophenyl)-O-(2-chlorophenyl)]*|
|(75)|*[chemical structure: pyrimidine-5-carboxamide-N-cyclopropane-C(O)NH-CH(CH3)-(2-chlorophenyl)-O-(2-chlorophenyl)]*|
|(76)|*[chemical structure: pyrimidine-5-carboxamide-N-cyclopropane-C(O)NH-CH2-(2-chlorophenyl)-O-(2-chloro-4-hydroxyphenyl)]*|
|(77)|*[chemical structure: trifluoroacetyl-N-cyclopropane-C(O)NH-CH2-(phenyl)-O-(2-chloro-4-methoxyphenyl)]*|
|(78)|*[chemical structure: pyrimidine-5-carboxamide-N-cyclopropane-C(O)NH-CH2-(phenyl)-O-(2-chloro-4-bromophenyl)]*|
|(79)|*[chemical structure: pyrimidine-5-carboxamide-N-cyclopropane-C(O)NH-CH2-(phenyl)-O-(4-bromo-2-trifluoromethylphenyl)]*|
|(80)|*[chemical structure: pyrimidine-5-carboxamide-N-cyclopropane-C(O)NH-CH2-(phenyl)-O-(2-bromo-4-chlorophenyl)]*|

| No. | Structure |
|---|---|
| (81) | 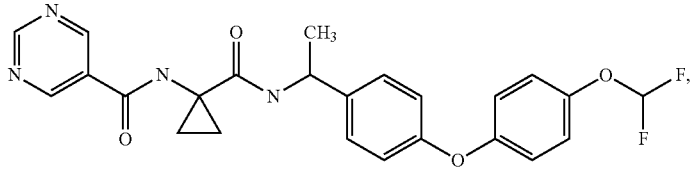 [SMILES: CC(NC(=O)C1(NC(=O)c2cncnc2)CC1)c1ccc(Oc2ccc(OC(F)F)cc2)cc1] |
| (82) | 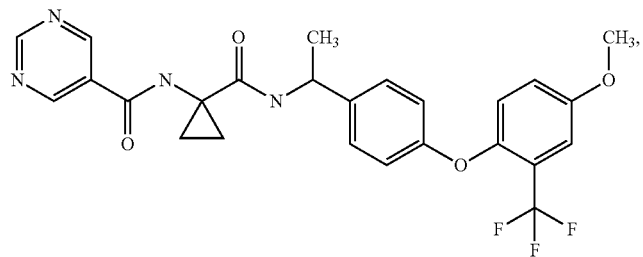 [SMILES: COc1ccc(Oc2ccc(C(C)NC(=O)C3(NC(=O)c4cncnc4)CC3)cc2)c(C(F)(F)F)c1] |
| (83) | 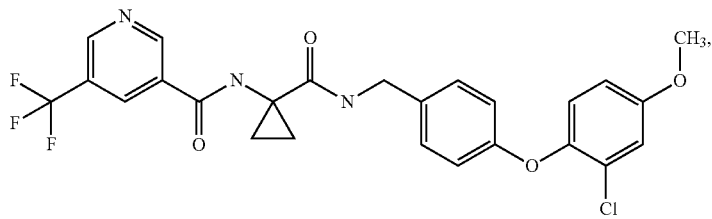 [SMILES: COc1ccc(Oc2ccc(CNC(=O)C3(NC(=O)c4cncc(C(F)(F)F)c4)CC3)cc2)c(Cl)c1] |
| (84) | 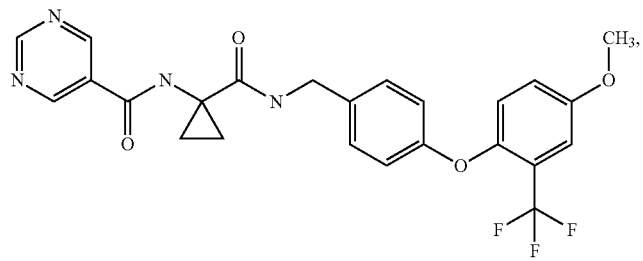 [SMILES: COc1ccc(Oc2ccc(CNC(=O)C3(NC(=O)c4cncnc4)CC3)cc2)c(C(F)(F)F)c1] |
| (85) | 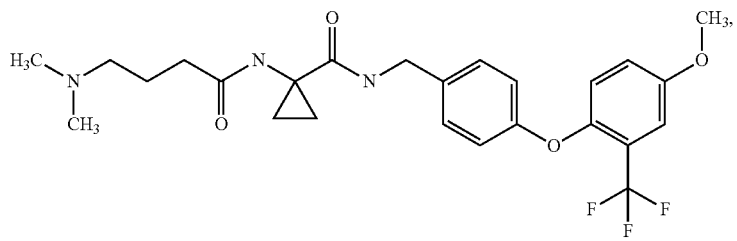 [SMILES: COc1ccc(Oc2ccc(CNC(=O)C3(NC(=O)CCCN(C)C)CC3)cc2)c(C(F)(F)F)c1] |
| (86) | 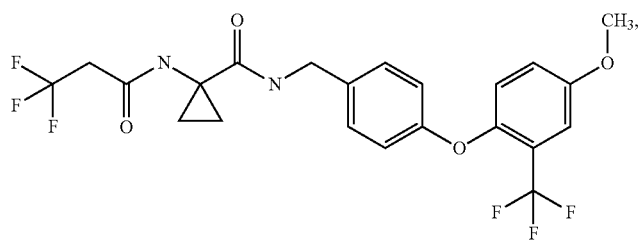 [SMILES: COc1ccc(Oc2ccc(CNC(=O)C3(NC(=O)CC(F)(F)F)CC3)cc2)c(C(F)(F)F)c1] |

| No. | Structure |
|---|---|
| (87) | *(chemical structure)* |
| (88) | *(chemical structure)* |
| (89) | *(chemical structure)* |
| (90) | *(chemical structure)* |
| (91) | *(chemical structure)* |
| (92) | *(chemical structure)* |

| No. | Structure |
|---|---|
| (93) | 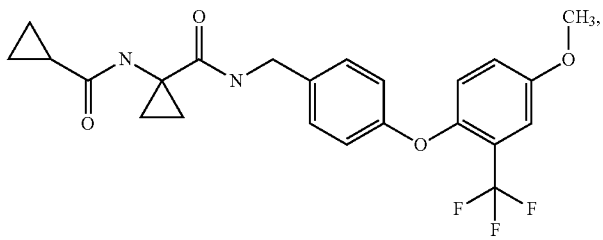 [SMILES: COc1ccc(Oc2ccc(CNC(=O)C3(NC(=O)C4CC4)CC3)cc2)c(C(F)(F)F)c1] |
| (94) | 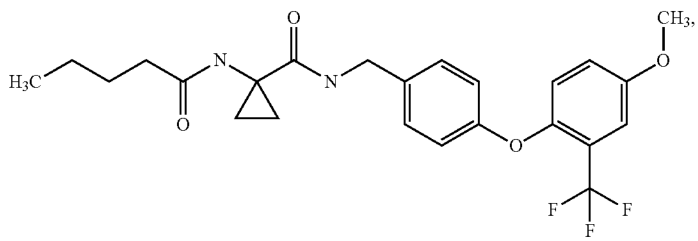 [SMILES: CCCCC(=O)NC1(C(=O)NCc2ccc(Oc3ccc(OC)cc3C(F)(F)F)cc2)CC1] |
| (95) | 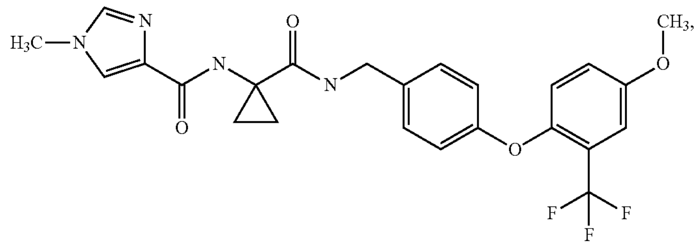 [SMILES: COc1ccc(Oc2ccc(CNC(=O)C3(NC(=O)c4cn(C)cn4)CC3)cc2)c(C(F)(F)F)c1] |
| (96) | 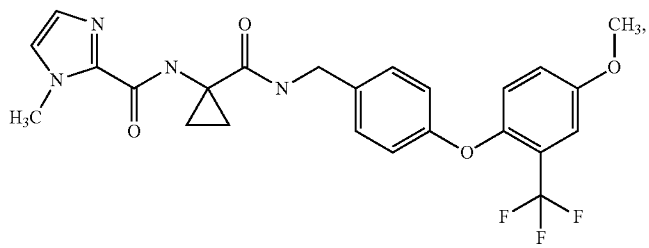 [SMILES: COc1ccc(Oc2ccc(CNC(=O)C3(NC(=O)c4nccn4C)CC3)cc2)c(C(F)(F)F)c1] |
| (97) | 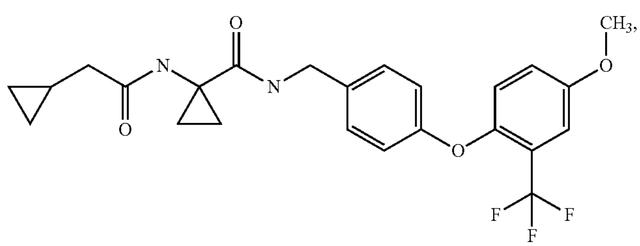 [SMILES: COc1ccc(Oc2ccc(CNC(=O)C3(NC(=O)CC4CC4)CC3)cc2)c(C(F)(F)F)c1] |
| (98) | 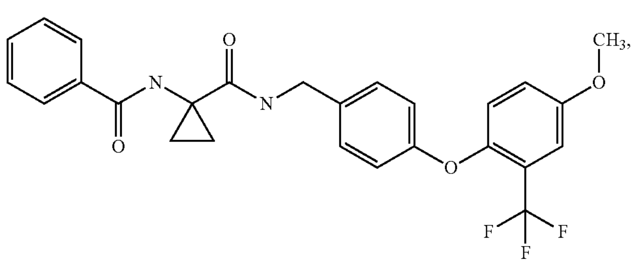 [SMILES: COc1ccc(Oc2ccc(CNC(=O)C3(NC(=O)c4ccccc4)CC3)cc2)c(C(F)(F)F)c1] |

| No. | Structure |
|---|---|
| (99) | 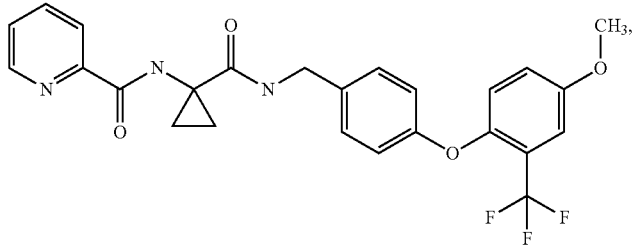 [SMILES: COc1ccc(Oc2ccc(CNC(=O)C3(NC(=O)c4ccccn4)CC3)cc2)c(C(F)(F)F)c1] |
| (100) | 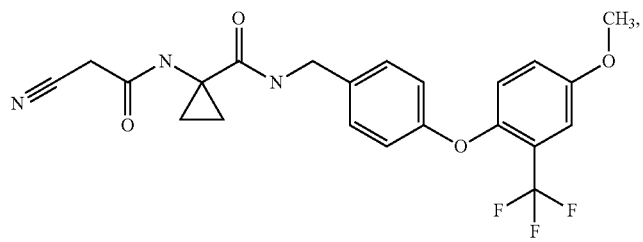 [SMILES: COc1ccc(Oc2ccc(CNC(=O)C3(NC(=O)CC#N)CC3)cc2)c(C(F)(F)F)c1] |
| (101) | 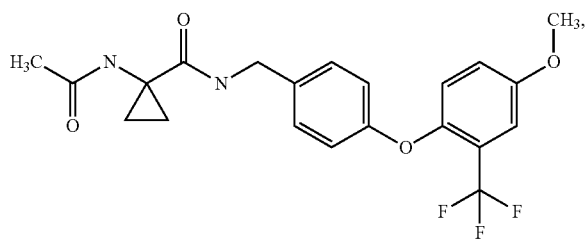 [SMILES: COc1ccc(Oc2ccc(CNC(=O)C3(NC(C)=O)CC3)cc2)c(C(F)(F)F)c1] |
| (102) | 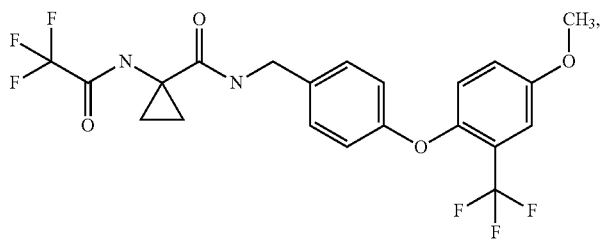 [SMILES: COc1ccc(Oc2ccc(CNC(=O)C3(NC(=O)C(F)(F)F)CC3)cc2)c(C(F)(F)F)c1] |
| (103) | 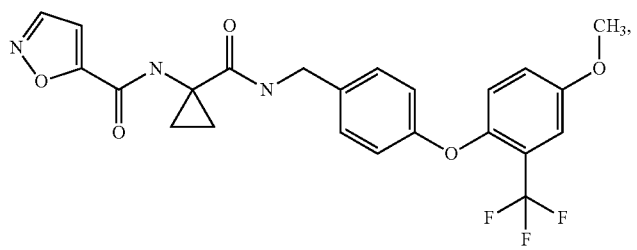 [SMILES: COc1ccc(Oc2ccc(CNC(=O)C3(NC(=O)c4ccno4)CC3)cc2)c(C(F)(F)F)c1] |
| (104) | 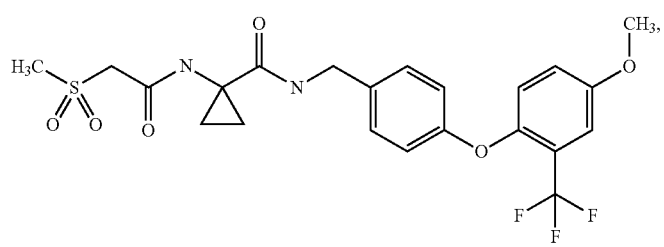 [SMILES: COc1ccc(Oc2ccc(CNC(=O)C3(NC(=O)CS(C)(=O)=O)CC3)cc2)c(C(F)(F)F)c1] |

| No. | Structure |
|---|---|
| (105) | 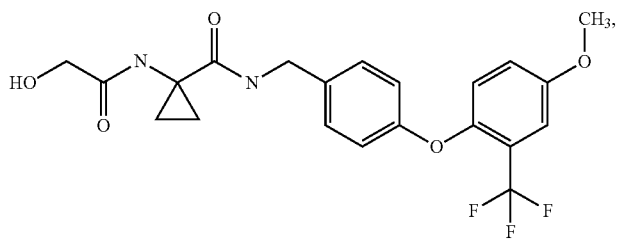 [SMILES: COc1ccc(Oc2ccc(CNC(=O)C3(NC(=O)CO)CC3)cc2)c(C(F)(F)F)c1] |
| (106) | 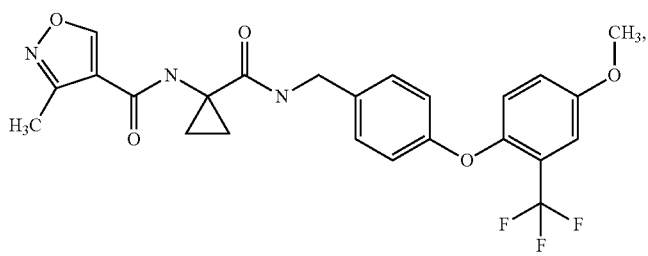 [SMILES: COc1ccc(Oc2ccc(CNC(=O)C3(NC(=O)c4conc4C)CC3)cc2)c(C(F)(F)F)c1] |
| (107) | 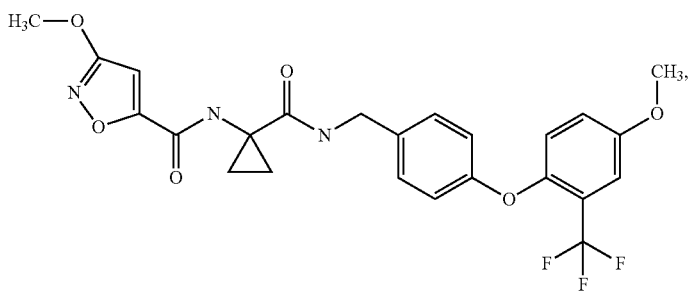 [SMILES: COc1ccc(Oc2ccc(CNC(=O)C3(NC(=O)c4cc(OC)no4)CC3)cc2)c(C(F)(F)F)c1] |
| (108) | 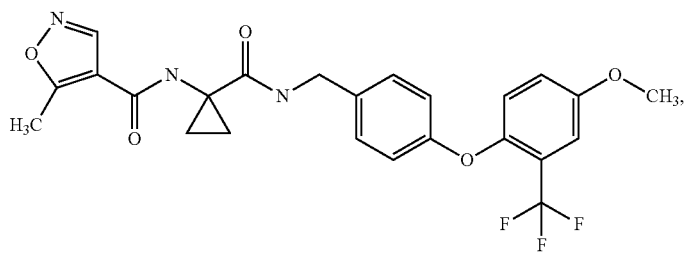 [SMILES: COc1ccc(Oc2ccc(CNC(=O)C3(NC(=O)c4cnoc4C)CC3)cc2)c(C(F)(F)F)c1] |
| (109) | 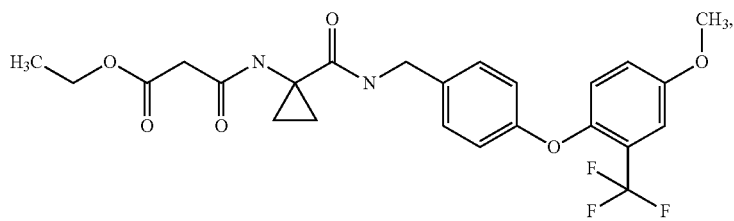 [SMILES: CCOC(=O)CC(=O)NC1(C(=O)NCc2ccc(Oc3ccc(OC)cc3C(F)(F)F)cc2)CC1] |
| (110) | 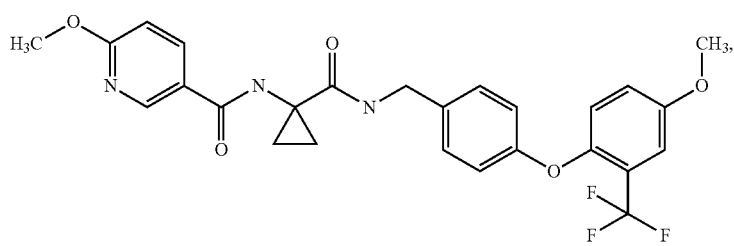 [SMILES: COc1ccc(Oc2ccc(CNC(=O)C3(NC(=O)c4ccc(OC)nc4)CC3)cc2)c(C(F)(F)F)c1] |

| No. | Structure |
|---|---|
| (111) | 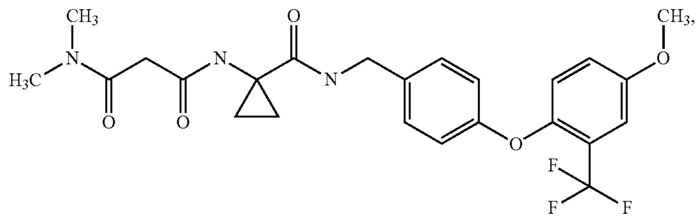 [SMILES: COc1ccc(Oc2ccc(CNC(=O)C3(NC(=O)CC(=O)N(C)C)CC3)cc2)c(C(F)(F)F)c1] |
| (112) | 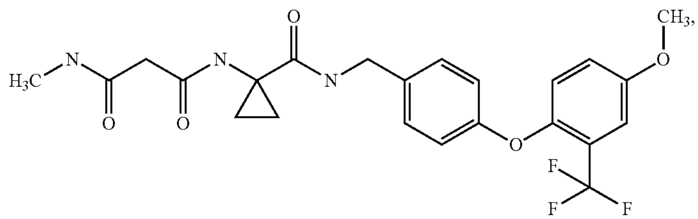 [SMILES: CNC(=O)CC(=O)NC1(C(=O)NCc2ccc(Oc3ccc(OC)cc3C(F)(F)F)cc2)CC1] |
| (113) | 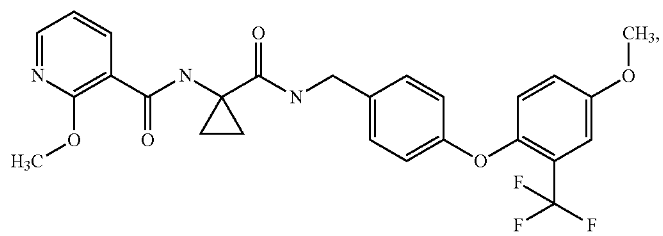 [SMILES: COc1ccc(Oc2ccc(CNC(=O)C3(NC(=O)c4cccnc4OC)CC3)cc2)c(C(F)(F)F)c1] |
| (114) | 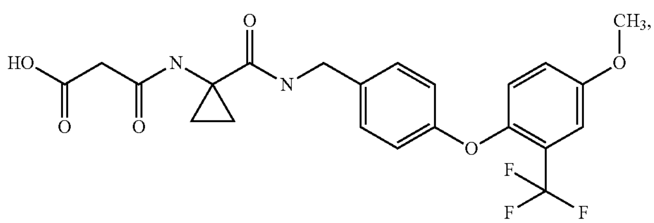 [SMILES: COc1ccc(Oc2ccc(CNC(=O)C3(NC(=O)CC(=O)O)CC3)cc2)c(C(F)(F)F)c1] |
| (115) | 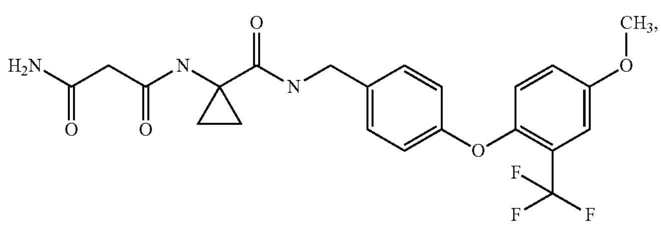 [SMILES: COc1ccc(Oc2ccc(CNC(=O)C3(NC(=O)CC(N)=O)CC3)cc2)c(C(F)(F)F)c1] |
| (116) | 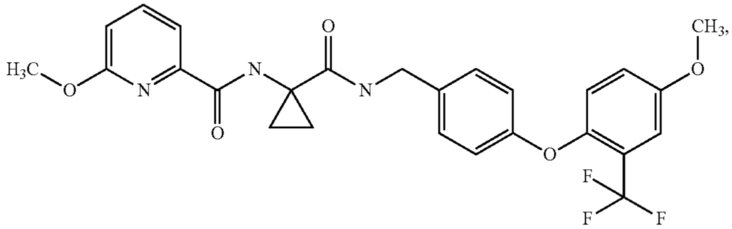 [SMILES: COc1ccc(Oc2ccc(CNC(=O)C3(NC(=O)c4cccc(OC)n4)CC3)cc2)c(C(F)(F)F)c1] |
| (117) | 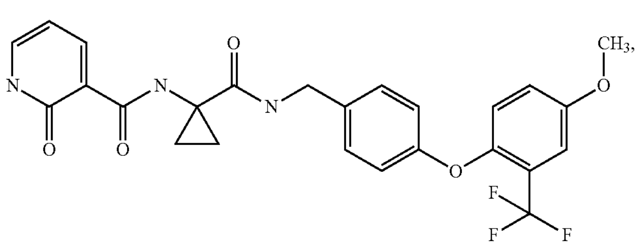 [SMILES: COc1ccc(Oc2ccc(CNC(=O)C3(NC(=O)c4ccc[nH]c4=O)CC3)cc2)c(C(F)(F)F)c1] |

| No. | Structure |
|---|---|
| (118) | 6-hydroxypyridine-2-carbonyl-NH-cyclopropyl-C(O)-NH-CH2-(4-(4-methoxy-2-(trifluoromethyl)phenoxy)phenyl) |
| (119) | 2-methoxypyridine-4-carbonyl-NH-cyclopropyl-C(O)-NH-CH2-(4-(4-methoxy-2-(trifluoromethyl)phenoxy)phenyl) |
| (120) | 2-fluoropyridine-4-carbonyl-NH-cyclopropyl-C(O)-NH-CH2-(4-(4-methoxy-2-(trifluoromethyl)phenoxy)phenyl) |
| (121) | pyridazine-4-carbonyl-NH-cyclopropyl-C(O)-NH-CH2-(4-(4-methoxy-2-(trifluoromethyl)phenoxy)phenyl) |
| (122) | 2-(trifluoromethyl)pyridine-4-carbonyl-NH-cyclopropyl-C(O)-NH-CH2-(4-(4-methoxy-2-(trifluoromethyl)phenoxy)phenyl) |
| (123) | 2-hydroxypyridine-4-carbonyl-NH-cyclopropyl-C(O)-NH-CH2-(4-(4-methoxy-2-(trifluoromethyl)phenoxy)phenyl) |

| No. | Structure |
|---|---|
| (124) | 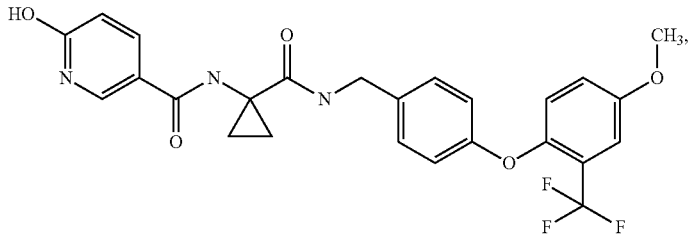 [SMILES: COc1ccc(Oc2ccc(CNC(=O)C3(NC(=O)c4ccc(O)nc4)CC3)cc2)c(C(F)(F)F)c1] |
| (125) | 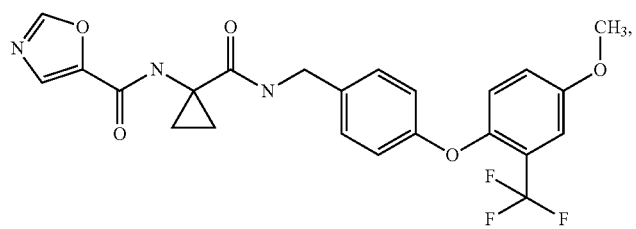 [SMILES: COc1ccc(Oc2ccc(CNC(=O)C3(NC(=O)c4cnco4)CC3)cc2)c(C(F)(F)F)c1] |
| (126) | 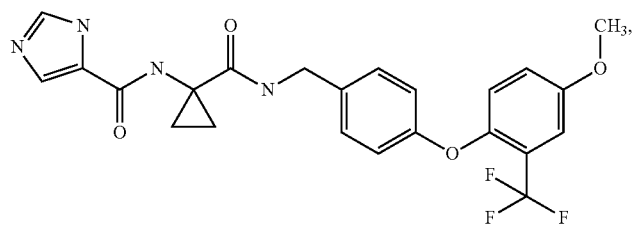 |
| (127) | 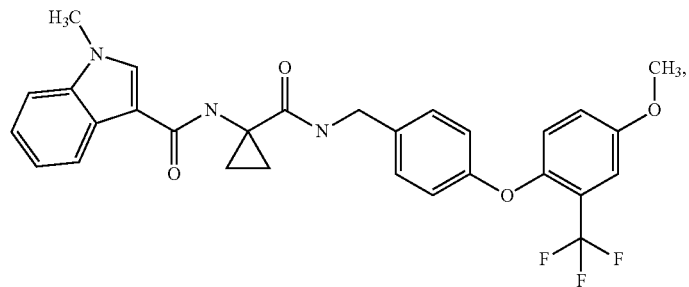 [SMILES: COc1ccc(Oc2ccc(CNC(=O)C3(NC(=O)c4cn(C)c5ccccc45)CC3)cc2)c(C(F)(F)F)c1] |
| (128) | 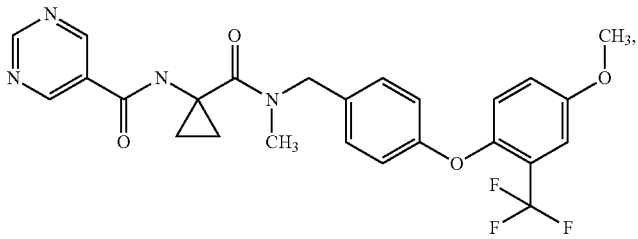 [SMILES: COc1ccc(Oc2ccc(CN(C)C(=O)C3(NC(=O)c4cncnc4)CC3)cc2)c(C(F)(F)F)c1] |
| (129) | 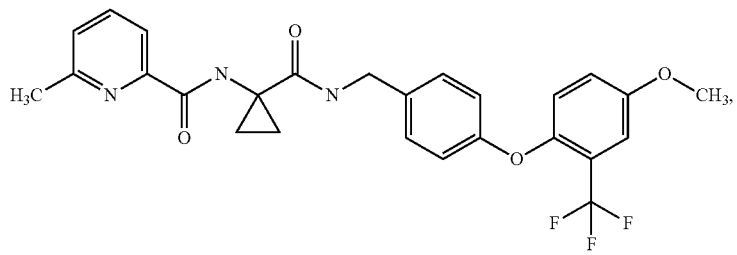 [SMILES: COc1ccc(Oc2ccc(CNC(=O)C3(NC(=O)c4cccc(C)n4)CC3)cc2)c(C(F)(F)F)c1] |

-continued
| No. | Structure |
|---|---|
| (130) | 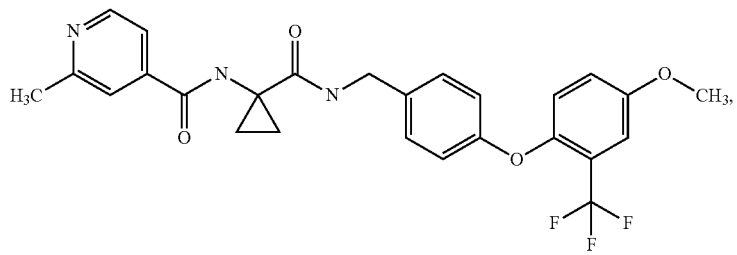 [SMILES: COc1ccc(Oc2ccc(CNC(=O)C3(NC(=O)c4ccnc(C)c4)CC3)cc2)c(C(F)(F)F)c1] |
| (131) | 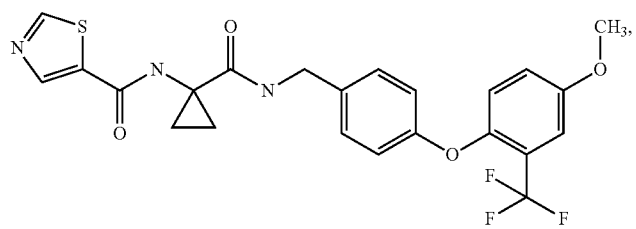 [SMILES: COc1ccc(Oc2ccc(CNC(=O)C3(NC(=O)c4cncs4)CC3)cc2)c(C(F)(F)F)c1] |
| (132) | 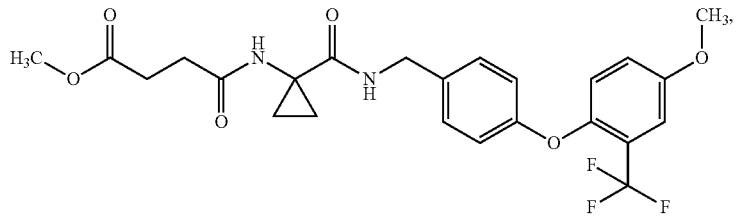 [SMILES: COC(=O)CCC(=O)NC1(C(=O)NCc2ccc(Oc3ccc(OC)cc3C(F)(F)F)cc2)CC1] |
| (133) | 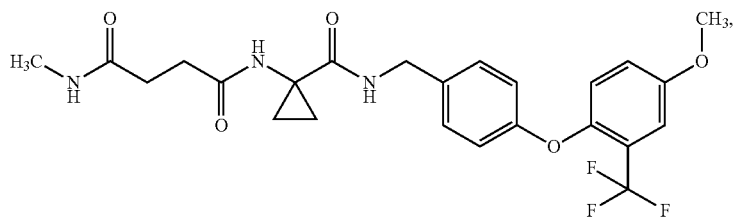 [SMILES: CNC(=O)CCC(=O)NC1(C(=O)NCc2ccc(Oc3ccc(OC)cc3C(F)(F)F)cc2)CC1] |
| (134) | 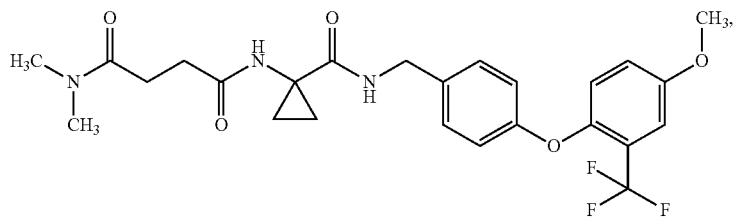 [SMILES: COc1ccc(Oc2ccc(CNC(=O)C3(NC(=O)CCC(=O)N(C)C)CC3)cc2)c(C(F)(F)F)c1] |
| (135) | 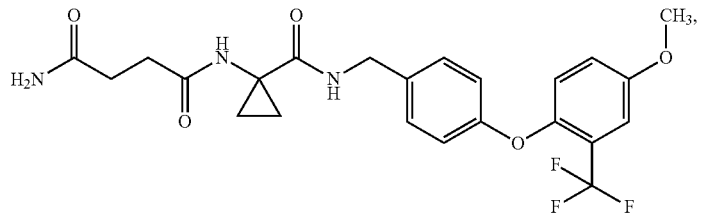 [SMILES: COc1ccc(Oc2ccc(CNC(=O)C3(NC(=O)CCC(N)=O)CC3)cc2)c(C(F)(F)F)c1] |

| No. | Structure |
|---|---|
| (136) | 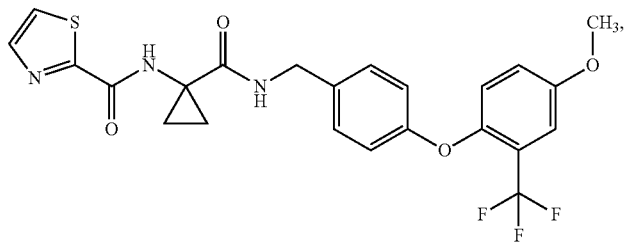 [SMILES: COc1ccc(Oc2ccc(CNC(=O)C3(NC(=O)c4nccs4)CC3)cc2)c(C(F)(F)F)c1] |
| (137) | 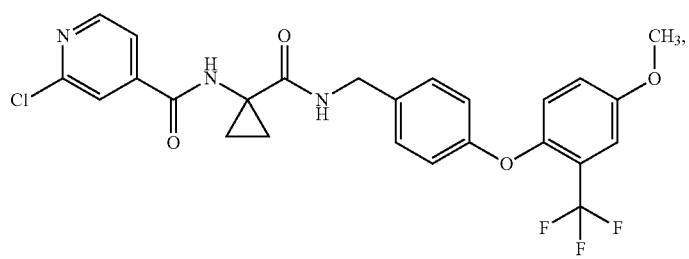 [SMILES: COc1ccc(Oc2ccc(CNC(=O)C3(NC(=O)c4ccnc(Cl)c4)CC3)cc2)c(C(F)(F)F)c1] |
| (138) | 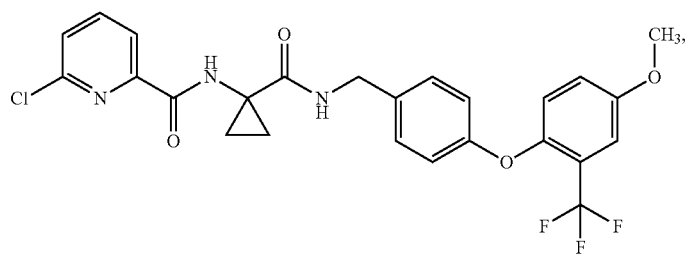 [SMILES: COc1ccc(Oc2ccc(CNC(=O)C3(NC(=O)c4cccc(Cl)n4)CC3)cc2)c(C(F)(F)F)c1] |
| (139) | 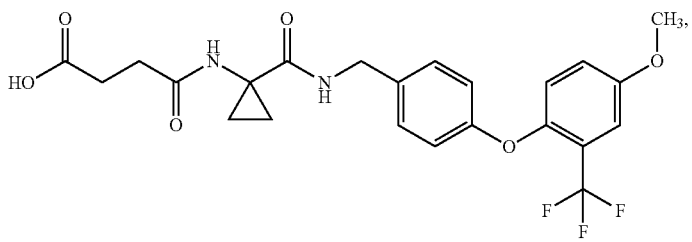 [SMILES: COc1ccc(Oc2ccc(CNC(=O)C3(NC(=O)CCC(=O)O)CC3)cc2)c(C(F)(F)F)c1] |
| (140) | 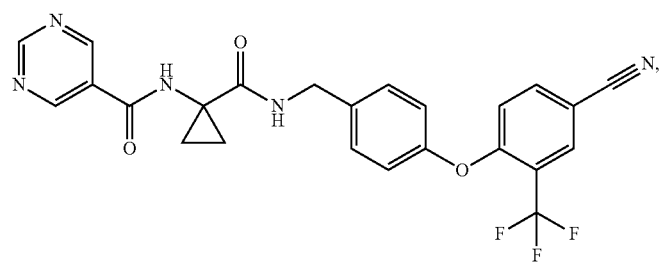 [SMILES: N#Cc1ccc(Oc2ccc(CNC(=O)C3(NC(=O)c4cncnc4)CC3)cc2)c(C(F)(F)F)c1] |
| (141) | 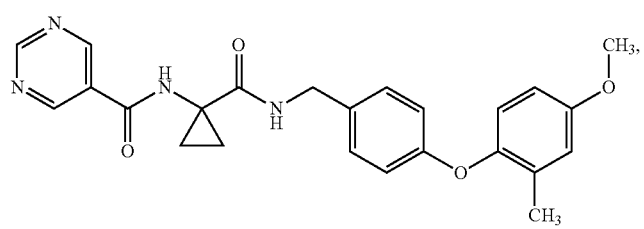 [SMILES: COc1ccc(Oc2ccc(CNC(=O)C3(NC(=O)c4cncnc4)CC3)cc2)c(C)c1] |

| No. | Structure |
|---|---|
| (142) | 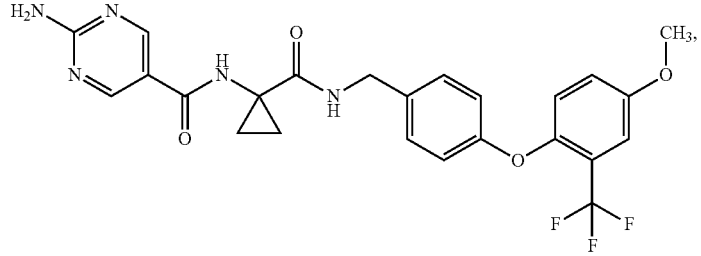 [SMILES: COc1ccc(Oc2ccc(CNC(=O)C3(NC(=O)c4cnc(N)nc4)CC3)cc2)c(C(F)(F)F)c1] |
| (143) | 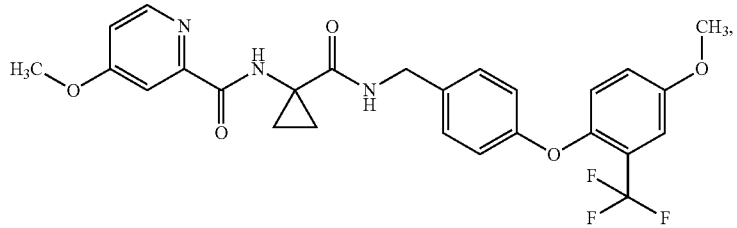 [SMILES: COc1ccnc(C(=O)NC2(C(=O)NCc3ccc(Oc4ccc(OC)cc4C(F)(F)F)cc3)CC2)c1] |
| (144) | 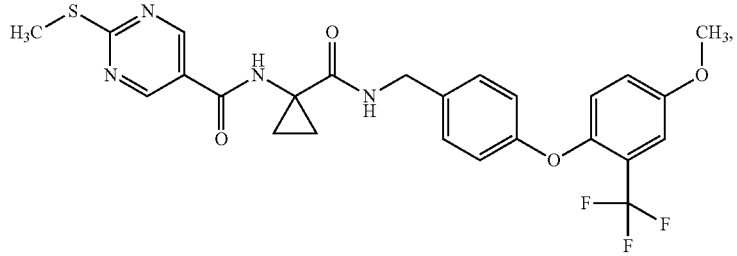 [SMILES: COc1ccc(Oc2ccc(CNC(=O)C3(NC(=O)c4cnc(SC)nc4)CC3)cc2)c(C(F)(F)F)c1] |
| (145) | 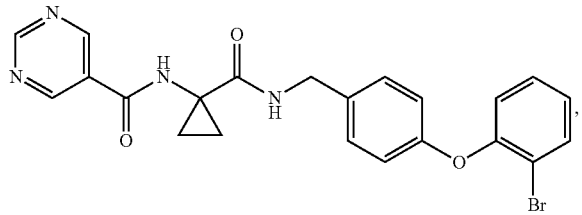 [SMILES: O=C(NC1(C(=O)NCc2ccc(Oc3ccccc3Br)cc2)CC1)c1cncnc1] |
| (146) | 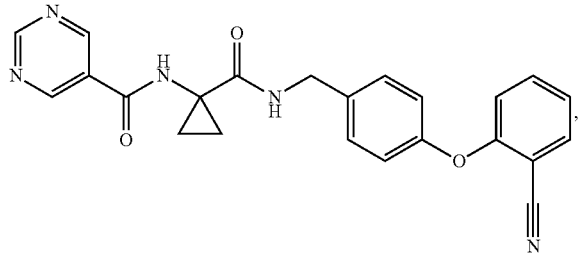 [SMILES: N#Cc1ccccc1Oc1ccc(CNC(=O)C2(NC(=O)c3cncnc3)CC2)cc1] |
| (147) | 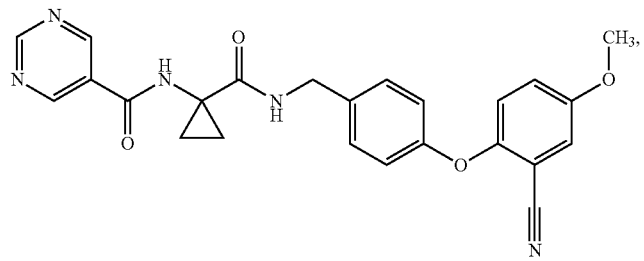 [SMILES: COc1ccc(Oc2ccc(CNC(=O)C3(NC(=O)c4cncnc4)CC3)cc2)c(C#N)c1] |

-continued

| No. | Structure |
|---|---|
| (148) | 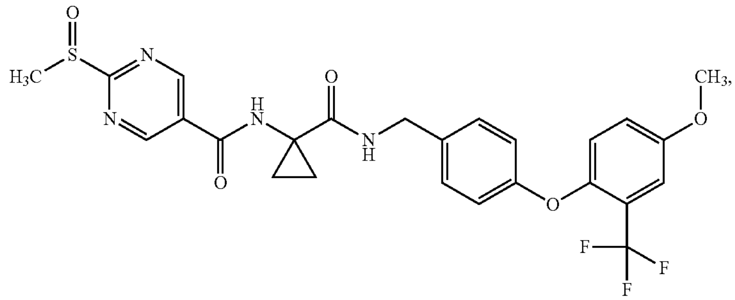 [SMILES: COc1ccc(Oc2ccc(CNC(=O)C3(NC(=O)c4cnc(S(C)=O)nc4)CC3)cc2)c(C(F)(F)F)c1] |
| (149) | 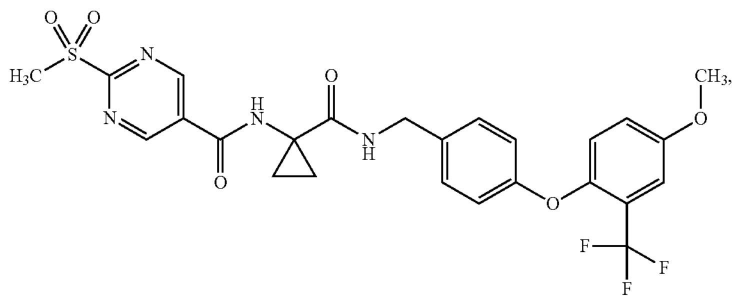 [SMILES: COc1ccc(Oc2ccc(CNC(=O)C3(NC(=O)c4cnc(S(C)(=O)=O)nc4)CC3)cc2)c(C(F)(F)F)c1] |
| (150) | 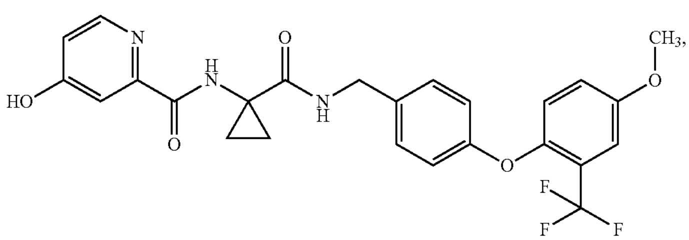 [SMILES: COc1ccc(Oc2ccc(CNC(=O)C3(NC(=O)c4cc(O)ccn4)CC3)cc2)c(C(F)(F)F)c1] |
| (151) | 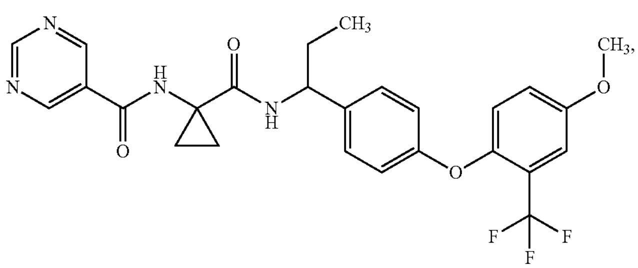 [SMILES: CCC(NC(=O)C1(NC(=O)c2cncnc2)CC1)c1ccc(Oc2ccc(OC)cc2C(F)(F)F)cc1] |
| (152) | 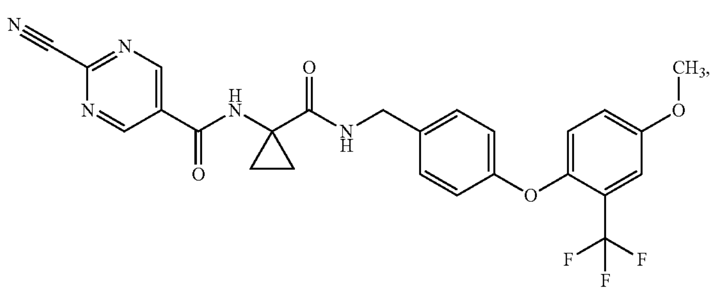 [SMILES: COc1ccc(Oc2ccc(CNC(=O)C3(NC(=O)c4cnc(C#N)nc4)CC3)cc2)c(C(F)(F)F)c1] |

| No. | Structure |
|---|---|
| (153) | 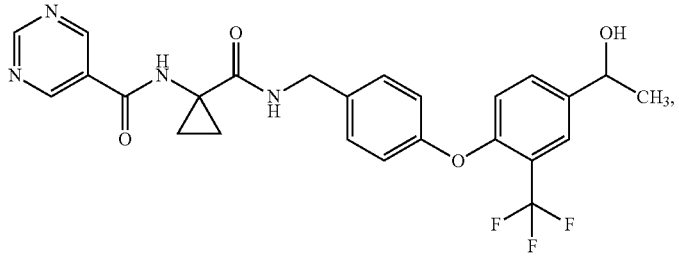 [SMILES: CC(O)c1ccc(Oc2ccc(CNC(=O)C3(NC(=O)c4cncnc4)CC3)cc2)c(C(F)(F)F)c1] |
| (154) | 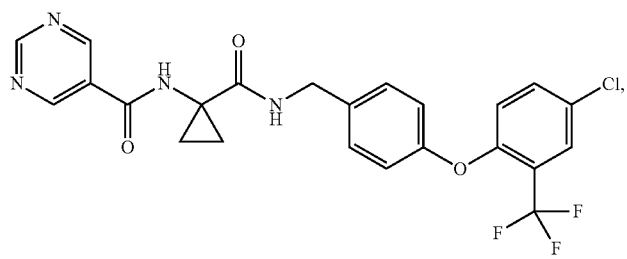 [SMILES: O=C(NC1(C(=O)NCc2ccc(Oc3ccc(Cl)cc3C(F)(F)F)cc2)CC1)c1cncnc1] |
| (155) | 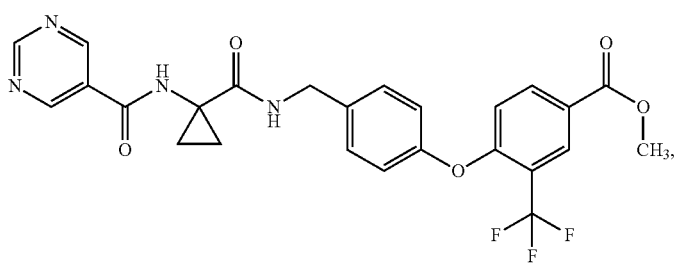 [SMILES: COC(=O)c1ccc(Oc2ccc(CNC(=O)C3(NC(=O)c4cncnc4)CC3)cc2)c(C(F)(F)F)c1] |
| (156) | 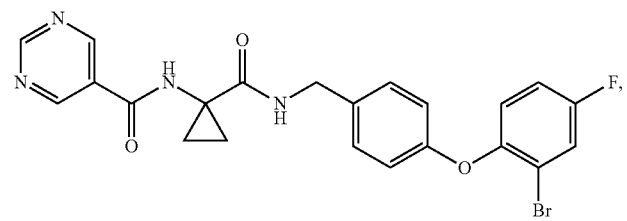 |
| (157) | 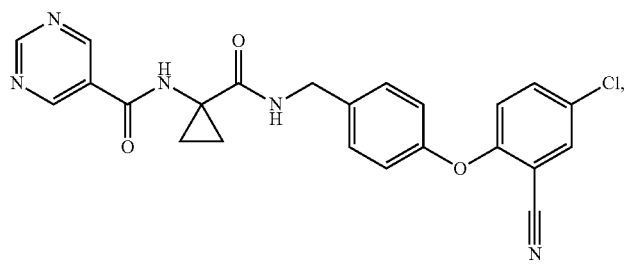 [SMILES: N#Cc1cc(Br)ccc1Oc1ccc(CNC(=O)C2(NC(=O)c3cncnc3)CC2)cc1] |
| (158) | 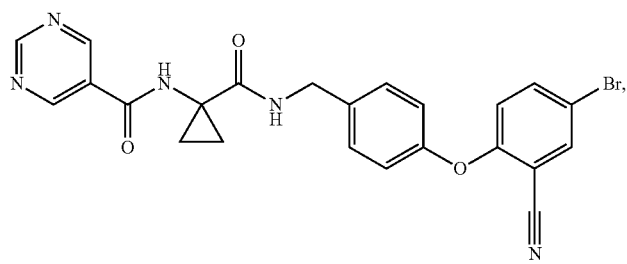 |

| No. | Structure |
|---|---|
| (159) | 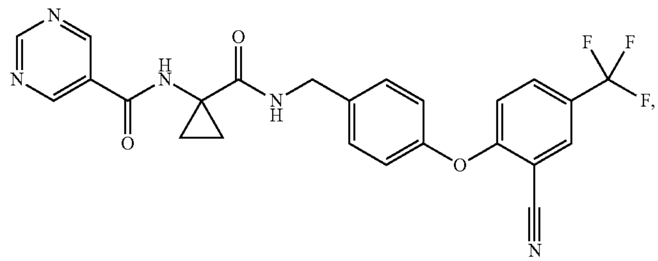 [SMILES: N#Cc1cc(C(F)(F)F)ccc1Oc1ccc(CNC(=O)C2(NC(=O)c3cncnc3)CC2)cc1] |
| (160) | 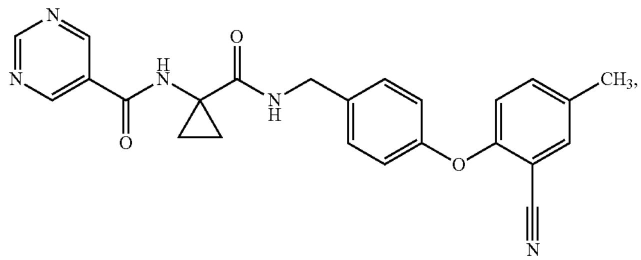 [SMILES: Cc1ccc(Oc2ccc(CNC(=O)C3(NC(=O)c4cncnc4)CC3)cc2)c(C#N)c1] |
| (161) | 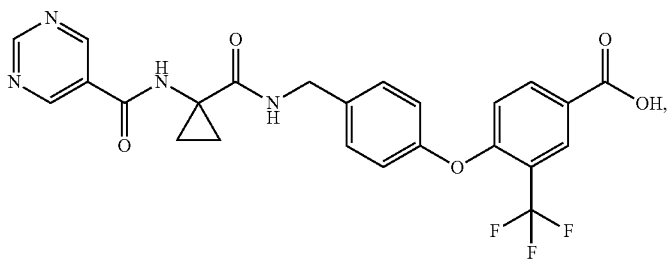 [SMILES: O=C(O)c1ccc(Oc2ccc(CNC(=O)C3(NC(=O)c4cncnc4)CC3)cc2)c(C(F)(F)F)c1] |
| (162) | and |
| (163) | | or a salt thereof.

16. A physiologically acceptable salt of a compound as in any one of claims 1-15.

17. A pharmaceutical composition comprising a compound as in any one of claims 1-15, or a physiologically acceptable salt thereof together with an inert carrier or diluents.

18. A method for treating acute pain, visceral pain, neuropathic pain, inflammatory/pain receptor-mediated pain, tumour pain and headache diseases, which method comprises administering to a host suffering from the same a therapeutically effective amount of a compound as in any one of claims 1-15, or a physiologically acceptable salt thereof.

* * * * *